US011788066B2

(12) United States Patent
Kim et al.

(10) Patent No.: US 11,788,066 B2
(45) Date of Patent: Oct. 17, 2023

(54) ANTIBODY CONJUGATES AND METHODS OF MAKING AND USING THE SAME

(71) Applicant: R.P. Scherer Technologies, LLC, Carson City, NV (US)

(72) Inventors: Yun Cheol Kim, Walnut Creek, CA (US); Chao Bai Huang, San Leandro, CA (US); David Rabuka, Kensington, CA (US)

(73) Assignee: R.P. Scherer Technologies, LLC, Carson City, NV (US)

( * ) Notice: Subject to any disclaimer, the term of this patent is extended or adjusted under 35 U.S.C. 154(b) by 136 days.

(21) Appl. No.: 17/532,797

(22) Filed: Nov. 22, 2021

(65) Prior Publication Data
US 2022/0145270 A1 May 12, 2022

Related U.S. Application Data

(62) Division of application No. 15/495,431, filed on Apr. 24, 2017, now Pat. No. 11,208,632.
(Continued)

(51) Int. Cl.
*C12N 9/02* (2006.01)
*A61K 47/68* (2017.01)
(Continued)

(52) U.S. Cl.
CPC ............ *C12N 9/0051* (2013.01); *A61K 47/60* (2017.08); *A61K 47/6851* (2017.08);
(Continued)

(58) Field of Classification Search
None
See application file for complete search history.

(56) References Cited

U.S. PATENT DOCUMENTS

| | | |
|---|---|---|
| 4,332,717 A | 6/1982 | Kanaoka et al. |
| 4,342,832 A | 8/1982 | Goeddel et al. |

(Continued)

FOREIGN PATENT DOCUMENTS

| | | |
|---|---|---|
| EP | 1391213 | 2/2004 |
| EP | 2325301 | 5/2011 |

(Continued)

OTHER PUBLICATIONS

Drake et al., (2014) "Aldehyde Tag Coupled with HIPS Chemistry Enables the Production of ADCs Conjugated Site-Specifically to Different Antibody Regions with Distinct in Vivo Efficacy and PK Outcomes", Bioconjugate Chemistry 24 (7):1331-1341.

(Continued)

*Primary Examiner* — Karl J Puttlitz
(74) *Attorney, Agent, or Firm* — Carol L. Francis; Rudy J. Ng; Bozicevic, Field & Francis LLP

(57) ABSTRACT

Antibodies that include a sulfatase motif-containing tag in a constant region of an immunoglobulin (Ig) light chain polypeptide are disclosed. The sulfatase motif can be converted by a formylglycine-generating enzyme (FGE) to produce a formylglycine (fGly)-modified Ig light chain polypeptide. An fGly-modified Ig light chain polypeptide of the antibody can be covalently and site-specifically bound to a moiety of interest to provide an antibody conjugate. The disclosure also encompasses methods of production of such tagged Ig light chain polypeptides, fGly-modified Ig light chain polypeptides, and antibody conjugates, as well as methods of use of same.

29 Claims, 26 Drawing Sheets

Specification includes a Sequence Listing.

Related U.S. Application Data

(60) Provisional application No. 62/327,906, filed on Apr. 26, 2016.

(51) Int. Cl.
*C07K 16/00* (2006.01)
*A61K 47/60* (2017.01)
*C07K 16/30* (2006.01)

(52) U.S. Cl.
CPC ............. *C07K 16/00* (2013.01); *C07K 16/30* (2013.01); *C12Y 108/99* (2013.01); *C07K 2317/14* (2013.01); *C07K 2317/515* (2013.01); *C07K 2317/52* (2013.01); *C07K 2317/56* (2013.01); *C07K 2317/94* (2013.01); *C07K 2319/40* (2013.01)

(56) References Cited

U.S. PATENT DOCUMENTS

| | | |
|---|---|---|
| 4,671,958 A | 6/1987 | Rodwell et al. |
| 4,952,394 A | 8/1990 | Senter |
| 5,200,534 A | 4/1993 | Rao |
| 5,202,448 A | 4/1993 | Carver et al. |
| 5,204,449 A | 4/1993 | Puri |
| 5,208,020 A | 5/1993 | Chari et al. |
| 5,229,529 A | 7/1993 | Ueno et al. |
| 5,274,137 A | 12/1993 | Nicolaou et al. |
| 5,279,949 A | 1/1994 | Nair |
| 5,294,637 A | 3/1994 | Chen et al. |
| 5,415,869 A | 5/1995 | Straubinger et al. |
| 5,416,064 A | 5/1995 | Chari et al. |
| 5,428,130 A | 6/1995 | Capon et al. |
| 5,455,165 A | 10/1995 | Capon et al. |
| 5,475,092 A | 12/1995 | Chari et al. |
| 5,484,892 A | 1/1996 | Tedder et al. |
| 5,514,582 A | 5/1996 | Capon et al. |
| 5,585,499 A | 12/1996 | Chari et al. |
| 5,624,821 A | 4/1997 | Winter et al. |
| 5,681,566 A | 10/1997 | Stevenson |
| 5,686,072 A | 11/1997 | Uhr et al. |
| 5,698,672 A | 12/1997 | Labroo et al. |
| 5,789,554 A | 8/1998 | Leung et al. |
| 5,821,263 A | 10/1998 | Scola et al. |
| 5,824,701 A | 10/1998 | Greenwald et al. |
| 5,831,000 A | 11/1998 | Murayama et al. |
| 5,846,545 A | 12/1998 | Chari et al. |
| 5,869,680 A | 2/1999 | Mas et al. |
| 5,885,573 A | 3/1999 | Bluestone et al. |
| 5,980,895 A | 11/1999 | Pastan et al. |
| 5,981,485 A | 11/1999 | O'Connor et al. |
| 5,981,488 A | 11/1999 | Hoffman |
| 6,103,236 A | 8/2000 | Suzawa et al. |
| 6,121,022 A | 9/2000 | Presta et al. |
| 6,183,744 B1 | 2/2001 | Goldenberg |
| 6,187,287 B1 | 2/2001 | Leung et al. |
| 6,194,551 B1 | 2/2001 | Idusogie et al. |
| 6,254,868 B1 | 7/2001 | Leung et al. |
| 6,268,343 B1 | 7/2001 | Knudsen et al. |
| 6,284,727 B1 | 9/2001 | Kim et al. |
| 6,323,315 B1 | 11/2001 | Pettit et al. |
| 6,395,226 B1 | 5/2002 | Plunkett |
| 6,441,163 B1 | 8/2002 | Chari et al. |
| 6,528,624 B1 | 3/2003 | Idusogie et al. |
| 6,538,124 B1 | 3/2003 | Idusogie et al. |
| 6,548,644 B1 | 4/2003 | Pettit |
| 6,570,040 B2 | 5/2003 | Saxon et al. |
| 6,576,744 B1 | 6/2003 | Presnell et al. |
| 6,608,183 B1 | 8/2003 | Cox, III |
| 6,608,196 B2 | 8/2003 | Wang et al. |
| 6,653,104 B2 | 11/2003 | Goldenberg |
| 6,660,843 B1 | 12/2003 | Feige et al. |
| 6,692,924 B2 | 2/2004 | Presnell et al. |
| 6,710,169 B2 | 3/2004 | Capon et al. |
| 6,716,821 B2 | 4/2004 | Zhao et al. |
| 6,737,056 B1 | 5/2004 | Presta |
| 6,756,480 B2 | 6/2004 | Kostenuik et al. |
| 6,770,625 B2 | 8/2004 | Soltero et al. |
| 6,777,539 B2 | 8/2004 | Sprecher et al. |
| 6,800,740 B1 | 10/2004 | Cunningham et al. |
| 6,803,451 B2 | 10/2004 | Presnell et al. |
| 6,825,166 B2 | 11/2004 | McChesney et al. |
| 6,875,845 B2 | 4/2005 | Presnell et al. |
| 6,884,869 B2 | 4/2005 | Senter et al. |
| 6,897,044 B1 | 5/2005 | Braslawsky et al. |
| 6,897,292 B2 | 5/2005 | Presnell et al. |
| 6,900,218 B2 | 5/2005 | Wang et al. |
| 6,900,304 B2 | 5/2005 | Tsien et al. |
| 6,913,748 B2 | 7/2005 | Widdison |
| 6,927,042 B2 | 8/2005 | Schultz et al. |
| 6,989,366 B2 | 1/2006 | Beeley et al. |
| 6,989,452 B2 | 1/2006 | Ng et al. |
| 6,998,253 B1 | 2/2006 | Presta et al. |
| 7,045,337 B2 | 5/2006 | Schultz et al. |
| 7,045,498 B2 | 5/2006 | Kindsvogel et al. |
| 7,045,605 B2 | 5/2006 | Bader et al. |
| 7,049,316 B2 | 5/2006 | Zhao et al. |
| 7,056,701 B2 | 6/2006 | Heer et al. |
| 7,087,600 B2 | 8/2006 | Ng et al. |
| 7,091,186 B2 | 8/2006 | Senter et al. |
| 7,097,840 B2 | 8/2006 | Erickson et al. |
| 7,098,308 B2 | 8/2006 | Senter et al. |
| 7,112,439 B2 | 9/2006 | Johnson et al. |
| 7,115,573 B2 | 10/2006 | Pickford et al. |
| 7,122,637 B2 | 10/2006 | Presta |
| 7,138,371 B2 | 11/2006 | DeFrees |
| 7,141,547 B2 | 11/2006 | Rosen et al. |
| 7,176,278 B2 | 2/2007 | Prior |
| 7,183,387 B1 | 2/2007 | Presta |
| 7,189,811 B2 | 3/2007 | Panda et al. |
| 7,189,835 B2 | 3/2007 | Raymond et al. |
| 7,189,839 B2 | 3/2007 | Presnell et al. |
| 7,214,663 B2 | 5/2007 | Bebbington et al. |
| 7,214,685 B2 | 5/2007 | Tietze et al. |
| 7,226,990 B2 | 6/2007 | Knudsen et al. |
| 7,230,068 B2 | 6/2007 | Wilson |
| 7,255,012 B2 | 8/2007 | Hedtke |
| 7,256,257 B2 | 8/2007 | Doronina et al. |
| 7,265,203 B2 | 9/2007 | Presnell et al. |
| 7,271,149 B2 | 9/2007 | Glaesner et al. |
| 7,271,255 B2 | 9/2007 | Raymond et al. |
| 7,276,497 B2 | 10/2007 | Chari et al. |
| 7,276,585 B2 | 10/2007 | Lazar et al. |
| 7,276,947 B2 | 10/2007 | Becker et al. |
| 7,297,775 B2 | 11/2007 | Idusogie et al. |
| 7,317,091 B2 | 1/2008 | Lazar et al. |
| 7,319,139 B2 | 1/2008 | Braslawsky et al. |
| 7,321,026 B2 | 1/2008 | Leung |
| 7,332,571 B2 | 2/2008 | Miao et al. |
| 7,332,581 B2 | 2/2008 | Presta |
| 7,335,742 B2 | 2/2008 | Presta |
| 7,338,659 B2 | 3/2008 | Leung |
| 7,351,555 B2 | 4/2008 | Presnell et al. |
| 7,355,008 B2 | 4/2008 | Stavenhagen et al. |
| 7,355,011 B2 | 4/2008 | Popplewell et al. |
| 7,355,012 B2 | 4/2008 | Pastan et al. |
| 7,361,347 B2 | 4/2008 | Adolf et al. |
| 7,368,565 B2 | 5/2008 | Chari et al. |
| 7,371,826 B2 | 5/2008 | Presta |
| 7,374,762 B2 | 5/2008 | Amphlett |
| 7,381,408 B2 | 6/2008 | Mezo et al. |
| 7,385,028 B2 | 6/2008 | Miao et al. |
| 7,388,026 B2 | 6/2008 | Zhao et al. |
| 7,404,956 B2 | 7/2008 | Peters et al. |
| 7,364,731 B2 | 8/2008 | Idusogie et al. |
| 7,410,779 B2 | 8/2008 | Heer et al. |
| 7,411,056 B2 | 8/2008 | Presnell et al. |
| 7,416,727 B2 | 8/2008 | Presta |
| 7,423,116 B2 | 9/2008 | Doronina et al. |
| 7,425,541 B2 | 9/2008 | Dubois et al. |
| 7,435,416 B2 | 10/2008 | Devaux et al. |
| 7,435,550 B2 | 10/2008 | Novak et al. |
| 7,442,778 B2 | 10/2008 | Gegg et al. |
| 7,445,764 B1 | 11/2008 | Kratz |

(56) References Cited

U.S. PATENT DOCUMENTS

| | | |
|---|---|---|
| 7,456,260 B2 | 11/2008 | Rybak et al. |
| 7,473,796 B2 | 1/2009 | Chari et al. |
| 7,488,590 B2 | 2/2009 | Feige et al. |
| 7,491,809 B2 | 2/2009 | Presnell et al. |
| 7,494,649 B2 | 2/2009 | Amphlett et al. |
| 7,498,298 B2 | 3/2009 | Doronina et al. |
| 7,498,302 B2 | 3/2009 | Ng et al. |
| 7,501,120 B2 | 3/2009 | Amphlett et al. |
| 7,501,497 B2 | 3/2009 | Rixon et al. |
| 7,507,420 B2 | 3/2009 | Ng et al. |
| 7,514,080 B2 | 4/2009 | Amphlett et al. |
| 7,517,903 B2 | 4/2009 | Chen et al. |
| 7,521,541 B2 | 4/2009 | Eigenbrot et al. |
| 7,521,542 B2 | 4/2009 | Johnson et al. |
| 7,534,427 B2 | 5/2009 | Goldenberg et al. |
| 7,541,034 B1 | 6/2009 | Fitzgerald et al. |
| 7,553,816 B2 | 6/2009 | Senter et al. |
| 7,572,456 B2 | 8/2009 | Johnson et al. |
| 7,572,892 B2 | 8/2009 | Novak et al. |
| 7,575,748 B1 | 8/2009 | Erickson et al. |
| 7,601,354 B2 | 10/2009 | Chari |
| 7,608,686 B2 | 10/2009 | Gross et al. |
| 7,618,628 B2 | 11/2009 | Johnson et al. |
| 7,622,116 B2 | 11/2009 | Kuestner et al. |
| 7,629,452 B2 | 12/2009 | Sprecher et al. |
| 7,632,497 B2 | 12/2009 | Stavenhagen |
| 7,635,767 B2 | 12/2009 | Rixon et al. |
| 7,642,228 B2 | 1/2010 | Carter et al. |
| 7,655,660 B2 | 2/2010 | Zhao et al. |
| 7,655,661 B2 | 2/2010 | Zhao et al. |
| 7,657,380 B2 | 2/2010 | Lazar et al. |
| 7,659,241 B2 | 2/2010 | Senter et al. |
| 7,662,387 B2 | 2/2010 | Law et al. |
| 7,662,925 B2 | 2/2010 | Lazar et al. |
| 7,662,936 B2 | 2/2010 | Kadkhodayan et al. |
| 7,691,962 B2 | 4/2010 | Boyd et al. |
| 7,722,865 B2 | 5/2010 | Vellard et al. |
| 7,723,485 B2 | 5/2010 | Junutula et al. |
| 7,729,232 B2 | 6/2010 | Wang et al. |
| 7,745,394 B2 | 6/2010 | Doronina et al. |
| 7,750,116 B1 | 7/2010 | Doronina et al. |
| 7,754,681 B2 | 7/2010 | Feng |
| 7,771,727 B2 | 8/2010 | Fuselier et al. |
| 7,777,019 B2 | 8/2010 | Pastan et al. |
| 7,803,915 B2 | 9/2010 | Cairns et al. |
| 7,816,317 B2 | 10/2010 | Bebbington et al. |
| 7,829,086 B2 | 11/2010 | Hilbert et al. |
| 7,829,531 B2 | 11/2010 | Senter et al. |
| 7,837,980 B2 | 11/2010 | Alley et al. |
| 7,847,105 B2 | 12/2010 | Gangwar et al. |
| 7,851,432 B2 | 12/2010 | Chari et al. |
| 7,851,437 B2 | 12/2010 | Senter et al. |
| 7,855,275 B2 | 12/2010 | Eigenbrot et al. |
| 7,858,759 B2 | 12/2010 | Brandt et al. |
| 7,893,023 B2 | 2/2011 | Tronet et al. |
| 7,906,545 B2 | 3/2011 | Zhao et al. |
| 7,960,512 B2 | 6/2011 | Stavenhagen et al. |
| 7,964,195 B2 | 6/2011 | Papkoff et al. |
| 7,964,566 B2 | 6/2011 | Doronina et al. |
| 7,964,567 B2 | 6/2011 | Doronina et al. |
| 7,978,319 B2 | 7/2011 | Okabe et al. |
| 7,985,783 B2 | 7/2011 | Carrico et al. |
| 8,097,701 B2 | 1/2012 | Carrico et al. |
| 8,163,882 B2 | 4/2012 | Presta |
| 8,192,737 B2 | 6/2012 | Stavenhagen et al. |
| 8,227,212 B2 | 7/2012 | Von Figura et al. |
| 8,349,910 B2 | 1/2013 | Carrico et al. |
| 8,765,437 B2 | 7/2014 | Koppaka et al. |
| 8,846,866 B2 | 9/2014 | Carrico et al. |
| 9,447,390 B2 | 9/2016 | Carrico et al. |
| 9,540,438 B2 | 1/2017 | Barfield et al. |
| 2002/0103345 A1 | 8/2002 | Zhu |
| 2002/0128448 A1 | 9/2002 | Reff |
| 2002/0146504 A1 | 10/2002 | Schwartz |
| 2002/0177756 A1 | 11/2002 | Pierre Godinot et al. |
| 2003/0082575 A1 | 5/2003 | Schultz et al. |
| 2003/0108609 A1 | 6/2003 | Berry et al. |
| 2003/0109682 A1 | 6/2003 | Santi et al. |
| 2003/0124669 A1 | 7/2003 | Pan et al. |
| 2003/0157108 A1 | 8/2003 | Presta |
| 2003/0166868 A1 | 9/2003 | Presta et al. |
| 2003/0171285 A1 | 9/2003 | Finn et al. |
| 2003/0186229 A1 | 10/2003 | Tsien et al. |
| 2004/0010124 A1 | 1/2004 | Johnson et al. |
| 2004/0048395 A1 | 3/2004 | Lee et al. |
| 2004/0110226 A1 | 6/2004 | Lazar et al. |
| 2004/0115774 A1 | 6/2004 | Kochendorfer et al. |
| 2004/0132101 A1 | 7/2004 | Lazar et al. |
| 2004/0197866 A1 | 10/2004 | Johnson et al. |
| 2004/0219156 A1 | 11/2004 | Goldenberg et al. |
| 2004/0229250 A1 | 11/2004 | Figura et al. |
| 2004/0265952 A1 | 12/2004 | Deiters et al. |
| 2005/0026234 A1 | 2/2005 | Violin et al. |
| 2005/0037000 A1 | 2/2005 | Stavenhagen et al. |
| 2005/0064514 A1 | 3/2005 | Stavenhagen et al. |
| 2005/0084862 A1 | 4/2005 | Lee et al. |
| 2005/0118174 A1 | 6/2005 | Presta |
| 2005/0118182 A1 | 6/2005 | Pastan et al. |
| 2005/0142133 A1 | 6/2005 | Lazar |
| 2005/0147618 A1 | 7/2005 | Rivera et al. |
| 2005/0170404 A1 | 8/2005 | Cho et al. |
| 2005/0177878 A1 | 8/2005 | Melo et al. |
| 2005/0220762 A1 | 10/2005 | Cho et al. |
| 2005/0249723 A1 | 11/2005 | Lazar |
| 2005/0260711 A1 | 11/2005 | Datta et al. |
| 2005/0281829 A1 | 12/2005 | Hehir et al. |
| 2006/0013810 A1 | 1/2006 | Johnson et al. |
| 2006/0019347 A1 | 1/2006 | Cho et al. |
| 2006/0024298 A1 | 2/2006 | Lazar et al. |
| 2006/0035305 A1 | 2/2006 | Bertozzi |
| 2006/0057149 A1 | 3/2006 | Johnson et al. |
| 2006/0121032 A1 | 6/2006 | Dahiyat et al. |
| 2006/0134105 A1 | 6/2006 | Lazar et al. |
| 2006/0134709 A1 | 6/2006 | Stavenhagen et al. |
| 2006/0135427 A1 | 6/2006 | Hays et al. |
| 2006/0153860 A1 | 7/2006 | Cho et al. |
| 2006/0173170 A1 | 8/2006 | Chamberlain et al. |
| 2006/0182750 A1 | 8/2006 | Chari et al. |
| 2006/0183198 A1 | 8/2006 | Buechler et al. |
| 2006/0189529 A1 | 8/2006 | Cho et al. |
| 2006/0194290 A1 | 8/2006 | Presta |
| 2006/0194957 A1 | 8/2006 | Presta |
| 2006/0217289 A1 | 9/2006 | Miao et al. |
| 2006/0235208 A1 | 10/2006 | Lazar et al. |
| 2006/0275254 A1 | 12/2006 | Kim et al. |
| 2007/0004909 A1 | 1/2007 | Johnson et al. |
| 2007/0009523 A1 | 1/2007 | Presta |
| 2007/0020258 A1 | 1/2007 | Jardieu et al. |
| 2007/0020260 A1 | 1/2007 | Presta |
| 2007/0024389 A1 | 2/2007 | Mizutani |
| 2007/0031922 A1 | 2/2007 | Presta et al. |
| 2007/0036799 A1 | 2/2007 | Stavehagen et al. |
| 2007/0037216 A1 | 2/2007 | Johnson et al. |
| 2007/0053901 A1 | 3/2007 | Lazar et al. |
| 2007/0077429 A1 | 4/2007 | Mirkin et al. |
| 2007/0122408 A1 | 5/2007 | Barbas, III |
| 2007/0123691 A1 | 5/2007 | Wilson |
| 2007/0123693 A1 | 5/2007 | Wilson |
| 2007/0135620 A1 | 6/2007 | Chamberlain et al. |
| 2007/0148170 A1 | 6/2007 | Desjarlais et al. |
| 2007/0148171 A1 | 6/2007 | Lazar et al. |
| 2007/0160597 A1 | 7/2007 | Lazar et al. |
| 2007/0166309 A1 | 7/2007 | Lazar et al. |
| 2007/0189962 A1 | 8/2007 | Pastan et al. |
| 2007/0198996 A1 | 8/2007 | Chiu et al. |
| 2007/0202098 A1 | 8/2007 | Lazar et al. |
| 2007/0219133 A1 | 9/2007 | Lazar et al. |
| 2007/0224189 A1 | 9/2007 | Lazar et al. |
| 2007/0224192 A1 | 9/2007 | Lazar et al. |
| 2007/0231329 A1 | 10/2007 | Lazar et al. |
| 2007/0237765 A1 | 10/2007 | Lazar et al. |
| 2007/0237766 A1 | 10/2007 | Lazar et al. |
| 2007/0237767 A1 | 10/2007 | Lazar et al. |
| 2007/0238665 A1 | 10/2007 | Lazar et al. |

(56) References Cited

U.S. PATENT DOCUMENTS

| | | |
|---|---|---|
| 2007/0243188 A1 | 10/2007 | Lazar et al. |
| 2007/0244303 A1 | 10/2007 | Johnson et al. |
| 2007/0248602 A1 | 10/2007 | Lazar et al. |
| 2007/0248603 A1 | 10/2007 | Lazar et al. |
| 2007/0264260 A1 | 11/2007 | Tuscano et al. |
| 2007/0269369 A1 | 11/2007 | Gegg et al. |
| 2007/0275460 A1 | 11/2007 | Desjarlais et al. |
| 2007/0286859 A1 | 12/2007 | Lazar et al. |
| 2008/0044417 A1 | 2/2008 | Johnson et al. |
| 2008/0044429 A1 | 2/2008 | Johnson et al. |
| 2008/0050310 A1 | 2/2008 | Ebens et al. |
| 2008/0050371 A1 | 2/2008 | Johnson et al. |
| 2008/0050374 A1 | 2/2008 | Cho et al. |
| 2008/0051563 A1 | 2/2008 | Lazar et al. |
| 2008/0057056 A1 | 3/2008 | Lazar et al. |
| 2008/0081038 A1 | 4/2008 | Cho et al. |
| 2008/0085277 A1 | 4/2008 | Cho et al. |
| 2008/0085538 A1 | 4/2008 | Buechler et al. |
| 2008/0095762 A1 | 4/2008 | Presta |
| 2008/0097083 A1 | 4/2008 | Cho et al. |
| 2008/0102124 A1 | 5/2008 | Cho et al. |
| 2008/0102125 A1 | 5/2008 | Cho et al. |
| 2008/0103293 A1 | 5/2008 | Cho et al. |
| 2008/0103294 A1 | 5/2008 | Cho et al. |
| 2008/0108791 A1 | 5/2008 | Cho et al. |
| 2008/0108792 A1 | 5/2008 | Hays et al. |
| 2008/0108797 A1 | 5/2008 | Cho et al. |
| 2008/0112943 A1 | 5/2008 | Mariani et al. |
| 2008/0112961 A1 | 5/2008 | Stavehagen et al. |
| 2008/0113408 A1 | 5/2008 | Mariani et al. |
| 2008/0113411 A1 | 5/2008 | Sheffer et al. |
| 2008/0113412 A1 | 5/2008 | Sheffer et al. |
| 2008/0113457 A1 | 5/2008 | Tsay et al. |
| 2008/0113912 A1 | 5/2008 | Hays et al. |
| 2008/0113913 A1 | 5/2008 | Hays et al. |
| 2008/0113914 A1 | 5/2008 | Hays et al. |
| 2008/0114154 A1 | 5/2008 | Cho et al. |
| 2008/0114155 A1 | 5/2008 | Cho et al. |
| 2008/0118505 A1 | 5/2008 | Tedder |
| 2008/0119640 A1 | 5/2008 | Hays et al. |
| 2008/0125574 A1 | 5/2008 | Sheffer et al. |
| 2008/0131435 A1 | 6/2008 | Stavehagen et al. |
| 2008/0132681 A1 | 6/2008 | Hays et al. |
| 2008/0138338 A1 | 6/2008 | Idusogie et al. |
| 2008/0138344 A1 | 6/2008 | Stavenhagen et al. |
| 2008/0138349 A1 | 6/2008 | Stavenhagen et al. |
| 2008/0146781 A1 | 6/2008 | Cho et al. |
| 2008/0152649 A1 | 6/2008 | Chamberlain et al. |
| 2008/0154025 A1 | 6/2008 | Lazar et al. |
| 2008/0161539 A1 | 7/2008 | Cho et al. |
| 2008/0161541 A1 | 7/2008 | Lazar et al. |
| 2008/0166759 A1 | 7/2008 | Presta et al. |
| 2008/0167452 A1 | 7/2008 | Maiti et al. |
| 2008/0177027 A1 | 7/2008 | Miao et al. |
| 2008/0177038 A1 | 7/2008 | Miao et al. |
| 2008/0181890 A1 | 7/2008 | Lazar et al. |
| 2008/0182968 A1 | 7/2008 | Lazar et al. |
| 2008/0182969 A1 | 7/2008 | Miao et al. |
| 2008/0187491 A1 | 8/2008 | Miao et al. |
| 2008/0187956 A1 | 8/2008 | Carrico et al. |
| 2008/0194459 A1 | 8/2008 | Miao et al. |
| 2008/0199471 A1 | 8/2008 | Bernett et al. |
| 2008/0199909 A1 | 8/2008 | Buechler et al. |
| 2008/0206242 A1 | 8/2008 | Lawrence et al. |
| 2008/0206853 A1 | 8/2008 | Lee et al. |
| 2008/0206867 A1 | 8/2008 | Desjarlais et al. |
| 2008/0207877 A1 | 8/2008 | Cho et al. |
| 2008/0213840 A1 | 9/2008 | Miao et al. |
| 2008/0219974 A1 | 9/2008 | Bernett et al. |
| 2008/0225287 A1 | 9/2008 | Mirkin et al. |
| 2008/0227205 A1 | 9/2008 | Cho |
| 2008/0242845 A1 | 10/2008 | Lazar et al. |
| 2008/0244222 A1 | 10/2008 | Supalov et al. |
| 2008/0248028 A1 | 10/2008 | Lazar et al. |
| 2008/0249288 A1 | 10/2008 | Mezo et al. |
| 2008/0254027 A1 | 10/2008 | Bernett et al. |
| 2008/0255045 A1 | 10/2008 | Cujec et al. |
| 2008/0260731 A1 | 10/2008 | Bernett et al. |
| 2008/0268518 A1 | 10/2008 | Miao et al. |
| 2008/0268519 A1 | 10/2008 | Miao et al. |
| 2008/0274105 A1 | 11/2008 | Presta |
| 2008/0274108 A1 | 11/2008 | Presta |
| 2008/0274506 A1 | 11/2008 | Presta |
| 2008/0292621 A1 | 11/2008 | Lazar et al. |
| 2008/0317758 A9 | 12/2008 | Presta |
| 2009/0004734 A1 | 1/2009 | Pastan et al. |
| 2009/0005312 A1 | 1/2009 | Hansen et al. |
| 2009/0010920 A1 | 1/2009 | Lazar et al. |
| 2009/0041758 A1 | 2/2009 | Glaser et al. |
| 2009/0041770 A1 | 2/2009 | Chamberlain et al. |
| 2009/0042291 A1 | 2/2009 | Chu et al. |
| 2009/0053211 A9 | 2/2009 | Lazar et al. |
| 2009/0053240 A1 | 2/2009 | Lazar et al. |
| 2009/0060910 A1 | 3/2009 | Johnson et al. |
| 2009/0068175 A1 | 3/2009 | Lazar et al. |
| 2009/0068177 A1 | 3/2009 | Lazar et al. |
| 2009/0081208 A1 | 3/2009 | Lazar et al. |
| 2009/0092599 A1 | 4/2009 | Lazar et al. |
| 2009/0098124 A1 | 4/2009 | Stavehagen et al. |
| 2009/0136485 A1 | 5/2009 | Chu et al. |
| 2009/0142340 A1 | 6/2009 | Lazar et al. |
| 2009/0143246 A1 | 6/2009 | Mirkin et al. |
| 2009/0155587 A1 | 6/2009 | Mirkin et al. |
| 2009/0162353 A1 | 6/2009 | Johnson et al. |
| 2009/0162382 A1 | 6/2009 | Bernett et al. |
| 2009/0163699 A1 | 6/2009 | Chamberlain et al. |
| 2009/0185290 A1 | 7/2009 | Li et al. |
| 2009/0202536 A1 | 8/2009 | Ebens et al. |
| 2009/0202537 A1 | 8/2009 | Johnson et al. |
| 2009/0214526 A1 | 8/2009 | Lazar et al. |
| 2009/0215991 A1 | 8/2009 | Lazar et al. |
| 2009/0281286 A1 | 11/2009 | Gregg et al. |
| 2009/0286964 A1 | 11/2009 | Gregg et al. |
| 2009/0305411 A1 | 12/2009 | FitzGerald et al. |
| 2009/0324593 A1 | 12/2009 | Johnson et al. |
| 2010/0129908 A1 | 5/2010 | Fang et al. |
| 2010/0143368 A1 | 6/2010 | King et al. |
| 2010/0204454 A1 | 8/2010 | Chamberlain et al. |
| 2010/0210543 A1 | 8/2010 | Rabuka et al. |
| 2010/0234571 A1 | 9/2010 | Chamberlain et al. |
| 2010/0234572 A1 | 9/2010 | Chamberlain et al. |
| 2010/0234573 A1 | 9/2010 | Chamberlain et al. |
| 2010/0234574 A1 | 9/2010 | Chamberlain et al. |
| 2010/0234575 A1 | 9/2010 | Chamberlain et al. |
| 2010/0311954 A1 | 12/2010 | Chamberlain et al. |
| 2011/0020344 A1 | 1/2011 | Dimitrov et al. |
| 2011/0065185 A1 | 3/2011 | Pastan et al. |
| 2011/0142859 A1 | 6/2011 | Ebens et al. |
| 2011/0293632 A1 | 12/2011 | Presta |
| 2012/0183566 A1 | 7/2012 | Barfield et al. |
| 2013/0028881 A1 | 1/2013 | Von Figura et al. |
| 2013/0172403 A1 | 7/2013 | Von Figura et al. |
| 2014/0141025 A1 | 5/2014 | Kudirka et al. |
| 2014/0341878 A1 | 11/2014 | Koppaka et al. |
| 2015/0010898 A1 | 1/2015 | Ng |
| 2015/0023956 A1 | 1/2015 | Pardridge et al. |
| 2015/0044715 A1 | 2/2015 | Yokoyama |
| 2015/0141617 A1 | 5/2015 | Dierks et al. |
| 2015/0157736 A1 | 6/2015 | Rabuka et al. |
| 2017/0121389 A1 | 5/2017 | Carrico et al. |
| 2017/0166639 A1 | 6/2017 | Barfield et al. |

FOREIGN PATENT DOCUMENTS

| | | |
|---|---|---|
| EP | 2325302 | 5/2011 |
| WO | WO 1990004413 | 5/1990 |
| WO | WO1993010076 | 5/1993 |
| WO | WO 1993012812 | 7/1993 |
| WO | WO1993023555 | 11/1993 |
| WO | WO1994007876 | 4/1994 |
| WO | WO1994007880 | 4/1994 |
| WO | WO 1994007881 | 4/1994 |
| WO | WO 1994007882 | 4/1994 |
| WO | WO 1994026778 | 11/1994 |

(56) References Cited

FOREIGN PATENT DOCUMENTS

| | | |
|---|---|---|
| WO | WO 1996004925 | 2/1996 |
| WO | WO 1996014856 | 5/1996 |
| WO | WO 1996033212 | 10/1996 |
| WO | WO1998013059 | 4/1998 |
| WO | WO1998022451 | 5/1998 |
| WO | WO1998028288 | 7/1998 |
| WO | WO1998058927 | 12/1998 |
| WO | WO1999009021 | 2/1999 |
| WO | WO1999014209 | 3/1999 |
| WO | WO1999018113 | 4/1999 |
| WO | WO 1999058572 | 11/1999 |
| WO | WO 2000042072 | 7/2000 |
| WO | WO 2001081415 | 1/2001 |
| WO | WO 2001060991 | 8/2001 |
| WO | WO 2003027135 | 4/2003 |
| WO | WO 2003105782 | 12/2003 |
| WO | WO 2004072275 | 8/2004 |
| WO | WO 2004082640 | 9/2004 |
| WO | WO 2004099249 | 11/2004 |
| WO | WO 2005000892 | 1/2005 |
| WO | WO 2005035727 | 4/2005 |
| WO | WO 2005047336 | 5/2005 |
| WO | WO 2005052006 | 6/2005 |
| WO | WO 2005074524 | 8/2005 |
| WO | WO 2005074546 | 8/2005 |
| WO | WO 2005074650 | 8/2005 |
| WO | WO 2005113765 | 12/2005 |
| WO | WO 2006009901 | 1/2006 |
| WO | WO 2006068802 | 6/2006 |
| WO | WO 2006069220 | 6/2006 |
| WO | WO 2006071840 | 7/2006 |
| WO | WO 2006073846 | 7/2006 |
| WO | WO 2006091231 | 8/2006 |
| WO | WO 2006069246 | 9/2006 |
| WO | WO 2006132969 | 12/2006 |
| WO | WO 2006133089 | 12/2006 |
| WO | WO 2007021297 | 2/2007 |
| WO | WO 2007056083 | 5/2007 |
| WO | WO 2007056448 | 5/2007 |
| WO | WO 2007059312 | 5/2007 |
| WO | WO 2007070659 | 6/2007 |
| WO | WO 2007079130 | 7/2007 |
| WO | WO 2007094916 | 8/2007 |
| WO | WO 2007103470 | 9/2007 |
| WO | WO 2007140371 | 12/2007 |
| WO | WO 2008011446 | 1/2008 |
| WO | WO 2008030558 | 3/2008 |
| WO | WO 2008030612 | 3/2008 |
| WO | WO 2008030613 | 3/2008 |
| WO | WO 2008030614 | 3/2008 |
| WO | WO 2008036350 | 3/2008 |
| WO | WO 2008070569 | 6/2008 |
| WO | WO 2008077079 | 6/2008 |
| WO | WO 2008083346 | 7/2008 |
| WO | WO 2008121563 | 10/2008 |
| WO | WO 2008137471 | 11/2008 |
| WO | WO 2009058492 | 5/2009 |
| WO | WO 2009120611 | 10/2009 |
| WO | WO 2010096394 | 8/2010 |
| WO | WO 2012097333 | 7/2012 |
| WO | WO 2014074218 | 5/2014 |
| WO | WO 2014136065 | 9/2014 |
| WO | WO 2015/187428 | 12/2015 |

OTHER PUBLICATIONS

York et al., (2016) "Generating Aldehyde-Tagged Antibodies with High Titers and High Formylglycine Yields by Supplementing Culture Media with Copper(II)", BMC Biotechnology 16(23):11 pages.
Adams, et al., "New Biarsenical Ligands and Tetracysteine Labeling in Vitro and in Vivo: Synthesis Applications" *J. Amer. Chem. Soc.* 124(21), (2002):6063-6076.
Adams, et al. (2003) "Safety and Utilization of Blood Components as Therapeutic Delivery Systems" *Curr Pharm Biotechnol* 4(5):275-282.
Advani et al. (2010) "Safety, pharmacokinetics, and preliminary clinical activity of inotuzumab ozogamicin, a novel immunoconjugate for the treatment of B-cell non-Hodgkin's lymphoma: results of a phase I study" *J Clin Oncol* 28(12):2085-2093.
Amlot et al. (1993) "A phase I study of an anti-CD22-deglycosylated ricin A chain immunotoxin in the treatment of B-cell lymphomas resistant to conventional therapy" *Blood* 82(9):2624-2633.
Andreotti, et al. (2006) "Structural determinants of salmon calcitonin bioactivity: the role of the Leu-based amphipathic α-helix" *J. Biol. Chem.* 281(34):24193-24203.
Asai et al. (1999) "Synthesis and antitumor activity of water-soluble duocarmycin B1 prodrugs" *Bioorg Med Chem Lett* 9(20):2995-2998.
Baenziger (2003) "A major step on the road to understanding a unique posttranslational modification and its role in a genetic disease" *Cell* 113(4):421-422.
Baggio, et al. (2008) "An albumin-exendin-4 conjugate engages central and peripheral circuits regulating murine energy and glucose homeostasis" *Gastroenterology* 134(4):1137-1147.
Bain et al. (1989) "Biosynthetic site-specific incorporation of a non-natural amino acid into a polypeptide" *J Am Chem Soc* 111(20):8013-8014.
Baird & Holowka (1985) "Structural mapping of Fc receptor bound immunoglobulin E: proximity to the membrane surface of the antibody combining site and another site in the Fab segments" *Biochem* 24(22):6252-6259.
Baker (2002) "Albumin, steroid hormones and the origin of vertebrates" *J Endocrinol* 175(1):121-127.
Banghart, et al., "Light-Activated Ion Channels for Remote Control of Neuronal Firing" *Nat. Neurosci.* 7(12), (2004):1381-6.
Berteau et al. (2006) "A new type of bacterial sulfatase reveals a novel maturation pathway in prokaryotes" *J. Biol. Chem.* 281(32):22464-22470.
Boer et al. (2003) "The genome-wide transcriptional responses of *Saccharomyces cerevisiae* grown on glucose in aerobic chemostat cultures limited for carbon, nitrogen, phosphorus, or sulfur" *J Biol Chem* 278(5):3265-3274.
Boghaert et al. (2008) "Determination of pharmacokinetic values of calicheamicin-antibody conjugates in mice by plasmon resonance analysis of small (5 microl) blood samples" *Cancer Chemother Pharmacol* 61(6):1027-1035.
Brubaker (2007) "Incretin-based therapies: mimetics versus protease inhibitors" *TRENDS Endoccrinol. Metab.* 18(6):240-245.
Carrico et al. (2007) "Introducing genetically encoded aldehydes into proteins" Nature Chemical Biology, 3(6):321-322.
Carter & Senter (2008) "Antibody-Drug Conjugates for Cancer Therapy" *Cancer J* 14(3):154-619.
Chen et al., "Synthetic Erythropoietic Proteins: Tuning Biological Performance by Site-Specific Polymer Attachment" *Chem. Biol.* 12(3), (2005):371-383.
Chen, et al., "Site-Specific Labeling of Cell Surface Proteins with Biophysical Probes Using Biotin Ligase" *Nature Methods* 2(2), (2005):99-104.
Connolly "Analytical molecular surface calculation" *J. Appl. Cryst.* (1983) 16:548-558.
Cornish et al. (1994) "Site-specific incorporation of biophysical probes into proteins" *Proc Natl Acad Sci USA* 91(8):2910-2914.
Cornish et al. (1995) "Probing Protein Structure and Function with an Expanded Genetic Code" *Angew Chem Int Ed Engl* 34:621-633.
Cosma et al. (2003) "The multiple sulfatase deficiency gene encodes an essential and limiting factor for the activity of sulfatases" *Cell* 113(4):445-456.
Cosma et al. (2004) "Molecular and functional analysis of SUMF1 mutations in multiple sulfatase deficiency" *Hum. Mutat.* 23, 576-581.
Deghenghi, et al. "Somatostatin octapeptides (lanreotide, octreotide, vapreotide, and their analogs) share the growth hormone-releasing peptide receptor in the human pituitary gland", Endocrine, Feb. 2001, vol. 14, Issue 1, pp. 29-33.

(56) References Cited

OTHER PUBLICATIONS

Deiters et al. (2003) "Adding amino acids with novel reactivity to the genetic code of *Saccharomyces cerevisiae*" *J Am Chem Soc* 125(39):11782-11783.

Dierks et al. (1997) "Conversion of cysteine to formylglycine: a protein modification in the endoplasmic reticulum" *Proc Natl Acad Sci U S A* 94(22):11963-8.

Dierks et al. (1998) "Conversion of cysteine to formylglycine in eukaryotic sulfatases occurs by a common mechanism in the endoplasmic reticulum" *FEBS Lett.* 423(1):61-5.

Dierks et al. (1999) "Sequence determinants directing conversion of cysteine to formylglycine in eukaryotic sulfatases" *EMBO J* 18(8):2084-2091.

Dierks et al. (2003) "Multiple sulfatase deficiency is caused by mutations in the gene encoding the human Cα-formylglycine generating enzyme" *Cell* 113(4):435-444.

Dierks et al. (2005) "Molecular basis for multiple sulfatase deficiency and mechanism for formylglycine generation of the human formylglycine-generating enzyme" *Cell.* 121(4):541-552.

Dierks, et al., (1998) "Posttranslational Formation of Formylglycine in Prokaryotic Sulfatases by Modification of Either Cysteine or Serine" *J Biol Chem*, 273(40):25560-25564.

Dijoseph et al. (2004) "Antibody-targeted chemotherapy with CMC-544: a CD22-targeted immunoconjugate of calicheamicin for the treatment of B-lymphoid malignancies" *Blood* 103(5):1807-1814.

Dijoseph et al. (2004) "Potent and specific antitumor efficacy of CMC-544, a CD22-targeted immunoconjugate of calicheamicin, against systemically disseminated B-cell lymphoma" *Clin Cancer Res* 10:8620-8629.

Dijoseph et al. (2006) "Antitumor efficacy of a combination of CMC-544 (inotuzumab ozogamicin), a CD22-targeted cytotoxic immunoconjugate of calicheamicin, and rituximab against non-Hodgkin's B-cell lymphoma" Clin Cancer Res 12(1):242-249.

Dijoseph et al. (2007) "Therapeutic potential of CD22-specific antibody-targeted chemotherapy using inotuzumab ozogamicin (CMC-544) for the treatment of acute lymphoblastic leukemia" *Leukemia* 21(11):2240-2245.

Doronina, et al. (2008) "Novel peptide linkers for highly potent antibody-auristatin conjugate" *Bioconjugate Chem* 19(10):1960-1963.

Dou, et al. (2008) "Expression, purification, and characterization of recombinant human serum albumin fusion protein with two human glucagon-like peptide-1 mutants in Pichia pastoris" *Protein Expr Purif* 61(1):45-49.

Fang et al. (2004) "Post-translational formylglycine modification of bacterial sulfatases by the radical S-adenosylmethionine protein AtsB" *J Biol Chem.* 79(15):14570-8.

Fanslow et al. (1992) "Soluble forms of CD40 inhibit biologic responses of human B cells" *J Immunol* 149(2):655-660.

Figura, et al. "A Novel Protein Modification Generating an Aldehyde Group in Sulfatases: Its Role in Catalysis and Disease" *Bioessays.* 20(6), (1998):505-10.

GenBank Acc. No. NP_215226 (Jan. 6, 2005).

GenBank Acc. No. NP_215226 (May 24, 2007).

GenBank Accession No. AAG00909 "recombinant IgG1 heavy chain [*Homo sapiens*]" dated May 11, 2001.

GenBank Accession No. NM_182760 "*Homo sapiens* sulfatase modifying factor 1 (SUMF1), transcript variant 1, mRNA" dated Nov. 28, 2012.

George, et al. "Specific Labeling of Cell Surface Proteins with Chemically Diverse Compounds" *J. Amer. Chem. Soc.* 126(29), (2004):8896-8897.

Ghetie et al. (1991) "Antitumor activity of Fab' and IgG-anti-CD22 immunotoxins in disseminated human B lymphoma grown in mice with severe combined immunodeficiency disease: effect on tumor cells in extranodal sites" *Cancer Res* 51(21):5876-5880.

Gilon et al. (1967) "Synthesis of co-aminooxy acids by oxygen-alkyl fission of lactones: An improved synthesis of DL-canaline" *Tetrahedron* 23(11):4441-4447.

Griffin, et al., "Specific Covalent Labeling of Recombinant Protein Molecules Inside Live Cells" Science 281(5374), (1998):269-272.

Guignet, et al., "Reversible Site-Selective Labeling of Membrane Proteins in Live Cells" *Nature Biotechnol* 22(4), (2004):440-444.

Hall et al. (2005) "Contribution of horizontal gene transfer to the evolution of *Saccharomyces cerevisiae*" *Eukaryot Cell* 4(6):1102-1115.

Harohalli, et al. (2002) "Site-directed mutagenesis studies of human serum albumin define tryptophan at amino acid position 214 as the principal site for nitrosation" *J Biomed Sci* 9(1):47-58.

Hecht (1992) "Probing the Synthetic Capabilities of a Center of Biochemical Catalysis" *Acc Chem Res* 25(12):545-552.

Hortin & Boime (1983) "Applications of amino acid analogs for studying co- and posttranslational modifications of proteins" *Meth Enzymol* 96:777-784.

Idusogie et al. (2000) "Mapping of the C1q binding site on rituxan, a chimeric antibody with a human IgG1 70" *J Immunol* 164(8):4178-4184.

Immunogen, Inc. (2008) "ImmunoGen, Inc. Announces Clinical Findings Reported at ASCO with Targeted Anticancer Compounds IMGN242 and AVE1642" http://www.drugs.com/clinical_trials/immunogen-inc-announces-clinical-findings-reported-asco-targeted-anticancer-compounds-imgn242-4545.html#ixzz0r9nPIIXM.

Jefferis & Lefranc (2009) "Human Immunoglobulin Allotypes" *MAbs* 1(4):332-338.

Jeffrey et al. (2005) "Design, synthesis, and in vitro evaluation of dipeptide-based antibody minor groove binder conjugates" *J Med Chem* 48(5):1344-1358.

Johnson & Wu (2000) "Kabat database and its applications: 30 years after the first variability plot" *Nucl Acids Res* 28(1):214-218.

Jones et al. (2000) "A convenient synthesis of N-(tert-butyloxycarbonyl)aminooxy ethers" *Tetrahedron Lett* 41(10):1531-1533.

Junutula, et al. (2008) "Site-specific conjugation of a cytotoxic drug to an antibody improves the therapeutic index" *Nat Biotechnol* 26(8):925-932.

Kabsch & Sander (1983) "Dictionary of protein secondary structure: pattern recognition of hydrogen-bonded and geometrical features" *Biopolymers* 22: 2577-637.

Kan (2001) "Thioether-bonded constructs of Fab'gamma and Fc gamma modules utilizing differential reduction of interchain disulfide bonds" *J Immunol* 166(2):1320-1326.

Kirshenbaum et al. (2002) "Biosynthesis of proteins incorporating a versatile set of phenylalanine analogues" *Chembiochem* 3(2-3):235-237.

Knaust et al., "Residues Critical for Formylglycine Formation and/or Catalytic Activity of Arylsulfatase A," *Biochemistry*, 37(40), (1998): 13941-13946.

Komarova (2003) "Regulation of Osteoclasts by Calcitonin and Amphiphilic Calcitonin Conjugates: Role of Cytosolic Calcium" *Calcif Tissue Int* 73(3):265-273.

Kubota, "Engineered therapeutic antibodies with improved effector functions", Cancer Science, vol. 1 00, No. 9, p. 1566-1572, 2009.

Kumar, et al. (2007) "Gene therapy of diabetes using a novel GLP-1/IgG1-Fc fusion construct normalizes glucose levels in db/db mice" *Gene Ther.* 14(2): 162-172.

Landgrebe et al. (2003) "The human SUMF1 gene, required for posttranslational sulfatase modification, defines a new gene family which is conserved from pro- to eukaryotes" *Gene*. 316:47-56.

Lee & Richards (1971) "The interpretation of protein structures: estimation of static accessibility" *J. Mol. Biol.* 55(3):379-400.

Léger, et al. (2004) "Identification of CJC-1131-albumin bioconjugate as a stable and bioactive GLP-1(7-36) analog" *Bioorg. Med. Chem. Lett.* 14(17):4395-4398.

Lemieux, et al., "Chemoselective Ligation Reactions with Proteins, Oligosaccharides and Cells" *Trends Biotechnol* 16(12), (1998):506-13.

Lisenbee, et al., "Overexpression and Mislocalization of a Tail-Anchored GFP Redefines the Identity of Peroxisomal ER" *Traffic* 4(7), (2003):491-501.

Liu, et al. "Eradication of large colon tumor xenografts by targeted delivery of maytansinoids", *Proc Natl Acad Sci U S A*. Aug. 6, 1996;93(16):8618-23.

(56) References Cited

OTHER PUBLICATIONS

Lukatela, et al., "Crystal Structure of Human Arylsulfatase A: the Aldehyde Function and the Metal ion at the Active Site Suggest a Novel Mechanism for Sulfate Ester Hydrolysis" *Biochemistry* 37(11), (1998):3654-3664.

Mahal et al. (1997) "Engineering chemical reactivity on cell surfaces through oligosaccharide biosynthesis" *Science* 276(5315):1125-1128.

Mariappan, et al., "Expression, Localization, Structural, and Functional Characterization of pFGE, the Paralog of the Cα-Formylglycine-generating Enzyme" *J. Biol. Chem.* 280(15), (2005):15173-9.

Matos, et al. "HIV-1 Fusion Inhibitor Peptides Enfuvirtide and T-1249 Interact with Erythrocyte and Lymphocyte Membranes", *PLoS One.* Mar. 23, 2010;5(3):e9830.

Matthews, (2008) et al. "Pharmacodynamics, Pharmacokinetics, Safety, and Tolerability of Albiglutide, a Long-Acting Glucagon-Like Peptide-1 Mimetic, in Patients with Type 2 Diabetes" *J. Clin. Endocrinol. Metab.* 93(12):4810-4817.

McDonagh, et al. (2006) "Engineered antibody-drug conjugates with defined sites and stoichiometries of drug attachment" *Protein Eng Des Sel* 19(7):299-307.

Montano, "Influence of the Isotype of the Light Chain on the Properties of IgG1", The Journal of Immunology, vol. 168, p. 224-231, 2002.

Mougous et al., "Identification, Function and Structure of the Mycobacterial Sulfotransferase that Initiates Sulfolipid-1 Biosynthesis" *Nat. Struc. Mol. Biol.* 11(8), (2004):721-729.

Müller, et al. (2007) "Improved pharmacokinetics of recombinant bispecific antibody molecules by fusion to human serum albumin" *J Bio Chem* 282(17):12650-12660.

Ogura et al. (2010) "Phase I Study of Inotuzumab Ozogamicin (CMC-544) in Japanese Patients with Follicular Lymphoma Pretreated with Rituximab-Based Therapy" *Cancer Sci* 101(8):1840-1845. Epub Apr. 23, 2012 doi:10.1111/j. 1349-7006.2010.01601.x.

Peterson, et al. (2002) "Probing the structure of the warfarin-binding site on human serum albumin using site-directed mutagenesis" *Proteins* 47(2):116-125.

Pettit (1996) "Progress in the discovery of biosynthetic anticancer drugs" *J Nat Prod* 59(8):812-821.

Picha, et al. (2008) "Protein Engineering Strategies for Sustained Glucagon-Like Peptide-1 Receptor—Dependent Control of Glucose Homeostasis" *Diabetes* 57(7):1926-1934.

Pleass (1999) "Identification of residues in the CH2/CH3 domain interface of IgA essential for interaction with the human fcalpha receptor (FcalphaR) CD89" *J Biol Chem* 274(33):23508-23514.

Prescher and Bertozzi (2005) "Chemistry in living systems" Nature Chemical Biology, 1(1):13-21.

Presta (2002) "Engineering therapeutic antibodies for improved function" *Biochem Soc Trans* 30(4):487-490.

Presta (2008) "Molecular engineering and design of therapeutic antibodies" Current Opinion in Immunology 20: 460-470.

Preusser-Kunze et al. (2005) "Molecular characterization of the human Cα-formylglycine-generating enzyme" *J. Biol. Chem.* 280(15):14900-10.

Rabuka, "Site-specific chemical protein conjugation using genetically encoded aldehyde tags", Nature Protocols, vol. 7, No. 6, p. 1052-1067,2012.

Rakestraw et al. (1990) "Preparation and characterization of immunoconjugates for antibody-targeted photolysis" *Bioconjugate Chem* 1(3):212-221.

Roeser et al. (2006) "A general binding mechanism for all human sulfatases by the formylglycine-generating enzyme" *Proc Natl Acad Sci USA* 103(1):81-86.

Rush, et al., "An α-Formylglycine Building Block for Fmoc-Based Solid-Phase Peptide Synthesis" *Org Lett.* 8(1), (2006):131-4.

Rutishauser et al. (1968) "Amino Acid Sequence of the Fc Region of a Human γ G-Immunoglobulin" *Proc Natl Acad Sci USA* 61(4)1414-1421.

Samuel, et al., "Chemical Tools for the Study of Polysialic Acid", (2004) *Trends In Glycoscience and Technology* 16(91), (2004):305-318.

Sardiello et al. (2005) "Sulfatases and sulfatase modifying factors: an exclusive and promiscuous relationship" *Hum Mol Genet.* 14(21):3203-3217.

Sayers et al. (1998) "Amino acid residues that influence Fc epsilon RI-mediated effector functions of human immunoglobulin E" *Biochemistry* 37(46):16152-16164.

Schirmer, et al., "Computational Analysis of Bacterial Sulfatases and Their Modifying Enzymes", *Chem Biol* 5(8), (1998):R181-R186.

Schmidt, et al., "A Novel Amino Acid Modification in Sulfatases that Is Defective in Multiple Sulfatase Deficiency" *Cell* 82(2), (1995):271-8.

Shields et al. "High resolution mapping of the binding site on human IgG1 for Fc gamma RI, Fc gamma RII, Fc gamma RIII, and FcRn and design of IgGl variants with improved binding to the Fc gamma R" *J Biol Chem* 276(9):6591-6604, (2001).

Singh & Francis (1978) "A direct binding assay for rheumatoid factor serum antiglobulins using fluorescein-labelled Fc fragment of human immunoglobulin-G" *J Clin Path* 31(10):963-973.

Singh et al. (2008) "Recent Trends in Targeted Anticancer Prodrug and Conjugate Design" *Curr Med Chem* 15(18):1802-1826.

Sjogren "Thymalfasin: an immune system enhancer for the treatment of liver disease", J Gastroenterol Hepatol. Dec. 2004;19(12):S69-72.

Smith et al. (2014) "Chemoenzymatic Fc Glycosylation via Engineered Aldehyde Tags" Bioconjugate Chemistry, 25(4):788-795.

Sondermann & Oosthuizen (2002) "Mediation and Modulation of Antibody Function" *Biochem Soc Trans* 30(pt.4):481-486.

Stevenson et al. (1997) "Conjugation of human Fc gamma in closed-hinge or open-hinge configuration to Fab'gamma and analogous ligands" *J Immunol* 158(5):2242-2250.

Stevenson et al. (1999) "Preparation of fcgamma for addition to sulfhydryl-expressing ligands with minimal disturbance of the hinge" *J Immunol Meth* 231(1-2):169-175.

Stimmel et al. (2000) "Site-specific conjugation on serine → cysteine variant monoclonal antibodies" *J Biol Chem* 275(39):30445-30450.

Stroffekova, et al. "The Protein-Labeling Reagent FLASH-EDT2 Binds Not Only to CCXXCC Motifs but Also Non-Specifically to Endogenous Cysteine-Rich Proteins" *Archiv-Europ. J. Physiol.* 442(6), (2001):859-866.

Szameit et al. (1999) "The iron sulfur protein AtsB is required for posttranslational formation of formylglycine in the Klebsiella sulfatase" *J Biol Chem* 274(22):15375-15381.

Takabe (1988) "SR alpha promoter: an efficient and versatile mammalian cDNA expression system composed of the simian virus 40 early promoter and the R-U5 segment of human T-cell leukemia virus type 1 long terminal repeat" *Mol Cell Biol* 8(1):466-472.

Takeshita (2009) "CMC-544 (inotuzumab ozogamicin) shows less effect on multidrug resistant cells: analyses in cell lines and cells from patients with B-cell chronic lymphocytic leukaemia and lymphoma" *Br J Haematol* 146:34-43.

Taylor (2010) ""Mutations in an avian IgY-Fc fragment reveal the locations of monocyte Fc receptor binding sites *Dev Comp Immunol* 34(2):97-101.

Thrasher et al. (1975) "The effect of fluorescein conjugation on Fc-dependent properties of rabbit antibody" *J Immunol* 114(2 pt. 2):762-764.

Tirat et al., "Evaluation of Two Novel Tag-Based Labelling Technologies for Site-Specific modification of Proteins" *International Journal of Biological Macromolecules* 39(1-3), (2006):66-76.

Villani et al., "Expression of Five Iduronate-2-Sulfatase Site-Directed Mutations" *Biochimica et Biophysica Acta* 1501(2-3), (2000):71-80.

Vitetta et al. (1991) "Phase I immunotoxin trial in patients with B-cell lymphoma" *Cancer Res* 51(15):4052-4058.

Wooley et al. (1993) "Influence of a recombinant human soluble tumor necrosis factor receptor FC fusion protein on type II collagen-induced arthritis in mice" *J Immunol* 151(11):6602-6607.

(56) References Cited

OTHER PUBLICATIONS

Wu & Senter (2005) "Arming antibodies: prospects and challenges for immunoconjugates" *Nat Biotechnol* 23(9):1137-1146.

Wu et al., (2009) "Site-specific chemical modification of recombinant proteins produced in mammalian cells by using the genetically encoded aldehyde tag" Proc. Natl. Acad. Sci. 106(9):3000-3005.

Xu et al. (1999) "Bis(Hydroxamamide)-Based Bifunctional Chelating Agent $^{99m}$Tc Labeling of Polypeptides" *Bioconjug Chem* 10(1):9-17.

Yin, et al., "Genetically Encoded Short Peptide Tag for Versatile Protein Labeling by Sfp Phosphopantetheinyl Transferase" *Proc. Natl. Acad. Sci. USA*_102(44), (2005):15815-15820.

Youn, et al. (2007) "High-yield production of biologically active mono-PEGylated salmon calcitonin by site-specific PEGylation" *J. Control. Release* 117(3):371-379.

(% aggregation by SEC)

| Tag insertion site | 20 ml expression | 6 ml expression |
|---|---|---|
| 2V | 7.9 | 0.80 |
| 4A | 15.6 | 0.70 |
| 5P | 9.9 | 1.10 |
| 20G | 5.0 | 2.60 |
| 21T | 8.4 | 3.70 |
| 22A | 10.8 | 2.80 |
| 46L | 7.0 | 1.90 |
| 48S | 7.6 | 1.60 |
| 49G | 7.4 | 2.60 |
| 50N | 7.4 | 2.00 |
| 51S | 5.5 | 3.10 |
| 65Y | 16.8 | 5.10 |
| 91Q | 16.7 | |
| 93L | 8.4 | 3.20 |
| 95S | 9.7 | 5.20 |
| 96P | 6.7 | 2.60 |
| WT Ab | 1.7 | |

FIG. 6A
FIG. 6B
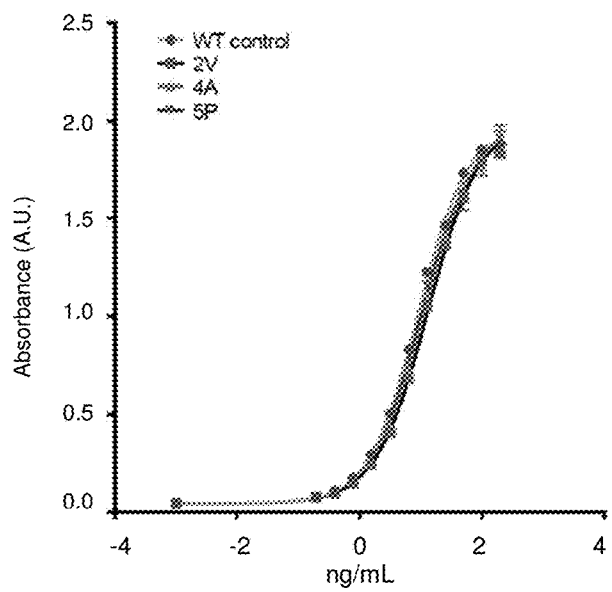
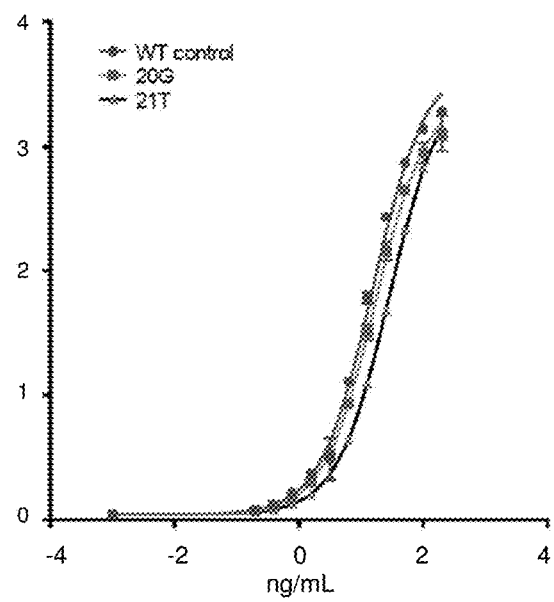
FIG. 6C
FIG. 6D
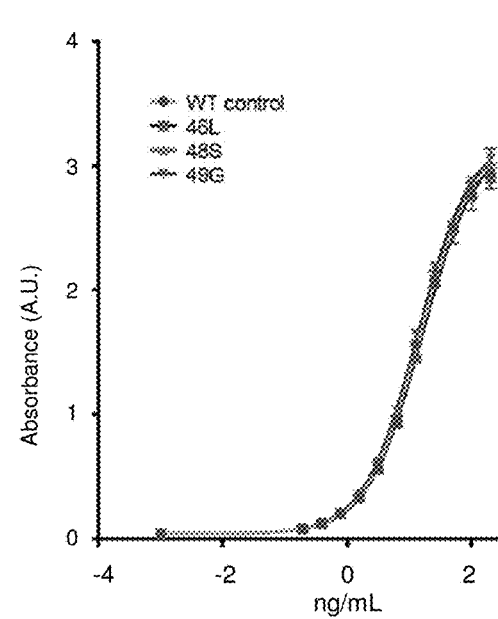
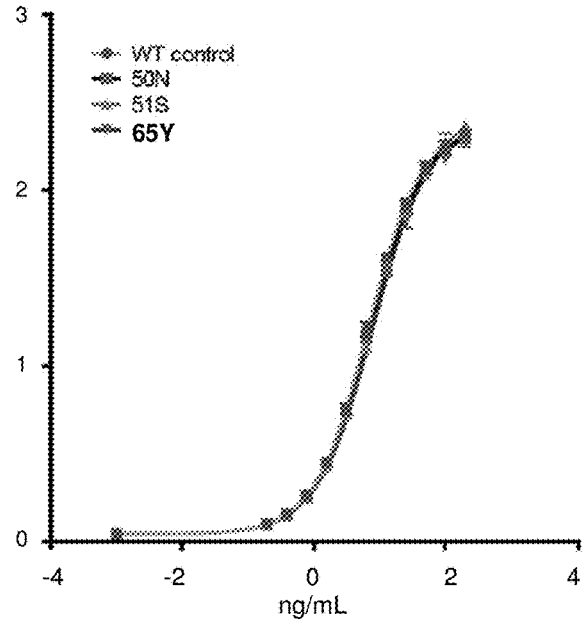

FIG. 9

```
              |       |       |       |       |       |
Kappa    TVAAPSVFIFPPSDEQLKSGTASVVCLLNNFYPREAKVQWKVDNALQSGNSQESVTEQDS  60
Km*      ............................................V..................

|       |       |       |
Kappa    KDSTYSLSSTLTLSKADYEKHKVYACEVTHQGLSSPVTKSFNRGEC  106 (SEQ ID NO:1)
Km*      ...........................L.................
```

FIG. 10A

Wildtype, Ig Kappa light chain constant region
TVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC (SEQ ID NO:1)

1T
TLCTPSRVAAPSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC (SEQ ID NO:2)

2V
TVLCTPSRAAPSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC (SEQ ID NO:3)

3A
TVALCTPSRAPSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC (SEQ ID NO:4)

4A
TVAALCTPSRPSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC (SEQ ID NO:5)

5P
TVAAPLCTPSRSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC (SEQ ID NO:6)

6S
TVAAPSLCTPSRVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC (SEQ ID NO:7)

19S
TVAAPSVFIFPPSDEQLKSLCTPSRGTASVVCLLNNFYPREAKVQWKVDNALQSGNSQESVTEQDSKDST
YSLSSTLTLSKADYEKHKVYACEVTHQGLSSPVTKSFNRGEC (SEQ ID NO:15)

20G
TVAAPSVFIFPPSDEQLKSGLCTPSRTASVVCLLNNFYPREAKVQWKVDNALQSGNSQESVTEQDSKDST
YSLSSTLTLSKADYEKHKVYACEVTHQGLSSPVTKSFNRGEC (SEQ ID NO:16)

21T
TVAAPSVFIFPPSDEQLKSGTLCTPSRASVVCLLNNFYPREAKVQWKVDNALQSGNSQESVTEQDSKDST
YSLSSTLTLSKADYEKHKVYACEVTHQGLSSPVTKSFNRGEC (SEQ ID NO:17)

22A
TVAAPSVFIFPPSDEQLKSGTALCTPSRSVVCLLNNFYPREAKVQWKVDNALQSGNSQESVTEQDSKDST
YSLSSTLTLSKADYEKHKVYACEVTHQGLSSPVTKSFNRGEC (SEQ ID NO:18)

TVAAPSVFIFPPSDEQLKSGTASVVCLLNLCTPSRNFYPREAKVQWKVDNALQSGNSQESVTEQDSKDST
YSLSSTLTLSKADYEKHKVYACEVTHQGLSSPVTKSFNRGEC (SEQ ID NO:19)

30N

TVAAPSVFIFPPSDEQLKSGTASVVCLLNNLCTPSRFYPREAKVQWKVDNALQSGNSQESVTEQDSKDST
YSLSSTLTLSKADYEKHKVYACEVTHQGLSSPVTKSFNRGEC (SEQ ID NO:20)

31F

TVAAPSVFIFPPSDEQLKSGTASVVCLLNNFLCTPSRYPREAKVQWKVDNALQSGNSQESVTEQDSKDST
YSLSSTLTLSKADYEKHKVYACEVTHQGLSSPVTKSFNRGEC (SEQ ID NO:21)

32Y

TVAAPSVFIFPPSDEQLKSGTASVVCLLNNFYLCTPSRPREAKVQWKVDNALQSGNSQESVTEQDSKDST
YSLSSTLTLSKADYEKHKVYACEVTHQGLSSPVTKSFNRGEC (SEQ ID NO:22)

42V

TVAAPSVFIFPPSDEQLKSGTASVVCLLNNFYPREAKVQWKVLCTPSRDNALQSGNSQESVTEQDSKDST
YSLSSTLTLSKADYEKHKVYACEVTHQGLSSPVTKSFNRGEC (SEQ ID NO:23)

43D

TVAAPSVFIFPPSDEQLKSGTASVVCLLNNFYPREAKVQWKVDLCTPSRNALQSGNSQESVTEQDSKDST
YSLSSTLTLSKADYEKHKVYACEVTHQGLSSPVTKSFNRGEC (SEQ ID NO:24)

45A

TVAAPSVFIFPPSDEQLKSGTASVVCLLNNFYPREAKVQWKVDNALCTPSRLQSGNSQESVTEQDSKDST
YSLSSTLTLSKADYEKHKVYACEVTHQGLSSPVTKSFNRGEC (SEQ ID NO:25)

46L

TVAAPSVFIFPPSDEQLKSGTASVVCLLNNFYPREAKVQWKVDNALLCTPSRQSGNSQESVTEQDSKDST
YSLSSTLTLSKADYEKHKVYACEVTHQGLSSPVTKSFNRGEC (SEQ ID NO:26)

47Q

TVAAPSVFIFPPSDEQLKSGTASVVCLLNNFYPREAKVQWKVDNALQLCTPSRGNSQESVTEQDSKDST
YSLSSTLTLSKADYEKHKVYACEVTHQGLSSPVTKSFNRGEC (SEQ ID NO:27)

48S

TVAAPSVFIFPPSDEQLKSGTASVVCLLNNFYPREAKVQWKVDNALQSLCTPSRGNSQESVTEQDSKDST
YSLSSTLTLSKADYEKHKVYACEVTHQGLSSPVTKSFNRGEC (SEQ ID NO:28)

FIG. 10C

49G
TVAAPSVFIFPPSDEQLKSGTASVVCLLNNFYPREAKVQWKVDNALQSGLCTPSRNSQESVTEQDSKDST
YSLSSTLTLSKADYEKHKVYACEVTHQGLSSPVTKSFNRGEC (SEQ ID NO:29)

50N
TVAAPSVFIFPPSDEQLKSGTASVVCLLNNFYPREAKVQWKVDNALQSGNLCTPSRSQESVTEQDSKDST
YSLSSTLTLSKADYEKHKVYACEVTHQGLSSPVTKSFNRGEC (SEQ ID NO:30)

51S
TVAAPSVFIFPPSDEQLKSGTASVVCLLNNFYPREAKVQWKVDNALQSGNSLCTPSRQESVTEQDSKDST
YSLSSTLTLSKADYEKHKVYACEVTHQGLSSPVTKSFNRGEC (SEQ ID NO:31)

52Q
TVAAPSVFIFPPSDEQLKSGTASVVCLLNNFYPREAKVQWKVDNALQSGNSQLCTPSRESVTEQDSKDST
YSLSSTLTLSKADYEKHKVYACEVTHQGLSSPVTKSFNRGEC (SEQ ID NO:32)

60S
TVAAPSVFIFPPSDEQLKSGTASVVCLLNNFYPREAKVQWKVDNALQSGNSQESVTEQDSLCTPSRKDST
YSLSSTLTLSKADYEKHKVYACEVTHQGLSSPVTKSFNRGEC (SEQ ID NO:33)

62D
TVAAPSVFIFPPSDEQLKSGTASVVCLLNNFYPREAKVQWKVDNALQSGNSQESVTEQDSKDLCTPSRST
YSLSSTLTLSKADYEKHKVYACEVTHQGLSSPVTKSFNRGEC (SEQ ID NO:34)

63S
TVAAPSVFIFPPSDEQLKSGTASVVCLLNNFYPREAKVQWKVDNALQSGNSQESVTEQDSKDSLCTPSRT
YSLSSTLTLSKADYEKHKVYACEVTHQGLSSPVTKSFNRGEC (SEQ ID NO:35)

64T
TVAAPSVFIFPPSDEQLKSGTASVVCLLNNFYPREAKVQWKVDNALQSGNSQESVTEQDSKDSTLCTPSR
YSLSSTLTLSKADYEKHKVYACEVTHQGLSSPVTKSFNRGEC (SEQ ID NO:36)

65Y
TVAAPSVFIFPPSDEQLKSGTASVVCLLNNFYPREAKVQWKVDNALQSGNSQESVTEQDSKDSTYLCTPS
RSLSSTLTLSKADYEKHKVYACEVTHQGLSSPVTKSFNRGEC (SEQ ID NO:37)

89T
TVAAPSVFIFPPSDEQLKSGTASVVCLLNNFYPREAKVQWKVDNALQSGNSQESVTEQDSKDSTYSLSST
LTLSKADYEKHKVYACEVTLCTPSRHQGLSSPVTKSFNRGEC (SEQ ID NO:38)

FIG. 10D

90H
TVAAPSVFIFPPSDEQLKSGTASVVCLLNNFYPREAKVQWKVDNALQSGNSQESVTEQDSKDSTYSLSST
LTLSKADYEKHKVYACEVTHLCTPSRQGLSSPVTKSFNRGEC (SEQ ID NO:39)

91Q
TVAAPSVFIFPPSDEQLKSGTASVVCLLNNFYPREAKVQWKVDNALQSGNSQESVTEQDSKDSTYSLSST
LTLSKADYEKHKVYACEVTHQLCTPSRGLSSPVTKSFNRGEC (SEQ ID NO:40)

92G
TVAAPSVFIFPPSDEQLKSGTASVVCLLNNFYPREAKVQWKVDNALQSGNSQESVTEQDSKDSTYSLSST
LTLSKADYEKHKVYACEVTHQGLCTPSRLSSPVTKSFNRGEC (SEQ ID NO:41)

93L
TVAAPSVFIFPPSDEQLKSGTASVVCLLNNFYPREAKVQWKVDNALQSGNSQESVTEQDSKDSTYSLSST
LTLSKADYEKHKVYACEVTHQGLLCTPSRSSPVTKSFNRGEC (SEQ ID NO:42)

94S
TVAAPSVFIFPPSDEQLKSGTASVVCLLNNFYPREAKVQWKVDNALQSGNSQESVTEQDSKDSTYSLSST
LTLSKADYEKHKVYACEVTHQGLSLCTPSRSPVTKSFNRGEC (SEQ ID NO:43)

95S
TVAAPSVFIFPPSDEQLKSGTASVVCLLNNFYPREAKVQWKVDNALQSGNSQESVTEQDSKDSTYSLSST
LTLSKADYEKHKVYACEVTHQGLSSLCTPSRPVTKSFNRGEC (SEQ ID NO:44)

96P
TVAAPSVFIFPPSDEQLKSGTASVVCLLNNFYPREAKVQWKVDNALQSGNSQESVTEQDSKDSTYSLSST
LTLSKADYEKHKVYACEVTHQGLSSPLCTPSRVTKSFNRGEC (SEQ ID NO:45)

FIG. 14A

Table 3. Primer sets for clones

| Clone name | Forward Primers (5' to 3') | SEQ ID NO: | Reverse Primers (5' to 3') | SEQ ID NO: |
|---|---|---|---|---|
| 1T | CTGTGTACCCCTTCCAGGgtggctgcaccatctgtcttcatct | 252 | CCTGGAAGGGGTACACAGagttcCTgaggaaagaagcaaacag | 276 |
| 2V | CTGTGTACCCCTTCCAGGgctgcaccatctgtcttcatcttcc | 253 | CCTGGAAGGGGTACACAGcacagttcCTgaggaaagaagcaaa | 277 |
| 3A | CTGTGTACCCCTTCCAGGcaccatctgtcttcatcttcccgc | 254 | CCTGGAAGGGGTACACAGagccacagttcCTgaggaaagaagc | 278 |
| 4A | CTGTGTACCCCTTCCAGGccatctgtcttcatcttcccgccat | 255 | CCTGGAAGGGGTACACAGtgcagccacagttcCTgaggaaaga | 279 |
| 5P | CTGTGTACCCCTTCCAGGtctgtcttcatcttcccgccatctg | 256 | CCTGGAAGGGGTACACAGtggtgcagccacagttcCTgaggaa | 280 |
| 6S | CTGTGTACCCCTTCCAGGgtcttcatcttcccgccatctgatg | 257 | CCTGGAAGGGGTACACAGagatggtgcagccacagttcCTgag | 281 |
| 7V | CTGTGTACCCCTTCCAGGttcatcttcccgccatctgatgagc | 258 | CCTGGAAGGGGTACACAGacagatggtgcagccacagttcCT | 282 |
| 8F | CTGTGTACCCCTTCCAGGatcttcccgccatctgatgagcagt | 259 | CCTGGAAGGGGTACACAGaagacagatggtgcagccacagtt | 283 |
| 9I | CTGTGTACCCCTTCCAGGttcccgccatctgatgagcagttga | 260 | CCTGGAAGGGGTACACAGatgaagacagatggtgcagccaca | 284 |
| 10F | CTGTGTACCCCTTCCAGGccgccatctgatgagcagttgaaat | 261 | CCTGGAAGGGGTACACAGaagatgaagacagatggtgcagcc | 285 |
| 11P | CTGTGTACCCCTTCCAGGccatctgatgagcagttgaaatctg | 262 | CCTGGAAGGGGTACACAGcgggaagatgaagacagatggtgca | 286 |
| 12P | CTGTGTACCCCTTCCAGGtctgatgagcagttgaaatctggaa | 263 | CCTGGAAGGGGTACACAGtggcgggaagatgaagacagatggt | 287 |
| 13S | CTGTGTACCCCTTCCAGGatgagcagttgaaatctggaactg | 264 | CCTGGAAGGGGTACACAGagatggcgggaagatgaagacagat | 288 |
| 14D | CTGTGTACCCCTTCCAGGagcagttgaaatctggaactgcct | 265 | CCTGGAAGGGGTACACAGatcagatggcgggaagatgaagaca | 289 |
| 15E | CTGTGTACCCCTTCCAGGcagttgaaatctggaactgcctctg | 266 | CCTGGAAGGGGTACACAGctcatcagatggcgggaagatgaag | 290 |
| 16Q | CTGTGTACCCCTTCCAGGttgaaatctggaactgcctctgttg | 267 | CCTGGAAGGGGTACACAGctgctcatcagatggcgggaagatg | 291 |
| 17L | CTGTGTACCCCTTCCAGGaaatctggaactgcctctgttgtgt | 268 | CCTGGAAGGGGTACACAGcaactgctcatcagatggcgggaag | 292 |
| 18K | CTGTGTACCCCTTCCAGGtctggaactgcctctgttgtgtgcc | 269 | CCTGGAAGGGGTACACAGtttcaactgctcatcagatggcggg | 293 |
| 19S | CTGTGTACCCCTTCCAGGggaactgcctctgttgtgtgcctgc | 270 | CCTGGAAGGGGTACACAGagatttcaactgctcatcagatggc | 294 |
| 20G | CTGTGTACCCCTTCCAGGactgcctctgttgtgtgcctgctga | 271 | CCTGGAAGGGGTACACAGtccagatttcaactgctcatcagat | 295 |
| 21T | CTGTGTACCCCTTCCAGGcctctgttgtgtgcctgctgaata | 272 | CCTGGAAGGGGTACACAGagttccagatttcaactgctcatca | 296 |
| 22A | CTGTGTACCCCTTCCAGGtctgttgtgtgcctgctgaataact | 273 | CCTGGAAGGGGTACACAGggcagttccagatttcaactgctca | 297 |
| 23S | CTGTGTACCCCTTCCAGGttgtgtgcctgctgaataacttct | 274 | CCTGGAAGGGGTACACAGagaggcagttccagatttcaactgc | 298 |
| 24V | CTGTGTACCCCTTCCAGGgtgtgcctgctgaataacttctatc | 275 | CCTGGAAGGGGTACACAGaacagaggcagttccagatttcaac | 299 |

FIG. 14B

| Clone name | Forward Primers (5' to 3') | SEQ ID NO: | Reverse Primers (5' to 3') | SEQ ID NO: |
|---|---|---|---|---|
| 25V | CTGTGTACCCCTTCCAGGtgcctgctgaataacttctatccca | 300 | CCTGGAAGGGGTACACAGcacaacagaggcagttccagatttc | 325 |
| 26C | CTGTGTACCCCTTCCAGGctgctgaataacttctatcccagag | 301 | CCTGGAAGGGGTACACAGgcacacaacagaggcagttccagat | 326 |
| 27L | CTGTGTACCCCTTCCAGGctgaataacttctatcccagagagg | 302 | CCTGGAAGGGGTACACAGcaggcacacaacagaggcagttcca | 327 |
| 28L | CTGTGTACCCCTTCCAGGaataacttctatcccagagaggcca | 303 | CCTGGAAGGGGTACACAGcagcaggcacacaacagaggcagtt | 328 |
| 29N | CTGTGTACCCCTTCCAGGaacttctatcccagagaggccaaag | 304 | CCTGGAAGGGGTACACAGattcagcaggcacacaacagaggca | 329 |
| 30N | CTGTGTACCCCTTCCAGGttctatcccagagaggccaaagtac | 305 | CCTGGAAGGGGTACACAGgttattcagcaggcacacaacagag | 330 |
| 31F | CTGTGTACCCCTTCCAGGtatcccagagaggccaaagtacagt | 306 | CCTGGAAGGGGTACACAGaagttattcagcaggcacacaaca | 331 |
| 32Y | CTGTGTACCCCTTCCAGGcccagagaggccaaagtacagtgga | 307 | CCTGGAAGGGGTACACAGatagaagttattcagcaggcacaca | 332 |
| 33P | CTGTGTACCCCTTCCAGGagagaggccaaagtacagtggaagg | 308 | CCTGGAAGGGGTACACAGgggatagaagttattcagcaggcac | 333 |
| 34R | CTGTGTACCCCTTCCAGGgaggccaaagtacagtggaaggtgg | 309 | CCTGGAAGGGGTACACAGtctgggatagaagttattcagcagg | 334 |
| 35E | CTGTGTACCCCTTCCAGGgccaaagtacagtggaaggtggata | 310 | CCTGGAAGGGGTACACAGctctctgggatagaagttattcagc | 335 |
| 36A | CTGTGTACCCCTTCCAGGaaagtacagtggaaggtggataacg | 311 | CCTGGAAGGGGTACACAGggcctctctgggatagaagttattc | 336 |
| 37K | CTGTGTACCCCTTCCAGGgtacagtggaaggtggataacgccc | 312 | CCTGGAAGGGGTACACAGtttggcctctctgggatagaagtta | 337 |
| 38V | CTGTGTACCCCTTCCAGGcagtggaaggtggataacgccctcc | 313 | CCTGGAAGGGGTACACAGactttggcctctctgggatagaag | 338 |
| 39Q | CTGTGTACCCCTTCCAGGtggaaggtggataacgccctccaat | 314 | CCTGGAAGGGGTACACAGctgtactttggcctctctgggatag | 339 |
| 40W | CTGTGTACCCCTTCCAGGaaggtggataacgccctccaatcgg | 315 | CCTGGAAGGGGTACACAGccactgtactttggcctctctggga | 340 |
| 41K | CTGTGTACCCCTTCCAGGgtggataacgccctccaatcgggta | 316 | CCTGGAAGGGGTACACAGcttccactgtactttggcctctctg | 341 |
| 42V | CTGTGTACCCCTTCCAGGgataacgccctccaatcgggtaact | 317 | CCTGGAAGGGGTACACAGcaccttccactgtactttggcctct | 342 |
| 43D | CTGTGTACCCCTTCCAGGaacgccctccaatcgggtaactccc | 318 | CCTGGAAGGGGTACACAGatccaccttccactgtactttggcc | 343 |
| 44N | CTGTGTACCCCTTCCAGGgccctccaatcgggtaactcccagg | 319 | CCTGGAAGGGGTACACAGgttatccaccttccactgtactttg | 344 |
| 45A | CTGTGTACCCCTTCCAGGctccaatcgggtaactcccaggaga | 320 | CCTGGAAGGGGTACACAGggcgttatccaccttccactgtact | 345 |
| 46L | CTGTGTACCCCTTCCAGGcaatcgggtaactcccaggagagtg | 321 | CCTGGAAGGGGTACACAGgagggcgttatccaccttccactgt | 346 |
| 47Q | CTGTGTACCCCTTCCAGGtcgggtaactcccaggagagtgtca | 322 | CCTGGAAGGGGTACACAGttggagggcgttatccaccttccac | 347 |
| 48S | CTGTGTACCCCTTCCAGGggtaactcccaggagagtgtcacag | 323 | CCTGGAAGGGGTACACAGcgattgagggcgttatccaccttc | 348 |
| 49G | CTGTGTACCCCTTCCAGGaactcccaggagagtgtcacagagc | 324 | CCTGGAAGGGGTACACAGacccgattgagggcgttatccacc | 349 |

FIG. 14C

| Clone name | Forward Primers (5' to 3') | SEQ ID NO: | Reverse Primers (5' to 3') | SEQ ID NO: |
|---|---|---|---|---|
| 50N | CTGTGTACCCCTTCCAGGtcccaggagagtgtcacagagcagg | 350 | CCTGGAAGGGGTACACAGgttacccgattggagggcgttatcc | 375 |
| 51S | CTGTGTACCCCTTCCAGGcaggagagtgtcacagagcaggaca | 351 | CCTGGAAGGGGTACACAGggagttacccgattggagggcgtta | 376 |
| 52Q | CTGTGTACCCCTTCCAGGgagagtgtcacagagcaggacagca | 352 | CCTGGAAGGGGTACACAGctgggagttacccgattggagggcg | 377 |
| 53E | CTGTGTACCCCTTCCAGGagtgtcacagagcaggacagcaagg | 353 | CCTGGAAGGGGTACACAGctcctgggagttacccgattggagg | 378 |
| 54S | CTGTGTACCCCTTCCAGGgtcacagagcaggacagcaaggaca | 354 | CCTGGAAGGGGTACACAGactctcctgggagttacccgattgg | 379 |
| 55V | CTGTGTACCCCTTCCAGGacagagcaggacagcaaggacagca | 355 | CCTGGAAGGGGTACACAGacactctcctgggagttacccgat | 380 |
| 56T | CTGTGTACCCCTTCCAGGgagcaggacagcaaggacagcacct | 356 | CCTGGAAGGGGTACACAGtgtgacactctcctgggagttaccc | 381 |
| 57E | CTGTGTACCCCTTCCAGGcaggacagcaaggacagcacctaca | 357 | CCTGGAAGGGGTACACAGctctgtgacactctcctgggagtta | 382 |
| 58Q | CTGTGTACCCCTTCCAGGgacagcaaggacagcacctacagcc | 358 | CCTGGAAGGGGTACACAGctgctctgtgacactctcctgggag | 383 |
| 59D | CTGTGTACCCCTTCCAGGagcaaggacagcacctacagcctca | 359 | CCTGGAAGGGGTACACAGgtcctgctctgtgacactctcctgg | 384 |
| 60S | CTGTGTACCCCTTCCAGGaaggacagcacctacagcctcagca | 360 | CCTGGAAGGGGTACACAGgctgtcctgctctgtgacactctcc | 385 |
| 61K | CTGTGTACCCCTTCCAGGgacagcacctacagcctcagcagca | 361 | CCTGGAAGGGGTACACAGcttgctgtcctgctctgtgacactc | 386 |
| 62D | CTGTGTACCCCTTCCAGGagcacctacagcctcagcagcaccc | 362 | CCTGGAAGGGGTACACAGgtccttgctgtcctgctctgtgaca | 387 |
| 63S | CTGTGTACCCCTTCCAGGacctacagcctcagcagcaccctga | 363 | CCTGGAAGGGGTACACAGgctgtccttgctgtcctgctctgtg | 388 |
| 64T | CTGTGTACCCCTTCCAGGtacagcctcagcagcaccctgacgc | 364 | CCTGGAAGGGGTACACAGggtgctgtccttgctgtcctgctct | 389 |
| 65Y | CTGTGTACCCCTTCCAGGagcctcagcagcaccctgacgctga | 365 | CCTGGAAGGGGTACACAGgtaggtgctgtccttgctgtcctgc | 390 |
| 66S | CTGTGTACCCCTTCCAGGctcagcagcaccctgacgctgagca | 366 | CCTGGAAGGGGTACACAGgctgtaggtgctgtccttgctgtcc | 391 |
| 67L | CTGTGTACCCCTTCCAGGagcagcaccctgacgctgagcaaag | 367 | CCTGGAAGGGGTACACAGgaggctgtaggtgctgtccttgctg | 392 |
| 68S | CTGTGTACCCCTTCCAGGagcaccctgacgctgagcaaagcag | 368 | CCTGGAAGGGGTACACAGgctgagctgtaggtgctgtccttg | 393 |
| 69S | CTGTGTACCCCTTCCAGGaccctgacgctgagcaaagcagact | 369 | CCTGGAAGGGGTACACAGgctgctgaggctgtaggtgctgtcc | 394 |
| 70T | CTGTGTACCCCTTCCAGGctgacgctgagcaaagcagactacg | 370 | CCTGGAAGGGGTACACAGggtgctgctgaggctgtaggtgct | 395 |
| 71L | CTGTGTACCCCTTCCAGGacgctgagcaaagcagactacgaga | 371 | CCTGGAAGGGGTACACAGcagggtgctgctgaggctgtaggtg | 396 |
| 72T | CTGTGTACCCCTTCCAGGctgagcaaagcagactacgagaaac | 372 | CCTGGAAGGGGTACACAGcgtcagggtgctgctgaggctgtag | 397 |
| 73L | CTGTGTACCCCTTCCAGGagcaaagcagactacgagaaacaca | 373 | CCTGGAAGGGGTACACAGcagcgtcagggtgctgctgaggct | 398 |
| 74S | CTGTGTACCCCTTCCAGGaaagcagactacgagaaacacaaag | 374 | CCTGGAAGGGGTACACAGgctcagcgtcagggtgctgctgagg | 399 |

FIG. 14D

| Clone name | Forward Primers (5' to 3') | SEQ ID NO: | Reverse Primers (5' to 3') | SEQ ID NO: |
|---|---|---|---|---|
| 75K | CTGTGTACCCCTTCCAGGgcagactacgagaaacacaaagtct | 400 | CCTGGAAGGGGTACACAGtttgctcagcgtcagggtgctgctg | 425 |
| 76A | CTGTGTACCCCTTCCAGGgactacgagaaacacaaagtctacg | 401 | CCTGGAAGGGGTACACAGtgctttgctcagcgtcagggtgct | 426 |
| 77D | CTGTGTACCCCTTCCAGGtacgagaaacacaaagtctacgcct | 402 | CCTGGAAGGGGTACACAGgtctgctttgctcagcgtcaggtg | 427 |
| 78Y | CTGTGTACCCCTTCCAGGgagaaacacaaagtctacgcctgcg | 403 | CCTGGAAGGGGTACACAGgtagtctgctttgctcagcgtcagg | 428 |
| 79E | CTGTGTACCCCTTCCAGGaaacacaaagtctacgcctgcgaag | 404 | CCTGGAAGGGGTACACAGctcgtagtctgctttgctcagcgtc | 429 |
| 80K | CTGTGTACCCCTTCCAGGcacaaagtctacgcctgcgaagtca | 405 | CCTGGAAGGGGTACACAGtttctcgtagtctgctttgctcagc | 430 |
| 81H | CTGTGTACCCCTTCCAGGaaagtctacgcctgcgaagtcaccc | 406 | CCTGGAAGGGGTACACAGgtgtttctcgtagtctgctttgctc | 431 |
| 82K | CTGTGTACCCCTTCCAGGgtctacgcctgcgaagtcacccatc | 407 | CCTGGAAGGGGTACACAGtttgtgtttctcgtagtctgctttg | 432 |
| 83V | CTGTGTACCCCTTCCAGGtacgcctgcgaagtcacccatcagg | 408 | CCTGGAAGGGGTACACAGgactttgtgtttctcgtagtctgct | 433 |
| 84Y | CTGTGTACCCCTTCCAGGgcctgcgaagtcacccatcagggcc | 409 | CCTGGAAGGGGTACACAGgtagactttgtgtttctcgtagtct | 434 |
| 85A | CTGTGTACCCCTTCCAGGtgcgaagtcacccatcagggcctga | 410 | CCTGGAAGGGGTACACAGgcgtagactttgtgtttctcgtag | 435 |
| 86C | CTGTGTACCCCTTCCAGGgaagtcacccatcagggcctgagct | 411 | CCTGGAAGGGGTACACAGgcaggcgtagactttgtgtttctcg | 436 |
| 87E | CTGTGTACCCCTTCCAGGgtcacccatcagggcctgagctcgc | 412 | CCTGGAAGGGGTACACAGttcgcaggcgtagactttgtgttc | 437 |
| 88V | CTGTGTACCCCTTCCAGGacccatcagggcctgagctcgcccg | 413 | CCTGGAAGGGGTACACAGgacttcgcaggcgtagactttgtgt | 438 |
| 89T | CTGTGTACCCCTTCCAGGcatcagggcctgagctcgccgtca | 414 | CCTGGAAGGGGTACACAGggtgacttcgcaggcgtagacttg | 439 |
| 90H | CTGTGTACCCCTTCCAGGcagggcctgagctcgcccgtcacaa | 415 | CCTGGAAGGGGTACACAGatgggtgacttcgcaggcgtagact | 440 |
| 91Q | CTGTGTACCCCTTCCAGGggcctgagctcgcccgtcacaaga | 416 | CCTGGAAGGGGTACACAGctgatgggtgacttcgcaggcgtag | 441 |
| 92G | CTGTGTACCCCTTCCAGGctgagctcgcccgtcacaagagct | 417 | CCTGGAAGGGGTACACAGgccctgatgggtgacttcgcaggcg | 442 |
| 93L | CTGTGTACCCCTTCCAGGagctcgcccgtcacaagagcttca | 418 | CCTGGAAGGGGTACACAGcaggccctgatgggtgacttcgcag | 443 |
| 94S | CTGTGTACCCCTTCCAGGtcgcccgtcacaaagagcttcaaca | 419 | CCTGGAAGGGGTACACAGgctcaggccctgatgggtgacttcg | 444 |
| 95S | CTGTGTACCCCTTCCAGGcccgtcacaaagagcttcaacaggg | 420 | CCTGGAAGGGGTACACAGcgagctcaggccctgatgggtgact | 445 |
| 96P | CTGTGTACCCCTTCCAGGgtcacaaagagcttcaacaggggag | 421 | CCTGGAAGGGGTACACAGggcgagctcaggccctgatgggt | 446 |
| 97V | CTGTGTACCCCTTCCAGGacaaagagcttcaacaggggagagt | 422 | CCTGGAAGGGGTACACAGgacgggcgagctcaggccctgatgg | 447 |
| 98T | CTGTGTACCCCTTCCAGGaagagcttcaacaggggagagtgtt | 423 | CCTGGAAGGGGTACACAGtgtgacgggcgagctcaggccctga | 448 |
| 99K | CTGTGTACCCCTTCCAGGagcttcaacaggggagagtgttagC | 424 | CCTGGAAGGGGTACACAGctttgtgacgggcgagctcaggccc | 449 |

FIG. 14E

| Clone name | Forward Primers (5' to 3') | SEQ ID NO: | Reverse Primers (5' to 3') | SEQ ID NO: |
|---|---|---|---|---|
| 100S | CTGTGTACCCCTTCCAGGttcaacaggggagagtgttagCCTG | 450 | CCTGGAAGGGGTACACAGgctctttgtgacgggcgagctcagg | 457 |
| 101F | CTGTGTACCCCTTCCAGGaacaggggagagtgttagCCTGCAG | 451 | CCTGGAAGGGGTACACAGgaagctctttgtgacgggcgagctc | 458 |
| 102N | CTGTGTACCCCTTCCAGGaggggagagtgttagCCTGCAGGCA | 452 | CCTGGAAGGGGTACACAGgttgaagctctttgtgacgggcgag | 459 |
| 103R | CTGTGTACCCCTTCCAGGggagagtgttagCCTGCAGGCATGA | 453 | CCTGGAAGGGGTACACAGcctgttgaagctctttgtgacgggc | 460 |
| 104G | CTGTGTACCCCTTCCAGGgagtgttagCCTGCAGGCATGATCA | 454 | CCTGGAAGGGGTACACAGtcccctgttgaagctctttgtgacg | 461 |
| 105E | CTGTGTACCCCTTCCAGGtgttagCCTGCAGGCATGATCATAA | 455 | CCTGGAAGGGGTACACAGctctcccctgttgaagctctttgtg | 462 |
| 106C | CTGTGTACCCCTTCCAGGtagCCTGCAGGCATGATCATAATCA | 456 | CCTGGAAGGGGTACACAGacactctcccctgttgaagctcttt | 463 |

FIG. 15

| LC | DAR |
|----|-----|
| 1T | 1.18 |
| 2V | 1.62 |
| 3A | 1.21 |
| 4A | 1.54 |
| 5P | 1.44 |
| 6S | 0.87 |
| 11P | 0.00 |
| 12P | 0.00 |
| 13S | 0.00 |
| 14D | 0.00 |
| 15E | 0.02 |
| 16Q | 0.22 |
| 17L | 0.14 |
| 18K | 0.15 |
| 19S | 0.63 |
| 20G | 1.40 |
| 21T | 1.65 |
| 22A | 1.66 |
| 27L | 0.21 |
| 29N | 0.54 |
| 30N | 1.05 |
| 31F | 0.63 |
| 32Y | 0.79 |
| 33P | 0.24 |
| 34R | 0.31 |
| 35E | 0.27 |
| 36A | 0.00 |
| 37K | 0.00 |
| 41K | 0.47 |
| 42V | 0.87 |
| 43D | 0.60 |
| 44N | 0.22 |
| 45A | 0.78 |
| 46L | 1.55 |
| 47Q | 0.95 |
| 48S | 1.60 |
| 49G | 1.31 |
| 50N | 1.36 |

| LC | DAR |
|----|-----|
| 51S | 1.49 |
| 52Q | 1.03 |
| 55V | 0.00 |
| 56T | 0.00 |
| 57E | 0.00 |
| 58Q | 0.31 |
| 59D | 0.13 |
| 60S | 0.76 |
| 62D | 0.58 |
| 63S | 0.68 |
| 64T | 0.94 |
| 65Y | 1.54 |
| 79E | 0.08 |
| 89T | 0.83 |
| 90H | 1.15 |
| 91Q | 1.47 |
| 92G | 0.98 |
| 93L | 1.40 |
| 94S | 1.13 |
| 95S | 1.60 |
| 96P | 1.77 |
| 101F | 0.25 |
| 102N | 0.00 |
| 103R | 0.00 |
| 104G | 0.17 |
| 105E | 0.00 |
| 106C | 0.18 |

Table 4. Conjugation yields for the light chain tags

SEQUENCE LISTING

<160> NUMBER OF SEQ ID NOS: 515

<210> SEQ ID NO 1
<211> LENGTH: 106
<212> TYPE: PRT
<213> ORGANISM: Homo sapiens

<400> SEQUENCE: 1

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 2
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 2

Thr Leu Cys Thr Pro Ser Arg Val Ala Ala Pro Ser Val Phe Ile Phe
1               5                   10                  15

Pro Pro Ser Asp Glu Gln Leu Lys Ser Gly Thr Ala Ser Val Val Cys
            20                  25                  30

Leu Leu Asn Asn Phe Tyr Pro Arg Glu Ala Lys Val Gln Trp Lys Val
        35                  40                  45

Asp Asn Ala Leu Gln Ser Gly Asn Ser Gln Glu Ser Val Thr Glu Gln
    50                  55                  60

Asp Ser Lys Asp Ser Thr Tyr Ser Leu Ser Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110

<210> SEQ ID NO 3
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 3

Thr Val Leu Cys Thr Pro Ser Arg Ala Ala Pro Ser Val Phe Ile Phe
1               5                   10                  15

Pro Pro Ser Asp Glu Gln Leu Lys Ser Gly Thr Ala Ser Val Val Cys
            20                  25                  30

Leu Leu Asn Asn Phe Tyr Pro Arg Glu Ala Lys Val Gln Trp Lys Val

```
                35                  40                  45
Asp Asn Ala Leu Gln Ser Gly Asn Ser Gln Glu Ser Val Thr Glu Gln
         50                  55                  60

Asp Ser Lys Asp Ser Thr Tyr Ser Leu Ser Thr Leu Thr Leu Ser
 65                  70                  75                  80

Lys Ala Asp Tyr Glu Lys His Lys Val Tyr Ala Cys Glu Val Thr His
                 85                  90                  95

Gln Gly Leu Ser Ser Pro Val Thr Lys Ser Phe Asn Arg Gly Glu Cys
            100                 105                 110

<210> SEQ ID NO 4
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 4

Thr Val Ala Leu Cys Thr Pro Ser Arg Ala Pro Ser Val Phe Ile Phe
  1               5                  10                  15

Pro Pro Ser Asp Glu Gln Leu Lys Ser Gly Thr Ala Ser Val Val Cys
                 20                  25                  30

Leu Leu Asn Asn Phe Tyr Pro Arg Glu Ala Lys Val Gln Trp Lys Val
             35                  40                  45

Asp Asn Ala Leu Gln Ser Gly Asn Ser Gln Glu Ser Val Thr Glu Gln
         50                  55                  60

Asp Ser Lys Asp Ser Thr Tyr Ser Leu Ser Thr Leu Thr Leu Ser
 65                  70                  75                  80

Lys Ala Asp Tyr Glu Lys His Lys Val Tyr Ala Cys Glu Val Thr His
                 85                  90                  95

Gln Gly Leu Ser Ser Pro Val Thr Lys Ser Phe Asn Arg Gly Glu Cys
            100                 105                 110

<210> SEQ ID NO 5
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 5

Thr Val Ala Ala Leu Cys Thr Pro Ser Arg Pro Ser Val Phe Ile Phe
  1               5                  10                  15

Pro Pro Ser Asp Glu Gln Leu Lys Ser Gly Thr Ala Ser Val Val Cys
                 20                  25                  30

Leu Leu Asn Asn Phe Tyr Pro Arg Glu Ala Lys Val Gln Trp Lys Val
             35                  40                  45

Asp Asn Ala Leu Gln Ser Gly Asn Ser Gln Glu Ser Val Thr Glu Gln
         50                  55                  60

Asp Ser Lys Asp Ser Thr Tyr Ser Leu Ser Ser Thr Leu Thr Leu Ser
 65                  70                  75                  80

Lys Ala Asp Tyr Glu Lys His Lys Val Tyr Ala Cys Glu Val Thr His
                 85                  90                  95

Gln Gly Leu Ser Ser Pro Val Thr Lys Ser Phe Asn Arg Gly Glu Cys
            100                 105                 110

<210> SEQ ID NO 6
<211> LENGTH: 112
```

```
<212> TYPE: PRT
<213> ORGANISM: Artificial sequence
<220> FEATURE:
<223> OTHER INFORMATION: Synthetic polypeptide

<400> SEQUENCE: 6

Thr Val Ala Ala Pro Leu Cys Thr Pro Ser Arg Ser Val Phe Ile Phe
1               5                   10                  15

Pro Pro Ser Asp Glu Gln Leu Lys Ser Gly Thr Ala Ser Val Val Cys
            20                  25                  30

Leu Leu Asn Asn Phe Tyr Pro Arg Glu Ala Lys Val Gln Trp Lys Val
        35                  40                  45

Asp Asn Ala Leu Gln Ser Gly Asn Ser Gln Glu Ser Val Thr Glu Gln
    50                  55                  60

Asp Ser Lys Asp Ser Thr Tyr Ser Leu Ser Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110

<210> SEQ ID NO 7
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 7

Thr Val Ala Ala Pro Ser Leu Cys Thr Pro Ser Arg Val Phe Ile Phe
1               5                   10                  15

Pro Pro Ser Asp Glu Gln Leu Lys Ser Gly Thr Ala Ser Val Val Cys
            20                  25                  30

Leu Leu Asn Asn Phe Tyr Pro Arg Glu Ala Lys Val Gln Trp Lys Val
        35                  40                  45

Asp Asn Ala Leu Gln Ser Gly Asn Ser Gln Glu Ser Val Thr Glu Gln
    50                  55                  60

Asp Ser Lys Asp Ser Thr Tyr Ser Leu Ser Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110

<210> SEQ ID NO 8
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 8

Thr Val Ala Ala Pro Ser Val Leu Cys Thr Pro Ser Arg Phe Ile Phe
1               5                   10                  15

Pro Pro Ser Asp Glu Gln Leu Lys Ser Gly Thr Ala Ser Val Val Cys
            20                  25                  30

Leu Leu Asn Asn Phe Tyr Pro Arg Glu Ala Lys Val Gln Trp Lys Val
        35                  40                  45

Asp Asn Ala Leu Gln Ser Gly Asn Ser Gln Glu Ser Val Thr Glu Gln
```

```
                    50                  55                  60
Asp Ser Lys Asp Ser Thr Tyr Ser Leu Ser Thr Leu Thr Leu Ser
 65                  70                  75                  80

Lys Ala Asp Tyr Glu Lys His Lys Val Tyr Ala Cys Glu Val Thr His
                 85                  90                  95

Gln Gly Leu Ser Ser Pro Val Thr Lys Ser Phe Asn Arg Gly Glu Cys
                100                 105                 110
```

<210> SEQ ID NO 9
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 9

```
Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Leu Cys Thr Pro Ser Arg Asn Arg Gly Glu Cys
                100                 105                 110
```

<210> SEQ ID NO 10
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 10

```
Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Leu Cys Thr Pro Ser Arg Arg Gly Glu Cys
                100                 105                 110
```

<210> SEQ ID NO 11
<211> LENGTH: 112
<212> TYPE: PRT
<213> ORGANISM: Artificial sequence
<220> FEATURE:

<223> OTHER INFORMATION: Synthetic polypeptide

<400> SEQUENCE: 11

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Leu Cys Thr Pro Ser Arg Gly Glu Cys
            100                 105                 110
```

<210> SEQ ID NO 12
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 12

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Leu Cys Thr Pro Ser Arg Glu Cys
            100                 105                 110
```

<210> SEQ ID NO 13
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 13

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
```

```
                65                  70                  75                  80
His Lys Val Tyr Ala Cys Glu Val Thr His Gln Gly Leu Ser Ser Pro
                    85                  90                  95

Val Thr Lys Ser Phe Asn Arg Gly Glu Leu Cys Thr Pro Ser Arg Cys
                100                 105                 110
```

<210> SEQ ID NO 14
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 14

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys Leu Cys Thr Pro Ser Arg
                100                 105                 110
```

<210> SEQ ID NO 15
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 15

```
Thr Val Ala Ala Pro Ser Val Phe Ile Phe Pro Pro Ser Asp Glu Gln
1               5                   10                  15

Leu Lys Ser Leu Cys Thr Pro Ser Arg Gly Thr Ala Ser Val Val Cys
                20                  25                  30

Leu Leu Asn Asn Phe Tyr Pro Arg Glu Ala Lys Val Gln Trp Lys Val
            35                  40                  45

Asp Asn Ala Leu Gln Ser Gly Asn Ser Gln Glu Ser Val Thr Glu Gln
50                  55                  60

Asp Ser Lys Asp Ser Thr Tyr Ser Leu Ser Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
                100                 105                 110
```

<210> SEQ ID NO 16
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 16

Thr Val Ala Ala Pro Ser Val Phe Ile Phe Pro Pro Ser Asp Glu Gln
1               5                   10                  15

Leu Lys Ser Gly Leu Cys Thr Pro Ser Arg Thr Ala Ser Val Val Cys
            20                  25                  30

Leu Leu Asn Asn Phe Tyr Pro Arg Glu Ala Lys Val Gln Trp Lys Val
        35                  40                  45

Asp Asn Ala Leu Gln Ser Gly Asn Ser Gln Glu Ser Val Thr Glu Gln
    50                  55                  60

Asp Ser Lys Asp Ser Thr Tyr Ser Leu Ser Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110

<210> SEQ ID NO 17
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 17

Thr Val Ala Ala Pro Ser Val Phe Ile Phe Pro Pro Ser Asp Glu Gln
1               5                   10                  15

Leu Lys Ser Gly Thr Leu Cys Thr Pro Ser Arg Ala Ser Val Val Cys
            20                  25                  30

Leu Leu Asn Asn Phe Tyr Pro Arg Glu Ala Lys Val Gln Trp Lys Val
        35                  40                  45

Asp Asn Ala Leu Gln Ser Gly Asn Ser Gln Glu Ser Val Thr Glu Gln
    50                  55                  60

Asp Ser Lys Asp Ser Thr Tyr Ser Leu Ser Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110

<210> SEQ ID NO 18
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 18

Thr Val Ala Ala Pro Ser Val Phe Ile Phe Pro Pro Ser Asp Glu Gln
1               5                   10                  15

Leu Lys Ser Gly Thr Ala Leu Cys Thr Pro Ser Arg Ser Val Val Cys
            20                  25                  30

Leu Leu Asn Asn Phe Tyr Pro Arg Glu Ala Lys Val Gln Trp Lys Val
        35                  40                  45

Asp Asn Ala Leu Gln Ser Gly Asn Ser Gln Glu Ser Val Thr Glu Gln
    50                  55                  60

Asp Ser Lys Asp Ser Thr Tyr Ser Leu Ser Ser Thr Leu Thr Leu Ser
65                  70                  75                  80

Lys Ala Asp Tyr Glu Lys His Lys Val Tyr Ala Cys Glu Val Thr His

Gln Gly Leu Ser Ser Pro Val Thr Lys Ser Phe Asn Arg Gly Glu Cys
            100                 105                 110

<210> SEQ ID NO 19
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 19

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Leu Cys Thr
            20                  25                  30

Pro Ser Arg Asn Phe Tyr Pro Arg Glu Ala Lys Val Gln Trp Lys Val
        35                  40                  45

Asp Asn Ala Leu Gln Ser Gly Asn Ser Gln Glu Ser Val Thr Glu Gln
    50                  55                  60

Asp Ser Lys Asp Ser Thr Tyr Ser Leu Ser Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110

<210> SEQ ID NO 20
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 20

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Leu Cys
            20                  25                  30

Thr Pro Ser Arg Phe Tyr Pro Arg Glu Ala Lys Val Gln Trp Lys Val
            35                  40                  45

Asp Asn Ala Leu Gln Ser Gly Asn Ser Gln Glu Ser Val Thr Glu Gln
    50                  55                  60

Asp Ser Lys Asp Ser Thr Tyr Ser Leu Ser Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110

<210> SEQ ID NO 21
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 21

Thr Val Ala Ala Pro Ser Val Phe Ile Phe Pro Pro Ser Asp Glu Gln
1               5                   10                  15

```
Leu Lys Ser Gly Thr Ala Ser Val Val Cys Leu Leu Asn Asn Phe Leu
            20                  25                  30

Cys Thr Pro Ser Arg Tyr Pro Arg Glu Ala Lys Val Gln Trp Lys Val
            35                  40                  45

Asp Asn Ala Leu Gln Ser Gly Asn Ser Gln Glu Ser Val Thr Glu Gln
    50                  55                  60

Asp Ser Lys Asp Ser Thr Tyr Ser Leu Ser Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110

<210> SEQ ID NO 22
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 22

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Leu Cys Thr Pro Ser Arg Pro Arg Glu Ala Lys Val Gln Trp Lys Val
            35                  40                  45

Asp Asn Ala Leu Gln Ser Gly Asn Ser Gln Glu Ser Val Thr Glu Gln
    50                  55                  60

Asp Ser Lys Asp Ser Thr Tyr Ser Leu Ser Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110

<210> SEQ ID NO 23
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 23

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Leu Cys Thr Pro Ser Arg
            35                  40                  45

Asp Asn Ala Leu Gln Ser Gly Asn Ser Gln Glu Ser Val Thr Glu Gln
    50                  55                  60

Asp Ser Lys Asp Ser Thr Tyr Ser Leu Ser Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
```

<210> SEQ ID NO 24
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 24

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Leu Cys Thr Pro Ser
        35                  40                  45

Arg Asn Ala Leu Gln Ser Gly Asn Ser Gln Glu Ser Val Thr Glu Gln
    50                  55                  60

Asp Ser Lys Asp Ser Thr Tyr Ser Leu Ser Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110

<210> SEQ ID NO 25
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 25

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Cys Thr
        35                  40                  45

Pro Ser Arg Leu Gln Ser Gly Asn Ser Gln Glu Ser Val Thr Glu Gln
    50                  55                  60

Asp Ser Lys Asp Ser Thr Tyr Ser Leu Ser Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110

<210> SEQ ID NO 26
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 26

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Leu Cys
            35                  40                  45

Thr Pro Ser Arg Gln Ser Gly Asn Ser Gln Glu Ser Val Thr Glu Gln
 50                  55                  60

Asp Ser Lys Asp Ser Thr Tyr Ser Leu Ser Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110

<210> SEQ ID NO 27
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 27

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Leu
            35                  40                  45

Cys Thr Pro Ser Arg Ser Gly Asn Ser Gln Glu Ser Val Thr Glu Gln
 50                  55                  60

Asp Ser Lys Asp Ser Thr Tyr Ser Leu Ser Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110

<210> SEQ ID NO 28
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 28

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
            35                  40                  45

Leu Cys Thr Pro Ser Arg Gly Asn Ser Gln Glu Ser Val Thr Glu Gln
         50                  55                  60

Asp Ser Lys Asp Ser Thr Tyr Ser Leu Ser Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110

<210> SEQ ID NO 29
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 29

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Leu Cys Thr Pro Ser Arg Asn Ser Gln Glu Ser Val Thr Glu Gln
    50                  55                  60

Asp Ser Lys Asp Ser Thr Tyr Ser Leu Ser Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110
```

<210> SEQ ID NO 30
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 30

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Leu Cys Thr Pro Ser Arg Ser Gln Glu Ser Val Thr Glu Gln
    50                  55                  60

Asp Ser Lys Asp Ser Thr Tyr Ser Leu Ser Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110
```

<210> SEQ ID NO 31
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 31

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45
```

Gly Asn Ser Leu Cys Thr Pro Ser Arg Gln Glu Ser Val Thr Glu Gln
            50                  55                  60

Asp Ser Lys Asp Ser Thr Tyr Ser Leu Ser Ser Thr Leu Thr Leu Ser
 65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110

<210> SEQ ID NO 32
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 32

Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Leu Cys Thr Pro Ser Arg Glu Ser Val Thr Glu Gln
            50                  55                  60

Asp Ser Lys Asp Ser Thr Tyr Ser Leu Ser Ser Thr Leu Thr Leu Ser
 65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110

<210> SEQ ID NO 33
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 33

Thr Val Ala Ala Pro Ser Val Phe Ile Phe Pro Pro Ser Asp Glu Gln
 1               5                  10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Leu Cys Thr Pro
            50                  55                  60

Ser Arg Lys Asp Ser Thr Tyr Ser Leu Ser Ser Thr Leu Thr Leu Ser
 65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110

<210> SEQ ID NO 34
<211> LENGTH: 112
<212> TYPE: PRT

<213> ORGANISM: Artificial sequence
<220> FEATURE:
<223> OTHER INFORMATION: Synthetic polypeptide

<400> SEQUENCE: 34

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Leu Cys
    50                  55                  60

Thr Pro Ser Arg Ser Thr Tyr Ser Leu Ser Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110
```

<210> SEQ ID NO 35
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 35

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Leu
    50                  55                  60

Cys Thr Pro Ser Arg Ser Thr Tyr Ser Leu Ser Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110
```

<210> SEQ ID NO 36
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 36

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60
```

Leu Cys Thr Pro Ser Arg Tyr Ser Leu Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110

<210> SEQ ID NO 37
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 37

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Leu Cys Thr Pro Ser Arg Ser Leu Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110

<210> SEQ ID NO 38
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 38

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr Leu Cys Thr Pro Ser Arg His
                85                  90                  95

Gln Gly Leu Ser Ser Pro Val Thr Lys Ser Phe Asn Arg Gly Glu Cys
            100                 105                 110

<210> SEQ ID NO 39
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 39

```
Thr Val Ala Ala Pro Ser Val Phe Ile Phe Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Leu Cys Thr Pro Ser Arg
                85                  90                  95

Gln Gly Leu Ser Ser Pro Val Thr Lys Ser Phe Asn Arg Gly Glu Cys
            100                 105                 110
```

<210> SEQ ID NO 40
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 40

```
Thr Val Ala Ala Pro Ser Val Phe Ile Phe Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Leu Cys Thr Pro Ser
                85                  90                  95

Arg Gly Leu Ser Ser Pro Val Thr Lys Ser Phe Asn Arg Gly Glu Cys
            100                 105                 110
```

<210> SEQ ID NO 41
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 41

```
Thr Val Ala Ala Pro Ser Val Phe Ile Phe Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80
```

His Lys Val Tyr Ala Cys Glu Val Thr His Gln Gly Leu Cys Thr Pro
                85                  90                  95

Ser Arg Leu Ser Ser Pro Val Thr Lys Ser Phe Asn Arg Gly Glu Cys
            100                 105                 110

<210> SEQ ID NO 42
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 42

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Leu Cys Thr
                85                  90                  95

Pro Ser Arg Ser Ser Pro Val Thr Lys Ser Phe Asn Arg Gly Glu Cys
            100                 105                 110

<210> SEQ ID NO 43
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 43

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Leu Cys
                85                  90                  95

Thr Pro Ser Arg Ser Pro Val Thr Lys Ser Phe Asn Arg Gly Glu Cys
            100                 105                 110

<210> SEQ ID NO 44
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 44

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Leu
                85                  90                  95

Cys Thr Pro Ser Arg Pro Val Thr Lys Ser Phe Asn Arg Gly Glu Cys
            100                 105                 110

<210> SEQ ID NO 45
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 45

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Leu Cys Thr Pro Ser Arg Val Thr Lys Ser Phe Asn Arg Gly Glu Cys
            100                 105                 110

<210> SEQ ID NO 46
<211> LENGTH: 9
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa at position 2 may be present or absent,
    and when present may be any amino acid
<220> FEATURE:
<221> NAME/KEY: MISC_FEATURE
<222> LOCATION: (3)..(3)
<223> OTHER INFORMATION: Xaa at position 3 is Cys, Ser, 2-
    formylglycine, or 2-formylglycine covalently bound to a moiety
<220> FEATURE:
<221> NAME/KEY: MISC_FEATURE
<222> LOCATION: (4)..(4)
<223> OTHER INFORMATION: Xaa at position 4 is any amino acid
<220> FEATURE:
<221> NAME/KEY: MISC_FEATURE
<222> LOCATION: (5)..(5)
<223> OTHER INFORMATION: Xaa at position 5 is Pro or Ala
<220> FEATURE:
<221> NAME/KEY: MISC_FEATURE

```
<222> LOCATION: (6)..(6)
<223> OTHER INFORMATION: Xaa at position 6 is any amino acid
<220> FEATURE:
<221> NAME/KEY: MISC_FEATURE
<222> LOCATION: (7)..(7)
<223> OTHER INFORMATION: Xaa at position 7 is an aliphatic amino acid
      or a basic amino acid

<400> SEQUENCE: 46

Thr Xaa Xaa Xaa Xaa Xaa Xaa Val Ala
1               5

<210> SEQ ID NO 47
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa at position 3 may be present or absent,
      and when present may be any amino acid
<220> FEATURE:
<221> NAME/KEY: MISC_FEATURE
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: MISC_FEATURE
<222> LOCATION: (5)..(5)
<223> OTHER INFORMATION: Xaa at position 5 is any amino acid
<220> FEATURE:
<221> NAME/KEY: MISC_FEATURE
<222> LOCATION: (6)..(6)
<223> OTHER INFORMATION: Xaa at position 6 is Pro or Ala
<220> FEATURE:
<221> NAME/KEY: MISC_FEATURE
<222> LOCATION: (7)..(7)
<223> OTHER INFORMATION: Xaa at position 7 is any amino acid
<220> FEATURE:
<221> NAME/KEY: MISC_FEATURE
<222> LOCATION: (8)..(8)
<223> OTHER INFORMATION: Xaa at position 8 is an aliphatic amino acid
      or a basic amino acid

<400> SEQUENCE: 47

Thr Val Xaa Xaa Xaa Xaa Xaa Xaa Ala Ala
1               5                   10

<210> SEQ ID NO 48
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa at position 3 may be present or absent,
      and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
<220> FEATURE:
<221> NAME/KEY: misc_feature
<222> LOCATION: (6)..(6)
<223> OTHER INFORMATION: Xaa at position 6 is Pro or Ala
<220> FEATURE:
```

```
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
      or a basic amino acid

<400> SEQUENCE: 48

Val Ala Xaa Xaa Xaa Xaa Xaa Xaa Ala Pro
1               5                   10

<210> SEQ ID NO 49
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa at position 3 may be present or absent,
      and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
<220> FEATURE:
<221> NAME/KEY: misc_feature
<222> LOCATION: (6)..(6)
<223> OTHER INFORMATION: Xaa at position 6 is Pro or Ala
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
      or a basic amino acid

<400> SEQUENCE: 49

Ala Ala Xaa Xaa Xaa Xaa Xaa Xaa Pro Ser Val
1               5                   10

<210> SEQ ID NO 50
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa at position 3 may be present or absent,
      and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
<220> FEATURE:
<221> NAME/KEY: misc_feature
<222> LOCATION: (6)..(6)
<223> OTHER INFORMATION: Xaa at position 6 is Pro or Ala
```

```
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
     or a basic amino acid

<400> SEQUENCE: 50

Ala Pro Xaa Xaa Xaa Xaa Xaa Xaa Ser Val Phe
1               5                   10

<210> SEQ ID NO 51
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa at position 3 may be present or absent,
     and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
     formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
<220> FEATURE:
<221> NAME/KEY: misc_feature
<222> LOCATION: (6)..(6)
<223> OTHER INFORMATION: Xaa at position 6 is Pro or Ala
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
     or a basic amino acid

<400> SEQUENCE: 51

Pro Ser Xaa Xaa Xaa Xaa Xaa Xaa Val Phe
1               5                   10

<210> SEQ ID NO 52
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa at position 3 may be present or absent,
     and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
     formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
<220> FEATURE:
<221> NAME/KEY: misc_feature
<222> LOCATION: (6)..(6)
```

```
<223> OTHER INFORMATION: Xaa at position 6 is Pro or Ala
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
      or a basic amino acid

<400> SEQUENCE: 52

Lys Ser Xaa Xaa Xaa Xaa Xaa Xaa Gly Thr
1               5                   10

<210> SEQ ID NO 53
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa at position 4 may be present or absent,
      and when present may be any amino acid
<220> FEATURE:
<221> NAME/KEY: misc_feature
<222> LOCATION: (5)..(5)
<223> OTHER INFORMATION: Xaa at position 5 is Cys, Ser, 2-
      formylglycine, or 2-formylglycine covalently bound to a moiety
<220> FEATURE:
<221> NAME/KEY: misc_feature
<222> LOCATION: (6)..(6)
<223> OTHER INFORMATION: Xaa at position 6 is any amino acid
<220> FEATURE:
<221> NAME/KEY: misc_feature
<222> LOCATION: (7)..(7)
<223> OTHER INFORMATION: Xaa at position 7 is Pro or Ala
<220> FEATURE:
<221> NAME/KEY: misc_feature
<222> LOCATION: (8)..(8)
<223> OTHER INFORMATION: Xaa at position 8 is any amino acid
<220> FEATURE:
<221> NAME/KEY: misc_feature
<222> LOCATION: (9)..(9)
<223> OTHER INFORMATION: Xaa at position 9 is an aliphatic amino acid
      or a basic amino acid

<400> SEQUENCE: 53

Lys Ser Gly Xaa Xaa Xaa Xaa Xaa Xaa Thr Ala
1               5                   10

<210> SEQ ID NO 54
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa at position 3 may be present or absent,
      and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
<220> FEATURE:
<221> NAME/KEY: misc_feature
```

<222> LOCATION: (6)..(6)
<223> OTHER INFORMATION: Xaa at position 6 is Pro or Ala
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
      or a basic amino acid

<400> SEQUENCE: 54

Gly Thr Xaa Xaa Xaa Xaa Xaa Xaa Ala Ser
1               5                   10

<210> SEQ ID NO 55
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa at position 3 may be present or absent,
      and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
<220> FEATURE:
<221> NAME/KEY: misc_feature
<222> LOCATION: (6)..(6)
<223> OTHER INFORMATION: Xaa at position 6 is Pro or Ala
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
      or a basic amino acid

<400> SEQUENCE: 55

Thr Ala Xaa Xaa Xaa Xaa Xaa Xaa Ser Val Val
1               5                   10

<210> SEQ ID NO 56
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa at position 3 may be present or absent,
      and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
<220> FEATURE:

-continued

```
<221> NAME/KEY: misc_feature
<222> LOCATION: (6)..(6)
<223> OTHER INFORMATION: Xaa at position 6 is Pro or Ala
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
      or a basic amino acid

<400> SEQUENCE: 56

Leu Asn Xaa Xaa Xaa Xaa Xaa Xaa Asn Phe
1               5                   10

<210> SEQ ID NO 57
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa at position 3 may be present or absent,
      and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
<220> FEATURE:
<221> NAME/KEY: misc_feature
<222> LOCATION: (6)..(6)
<223> OTHER INFORMATION: Xaa at position 6 is Pro or Ala
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
      or a basic amino acid

<400> SEQUENCE: 57

Asn Asn Xaa Xaa Xaa Xaa Xaa Xaa Phe Tyr
1               5                   10

<210> SEQ ID NO 58
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa at position 3 may be present or absent,
      and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
```

```
<220> FEATURE:
<221> NAME/KEY: misc_feature
<222> LOCATION: (6)..(6)
<223> OTHER INFORMATION: Xaa at position 6 is Pro or Ala
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
      or a basic amino acid

<400> SEQUENCE: 58

Asn Phe Xaa Xaa Xaa Xaa Xaa Xaa Tyr Pro
1               5                   10

<210> SEQ ID NO 59
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa at position 3 may be present or absent,
      and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
<220> FEATURE:
<221> NAME/KEY: misc_feature
<222> LOCATION: (6)..(6)
<223> OTHER INFORMATION: Xaa at position 6 is Pro or Ala
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
      or a basic amino acid

<400> SEQUENCE: 59

Phe Tyr Xaa Xaa Xaa Xaa Xaa Xaa Pro Arg
1               5                   10

<210> SEQ ID NO 60
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa at position 4 may be present or absent,
      and when present may be any amino acid
<220> FEATURE:
<221> NAME/KEY: misc_feature
<222> LOCATION: (5)..(5)
<223> OTHER INFORMATION: Xaa at position 5 is Cys, Ser, 2-
      formylglycine, or 2-formylglycine covalently bound to a moiety
<220> FEATURE:
<221> NAME/KEY: misc_feature
<222> LOCATION: (6)..(6)
```

```
<223> OTHER INFORMATION: Xaa at position 6 is any amino acid
<220> FEATURE:
<221> NAME/KEY: misc_feature
<222> LOCATION: (7)..(7)
<223> OTHER INFORMATION: Xaa at position 7 is Pro or Ala
<220> FEATURE:
<221> NAME/KEY: misc_feature
<222> LOCATION: (8)..(8)
<223> OTHER INFORMATION: Xaa at position 8 is any amino acid
<220> FEATURE:
<221> NAME/KEY: misc_feature
<222> LOCATION: (9)..(9)
<223> OTHER INFORMATION: Xaa at position 9 is an aliphatic amino acid
      or a basic amino acid

<400> SEQUENCE: 60

Trp Lys Val Xaa Xaa Xaa Xaa Xaa Xaa Asp Asn
1               5                   10

<210> SEQ ID NO 61
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa at position 3 may be present or absent,
      and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
<220> FEATURE:
<221> NAME/KEY: misc_feature
<222> LOCATION: (6)..(6)
<223> OTHER INFORMATION: Xaa at position 6 is Pro or Ala
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
      or a basic amino acid
<220> FEATURE:
<221> NAME/KEY: misc_feature
<222> LOCATION: (10)..(10)
<223> OTHER INFORMATION: Xaa can be Ala or Val

<400> SEQUENCE: 61

Val Asp Xaa Xaa Xaa Xaa Xaa Xaa Asn Xaa
1               5                   10

<210> SEQ ID NO 62
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa can be Ala or Val
<220> FEATURE:
<221> NAME/KEY: MISC_FEATURE
<222> LOCATION: (3)..(3)
<223> OTHER INFORMATION: Xaa at position 3 may be present or absent,
```

```
        and when present may be any amino acid
<220> FEATURE:
<221> NAME/KEY: MISC_FEATURE
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: MISC_FEATURE
<222> LOCATION: (5)..(5)
<223> OTHER INFORMATION: Xaa at position 5 is any amino acid
<220> FEATURE:
<221> NAME/KEY: MISC_FEATURE
<222> LOCATION: (6)..(6)
<223> OTHER INFORMATION: Xaa at position 6 is Pro or Ala
<220> FEATURE:
<221> NAME/KEY: MISC_FEATURE
<222> LOCATION: (7)..(7)
<223> OTHER INFORMATION: Xaa at position 7 is any amino acid
<220> FEATURE:
<221> NAME/KEY: MISC_FEATURE
<222> LOCATION: (8)..(8)
<223> OTHER INFORMATION: Xaa at position 8 is an aliphatic amino acid
      or a basic amino acid

<400> SEQUENCE: 62

Asn Xaa Xaa Xaa Xaa Xaa Xaa Xaa Leu Gln
1               5                   10

<210> SEQ ID NO 63
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Ala or Val
<220> FEATURE:
<221> NAME/KEY: misc_feature
<222> LOCATION: (3)..(3)
<223> OTHER INFORMATION: Xaa at position 3 may be present or absent,
      and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
<220> FEATURE:
<221> NAME/KEY: misc_feature
<222> LOCATION: (6)..(6)
<223> OTHER INFORMATION: Xaa at position 6 is Pro or Ala
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
      or a basic amino acid

<400> SEQUENCE: 63

Xaa Leu Xaa Xaa Xaa Xaa Xaa Xaa Gln Ser
1               5                   10

<210> SEQ ID NO 64
<211> LENGTH: 11
<212> TYPE: PRT
<213> ORGANISM: Artificial sequence
<220> FEATURE:
```

```
<223> OTHER INFORMATION: Synthetic polypeptide
<220> FEATURE:
<221> NAME/KEY: misc_feature
<222> LOCATION: (3)..(8)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa at position 3 may be present or absent,
      and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
<220> FEATURE:
<221> NAME/KEY: misc_feature
<222> LOCATION: (6)..(6)
<223> OTHER INFORMATION: Xaa at position 6 is Pro or Ala
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
      or a basic amino acid

<400> SEQUENCE: 64

Leu Gln Xaa Xaa Xaa Xaa Xaa Xaa Ser Gly Asn
1               5                   10

<210> SEQ ID NO 65
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa at position 3 may be present or absent,
      and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
<220> FEATURE:
<221> NAME/KEY: misc_feature
<222> LOCATION: (6)..(6)
<223> OTHER INFORMATION: Xaa at position 6 is Pro or Ala
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
      or a basic amino acid

<400> SEQUENCE: 65

Gln Ser Xaa Xaa Xaa Xaa Xaa Xaa Gly Asn
1               5                   10
```

```
<210> SEQ ID NO 66
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa at position 4 may be present or absent,
      and when present may be any amino acid
<220> FEATURE:
<221> NAME/KEY: misc_feature
<222> LOCATION: (5)..(5)
<223> OTHER INFORMATION: Xaa at position 5 is Cys, Ser, 2-
      formylglycine, or 2-formylglycine covalently bound to a moiety
<220> FEATURE:
<221> NAME/KEY: misc_feature
<222> LOCATION: (6)..(6)
<223> OTHER INFORMATION: Xaa at position 6 is any amino acid
<220> FEATURE:
<221> NAME/KEY: misc_feature
<222> LOCATION: (7)..(7)
<223> OTHER INFORMATION: Xaa at position 7 is Pro or Ala
<220> FEATURE:
<221> NAME/KEY: misc_feature
<222> LOCATION: (8)..(8)
<223> OTHER INFORMATION: Xaa at position 8 is any amino acid
<220> FEATURE:
<221> NAME/KEY: misc_feature
<222> LOCATION: (9)..(9)
<223> OTHER INFORMATION: Xaa at position 9 is an aliphatic amino acid
      or a basic amino acid

<400> SEQUENCE: 66

Gln Ser Gly Xaa Xaa Xaa Xaa Xaa Xaa Asn Ser
1               5                   10

<210> SEQ ID NO 67
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa at position 3 may be present or absent,
      and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
<220> FEATURE:
<221> NAME/KEY: misc_feature
<222> LOCATION: (6)..(6)
<223> OTHER INFORMATION: Xaa at position 6 is Pro or Ala
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
      or a basic amino acid

<400> SEQUENCE: 67

Gly Asn Xaa Xaa Xaa Xaa Xaa Xaa Ser Gln
1               5                   10
```

```
<210> SEQ ID NO 68
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa at position 3 may be present or absent,
      and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
<220> FEATURE:
<221> NAME/KEY: misc_feature
<222> LOCATION: (6)..(6)
<223> OTHER INFORMATION: Xaa at position 6 is Pro or Ala
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
      or a basic amino acid

<400> SEQUENCE: 68

Asn Ser Xaa Xaa Xaa Xaa Xaa Xaa Gln Glu
1               5                   10

<210> SEQ ID NO 69
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa at position 3 may be present or absent,
      and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
<220> FEATURE:
<221> NAME/KEY: misc_feature
<222> LOCATION: (6)..(6)
<223> OTHER INFORMATION: Xaa at position 6 is Pro or Ala
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
      or a basic amino acid

<400> SEQUENCE: 69

Ser Gln Xaa Xaa Xaa Xaa Xaa Xaa Glu Ser
1               5                   10
```

```
<210> SEQ ID NO 70
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa at position 4 may be present or absent,
      and when present may be any amino acid
<220> FEATURE:
<221> NAME/KEY: misc_feature
<222> LOCATION: (5)..(5)
<223> OTHER INFORMATION: Xaa at position 5 is Cys, Ser, 2-
      formylglycine, or 2-formylglycine covalently bound to a moiety
<220> FEATURE:
<221> NAME/KEY: misc_feature
<222> LOCATION: (6)..(6)
<223> OTHER INFORMATION: Xaa at position 6 is any amino acid
<220> FEATURE:
<221> NAME/KEY: misc_feature
<222> LOCATION: (7)..(7)
<223> OTHER INFORMATION: Xaa at position 7 is Pro or Ala
<220> FEATURE:
<221> NAME/KEY: misc_feature
<222> LOCATION: (8)..(8)
<223> OTHER INFORMATION: Xaa at position 8 is any amino acid
<220> FEATURE:
<221> NAME/KEY: misc_feature
<222> LOCATION: (9)..(9)
<223> OTHER INFORMATION: Xaa at position 9 is an aliphatic amino acid
      or a basic amino acid

<400> SEQUENCE: 70

Gln Asp Ser Xaa Xaa Xaa Xaa Xaa Xaa Lys Asp
1               5                   10

<210> SEQ ID NO 71
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa at position 3 may be present or absent,
      and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
<220> FEATURE:
<221> NAME/KEY: misc_feature
<222> LOCATION: (6)..(6)
<223> OTHER INFORMATION: Xaa at position 6 is Pro or Ala
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
      or a basic amino acid

<400> SEQUENCE: 71

Lys Asp Xaa Xaa Xaa Xaa Xaa Xaa Ser Thr Tyr
```

```
<210> SEQ ID NO 72
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa at position 4 may be present or absent,
      and when present may be any amino acid
<220> FEATURE:
<221> NAME/KEY: misc_feature
<222> LOCATION: (5)..(5)
<223> OTHER INFORMATION: Xaa at position 5 is Cys, Ser, 2-
      formylglycine, or 2-formylglycine covalently bound to a moiety
<220> FEATURE:
<221> NAME/KEY: misc_feature
<222> LOCATION: (6)..(6)
<223> OTHER INFORMATION: Xaa at position 6 is any amino acid
<220> FEATURE:
<221> NAME/KEY: misc_feature
<222> LOCATION: (7)..(7)
<223> OTHER INFORMATION: Xaa at position 7 is Pro or Ala
<220> FEATURE:
<221> NAME/KEY: misc_feature
<222> LOCATION: (8)..(8)
<223> OTHER INFORMATION: Xaa at position 6 is any amino acid
<220> FEATURE:
<221> NAME/KEY: misc_feature
<222> LOCATION: (9)..(9)
<223> OTHER INFORMATION: Xaa at position 7 is an aliphatic amino acid
      or a basic amino acid

<400> SEQUENCE: 72

Lys Asp Ser Xaa Xaa Xaa Xaa Xaa Xaa Thr Tyr
1               5                   10

<210> SEQ ID NO 73
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa at position 4 may be present or absent,
      and when present may be any amino acid
<220> FEATURE:
<221> NAME/KEY: misc_feature
<222> LOCATION: (5)..(5)
<223> OTHER INFORMATION: Xaa at position 5 is Cys, Ser, 2-
      formylglycine, or 2-formylglycine covalently bound to a moiety
<220> FEATURE:
<221> NAME/KEY: misc_feature
<222> LOCATION: (6)..(6)
<223> OTHER INFORMATION: Xaa at position 6 is any amino acid
<220> FEATURE:
<221> NAME/KEY: misc_feature
<222> LOCATION: (7)..(7)
<223> OTHER INFORMATION: Xaa at position 7 is Pro or Ala
<220> FEATURE:
<221> NAME/KEY: misc_feature
<222> LOCATION: (8)..(8)
<223> OTHER INFORMATION: Xaa at position 8 is any amino acid
<220> FEATURE:
<221> NAME/KEY: misc_feature
<222> LOCATION: (9)..(9)
<223> OTHER INFORMATION: Xaa at position 9 is an aliphatic amino acid
      or a basic amino acid

<400> SEQUENCE: 73
```

Asp Ser Thr Xaa Xaa Xaa Xaa Xaa Xaa Tyr Ser
1               5                   10

<210> SEQ ID NO 74
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa at position 3 may be present or absent,
      and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
<220> FEATURE:
<221> NAME/KEY: misc_feature
<222> LOCATION: (6)..(6)
<223> OTHER INFORMATION: Xaa at position 6 is Pro or Ala
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
      or a basic amino acid

<400> SEQUENCE: 74

Thr Tyr Xaa Xaa Xaa Xaa Xaa Xaa Ser Leu
1               5                   10

<210> SEQ ID NO 75
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa at position 4 may be present or absent,
      and when present may be any amino acid
<220> FEATURE:
<221> NAME/KEY: misc_feature
<222> LOCATION: (5)..(5)
<223> OTHER INFORMATION: Xaa at position 5 is Cys, Ser, 2-
      formylglycine, or 2-formylglycine covalently bound to a moiety
<220> FEATURE:
<221> NAME/KEY: misc_feature
<222> LOCATION: (6)..(6)
<223> OTHER INFORMATION: Xaa at position 6 is any amino acid
<220> FEATURE:
<221> NAME/KEY: misc_feature
<222> LOCATION: (7)..(7)
<223> OTHER INFORMATION: Xaa at position 7 is Pro or Ala
<220> FEATURE:
<221> NAME/KEY: misc_feature
<222> LOCATION: (8)..(8)
<223> OTHER INFORMATION: Xaa at position 8 is any amino acid
<220> FEATURE:
<221> NAME/KEY: misc_feature
<222> LOCATION: (9)..(9)
<223> OTHER INFORMATION: Xaa at position 9 is an aliphatic amino acid
      or a basic amino acid

<400> SEQUENCE: 75

```
Glu Val Thr Xaa Xaa Xaa Xaa Xaa Xaa His Gln
1               5                   10
```

<210> SEQ ID NO 76
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa at position 3 may be present or absent,
      and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
<220> FEATURE:
<221> NAME/KEY: misc_feature
<222> LOCATION: (6)..(6)
<223> OTHER INFORMATION: Xaa at position 6 is Pro or Ala
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
      or a basic amino acid

<400> SEQUENCE: 76

```
Thr His Xaa Xaa Xaa Xaa Xaa Xaa Gln Gly
1               5                   10
```

<210> SEQ ID NO 77
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa at position 3 may be present or absent,
      and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
<220> FEATURE:
<221> NAME/KEY: misc_feature
<222> LOCATION: (6)..(6)
<223> OTHER INFORMATION: Xaa at position 6 is Pro or Ala
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
      or a basic amino acid -continued

```
<400> SEQUENCE: 77

His Gln Xaa Xaa Xaa Xaa Xaa Xaa Gly Leu
1               5                   10

<210> SEQ ID NO 78
<211> LENGTH: 12
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa at position 3 may be present or absent,
      and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
<220> FEATURE:
<221> NAME/KEY: misc_feature
<222> LOCATION: (6)..(6)
<223> OTHER INFORMATION: Xaa at position 6 is Pro or Ala
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
      or a basic amino acid

<400> SEQUENCE: 78

Gln Gly Xaa Xaa Xaa Xaa Xaa Xaa Leu Ser Ser Pro
1               5                   10

<210> SEQ ID NO 79
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa at position 3 may be present or absent,
      and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
<220> FEATURE:
<221> NAME/KEY: misc_feature
<222> LOCATION: (6)..(6)
<223> OTHER INFORMATION: Xaa at position 6 is Pro or Ala
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
      or a basic amino acid
```

```
<400> SEQUENCE: 79

Gly Leu Xaa Xaa Xaa Xaa Xaa Xaa Ser Ser
1               5                   10

<210> SEQ ID NO 80
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa at position 4 may be present or absent,
      and when present may be any amino acid
<220> FEATURE:
<221> NAME/KEY: misc_feature
<222> LOCATION: (5)..(5)
<223> OTHER INFORMATION: Xaa at position 5 is Cys, Ser, 2-
      formylglycine, or 2-formylglycine covalently bound to a moiety
<220> FEATURE:
<221> NAME/KEY: misc_feature
<222> LOCATION: (6)..(6)
<223> OTHER INFORMATION: Xaa at position 6 is any amino acid
<220> FEATURE:
<221> NAME/KEY: misc_feature
<222> LOCATION: (7)..(7)
<223> OTHER INFORMATION: Xaa at position 7 is Pro or Ala
<220> FEATURE:
<221> NAME/KEY: misc_feature
<222> LOCATION: (8)..(8)
<223> OTHER INFORMATION: Xaa at position 8 is any amino acid
<220> FEATURE:
<221> NAME/KEY: misc_feature
<222> LOCATION: (9)..(9)
<223> OTHER INFORMATION: Xaa at position 9 is an aliphatic amino acid
      or a basic amino acid

<400> SEQUENCE: 80

Gly Leu Ser Xaa Xaa Xaa Xaa Xaa Xaa Ser Pro
1               5                   10

<210> SEQ ID NO 81
<211> LENGTH: 12
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (5)..(5)
<223> OTHER INFORMATION: Xaa at position 5 may be present or absent,
      and when present may be any amino acid
<220> FEATURE:
<221> NAME/KEY: misc_feature
<222> LOCATION: (6)..(6)
<223> OTHER INFORMATION: Xaa at position 6 is Cys, Ser, 2-
      formylglycine, or 2-formylglycine covalently bound to a moiety
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is Pro or Ala
<220> FEATURE:
<221> NAME/KEY: misc_feature
<222> LOCATION: (9)..(9)
<223> OTHER INFORMATION: Xaa at position 9 is any amino acid
<220> FEATURE:
<221> NAME/KEY: misc_feature
<222> LOCATION: (10)..(10)
<223> OTHER INFORMATION: Xaa at position 10 is an aliphatic amino acid
``` or a basic amino acid

<400> SEQUENCE: 81

Gly Leu Ser Ser Xaa Xaa Xaa Xaa Xaa Xaa Pro Val
1               5                   10

<210> SEQ ID NO 82
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa at position 3 may be present or absent,
      and when present may be any amino acid
<220> FEATURE:
<221> NAME/KEY: misc_feature
<222> LOCATION: (4)..(4)
<223> OTHER INFORMATION: Xaa at position 4 is Cys, Ser, 2-
      formylglycine, or 2-formylglycine covalently bound to a moiety
<220> FEATURE:
<221> NAME/KEY: misc_feature
<222> LOCATION: (5)..(5)
<223> OTHER INFORMATION: Xaa at position 5 is any amino acid
<220> FEATURE:
<221> NAME/KEY: misc_feature
<222> LOCATION: (6)..(6)
<223> OTHER INFORMATION: Xaa at position 6 is Pro or Ala
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is an aliphatic amino acid
      or a basic amino acid

<400> SEQUENCE: 82

Ser Pro Xaa Xaa Xaa Xaa Xaa Xaa Val Thr
1               5                   10

<210> SEQ ID NO 83
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 83

Thr Leu Cys Thr Pro Ser Arg Val Ala
1               5

<210> SEQ ID NO 84
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 84

Thr Val Leu Cys Thr Pro Ser Arg Ala Ala
1               5                   10

<210> SEQ ID NO 85
<211> LENGTH: 10
<212> TYPE: PRT
<213> ORGANISM: Artificial sequence
<220> FEATURE:

```
<223> OTHER INFORMATION: Synthetic polypeptide

<400> SEQUENCE: 85

Val Ala Leu Cys Thr Pro Ser Arg Ala Pro
1               5                   10

<210> SEQ ID NO 86
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 86

Ala Ala Leu Cys Thr Pro Ser Arg Pro Ser Val
1               5                   10

<210> SEQ ID NO 87
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 87

Ala Pro Leu Cys Thr Pro Ser Arg Ser Val Phe
1               5                   10

<210> SEQ ID NO 88
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 88

Pro Ser Leu Cys Thr Pro Ser Arg Val Phe
1               5                   10

<210> SEQ ID NO 89
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 89

Lys Ser Leu Cys Thr Pro Ser Arg Gly Thr
1               5                   10

<210> SEQ ID NO 90
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 90

Lys Ser Gly Leu Cys Thr Pro Ser Arg Thr Ala
1               5                   10

<210> SEQ ID NO 91
<211> LENGTH: 10
<212> TYPE: PRT
<213> ORGANISM: Artificial sequence
<220> FEATURE:
<223> OTHER INFORMATION: Synthetic polypeptide
```

<400> SEQUENCE: 91

Gly Thr Leu Cys Thr Pro Ser Arg Ala Ser
1               5                   10

<210> SEQ ID NO 92
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 92

Thr Ala Leu Cys Thr Pro Ser Arg Ser Val Val
1               5                   10

<210> SEQ ID NO 93
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 93

Leu Asn Leu Cys Thr Pro Ser Arg Asn Phe
1               5                   10

<210> SEQ ID NO 94
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 94

Asn Asn Leu Cys Thr Pro Ser Arg Phe Tyr
1               5                   10

<210> SEQ ID NO 95
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 95

Asn Phe Leu Cys Thr Pro Ser Arg Tyr Pro
1               5                   10

<210> SEQ ID NO 96
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 96

Phe Tyr Leu Cys Thr Pro Ser Arg Pro Arg
1               5                   10

<210> SEQ ID NO 97
<211> LENGTH: 11
<212> TYPE: PRT
<213> ORGANISM: Artificial sequence
<220> FEATURE:
<223> OTHER INFORMATION: Synthetic polypeptide

```
<400> SEQUENCE: 97

Trp Lys Val Leu Cys Thr Pro Ser Arg Asp Asn
1               5                   10

<210> SEQ ID NO 98
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (10)..(10)
<223> OTHER INFORMATION: Xaa can be Ala or Val

<400> SEQUENCE: 98

Val Asp Leu Cys Thr Pro Ser Arg Asn Xaa
1               5                   10

<210> SEQ ID NO 99
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be Ala or Val

<400> SEQUENCE: 99

Asn Xaa Leu Cys Thr Pro Ser Arg Leu Gln
1               5                   10

<210> SEQ ID NO 100
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Ala or Val

<400> SEQUENCE: 100

Xaa Leu Leu Cys Thr Pro Ser Arg Gln Ser
1               5                   10

<210> SEQ ID NO 101
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 101

Leu Gln Leu Cys Thr Pro Ser Arg Ser Gly Asn
1               5                   10

<210> SEQ ID NO 102
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 102
```

Gln Ser Leu Cys Thr Pro Ser Arg Gly Asn
1               5                   10

<210> SEQ ID NO 103
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 103

Gln Ser Gly Leu Cys Thr Pro Ser Arg Asn Ser
1               5                   10

<210> SEQ ID NO 104
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 104

Gly Asn Leu Cys Thr Pro Ser Arg Ser Gln
1               5                   10

<210> SEQ ID NO 105
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 105

Asn Ser Leu Cys Thr Pro Ser Arg Gln Glu
1               5                   10

<210> SEQ ID NO 106
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 106

Ser Gln Leu Cys Thr Pro Ser Arg Glu Ser
1               5                   10

<210> SEQ ID NO 107
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 107

Gln Asp Ser Leu Cys Thr Pro Ser Arg Lys Asp
1               5                   10

<210> SEQ ID NO 108
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 108

Lys Asp Leu Cys Thr Pro Ser Arg Ser Thr Tyr

```
1               5                   10
```

<210> SEQ ID NO 109
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 109

```
Lys Asp Ser Leu Cys Thr Pro Ser Arg Thr Tyr
1               5                   10
```

<210> SEQ ID NO 110
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 110

```
Asp Ser Thr Leu Cys Thr Pro Ser Arg Tyr Ser
1               5                   10
```

<210> SEQ ID NO 111
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 111

```
Thr Tyr Leu Cys Thr Pro Ser Arg Ser Leu
1               5                   10
```

<210> SEQ ID NO 112
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 112

```
Glu Val Thr Leu Cys Thr Pro Ser Arg His Gln
1               5                   10
```

<210> SEQ ID NO 113
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 113

```
Thr His Leu Cys Thr Pro Ser Arg Gln Gly
1               5                   10
```

<210> SEQ ID NO 114
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 114

```
His Gln Leu Cys Thr Pro Ser Arg Gly Leu
1               5                   10
```

<210> SEQ ID NO 115
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 115

Gln Gly Leu Cys Thr Pro Ser Arg Leu Ser Ser Pro
1               5                   10

<210> SEQ ID NO 116
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 116

Gly Leu Leu Cys Thr Pro Ser Arg Ser Ser
1               5                   10

<210> SEQ ID NO 117
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 117

Gly Leu Ser Leu Cys Thr Pro Ser Arg Ser Pro
1               5                   10

<210> SEQ ID NO 118
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 118

Gly Leu Ser Ser Leu Cys Thr Pro Ser Arg Pro Val
1               5                   10

<210> SEQ ID NO 119
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 119

Ser Pro Leu Cys Thr Pro Ser Arg Val Thr
1               5                   10

<210> SEQ ID NO 120
<211> LENGTH: 9
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa at position 2 may be present or absent,
      and when present may be any amino acid
<220> FEATURE:

```
<221> NAME/KEY: MOD_RES
<222> LOCATION: (3)..(3)
<223> OTHER INFORMATION: FORMYLATION, covalently bound to a moiety
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa at position 5 is Pro or Ala
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa at position 7 is an aliphatic or baisc
      amino acid

<400> SEQUENCE: 120

Thr Xaa Gly Xaa Xaa Xaa Xaa Val Ala
1               5

<210> SEQ ID NO 121
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid

<400> SEQUENCE: 121

Thr Val Xaa Gly Xaa Xaa Xaa Xaa Ala Ala
1               5                   10

<210> SEQ ID NO 122
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid

<400> SEQUENCE: 122

Val Ala Xaa Gly Xaa Xaa Xaa Xaa Ala Pro
1               5                   10

<210> SEQ ID NO 123
<211> LENGTH: 11
```

```
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid

<400> SEQUENCE: 123

Ala Ala Xaa Gly Xaa Xaa Xaa Xaa Pro Ser Val
1               5                   10

<210> SEQ ID NO 124
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid

<400> SEQUENCE: 124

Ala Pro Xaa Gly Xaa Xaa Xaa Xaa Ser Val Phe
1               5                   10

<210> SEQ ID NO 125
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid

<400> SEQUENCE: 125

Pro Ser Xaa Gly Xaa Xaa Xaa Xaa Val Phe
1               5                   10

<210> SEQ ID NO 126
<211> LENGTH: 10
<212> TYPE: PRT
<213> ORGANISM: Artificial sequence
<220> FEATURE:
<223> OTHER INFORMATION: Synthetic polypeptide
```

```
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid

<400> SEQUENCE: 126

Lys Ser Xaa Gly Xaa Xaa Xaa Xaa Gly Thr
1               5                   10

<210> SEQ ID NO 127
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MOD_RES
<222> LOCATION: (5)..(5)
<223> OTHER INFORMATION: FORMYLATION, covalently bound to a moiety
<220> FEATURE:
<221> NAME/KEY: misc_feature
<222> LOCATION: (6)..(9)
<223> OTHER INFORMATION: Xaa can be any naturally occurring amino acid

<400> SEQUENCE: 127

Lys Ser Gly Xaa Gly Xaa Xaa Xaa Xaa Thr Ala
1               5                   10

<210> SEQ ID NO 128
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid

<400> SEQUENCE: 128

Gly Thr Xaa Gly Xaa Xaa Xaa Xaa Ala Ser
1               5                   10

<210> SEQ ID NO 129
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid
```

```
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid

<400> SEQUENCE: 129

Thr Ala Xaa Gly Xaa Xaa Xaa Xaa Ser Val Val
1               5                   10

<210> SEQ ID NO 130
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid

<400> SEQUENCE: 130

Leu Asn Xaa Gly Xaa Xaa Xaa Xaa Asn Phe
1               5                   10

<210> SEQ ID NO 131
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid

<400> SEQUENCE: 131

Asn Asn Xaa Gly Xaa Xaa Xaa Xaa Phe Tyr
1               5                   10

<210> SEQ ID NO 132
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
```

```
<220> FEATURE:
<221> NAME/KEY: misc_feature
<222> LOCATION: (5)..(8)
<223> OTHER INFORMATION: Xaa can be any naturally occurring amino acid

<400> SEQUENCE: 132

Asn Phe Xaa Gly Xaa Xaa Xaa Xaa Tyr Pro
1               5                   10

<210> SEQ ID NO 133
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid

<400> SEQUENCE: 133

Phe Tyr Xaa Gly Xaa Xaa Xaa Xaa Pro Arg
1               5                   10

<210> SEQ ID NO 134
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MOD_RES
<222> LOCATION: (5)..(5)
<223> OTHER INFORMATION: FORMYLATION, covalently bound to a moiety
<220> FEATURE:
<221> NAME/KEY: misc_feature
<222> LOCATION: (6)..(9)
<223> OTHER INFORMATION: Xaa can be any naturally occurring amino acid

<400> SEQUENCE: 134

Trp Lys Val Xaa Gly Xaa Xaa Xaa Xaa Asp Asn
1               5                   10

<210> SEQ ID NO 135
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid
```

```
<220> FEATURE:
<221> NAME/KEY: misc_feature
<222> LOCATION: (10)..(10)
<223> OTHER INFORMATION: Xaa can be Ala or Val

<400> SEQUENCE: 135

Val Asp Xaa Gly Xaa Xaa Xaa Xaa Asn Xaa
1               5                   10

<210> SEQ ID NO 136
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be Ala or Val
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid

<400> SEQUENCE: 136

Asn Xaa Gly Xaa Xaa Xaa Xaa Xaa Leu Gln
1               5                   10

<210> SEQ ID NO 137
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa can be Ala or Val
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid

<400> SEQUENCE: 137

Xaa Leu Xaa Gly Xaa Xaa Xaa Xaa Gln Ser
1               5                   10

<210> SEQ ID NO 138
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
```

```
<220> FEATURE:
<221> NAME/KEY: misc_feature
<222> LOCATION: (5)..(8)
<223> OTHER INFORMATION: Xaa can be any naturally occurring amino acid

<400> SEQUENCE: 138

Leu Gln Xaa Gly Xaa Xaa Xaa Xaa Ser Gly Asn
1               5                   10

<210> SEQ ID NO 139
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid

<400> SEQUENCE: 139

Gln Ser Xaa Gly Xaa Xaa Xaa Xaa Gly Asn
1               5                   10

<210> SEQ ID NO 140
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MOD_RES
<222> LOCATION: (5)..(5)
<223> OTHER INFORMATION: FORMYLATION, covalently bound to a moiety
<220> FEATURE:
<221> NAME/KEY: misc_feature
<222> LOCATION: (6)..(9)
<223> OTHER INFORMATION: Xaa can be any naturally occurring amino acid

<400> SEQUENCE: 140

Gln Ser Gly Xaa Gly Xaa Xaa Xaa Xaa Asn Ser
1               5                   10

<210> SEQ ID NO 141
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid
```

<400> SEQUENCE: 141

Gly Asn Xaa Gly Xaa Xaa Xaa Xaa Ser Gln
1               5                   10

<210> SEQ ID NO 142
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid

<400> SEQUENCE: 142

Asn Ser Xaa Gly Xaa Xaa Xaa Xaa Gln Glu
1               5                   10

<210> SEQ ID NO 143
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid

<400> SEQUENCE: 143

Ser Gln Xaa Gly Xaa Xaa Xaa Xaa Glu Ser
1               5                   10

<210> SEQ ID NO 144
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MOD_RES
<222> LOCATION: (5)..(5)
<223> OTHER INFORMATION: FORMYLATION, covalently bound to a moiety
<220> FEATURE:
<221> NAME/KEY: misc_feature
<222> LOCATION: (6)..(9)
<223> OTHER INFORMATION: Xaa can be any naturally occurring amino acid

<400> SEQUENCE: 144

Gln Asp Ser Xaa Gly Xaa Xaa Xaa Xaa Lys Asp

<210> SEQ ID NO 145
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid

<400> SEQUENCE: 145

Lys Asp Xaa Gly Xaa Xaa Xaa Xaa Ser Thr Tyr
1               5                   10

<210> SEQ ID NO 146
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MOD_RES
<222> LOCATION: (5)..(5)
<223> OTHER INFORMATION: FORMYLATION, covalently bound to a moiety
<220> FEATURE:
<221> NAME/KEY: misc_feature
<222> LOCATION: (6)..(9)
<223> OTHER INFORMATION: Xaa can be any naturally occurring amino acid

<400> SEQUENCE: 146

Lys Asp Ser Xaa Gly Xaa Xaa Xaa Xaa Thr Tyr
1               5                   10

<210> SEQ ID NO 147
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MOD_RES
<222> LOCATION: (5)..(5)
<223> OTHER INFORMATION: FORMYLATION, covalently bound to a moiety
<220> FEATURE:
<221> NAME/KEY: misc_feature
<222> LOCATION: (6)..(9)
<223> OTHER INFORMATION: Xaa can be any naturally occurring amino acid

<400> SEQUENCE: 147

Asp Ser Thr Xaa Gly Xaa Xaa Xaa Xaa Tyr Ser
1               5                   10

<210> SEQ ID NO 148

```
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid

<400> SEQUENCE: 148

Thr Tyr Xaa Gly Xaa Xaa Xaa Xaa Ser Leu
1               5                   10

<210> SEQ ID NO 149
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MOD_RES
<222> LOCATION: (5)..(5)
<223> OTHER INFORMATION: FORMYLATION, covalently bound to a moiety
<220> FEATURE:
<221> NAME/KEY: misc_feature
<222> LOCATION: (6)..(9)
<223> OTHER INFORMATION: Xaa can be any naturally occurring amino acid

<400> SEQUENCE: 149

Glu Val Thr Xaa Gly Xaa Xaa Xaa Xaa His Gln
1               5                   10

<210> SEQ ID NO 150
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid

<400> SEQUENCE: 150

Thr His Xaa Gly Xaa Xaa Xaa Xaa Gln Gly
1               5                   10

<210> SEQ ID NO 151
<211> LENGTH: 10
<212> TYPE: PRT
<213> ORGANISM: Artificial sequence
<220> FEATURE:
```

<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid

<400> SEQUENCE: 151

His Gln Xaa Gly Xaa Xaa Xaa Xaa Gly Leu
1               5                   10

<210> SEQ ID NO 152
<211> LENGTH: 12
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid

<400> SEQUENCE: 152

Gln Gly Xaa Gly Xaa Xaa Xaa Xaa Leu Ser Ser Pro
1               5                   10

<210> SEQ ID NO 153
<211> LENGTH: 10
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid

<400> SEQUENCE: 153

Gly Leu Xaa Gly Xaa Xaa Xaa Xaa Ser Ser
1               5                   10

<210> SEQ ID NO 154
<211> LENGTH: 11
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (4)..(4)

```
<223> OTHER INFORMATION: Xaa can be any naturally occurring amino acid
<220> FEATURE:
<221> NAME/KEY: MOD_RES
<222> LOCATION: (5)..(5)
<223> OTHER INFORMATION: FORMYLATION, covalently bound to a moiety
<220> FEATURE:
<221> NAME/KEY: misc_feature
<222> LOCATION: (6)..(9)
<223> OTHER INFORMATION: Xaa can be any naturally occurring amino acid

<400> SEQUENCE: 154

Gly Leu Ser Xaa Gly Xaa Xaa Xaa Xaa Ser Pro
1               5                   10

<210> SEQ ID NO 155
<211> LENGTH: 12
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MOD_RES
<222> LOCATION: (6)..(6)
<223> OTHER INFORMATION: FORMYLATION, covalently bound to a moiety
<220> FEATURE:
<221> NAME/KEY: misc_feature
<222> LOCATION: (7)..(10)
<223> OTHER INFORMATION: Xaa can be any naturally occurring amino acid

<400> SEQUENCE: 155

Gly Leu Ser Ser Xaa Gly Xaa Xaa Xaa Xaa Pro Val
1               5                   10

<210> SEQ ID NO 156
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION, covalently bound to a moiety
<220> FEATURE:
<221> NAME/KEY: misc_feature
<222> LOCATION: (5)..(8)
<223> OTHER INFORMATION: Xaa can be any naturally occurring amino acid

<400> SEQUENCE: 156

Ser Pro Xaa Gly Xaa Xaa Xaa Xaa Val Thr
1               5                   10

<210> SEQ ID NO 157
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION

<400> SEQUENCE: 157
```

```
Leu Gly Thr Pro Ser Arg
1               5
```

<210> SEQ ID NO 158
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 158

```
Leu Cys Thr Pro Ser Arg
1               5
```

<210> SEQ ID NO 159
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 159

```
Leu Ser Thr Pro Ser Arg
1               5
```

<210> SEQ ID NO 160
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 160

```
Met Cys Thr Pro Ser Arg
1               5
```

<210> SEQ ID NO 161
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 161

```
Val Cys Thr Pro Ser Arg
1               5
```

<210> SEQ ID NO 162
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 162

```
Leu Cys Ser Pro Ser Arg
1               5
```

<210> SEQ ID NO 163
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 163

```
Leu Cys Ala Pro Ser Arg
```

```
1               5
```

<210> SEQ ID NO 164
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 164

```
Leu Cys Val Pro Ser Arg
1               5
```

<210> SEQ ID NO 165
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 165

```
Leu Cys Gly Pro Ser Arg
1               5
```

<210> SEQ ID NO 166
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 166

```
Ile Cys Thr Pro Ala Arg
1               5
```

<210> SEQ ID NO 167
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 167

```
Leu Cys Thr Pro Ser Lys
1               5
```

<210> SEQ ID NO 168
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 168

```
Met Cys Thr Pro Ser Lys
1               5
```

<210> SEQ ID NO 169
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 169

```
Val Cys Thr Pro Ser Lys
1               5
```

```
<210> SEQ ID NO 170
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 170

Leu Cys Ser Pro Ser Lys
1               5

<210> SEQ ID NO 171
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 171

Leu Cys Ala Pro Ser Lys
1               5

<210> SEQ ID NO 172
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 172

Leu Cys Val Pro Ser Lys
1               5

<210> SEQ ID NO 173
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 173

Leu Cys Gly Pro Ser Lys
1               5

<210> SEQ ID NO 174
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 174

Leu Cys Thr Pro Ser Ala
1               5

<210> SEQ ID NO 175
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 175

Ile Cys Thr Pro Ala Ala
1               5
```

<210> SEQ ID NO 176
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 176

Met Cys Thr Pro Ser Ala
1               5

<210> SEQ ID NO 177
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 177

Val Cys Thr Pro Ser Ala
1               5

<210> SEQ ID NO 178
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 178

Leu Cys Ser Pro Ser Ala
1               5

<210> SEQ ID NO 179
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 179

Leu Cys Ala Pro Ser Ala
1               5

<210> SEQ ID NO 180
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 180

Leu Cys Val Pro Ser Ala
1               5

<210> SEQ ID NO 181
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 181

Leu Cys Gly Pro Ser Ala
1               5

```
<210> SEQ ID NO 182
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 182

Met Ser Thr Pro Ser Arg
1               5

<210> SEQ ID NO 183
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 183

Val Ser Thr Pro Ser Arg
1               5

<210> SEQ ID NO 184
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 184

Leu Ser Ser Pro Ser Arg
1               5

<210> SEQ ID NO 185
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 185

Leu Ser Ala Pro Ser Arg
1               5

<210> SEQ ID NO 186
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 186

Leu Ser Val Pro Ser Arg
1               5

<210> SEQ ID NO 187
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 187

Leu Ser Gly Pro Ser Arg
1               5

<210> SEQ ID NO 188
```

```
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 188

Ile Ser Thr Pro Ala Arg
1               5

<210> SEQ ID NO 189
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 189

Leu Ser Thr Pro Ser Lys
1               5

<210> SEQ ID NO 190
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 190

Met Ser Thr Pro Ser Lys
1               5

<210> SEQ ID NO 191
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 191

Val Ser Thr Pro Ser Lys
1               5

<210> SEQ ID NO 192
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 192

Leu Ser Ser Pro Ser Lys
1               5

<210> SEQ ID NO 193
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 193

Leu Ser Ala Pro Ser Lys
1               5

<210> SEQ ID NO 194
<211> LENGTH: 6
```

```
<212> TYPE: PRT
<213> ORGANISM: Artificial sequence
<220> FEATURE:
<223> OTHER INFORMATION: Synthetic polypeptide

<400> SEQUENCE: 194

Leu Ser Val Pro Ser Lys
1               5

<210> SEQ ID NO 195
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 195

Leu Ser Gly Pro Ser Lys
1               5

<210> SEQ ID NO 196
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 196

Leu Ser Thr Pro Ser Ala
1               5

<210> SEQ ID NO 197
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 197

Ile Ser Thr Pro Ala Ala
1               5

<210> SEQ ID NO 198
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 198

Met Ser Thr Pro Ser Ala
1               5

<210> SEQ ID NO 199
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 199

Val Ser Thr Pro Ser Ala
1               5

<210> SEQ ID NO 200
<211> LENGTH: 6
<212> TYPE: PRT
```

```
<213> ORGANISM: Artificial sequence
<220> FEATURE:
<223> OTHER INFORMATION: Synthetic polypeptide

<400> SEQUENCE: 200

Leu Ser Ser Pro Ser Ala
1               5

<210> SEQ ID NO 201
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 201

Leu Ser Ala Pro Ser Ala
1               5

<210> SEQ ID NO 202
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 202

Leu Ser Val Pro Ser Ala
1               5

<210> SEQ ID NO 203
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 203

Leu Ser Gly Pro Ser Ala
1               5

<210> SEQ ID NO 204
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION

<400> SEQUENCE: 204

Met Gly Thr Pro Ser Arg
1               5

<210> SEQ ID NO 205
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION

<400> SEQUENCE: 205
```

```
Val Gly Thr Pro Ser Arg
1               5

<210> SEQ ID NO 206
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION

<400> SEQUENCE: 206

Leu Gly Ser Pro Ser Arg
1               5

<210> SEQ ID NO 207
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION

<400> SEQUENCE: 207

Leu Gly Ala Pro Ser Arg
1               5

<210> SEQ ID NO 208
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION

<400> SEQUENCE: 208

Leu Gly Val Pro Ser Arg
1               5

<210> SEQ ID NO 209
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION

<400> SEQUENCE: 209

Leu Gly Gly Pro Ser Arg
1               5

<210> SEQ ID NO 210
<211> LENGTH: 6
<212> TYPE: PRT
<213> ORGANISM: Artificial sequence
<220> FEATURE:
<223> OTHER INFORMATION: Synthetic polypeptide
<220> FEATURE:
```

```
<221> NAME/KEY: MOD_RES
<222> LOCATION: (2)..(2)
<223> OTHER INFORMATION: FORMYLATION

<400> SEQUENCE: 210

Ile Gly Thr Pro Ala Arg
1               5

<210> SEQ ID NO 211
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION

<400> SEQUENCE: 211

Leu Gly Thr Pro Ser Lys
1               5

<210> SEQ ID NO 212
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION

<400> SEQUENCE: 212

Met Gly Thr Pro Ser Lys
1               5

<210> SEQ ID NO 213
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION

<400> SEQUENCE: 213

Val Gly Thr Pro Ser Lys
1               5

<210> SEQ ID NO 214
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION

<400> SEQUENCE: 214

Leu Gly Ser Pro Ser Lys
1               5

<210> SEQ ID NO 215
```

```
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION

<400> SEQUENCE: 215

Leu Gly Ala Pro Ser Lys
 1               5

<210> SEQ ID NO 216
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION

<400> SEQUENCE: 216

Leu Gly Val Pro Ser Lys
 1               5

<210> SEQ ID NO 217
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION

<400> SEQUENCE: 217

Leu Gly Gly Pro Ser Lys
 1               5

<210> SEQ ID NO 218
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION

<400> SEQUENCE: 218

Leu Gly Thr Pro Ser Ala
 1               5

<210> SEQ ID NO 219
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION

<400> SEQUENCE: 219
```

```
Ile Gly Thr Pro Ala Ala
1               5

<210> SEQ ID NO 220
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION

<400> SEQUENCE: 220

Met Gly Thr Pro Ser Ala
1               5

<210> SEQ ID NO 221
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION

<400> SEQUENCE: 221

Val Gly Thr Pro Ser Ala
1               5

<210> SEQ ID NO 222
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION

<400> SEQUENCE: 222

Leu Gly Ser Pro Ser Ala
1               5

<210> SEQ ID NO 223
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION

<400> SEQUENCE: 223

Leu Gly Ala Pro Ser Ala
1               5

<210> SEQ ID NO 224
<211> LENGTH: 6
<212> TYPE: PRT
<213> ORGANISM: Artificial sequence
<220> FEATURE:
<223> OTHER INFORMATION: Synthetic polypeptide
```

```
<220> FEATURE:
<221> NAME/KEY: MOD_RES
<222> LOCATION: (2)..(2)
<223> OTHER INFORMATION: FORMYLATION

<400> SEQUENCE: 224

Leu Gly Val Pro Ser Ala
 1               5

<210> SEQ ID NO 225
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION

<400> SEQUENCE: 225

Leu Gly Gly Pro Ser Ala
 1               5

<210> SEQ ID NO 226
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION, covalently bound to a moiety

<400> SEQUENCE: 226

Leu Gly Thr Pro Ser Arg
 1               5

<210> SEQ ID NO 227
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION, covalently bound to a moiety

<400> SEQUENCE: 227

Met Gly Thr Pro Ser Arg
 1               5

<210> SEQ ID NO 228
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION, covalently bound to a moiety

<400> SEQUENCE: 228

Val Gly Thr Pro Ser Arg
 1               5
```

```
<210> SEQ ID NO 229
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION, covalently bound to a moiety

<400> SEQUENCE: 229

Leu Gly Ser Pro Ser Arg
1               5

<210> SEQ ID NO 230
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION, covalently bound to a moiety

<400> SEQUENCE: 230

Leu Gly Ala Pro Ser Arg
1               5

<210> SEQ ID NO 231
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION, covalently bound to a moiety

<400> SEQUENCE: 231

Leu Gly Val Pro Ser Arg
1               5

<210> SEQ ID NO 232
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION, covalently bound to a moiety

<400> SEQUENCE: 232

Leu Gly Gly Pro Ser Arg
1               5

<210> SEQ ID NO 233
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION, covalently bound to a moiety
```

```
<400> SEQUENCE: 233

Ile Gly Thr Pro Ala Arg
1               5

<210> SEQ ID NO 234
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION, covalently bound to a moiety

<400> SEQUENCE: 234

Leu Gly Thr Pro Ser Lys
1               5

<210> SEQ ID NO 235
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION, covalently bound to a moiety

<400> SEQUENCE: 235

Met Gly Thr Pro Ser Lys
1               5

<210> SEQ ID NO 236
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION, covalently bound to a moiety

<400> SEQUENCE: 236

Val Gly Thr Pro Ser Lys
1               5

<210> SEQ ID NO 237
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION, covalently bound to a moiety

<400> SEQUENCE: 237

Leu Gly Ser Pro Ser Lys
1               5

<210> SEQ ID NO 238
<211> LENGTH: 6
<212> TYPE: PRT
<213> ORGANISM: Artificial sequence
<220> FEATURE:
```

```
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION, covalently bound to a moiety

<400> SEQUENCE: 238

Leu Gly Ala Pro Ser Lys
1               5

<210> SEQ ID NO 239
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION, covalently bound to a moiety

<400> SEQUENCE: 239

Leu Gly Val Pro Ser Lys
1               5

<210> SEQ ID NO 240
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION, covalently bound to a moiety

<400> SEQUENCE: 240

Leu Gly Gly Pro Ser Lys
1               5

<210> SEQ ID NO 241
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION, covalently bound to a moiety

<400> SEQUENCE: 241

Leu Gly Thr Pro Ser Ala
1               5

<210> SEQ ID NO 242
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION, covalently bound to a moiety

<400> SEQUENCE: 242

Ile Gly Thr Pro Ala Ala
1               5
```

```
<210> SEQ ID NO 243
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION, covalently bound to a moiety

<400> SEQUENCE: 243

Met Gly Thr Pro Ser Ala
1               5

<210> SEQ ID NO 244
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION, covalently bound to a moiety

<400> SEQUENCE: 244

Val Gly Thr Pro Ser Ala
1               5

<210> SEQ ID NO 245
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION, covalently bound to a moiety

<400> SEQUENCE: 245

Leu Gly Ser Pro Ser Ala
1               5

<210> SEQ ID NO 246
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION, covalently bound to a moiety

<400> SEQUENCE: 246

Leu Gly Ala Pro Ser Ala
1               5

<210> SEQ ID NO 247
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION, covalently bound to a moiety
```

<400> SEQUENCE: 247

Leu Gly Val Pro Ser Ala
1               5

<210> SEQ ID NO 248
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (2)..(2)
<223> OTHER INFORMATION: FORMYLATION, covalently bound to a moiety

<400> SEQUENCE: 248

Leu Gly Gly Pro Ser Ala
1               5

<210> SEQ ID NO 249
<211> LENGTH: 8
<212> TYPE: PRT
<213> ORGANISM: Artificial sequence
<220> FEATURE:
<223> OTHER INFORMATION: Synthetic polypeptide

<400> SEQUENCE: 249

Asp Tyr Lys Asp Asp Asp Asp Lys
1               5

<210> SEQ ID NO 250
<211> LENGTH: 26
<212> TYPE: DNA
<213> ORGANISM: Artificial sequence
<220> FEATURE:
<223> OTHER INFORMATION: synthetic oligonucleotide

<400> SEQUENCE: 250
tcaaacgtga gtagaattta aacttt                                          26

<210> SEQ ID NO 251
<211> LENGTH: 25
<212> TYPE: DNA
<213> ORGANISM: Artificial sequence
<220> FEATURE:
<223> OTHER INFORMATION: synthetic oligonucleotide

<400> SEQUENCE: 251
aaagggcgaa aaaccgtcta tcagg                                           25

<210> SEQ ID NO 252
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 252
ctgtgtaccc cttccagggt ggctgcacca tctgtcttca tct                       43

<210> SEQ ID NO 253
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 253
ctgtgtaccc cttccagggc tgcaccatct gtcttcatct tcc                     43

<210> SEQ ID NO 254
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 254
ctgtgtaccc cttccagggc accatctgtc ttcatcttcc cgc                     43

<210> SEQ ID NO 255
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 255
ctgtgtaccc cttccaggcc atctgtcttc atcttcccgc cat                     43

<210> SEQ ID NO 256
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 256
ctgtgtaccc cttccaggtc tgtcttcatc ttcccgccat ctg                     43

<210> SEQ ID NO 257
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 257
ctgtgtaccc cttccagggt cttcatcttc ccgccatctg atg                     43

<210> SEQ ID NO 258
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 258
ctgtgtaccc cttccaggtt catcttcccg ccatctgatg agc                     43

<210> SEQ ID NO 259
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 259
ctgtgtaccc cttccaggat cttcccgcca tctgatgagc agt                     43

<210> SEQ ID NO 260

```
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 260
ctgtgtaccc cttccaggtt cccgccatct gatgagcagt tga          43

<210> SEQ ID NO 261
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 261
ctgtgtaccc cttccaggcc gccatctgat gagcagttga aat          43

<210> SEQ ID NO 262
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 262
ctgtgtaccc cttccaggcc atctgatgag cagttgaaat ctg          43

<210> SEQ ID NO 263
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 263
ctgtgtaccc cttccaggtc tgatgagcag ttgaaatctg gaa          43

<210> SEQ ID NO 264
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 264
ctgtgtaccc cttccaggga tgagcagttg aaatctggaa ctg          43

<210> SEQ ID NO 265
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 265
ctgtgtaccc cttccaggga gcagttgaaa tctggaactg cct          43

<210> SEQ ID NO 266
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 266
```

```
ctgtgtaccc cttccaggca gttgaaatct ggaactgcct ctg            43
```

<210> SEQ ID NO 267
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 267

```
ctgtgtaccc cttccaggtt gaaatctgga actgcctctg ttg            43
```

<210> SEQ ID NO 268
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 268

```
ctgtgtaccc cttccaggaa atctggaact gcctctgttg tgt            43
```

<210> SEQ ID NO 269
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 269

```
ctgtgtaccc cttccaggtc tggaactgcc tctgttgtgt gcc            43
```

<210> SEQ ID NO 270
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 270

```
ctgtgtaccc cttccagggg aactgcctct gttgtgtgcc tgc            43
```

<210> SEQ ID NO 271
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 271

```
ctgtgtaccc cttccaggac tgcctctgtt gtgtgcctgc tga            43
```

<210> SEQ ID NO 272
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 272

```
ctgtgtaccc cttccagggc tctgttgtgt gcctgctga ata             43
```

<210> SEQ ID NO 273
<211> LENGTH: 43
<212> TYPE: DNA

```
<213> ORGANISM: Artificial sequence
<220> FEATURE:
<223> OTHER INFORMATION: synthetic oligonucleotide

<400> SEQUENCE: 273
ctgtgtaccc cttccaggtc tgttgtgtgc ctgctgaata act           43

<210> SEQ ID NO 274
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 274
ctgtgtaccc cttccagggt tgtgtgcctg ctgaataact tct           43

<210> SEQ ID NO 275
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 275
ctgtgtaccc cttccagggt gtgcctgctg aataacttct atc           43

<210> SEQ ID NO 276
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 276
cctggaaggg gtacacagag ttcctgagga agaagcaaa cag            43

<210> SEQ ID NO 277
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 277
cctggaaggg gtacacagca cagttcctga ggaaagaagc aaa           43

<210> SEQ ID NO 278
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 278
cctggaaggg gtacacagag ccacagttcc tgaggaaaga agc           43

<210> SEQ ID NO 279
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 279
cctggaaggg gtacacagtg cagccacagt tcctgaggaa aga           43
```

<210> SEQ ID NO 280
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 280
cctggaaggg gtacacagtg gtgcagccac agttcctgag gaa                43

<210> SEQ ID NO 281
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 281
cctggaaggg gtacacagag atggtgcagc cacagttcct gag                43

<210> SEQ ID NO 282
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 282
cctggaaggg gtacacagga cagatggtgc agccacagtt cct                43

<210> SEQ ID NO 283
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 283
cctggaaggg gtacacagga agacagatgg tgcagccaca gtt                43

<210> SEQ ID NO 284
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 284
cctggaaggg gtacacagga tgaagacaga tggtgcagcc aca                43

<210> SEQ ID NO 285
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 285
cctggaaggg gtacacagga agatgaagac agatggtgca gcc                43

<210> SEQ ID NO 286
<211> LENGTH: 43
<212> TYPE: DNA
<213> ORGANISM: Artificial sequence
<220> FEATURE:

<223> OTHER INFORMATION: synthetic oligonucleotide

<400> SEQUENCE: 286
cctggaaggg gtacacagcg ggaagatgaa gacagatggt gca        43

<210> SEQ ID NO 287
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 287
cctggaaggg gtacacagtg gcgggaagat gaagacagat ggt        43

<210> SEQ ID NO 288
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 288
cctggaaggg gtacacagag atggcgggaa gatgaagaca gat        43

<210> SEQ ID NO 289
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 289
cctggaaggg gtacacagat cagatggcgg gaagatgaag aca        43

<210> SEQ ID NO 290
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 290
cctggaaggg gtacacagct catcagatgg cgggaagatg aag        43

<210> SEQ ID NO 291
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 291
cctggaaggg gtacacagct gctcatcaga tggcgggaag atg        43

<210> SEQ ID NO 292
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 292
cctggaaggg gtacacagca actgctcatc agatggcggg aag        43

<210> SEQ ID NO 293
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 293
cctggaaggg gtacacagtt tcaactgctc atcagatggc ggg        43

<210> SEQ ID NO 294
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 294
cctggaaggg gtacacagag atttcaactg ctcatcagat ggc        43

<210> SEQ ID NO 295
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 295
cctggaaggg gtacacagtc cagatttcaa ctgctcatca gat        43

<210> SEQ ID NO 296
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 296
cctggaaggg gtacacagag ttccagattt caactgctca tca        43

<210> SEQ ID NO 297
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 297
cctggaaggg gtacacaggg cagttccaga tttcaactgc tca        43

<210> SEQ ID NO 298
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 298
cctggaaggg gtacacagag aggcagttcc agatttcaac tgc        43

<210> SEQ ID NO 299
<211> LENGTH: 43
<212> TYPE: DNA
<213> ORGANISM: Artificial sequence
<220> FEATURE:
<223> OTHER INFORMATION: synthetic oligonucleotide

```
<400> SEQUENCE: 299
cctggaaggg gtacacagaa cagaggcagt tccagatttc aac         43

<210> SEQ ID NO 300
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 300
ctgtgtaccc cttccaggtg cctgctgaat aacttctatc cca         43

<210> SEQ ID NO 301
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 301
ctgtgtaccc cttccaggct gctgaataac ttctatccca gag         43

<210> SEQ ID NO 302
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 302
ctgtgtaccc cttccaggct gaataacttc tatcccagag agg         43

<210> SEQ ID NO 303
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 303
ctgtgtaccc cttccaggaa taacttctat cccagagagg cca         43

<210> SEQ ID NO 304
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 304
ctgtgtaccc cttccaggtt ctatcccaga gaggccaaag tac         43

<210> SEQ ID NO 305
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 305
ctgtgtaccc cttccaggtt ctatcccaga gaggccaaag tac         43

<210> SEQ ID NO 306
<211> LENGTH: 43
```

```
<212> TYPE: DNA
<213> ORGANISM: Artificial sequence
<220> FEATURE:
<223> OTHER INFORMATION: synthetic oligonucleotide

<400> SEQUENCE: 306
ctgtgtaccc cttccaggta tcccagagag gccaaagtac agt              43

<210> SEQ ID NO 307
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 307
ctgtgtaccc cttccaggcc cagagaggcc aaagtacagt gga              43

<210> SEQ ID NO 308
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 308
ctgtgtaccc cttccaggag agaggccaaa gtacagtgga agg              43

<210> SEQ ID NO 309
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 309
ctgtgtaccc cttccaggga ggccaaagta cagtggaagg tgg              43

<210> SEQ ID NO 310
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 310
ctgtgtaccc cttccagggc caaagtacag tggaaggtgg ata              43

<210> SEQ ID NO 311
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 311
ctgtgtaccc cttccaggaa agtacagtgg aaggtggata acg              43

<210> SEQ ID NO 312
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 312
```
ctgtgtaccc cttccagggt acagtggaag gtggataacg ccc                    43

<210> SEQ ID NO 313
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 313
ctgtgtaccc cttccaggca gtggaaggtg gataacgccc tcc                    43

<210> SEQ ID NO 314
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 314
ctgtgtaccc cttccaggtg gaaggtggat aacgccctcc aat                    43

<210> SEQ ID NO 315
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 315
ctgtgtaccc cttccaggaa ggtggataac gccctccaat cgg                    43

<210> SEQ ID NO 316
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 316
ctgtgtaccc cttccagggt ggataacgcc ctccaatcgg gta                    43

<210> SEQ ID NO 317
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 317
ctgtgtaccc cttccaggga taacgccctc caatcgggta act                    43

<210> SEQ ID NO 318
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 318
ctgtgtaccc cttccaggaa cgccctccaa tcgggtaact ccc                    43

<210> SEQ ID NO 319
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 319
ctgtgtaccc cttccagggc cctccaatcg ggtaactccc agg     43

<210> SEQ ID NO 320
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 320
ctgtgtaccc cttccaggct ccaatcgggt aactcccagg aga     43

<210> SEQ ID NO 321
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 321
ctgtgtaccc cttccaggca atcgggtaac tcccaggaga gtg     43

<210> SEQ ID NO 322
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 322
ctgtgtaccc cttccaggtc gggtaactcc caggagagtg tca     43

<210> SEQ ID NO 323
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 323
ctgtgtaccc cttccagggg taactcccag gagagtgtca cag     43

<210> SEQ ID NO 324
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 324
ctgtgtaccc cttccaggaa ctcccaggag agtgtcacag agc     43

<210> SEQ ID NO 325
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 325
cctggaaggg gtacacagca caacagaggc agttccagat ttc     43

<210> SEQ ID NO 326
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 326
cctggaaggg gtacacaggc acacaacaga ggcagttcca gat         43

<210> SEQ ID NO 327
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 327
cctggaaggg gtacacagca ggcacacaac agaggcagtt cca         43

<210> SEQ ID NO 328
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 328
cctggaaggg gtacacagca gcaggcacac aacagaggca gtt         43

<210> SEQ ID NO 329
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 329
cctggaaggg gtacacagat tcagcaggca cacaacagag gca         43

<210> SEQ ID NO 330
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 330
cctggaaggg gtacacaggt tattcagcag gcacacaaca gag         43

<210> SEQ ID NO 331
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 331
cctggaaggg gtacacagga agttattcag caggcacaca aca         43

<210> SEQ ID NO 332
<211> LENGTH: 43
<212> TYPE: DNA
<213> ORGANISM: Artificial sequence
<220> FEATURE:
<223> OTHER INFORMATION: synthetic oligonucleotide

```
<400> SEQUENCE: 332
cctggaaggg gtacacagat agaagttatt cagcaggcac aca         43

<210> SEQ ID NO 333
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 333
cctggaaggg gtacacaggg gatagaagtt attcagcagg cac         43

<210> SEQ ID NO 334
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 334
cctggaaggg gtacacagtc tgggatagaa gttattcagc agg         43

<210> SEQ ID NO 335
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 335
cctggaaggg gtacacagct ctctgggata gaagttattc agc         43

<210> SEQ ID NO 336
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 336
cctggaaggg gtacacaggg cctctctggg atagaagtta ttc         43

<210> SEQ ID NO 337
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 337
cctggaaggg gtacacagtt tggcctctct gggatagaag tta         43

<210> SEQ ID NO 338
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 338
cctggaaggg gtacacagta ctttggcctc tctgggatag aag         43

<210> SEQ ID NO 339
```

```
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 339
cctggaaggg gtacacagct gtactttggc ctctctggga tag              43

<210> SEQ ID NO 340
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 340
cctggaaggg gtacacagcc actgtacttt ggcctctctg gga              43

<210> SEQ ID NO 341
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 341
cctggaaggg gtacacagct tccactgtac tttggcctct ctg              43

<210> SEQ ID NO 342
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 342
cctggaaggg gtacacagca ccttccactg tactttggcc tct              43

<210> SEQ ID NO 343
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 343
cctggaaggg gtacacagat ccaccttcca ctgtactttg gcc              43

<210> SEQ ID NO 344
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 344
cctggaaggg gtacacaggt tatccacctt ccactgtact ttg              43

<210> SEQ ID NO 345
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 345
```
cctggaaggg gtacacaggg cgttatccac cttccactgt act         43

<210> SEQ ID NO 346
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 346
cctggaaggg gtacacagga gggcgttatc caccttccac tgt         43

<210> SEQ ID NO 347
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 347
cctggaaggg gtacacagtt ggagggcgtt atccaccttc cac         43

<210> SEQ ID NO 348
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 348
cctggaaggg gtacacagcg attggagggc gttatccacc ttc         43

<210> SEQ ID NO 349
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 349
cctggaaggg gtacacagac ccgattggag ggcgttatcc acc         43

<210> SEQ ID NO 350
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 350
ctgtgtaccc cttccaggtc ccaggagagt gtcacagagc agg         43

<210> SEQ ID NO 351
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 351
ctgtgtaccc cttccaggca ggagagtgtc acagagcagg aca         43

<210> SEQ ID NO 352
<211> LENGTH: 43
<212> TYPE: DNA

<213> ORGANISM: Artificial sequence
<220> FEATURE:
<223> OTHER INFORMATION: synthetic oligonucleotide

<400> SEQUENCE: 352
ctgtgtaccc cttccaggga gagtgtcaca gagcaggaca gca    43

<210> SEQ ID NO 353
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 353
ctgtgtaccc cttccaggag tgtcacagag caggacagca agg    43

<210> SEQ ID NO 354
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 354
ctgtgtaccc cttccagggt cacagagcag acagcaagg aca    43

<210> SEQ ID NO 355
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 355
ctgtgtaccc cttccaggac agagcaggac agcaaggaca gca    43

<210> SEQ ID NO 356
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 356
ctgtgtaccc cttccaggga gcaggacagc aaggacagca cct    43

<210> SEQ ID NO 357
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 357
ctgtgtaccc cttccaggca ggacagcaag gacagcacct aca    43

<210> SEQ ID NO 358
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 358
ctgtgtaccc cttccaggga cagcaaggac agcacctaca gcc    43

<210> SEQ ID NO 359
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 359
ctgtgtaccc cttccaggag caaggacagc acctacagcc tca       43

<210> SEQ ID NO 360
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 360
ctgtgtaccc cttccaggaa ggacagcacc tacagcctca gca       43

<210> SEQ ID NO 361
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 361
ctgtgtaccc cttccaggga cagcacctac agcctcagca gca       43

<210> SEQ ID NO 362
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 362
ctgtgtaccc cttccaggag cacctacagc ctcagcagca ccc       43

<210> SEQ ID NO 363
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 363
ctgtgtaccc cttccaggac ctacagcctc agcagcaccc tga       43

<210> SEQ ID NO 364
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 364
ctgtgtaccc cttccaggta cagcctcagc agcaccctga cgc       43

<210> SEQ ID NO 365
<211> LENGTH: 43
<212> TYPE: DNA
<213> ORGANISM: Artificial sequence
<220> FEATURE:

<223> OTHER INFORMATION: synthetic oligonucleotide

<400> SEQUENCE: 365
ctgtgtaccc cttccaggag cctcagcagc accctgacgc tga                43

<210> SEQ ID NO 366
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 366
ctgtgtaccc cttccaggct cagcagcacc ctgacgctga gca                43

<210> SEQ ID NO 367
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 367
ctgtgtaccc cttccaggag cagcaccctg acgctgagca aag                43

<210> SEQ ID NO 368
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 368
ctgtgtaccc cttccaggag caccctgacg ctgagcaaag cag                43

<210> SEQ ID NO 369
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 369
ctgtgtaccc cttccaggac cctgacgctg agcaaagcag act                43

<210> SEQ ID NO 370
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 370
ctgtgtaccc cttccaggct gacgctgagc aaagcagact acg                43

<210> SEQ ID NO 371
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 371
ctgtgtaccc cttccaggac gctgagcaaa gcagactacg aga                43

```
<210> SEQ ID NO 372
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 372
ctgtgtaccc cttccaggct gagcaaagca gactacgaga aac          43

<210> SEQ ID NO 373
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 373
ctgtgtaccc cttccaggag caaagcagac tacgagaaac aca          43

<210> SEQ ID NO 374
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 374
ctgtgtaccc cttccaggaa agcagactac gagaaacaca aag          43

<210> SEQ ID NO 375
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 375
cctggaaggg gtacacaggt tacccgattg gagggcgtta tcc          43

<210> SEQ ID NO 376
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 376
cctggaaggg gtacacaggg agttacccga ttggagggcg tta          43

<210> SEQ ID NO 377
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 377
cctggaaggg gtacacagct gggagttacc cgattggagg gcg          43

<210> SEQ ID NO 378
<211> LENGTH: 43
<212> TYPE: DNA
<213> ORGANISM: Artificial sequence
<220> FEATURE:
<223> OTHER INFORMATION: synthetic oligonucleotide
```

<400> SEQUENCE: 378
cctggaaggg gtacacagct cctgggagtt acccgattgg agg					43

<210> SEQ ID NO 379
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 379
cctggaaggg gtacacagac tctcctggga gttacccgat tgg					43

<210> SEQ ID NO 380
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 380
cctggaaggg gtacacagga cactctcctg ggagttaccc gat					43

<210> SEQ ID NO 381
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 381
cctggaaggg gtacacagtg tgacactctc ctgggagtta ccc					43

<210> SEQ ID NO 382
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 382
cctggaaggg gtacacagct ctgtgacact ctcctgggag tta					43

<210> SEQ ID NO 383
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 383
cctggaaggg gtacacagct gctctgtgac actctcctgg gag					43

<210> SEQ ID NO 384
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 384
cctggaaggg gtacacaggt cctgctctgt gacactctcc tgg					43

<210> SEQ ID NO 385
<211> LENGTH: 43

```
<212> TYPE: DNA
<213> ORGANISM: Artificial sequence
<220> FEATURE:
<223> OTHER INFORMATION: synthetic oligonucleotide

<400> SEQUENCE: 385
cctggaaggg gtacacaggc tgtcctgctc tgtgacactc tcc         43

<210> SEQ ID NO 386
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 386
cctggaaggg gtacacagct tgctgtcctg ctctgtgaca ctc         43

<210> SEQ ID NO 387
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 387
cctggaaggg gtacacaggt ccttgctgtc ctgctctgtg aca         43

<210> SEQ ID NO 388
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 388
cctggaaggg gtacacaggc tgtccttgct gtcctgctct gtg         43

<210> SEQ ID NO 389
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 389
cctggaaggg gtacacaggg tgctgtcctt gctgtcctgc tct         43

<210> SEQ ID NO 390
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 390
cctggaaggg gtacacaggt aggtgctgtc cttgctgtcc tgc         43

<210> SEQ ID NO 391
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 391
```
cctggaaggg gtacacaggc tgtaggtgct gtccttgctg tcc            43

<210> SEQ ID NO 392
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 392
cctggaaggg gtacacagga ggctgtaggt gctgtccttg ctg            43

<210> SEQ ID NO 393
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 393
cctggaaggg gtacacaggc tgaggctgta ggtgctgtcc ttg            43

<210> SEQ ID NO 394
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 394
cctggaaggg gtacacaggc tgctgaggct gtaggtgctg tcc            43

<210> SEQ ID NO 395
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 395
cctggaaggg gtacacaggg tgctgctgag gctgtaggtg ctg            43

<210> SEQ ID NO 396
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 396
cctggaaggg gtacacagca gggtgctgct gaggctgtag gtg            43

<210> SEQ ID NO 397
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 397
cctggaaggg gtacacagcg tcagggtgct gctgaggctg tag            43

<210> SEQ ID NO 398
<211> LENGTH: 43
<212> TYPE: DNA
<213> ORGANISM: Artificial sequence -continued
<220> FEATURE:
<223> OTHER INFORMATION: synthetic oligonucleotide

<400> SEQUENCE: 398
cctggaaggg gtacacagca gcgtcagggt gctgctgagg ctg        43

<210> SEQ ID NO 399
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 399
cctggaaggg gtacacaggc tcagcgtcag ggtgctgctg agg        43

<210> SEQ ID NO 400
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 400
ctgtgtaccc cttccagggc agactacgag aaacacaaag tct        43

<210> SEQ ID NO 401
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 401
ctgtgtaccc cttccaggga ctacgagaaa cacaaagtct acg        43

<210> SEQ ID NO 402
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 402
ctgtgtaccc cttccaggta cgagaaacac aaagtctacg cct        43

<210> SEQ ID NO 403
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 403
ctgtgtaccc cttccaggga gaaacacaaa gtctacgcct gcg        43

<210> SEQ ID NO 404
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 404
ctgtgtaccc cttccaggaa acacaaagtc tacgcctgcg aag        43

<210> SEQ ID NO 405
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 405
ctgtgtaccc cttccaggca caaagtctac gcctgcgaag tca         43

<210> SEQ ID NO 406
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 406
ctgtgtaccc cttccaggaa agtctacgcc tgcgaagtca ccc         43

<210> SEQ ID NO 407
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 407
ctgtgtaccc cttccagggt ctacgcctgc gaagtcaccc atc         43

<210> SEQ ID NO 408
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 408
ctgtgtaccc cttccaggta cgcctgcgaa gtcacccatc agg         43

<210> SEQ ID NO 409
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 409
ctgtgtaccc cttccagggc ctgcgaagtc acccatcagg gcc         43

<210> SEQ ID NO 410
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 410
ctgtgtaccc cttccaggtg cgaagtcacc catcagggcc tga         43

<210> SEQ ID NO 411
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 411
ctgtgtaccc cttccaggga agtcacccat cagggcctga gct            43

<210> SEQ ID NO 412
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 412
ctgtgtaccc cttccagggt cacccatcag ggcctgagct cgc            43

<210> SEQ ID NO 413
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 413
ctgtgtaccc cttccaggac ccatcagggc ctgagctcgc ccg            43

<210> SEQ ID NO 414
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 414
ctgtgtaccc cttccaggca tcagggcctg agctcgcccg tca            43

<210> SEQ ID NO 415
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 415
ctgtgtaccc cttccaggca gggcctgagc tcgcccgtca caa            43

<210> SEQ ID NO 416
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 416
ctgtgtaccc cttccagggg cctgagctcg cccgtcacaa aga            43

<210> SEQ ID NO 417
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 417
ctgtgtaccc cttccaggct gagctcgccc gtcacaaaga gct            43

<210> SEQ ID NO 418

```
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 418
ctgtgtaccc cttccaggag ctcgcccgtc acaaagagct tca                43

<210> SEQ ID NO 419
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 419
ctgtgtaccc cttccaggtc gcccgtcaca aagagcttca aca                43

<210> SEQ ID NO 420
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 420
ctgtgtaccc cttccaggcc cgtcacaaag agcttcaaca ggg                43

<210> SEQ ID NO 421
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 421
ctgtgtaccc cttccagggt cacaaagagc ttcaacaggg gag                43

<210> SEQ ID NO 422
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 422
ctgtgtaccc cttccaggac aaagagcttc aacagggggag agt                43

<210> SEQ ID NO 423
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 423
ctgtgtaccc cttccaggaa gagcttcaac aggggagagt gtt                43

<210> SEQ ID NO 424
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 424
```
ctgtgtaccc cttccaggag cttcaacagg ggagagtgtt agc                             43

<210> SEQ ID NO 425
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 425
cctggaaggg gtacacagtt tgctcagcgt cagggtgctg ctg                             43

<210> SEQ ID NO 426
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 426
cctggaaggg gtacacagtg ctttgctcag cgtcaggtg ctg                              43

<210> SEQ ID NO 427
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 427
cctggaaggg gtacacaggt ctgctttgct cagcgtcagg gtg                             43

<210> SEQ ID NO 428
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 428
cctggaaggg gtacacaggt agtctgcttt gctcagcgtc agg                             43

<210> SEQ ID NO 429
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 429
cctggaaggg gtacacagct cgtagtctgc tttgctcagc gtc                             43

<210> SEQ ID NO 430
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 430
cctggaaggg gtacacagtt tctcgtagtc tgctttgctc agc                             43

<210> SEQ ID NO 431
<211> LENGTH: 43
<212> TYPE: DNA

```
<213> ORGANISM: Artificial sequence
<220> FEATURE:
<223> OTHER INFORMATION: synthetic oligonucleotide

<400> SEQUENCE: 431
cctggaaggg gtacacaggt gtttctcgta gtctgctttg ctc                      43

<210> SEQ ID NO 432
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 432
cctggaaggg gtacacagtt tgtgtttctc gtagtctgct ttg                      43

<210> SEQ ID NO 433
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 433
cctggaaggg gtacacagga ctttgtgttt ctcgtagtct gct                      43

<210> SEQ ID NO 434
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 434
cctggaaggg gtacacaggt agactttgtg tttctcgtag tct                      43

<210> SEQ ID NO 435
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 435
cctggaaggg gtacacaggg cgtagacttt gtgtttctcg tag                      43

<210> SEQ ID NO 436
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 436
cctggaaggg gtacacaggc aggcgtagac tttgtgtttc tcg                      43

<210> SEQ ID NO 437
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 437
cctggaaggg gtacacagtt cgcaggcgta gactttgtgt ttc                      43
```

<210> SEQ ID NO 438
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 438
cctggaaggg gtacacagga cttcgcaggc gtagactttg tgt       43

<210> SEQ ID NO 439
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 439
cctggaaggg gtacacaggg tgacttcgca ggcgtagact ttg       43

<210> SEQ ID NO 440
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 440
cctggaaggg gtacacagat gggtgacttc gcaggcgtag act       43

<210> SEQ ID NO 441
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 441
cctggaaggg gtacacagct gatgggtgac ttcgcaggcg tag       43

<210> SEQ ID NO 442
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 442
cctggaaggg gtacacaggc cctgatgggt gacttcgcag gcg       43

<210> SEQ ID NO 443
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 443
cctggaaggg gtacacagca ggccctgatg ggtgacttcg cag       43

<210> SEQ ID NO 444
<211> LENGTH: 43
<212> TYPE: DNA
<213> ORGANISM: Artificial sequence
<220> FEATURE:

<223> OTHER INFORMATION: synthetic oligonucleotide

<400> SEQUENCE: 444
cctggaaggg gtacacaggc tcaggccctg atgggtgact tcg                              43

<210> SEQ ID NO 445
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 445
cctggaaggg gtacacagcg agctcaggcc ctgatgggtg act                              43

<210> SEQ ID NO 446
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 446
cctggaaggg gtacacaggg gcgagctcag gccctgatgg gtg                              43

<210> SEQ ID NO 447
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 447
cctggaaggg gtacacagga cgggcgagct caggccctga tgg                              43

<210> SEQ ID NO 448
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 448
cctggaaggg gtacacagtg tgacgggcga gctcaggccc tga                              43

<210> SEQ ID NO 449
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 449
cctggaaggg gtacacagct ttgtgacggg cgagctcagg ccc                              43

<210> SEQ ID NO 450
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 450
ctgtgtaccc cttccaggtt caacaggga gagtgttagc ctg                               43

```
<210> SEQ ID NO 451
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 451
ctgtgtaccc cttccaggaa caggggagag tgttagcctg cag             43

<210> SEQ ID NO 452
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 452
ctgtgtaccc cttccaggag gggagagtgt tagcctgcag gca             43

<210> SEQ ID NO 453
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 453
ctgtgtaccc cttccagggg agagtgttag cctgcaggca tga             43

<210> SEQ ID NO 454
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 454
ctgtgtaccc cttccaggga gtgttagcct gcaggcatga tca             43

<210> SEQ ID NO 455
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 455
ctgtgtaccc cttccaggtg ttagcctgca ggcatgatca taa             43

<210> SEQ ID NO 456
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 456
ctgtgtaccc cttccaggta gcctgcaggc atgatcataa tca             43

<210> SEQ ID NO 457
<211> LENGTH: 43
<212> TYPE: DNA
<213> ORGANISM: Artificial sequence
<220> FEATURE:
<223> OTHER INFORMATION: synthetic oligonucleotide
```

<400> SEQUENCE: 457
cctggaaggg gtacacaggc tctttgtgac gggcgagctc agg          43

<210> SEQ ID NO 458
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 458
cctggaaggg gtacacagga agctctttgt gacgggcgag ctc          43

<210> SEQ ID NO 459
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 459
cctggaaggg gtacacaggt tgaagctctt tgtgacgggc gag          43

<210> SEQ ID NO 460
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 460
cctggaaggg gtacacagcc tgttgaagct ctttgtgacg ggc          43

<210> SEQ ID NO 461
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 461
cctggaaggg gtacacagtc ccctgttgaa gctctttgtg acg          43

<210> SEQ ID NO 462
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 462
cctggaaggg gtacacagct ctcccctgtt gaagctcttt gtg          43

<210> SEQ ID NO 463
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 463
cctggaaggg gtacacagac actctcccct gttgaagctc ttt          43

<210> SEQ ID NO 464
<211> LENGTH: 5

```
<212> TYPE: PRT
<213> ORGANISM: Artificial sequence
<220> FEATURE:
<223> OTHER INFORMATION: synthetic polypeptide

<400> SEQUENCE: 464

Thr Val Ala Ala Pro
1               5

<210> SEQ ID NO 465
<211> LENGTH: 5
<212> TYPE: PRT
<213> ORGANISM: Artificial sequence
<220> FEATURE:
<223> OTHER INFORMATION: synthetic polypeptide

<400> SEQUENCE: 465

Tyr Pro Arg Glu Ala
1               5

<210> SEQ ID NO 466
<211> LENGTH: 4
<212> TYPE: PRT
<213> ORGANISM: Artificial sequence
<220> FEATURE:
<223> OTHER INFORMATION: synthetic polypeptide

<400> SEQUENCE: 466

Pro Arg Glu Ala
1

<210> SEQ ID NO 467
<211> LENGTH: 8
<212> TYPE: PRT
<213> ORGANISM: Artificial sequence
<220> FEATURE:
<223> OTHER INFORMATION: synthetic polypeptide

<400> SEQUENCE: 467

Asp Asn Ala Leu Gln Ser Gly Asn
1               5

<210> SEQ ID NO 468
<211> LENGTH: 9
<212> TYPE: PRT
<213> ORGANISM: Artificial sequence
<220> FEATURE:
<223> OTHER INFORMATION: synthetic polypeptide

<400> SEQUENCE: 468

Thr Glu Gln Asp Ser Lys Asp Ser Thr
1               5

<210> SEQ ID NO 469
<211> LENGTH: 6
<212> TYPE: PRT
<213> ORGANISM: Artificial sequence
<220> FEATURE:
<223> OTHER INFORMATION: synthetic polypeptide

<400> SEQUENCE: 469

His Gln Gly Leu Ser Ser
1               5

<210> SEQ ID NO 470
<211> LENGTH: 4
<212> TYPE: PRT
```

```
<213> ORGANISM: Artificial sequence
<220> FEATURE:
<223> OTHER INFORMATION: synthetic polypeptide

<400> SEQUENCE: 470

Arg Gly Glu Cys
1

<210> SEQ ID NO 471
<211> LENGTH: 6
<212> TYPE: PRT
<213> ORGANISM: Artificial sequence
<220> FEATURE:
<223> OTHER INFORMATION: synthetic polypeptide

<400> SEQUENCE: 471

Thr Val Ala Ala Pro Ser
1               5

<210> SEQ ID NO 472
<211> LENGTH: 4
<212> TYPE: PRT
<213> ORGANISM: Artificial sequence
<220> FEATURE:
<223> OTHER INFORMATION: synthetic polypeptide

<400> SEQUENCE: 472

Ser Gly Thr Ala
1

<210> SEQ ID NO 473
<211> LENGTH: 8
<212> TYPE: PRT
<213> ORGANISM: Artificial sequence
<220> FEATURE:
<223> OTHER INFORMATION: synthetic polypeptide

<400> SEQUENCE: 473

Asn Asn Phe Tyr Pro Arg Glu Ala
1               5

<210> SEQ ID NO 474
<211> LENGTH: 11
<212> TYPE: PRT
<213> ORGANISM: Artificial sequence
<220> FEATURE:
<223> OTHER INFORMATION: synthetic polypeptide

<400> SEQUENCE: 474

Val Asp Asn Ala Leu Gln Ser Gly Asn Ser Gln
1               5                   10

<210> SEQ ID NO 475
<211> LENGTH: 11
<212> TYPE: PRT
<213> ORGANISM: Artificial sequence
<220> FEATURE:
<223> OTHER INFORMATION: synthetic polypeptide

<400> SEQUENCE: 475

Val Thr Glu Gln Asp Ser Lys Asp Ser Thr Tyr
1               5                   10

<210> SEQ ID NO 476
<211> LENGTH: 8
<212> TYPE: PRT
<213> ORGANISM: Artificial sequence
```

<220> FEATURE:
<223> OTHER INFORMATION: synthetic polypeptide

<400> SEQUENCE: 476

Thr His Gln Gly Leu Ser Ser Pro
1               5

<210> SEQ ID NO 477
<211> LENGTH: 5
<212> TYPE: PRT
<213> ORGANISM: Artificial sequence
<220> FEATURE:
<223> OTHER INFORMATION: synthetic polypeptide

<400> SEQUENCE: 477

Asn Arg Gly Glu Cys
1               5

<210> SEQ ID NO 478
<211> LENGTH: 6
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (1)..(1)
<223> OTHER INFORMATION: Xaa at position 1 may be present or absent,
      and when present may be any amino acid
<220> FEATURE:
<221> NAME/KEY: MISC_FEATURE
<222> LOCATION: (2)..(2)
<223> OTHER INFORMATION: Xaa at position 2 is Cys, Ser, 2-
      formylglycine, or 2-formylglycine covalently bound to a moiety
<220> FEATURE:
<221> NAME/KEY: MISC_FEATURE
<222> LOCATION: (3)..(3)
<223> OTHER INFORMATION: Xaa at position 3 is any amino acid
<220> FEATURE:
<221> NAME/KEY: MISC_FEATURE
<222> LOCATION: (4)..(4)
<223> OTHER INFORMATION: Xaa at position 4 is Pro or Ala
<220> FEATURE:
<221> NAME/KEY: MISC_FEATURE
<222> LOCATION: (5)..(5)
<223> OTHER INFORMATION: Xaa at position 5 is any amino acid
<220> FEATURE:
<221> NAME/KEY: MISC_FEATURE
<222> LOCATION: (6)..(6)
<223> OTHER INFORMATION: Xaa at position 7 is an aliphatic amino acid
      or a basic amino acid

<400> SEQUENCE: 478

Xaa Xaa Xaa Xaa Xaa Xaa
1               5

<210> SEQ ID NO 479
<211> LENGTH: 9
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (2)..(2)
<223> OTHER INFORMATION: Xaa at position 2 may be present or absent,
      and when present may be any amino acid
<220> FEATURE:
<221> NAME/KEY: MOD_RES
<222> LOCATION: (3)..(3)
<223> OTHER INFORMATION: FORMYLATION
<220> FEATURE:
<221> NAME/KEY: MISC_FEATURE

```
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa at position 5 is Pro or Ala
<220> FEATURE:
<221> NAME/KEY: MISC_FEATURE
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa at position 7 is an aliphatic or baisc
      amino acid

<400> SEQUENCE: 479

Thr Xaa Gly Xaa Xaa Xaa Xaa Val Ala
1               5

<210> SEQ ID NO 480
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can be any naturally occurring amino acid

<400> SEQUENCE: 480

Thr Val Xaa Gly Xaa Xaa Xaa Xaa Ala Ala
1               5                   10

<210> SEQ ID NO 481
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can be any naturally occurring amino acid

<400> SEQUENCE: 481

Val Ala Xaa Gly Xaa Xaa Xaa Xaa Ala Pro
1               5                   10

<210> SEQ ID NO 482
<211> LENGTH: 11
<212> TYPE: PRT
<213> ORGANISM: Artificial sequence
<220> FEATURE:
<223> OTHER INFORMATION: synthetic sequence
<220> FEATURE:
```

```
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can be any naturally occurring amino acid

<400> SEQUENCE: 482

Ala Ala Xaa Gly Xaa Xaa Xaa Xaa Pro Ser Val
1               5                   10

<210> SEQ ID NO 483
<211> LENGTH: 11
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: Xaa can be any nautrally occuring amino acid
<220> FEATURE:
<221> NAME/KEY: MOD_RES
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can be any naturally occurring amino acid

<400> SEQUENCE: 483

Ala Pro Xaa Gly Xaa Xaa Xaa Xaa Ser Val Phe
1               5                   10

<210> SEQ ID NO 484
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: Xaa can be any nautrally occuring amino acid
<220> FEATURE:
<221> NAME/KEY: MOD_RES
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can be any naturally occurring amino acid

<400> SEQUENCE: 484

Pro Ser Xaa Gly Xaa Xaa Xaa Xaa Val Phe
1               5                   10

<210> SEQ ID NO 485
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: Xaa can be any nautrally occuring amino acid
<220> FEATURE:
```

```
<221> NAME/KEY: MOD_RES
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can be any naturally occurring amino acid

<400> SEQUENCE: 485

Lys Ser Xaa Gly Xaa Xaa Xaa Xaa Gly Thr
1               5                   10

<210> SEQ ID NO 486
<211> LENGTH: 11
<212> TYPE: PRT
<213> ORGANISM: Artificial sequence
<220> FEATURE:
<223> OTHER INFORMATION: synthetic sequence
<220> FEATURE:
<221> NAME/KEY: MOD_RES
<222> LOCATION: (3)..(3)
<223> OTHER INFORMATION: FORMYLATION
<220> FEATURE:
<221> NAME/KEY: MISC_FEATURE
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (6)..(9)
<223> OTHER INFORMATION: Xaa can be any naturally occurring amino acid

<400> SEQUENCE: 486

Lys Ser Gly Xaa Gly Xaa Xaa Xaa Xaa Thr Ala
1               5                   10

<210> SEQ ID NO 487
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can be any naturally occurring amino acid

<400> SEQUENCE: 487

Gly Thr Xaa Gly Xaa Xaa Xaa Xaa Ala Ser
1               5                   10

<210> SEQ ID NO 488
<211> LENGTH: 11
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION
<220> FEATURE:
```

```
<221> NAME/KEY: MISC_FEATURE
<222> LOCATION: (5)..(8)
<223> OTHER INFORMATION: Xaa can be any naturally occurring amino acid

<400> SEQUENCE: 488

Thr Ala Xaa Gly Xaa Xaa Xaa Xaa Ser Val Val
1               5                   10

<210> SEQ ID NO 489
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can be any naturally occurring amino acid

<400> SEQUENCE: 489

Leu Asn Xaa Gly Xaa Xaa Xaa Xaa Asn Phe
1               5                   10

<210> SEQ ID NO 490
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can be any naturally occurring amino acid

<400> SEQUENCE: 490

Asn Asn Xaa Gly Xaa Xaa Xaa Xaa Phe Tyr
1               5                   10

<210> SEQ ID NO 491
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can be any naturally occurring amino acid
```

```
<400> SEQUENCE: 491

Asn Phe Xaa Gly Xaa Xaa Xaa Xaa Tyr Pro
1               5                   10

<210> SEQ ID NO 492
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can be any naturally occurring amino acid

<400> SEQUENCE: 492

Phe Tyr Xaa Gly Xaa Xaa Xaa Xaa Pro Arg
1               5                   10

<210> SEQ ID NO 493
<211> LENGTH: 11
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: FORMYLATION
<220> FEATURE:
<221> NAME/KEY: MISC_FEATURE
<222> LOCATION: (6)..(9)
<223> OTHER INFORMATION: Xaa can be any naturally occurring amino acid

<400> SEQUENCE: 493

Trp Lys Val Xaa Gly Xaa Xaa Xaa Xaa Asp Asn
1               5                   10

<210> SEQ ID NO 494
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Xaa can be Ala or Val
```

```
<400> SEQUENCE: 494

Val Asp Xaa Gly Xaa Xaa Xaa Xaa Asn Xaa
1               5                   10

<210> SEQ ID NO 495
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (2)..(2)
<223> OTHER INFORMATION: Xaa can be Ala or Val
<220> FEATURE:
<221> NAME/KEY: MOD_RES
<222> LOCATION: (3)..(3)
<223> OTHER INFORMATION: FORMYLATION
<220> FEATURE:
<221> NAME/KEY: MISC_FEATURE
<222> LOCATION: (4)..(8)
<223> OTHER INFORMATION: Xaa can be any naturally occurring amino acid

<400> SEQUENCE: 495

Asn Xaa Gly Xaa Xaa Xaa Xaa Xaa Leu Gln
1               5                   10

<210> SEQ ID NO 496
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Xaa can be Ala or Val
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can be any naturally occurring amino acid

<400> SEQUENCE: 496

Xaa Leu Xaa Gly Xaa Xaa Xaa Xaa Gln Ser
1               5                   10

<210> SEQ ID NO 497
<211> LENGTH: 11
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: Xaa can be any naturaly occurring amino acid
<220> FEATURE:
<221> NAME/KEY: MOD_RES
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can be any naturally occurring amino acid
```

```
<400> SEQUENCE: 497

Leu Gln Xaa Gly Xaa Xaa Xaa Xaa Ser Gly Asn
1               5                   10

<210> SEQ ID NO 498
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can be any naturally occurring amino acid

<400> SEQUENCE: 498

Gln Ser Xaa Gly Xaa Xaa Xaa Xaa Gly Asn
1               5                   10

<210> SEQ ID NO 499
<211> LENGTH: 11
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (4)..(4)
<223> OTHER INFORMATION: Xaa can be any naturally occurring amino acid
<220> FEATURE:
<221> NAME/KEY: MOD_RES
<222> LOCATION: (5)..(5)
<223> OTHER INFORMATION: FORMYLATION
<220> FEATURE:
<221> NAME/KEY: MISC_FEATURE
<222> LOCATION: (6)..(9)
<223> OTHER INFORMATION: Xaa can be any naturally occurring amino acid

<400> SEQUENCE: 499

Gln Ser Gly Xaa Gly Xaa Xaa Xaa Xaa Asn Ser
1               5                   10

<210> SEQ ID NO 500
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can be any naturally occurring amino acid

<400> SEQUENCE: 500

Gly Asn Xaa Gly Xaa Xaa Xaa Xaa Ser Gln
1               5                   10
```

```
<210> SEQ ID NO 501
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can be any naturally occurring amino acid

<400> SEQUENCE: 501

Asn Ser Xaa Gly Xaa Xaa Xaa Xaa Gln Glu
1               5                   10

<210> SEQ ID NO 502
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can be any naturally occurring amino acid

<400> SEQUENCE: 502

Ser Gln Xaa Gly Xaa Xaa Xaa Xaa Glu Ser
1               5                   10

<210> SEQ ID NO 503
<211> LENGTH: 11
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (4)..(4)
<223> OTHER INFORMATION: Xaa can be any naturally occurring amino acid
<220> FEATURE:
<221> NAME/KEY: MOD_RES
<222> LOCATION: (5)..(5)
<223> OTHER INFORMATION: FORMYLATION
<220> FEATURE:
<221> NAME/KEY: MISC_FEATURE
<222> LOCATION: (6)..(9)
<223> OTHER INFORMATION: Xaa can be any naturally occurring amino acid

<400> SEQUENCE: 503

Gln Asp Ser Xaa Gly Xaa Xaa Xaa Xaa Lys Asp
1               5                   10

<210> SEQ ID NO 504
<211> LENGTH: 11
```

```
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can be any naturally occurring amino acid

<400> SEQUENCE: 504

Lys Asp Xaa Gly Xaa Xaa Xaa Xaa Ser Thr Tyr
1               5                   10

<210> SEQ ID NO 505
<211> LENGTH: 11
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (4)..(4)
<223> OTHER INFORMATION: Xaa can be any naturally occurring amino acid
<220> FEATURE:
<221> NAME/KEY: MOD_RES
<222> LOCATION: (5)..(5)
<223> OTHER INFORMATION: FORMYLATION
<220> FEATURE:
<221> NAME/KEY: MISC_FEATURE
<222> LOCATION: (6)..(9)
<223> OTHER INFORMATION: Xaa can be any naturally occurring amino acid

<400> SEQUENCE: 505

Lys Asp Ser Xaa Gly Xaa Xaa Xaa Xaa Thr Tyr
1               5                   10

<210> SEQ ID NO 506
<211> LENGTH: 11
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (4)..(4)
<223> OTHER INFORMATION: Xaa can be any naturally occurring amino acid
<220> FEATURE:
<221> NAME/KEY: MOD_RES
<222> LOCATION: (5)..(5)
<223> OTHER INFORMATION: FORMYLATION
<220> FEATURE:
<221> NAME/KEY: MISC_FEATURE
<222> LOCATION: (6)..(9)
<223> OTHER INFORMATION: Xaa can be any naturally occurring amino acid

<400> SEQUENCE: 506

Asp Ser Thr Xaa Gly Xaa Xaa Xaa Xaa Tyr Ser
1               5                   10

<210> SEQ ID NO 507
<211> LENGTH: 10
<212> TYPE: PRT
<213> ORGANISM: Artificial sequence
<220> FEATURE:
<223> OTHER INFORMATION: synthetic sequence
```

```
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can be any naturally occurring amino acid

<400> SEQUENCE: 507

Thr Tyr Xaa Gly Xaa Xaa Xaa Xaa Ser Leu
1               5                   10

<210> SEQ ID NO 508
<211> LENGTH: 11
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (4)..(4)
<223> OTHER INFORMATION: Xaa can be any naturally occurring amino acid
<220> FEATURE:
<221> NAME/KEY: MOD_RES
<222> LOCATION: (5)..(5)
<223> OTHER INFORMATION: FORMYLATION
<220> FEATURE:
<221> NAME/KEY: MISC_FEATURE
<222> LOCATION: (6)..(9)
<223> OTHER INFORMATION: Xaa can be any naturally occurring amino acid

<400> SEQUENCE: 508

Glu Val Thr Xaa Gly Xaa Xaa Xaa Xaa His Gln
1               5                   10

<210> SEQ ID NO 509
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can be any naturally occurring amino acid

<400> SEQUENCE: 509

Thr His Xaa Gly Xaa Xaa Xaa Xaa Gln Gly
1               5                   10

<210> SEQ ID NO 510
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: Xaa can be any naturally occurring amino acid
```

```
<220> FEATURE:
<221> NAME/KEY: MOD_RES
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can be any naturallyo ccurring amino acid

<400> SEQUENCE: 510

His Gln Xaa Gly Xaa Xaa Xaa Xaa Gly Leu
1               5                   10

<210> SEQ ID NO 511
<211> LENGTH: 12
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can be any naturally occurring amino acid

<400> SEQUENCE: 511

Gln Gly Xaa Gly Xaa Xaa Xaa Xaa Leu Ser Ser Pro
1               5                   10

<210> SEQ ID NO 512
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can be any naturally occurring amino acid

<400> SEQUENCE: 512

Gly Leu Xaa Gly Xaa Xaa Xaa Xaa Ser Ser
1               5                   10

<210> SEQ ID NO 513
<211> LENGTH: 11
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (4)..(4)
<223> OTHER INFORMATION: Xaa can be any naturally occurring amino acid
<220> FEATURE:
<221> NAME/KEY: MOD_RES
<222> LOCATION: (5)..(5)
<223> OTHER INFORMATION: FORMYLATION
```

```
<220> FEATURE:
<221> NAME/KEY: MISC_FEATURE
<222> LOCATION: (6)..(9)
<223> OTHER INFORMATION: Xaa can be any naturally occurring amino acid

<400> SEQUENCE: 513

Gly Leu Ser Xaa Gly Xaa Xaa Xaa Xaa Ser Pro
1               5                   10

<210> SEQ ID NO 514
<211> LENGTH: 12
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (5)..(5)
<223> OTHER INFORMATION: Xaa can be any naturally occurring amino acid
<220> FEATURE:
<221> NAME/KEY: MOD_RES
<222> LOCATION: (6)..(6)
<223> OTHER INFORMATION: FORMYLATION
<220> FEATURE:
<221> NAME/KEY: MISC_FEATURE
<222> LOCATION: (7)..(10)
<223> OTHER INFORMATION: Xaa can be any naturally occurring amino acid

<400> SEQUENCE: 514

Gly Leu Ser Ser Xaa Gly Xaa Xaa Xaa Xaa Pro Val
1               5                   10

<210> SEQ ID NO 515
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MOD_RES
<222> LOCATION: (4)..(4)
<223> OTHER INFORMATION: FORMYLATION
<220> FEATURE:
<221> NAME/KEY: MISC_FEATURE
<222> LOCATION: (5)..(8)
<223> OTHER INFORMATION: Xaa can eb any naturally occurring amino acid

<400> SEQUENCE: 515

Ser Pro Xaa Gly Xaa Xaa Xaa Xaa Val Thr
1               5                   10
```

ANTIBODY CONJUGATES AND METHODS OF MAKING AND USING THE SAME

CROSS-REFERENCE TO RELATED APPLICATION

This application claims priority benefit of U.S. provisional application Ser. No. 62/327,906, filed Apr. 26, 2016, which application is incorporated herein by reference in its entirety.

INTRODUCTION

Antibodies find use in various diagnostic and therapeutic applications. Antibodies can also be used to deliver drugs. However, conjugation of a drug to an antibody can be difficult to control, resulting in a heterogeneous mixture of conjugates that differ in the number of drug molecules attached. This can make controlling the amount administered to a patient difficult.

SUMMARY

Antibodies that include a sulfatase motif-containing tag in a constant region of an immunoglobulin (Ig) light chain polypeptide are disclosed. The sulfatase motif of the tag can be converted by a formylglycine-generating enzyme (FGE) to produce a formylglycine (fGly)-modified Ig light chain polypeptide. An fGly-modified Ig light chain polypeptide of the antibody can be covalently and site-specifically bound to a moiety of interest (i.e., a payload, e.g., drug) to provide an antibody conjugate. The disclosure also encompasses methods of production of such tagged Ig light chain polypeptides, fGly-modified Ig light chain polypeptides, and antibody conjugates, as well as methods of use of same.

Provided herein is an antibody that includes an immunoglobulin (Ig) light chain polypeptide containing in a constant region an amino acid sequence of the formula: $X^1Z^1X^2Z^2X^3Z^3$ (SEQ ID NO: 478), wherein $Z^1$ is cysteine, serine, 2-formylglycine (fGly), or fGly', wherein fGly' is an fGly residue covalently bound to a payload; $Z^2$ is proline or alanine; $Z^3$ is an aliphatic amino acid or a basic amino acid; $X^1$ is present or absent, and when present, can be any amino acid; and $X^2$ and $X^3$ are each independently any amino acid, wherein the amino acid sequence is positioned in the Ig light chain polypeptide such that when $Z^1$ is fGly, conjugation of the fGly (e.g., in a composition containing the present antibody) with the payload provides an average molar ratio of payload to antibody of at least 0.5. In some embodiments, the constant region of the Ig light chain polypeptide includes the amino acid sequence:

| | |
|---|---|
| $TXZ^1X^2Z^2X^3Z^3VA$; | (SEQ ID NO: 46) |
| $TVX^1Z^1X^2Z^2X^3Z^3AA$; | (SEQ ID NO: 47) |
| $VAX^1Z^1X^2Z^2X^3Z^3AP$; | (SEQ ID NO: 48) |
| $AAX^1Z^1X^2Z^2X^3Z^3PSV$; | (SEQ ID NO: 49) |
| $APX^1Z^1X^2Z^2X^3Z^3SVF$; | (SEQ ID NO: 50) |
| $PSX^1Z^1X^2Z^2X^3Z^3VF$; | (SEQ ID NO: 51) |
| $KSX^1Z^1X^2Z^2X^3Z^3GT$; | (SEQ ID NO: 52) |
| $KSGX^1Z^1X^2Z^2X^3Z^3TA$; | (SEQ ID NO: 53) |
| $GTX^1Z^1X^2Z^2X^3Z^3AS$; | (SEQ ID NO: 54) |
| $TAX^1Z^1X^2Z^2X^3Z^3SVV$; | (SEQ ID NO: 55) |
| $LNX^1Z^1X^2Z^2X^3Z^3NF$; | (SEQ ID NO: 56) |
| $NNX^1Z^1X^2Z^2X^3Z^3FY$; | (SEQ ID NO: 57) |
| $NFX^1Z^1X^2Z^2X^3Z^3YP$; | (SEQ ID NO: 58) |
| $FYX^1Z^1X^2Z^2X^3Z^3PR$; | (SEQ ID NO: 59) |
| $WKVX^1Z^1X^2Z^2X^3Z^3DN$; | (SEQ ID NO: 60) |
| $VDX^1Z^1X^2Z^2X^3Z^3N[A/V]$; | (SEQ ID NO: 61) |
| $N[A/V]X^1Z^1X^2Z^2X^3Z^3LQ$; | (SEQ ID NO: 62) |
| $[A/V]LX^1Z^1X^2Z^2X^3Z^3QS$; | (SEQ ID NO: 63) |
| $LQX^1Z^1X^2Z^2X^3Z^3SGN$; | (SEQ ID NO: 64) |
| $QSX^1Z^1X^2Z^2X^3Z^3GN$; | (SEQ ID NO: 65) |
| $QSGX^1Z^1X^2Z^2X^3Z^3NS$; | (SEQ ID NO: 66) |
| $GNX^1Z^1X^2Z^2X^3Z^3SQ$; | (SEQ ID NO: 67) |
| $NSX^1Z^1X^2Z^2X^3Z^3QE$; | (SEQ ID NO: 68) |
| $SQX^1Z^1X^2Z^2X^3Z^3ES$; | (SEQ ID NO: 69) |
| $QDSX^1Z^1X^2Z^2X^3Z^3KD$; | (SEQ ID NO: 70) |
| $KDX^1Z^1X^2Z^2X^3Z^3STY$; | (SEQ ID NO: 71) |
| $KDSX^1Z^1X^2Z^2X^3Z^3TY$; | (SEQ ID NO: 72) |
| $DSTX^1Z^1X^2Z^2X^3Z^3YS$; | (SEQ ID NO: 73) |
| $TYX^1Z^1X^2Z^2X^3Z^3SL$; | (SEQ ID NO: 74) |
| $EVTX^1Z^1X^2Z^2X^3Z^3HQ$; | (SEQ ID NO: 75) |
| $THX^1Z^1X^2Z^2X^3Z^3QG$; | (SEQ ID NO: 76) |
| $HQX^1Z^1X^2Z^2X^3Z^3GL$; | (SEQ ID NO: 77) |

-continued

QGX¹Z¹X²Z²X³Z³LSSP;  (SEQ ID NO: 78)

GLX¹Z¹X²Z²X³Z³SS;  (SEQ ID NO: 79)

GLSX¹Z¹X²Z²X³Z³SP;  (SEQ ID NO: 80)

GLSSX¹Z¹X²Z²X³Z³PV;  (SEQ ID NO: 81)
or

SPX¹Z¹X²Z²X³Z³VT.  (SEQ ID NO: 82)

([*/*] denotes alternative amino acids (or amino acid sequences) chosen from the amino acid residues (or sequences) separated by "/".) In some embodiments, $Z^3$ is arginine. In some embodiments, $X^1$ is present. In some embodiments, $X^1$ is glycine, leucine, isoleucine, methionine, histidine, tyrosine, valine, serine, cysteine or threonine. In some embodiments, $X^2$ and $X^3$ are each independently serine, threonine, alanine, valine, glycine or cysteine.

In any embodiment, the Ig light chain polypeptide constant region may contain two or more of SEQ ID NOs:46-82.

In any embodiment, the antibody may specifically bind a tumor antigen on a cancer cell.

In some embodiments, $X^1Z^1X^2Z^2X^3Z^3$ is LCTPSR (SEQ ID NO:158) or LSTPSR (SEQ ID NO:159). In some embodiments, $X^1Z^1X^2Z^2X^3Z^3$ is selected from MCTPSR (SEQ ID NO:160), VCTPSR (SEQ ID NO:161), LCSPSR (SEQ ID NO:162), LCAPSR (SEQ ID NO:163), LCVPSR (SEQ ID NO:164), LCGPSR (SEQ ID NO:165), ICTPAR (SEQ ID NO:166), LCTPSK (SEQ ID NO:167), MCTPSK (SEQ ID NO:168), VCTPSK (SEQ ID NO:169), LCSPSK (SEQ ID NO:170), LCAPSK (SEQ ID NO:171), LCVPSK (SEQ ID NO:172), LCGPSK (SEQ ID NO:173), LCTPSA (SEQ ID NO:174), ICTPAA (SEQ ID NO:175), MCTPSA (SEQ ID NO:176), VCTPSA (SEQ ID NO:177), LCSPSA (SEQ ID NO:178), LCAPSA (SEQ ID NO:179), LCVPSA (SEQ ID NO:180), LCGPSA (SEQ ID NO:181), MSTPSR (SEQ ID NO:182), VSTPSR (SEQ ID NO:183), LSSPSR (SEQ ID NO:184), LSAPSR (SEQ ID NO:185), LSVPSR (SEQ ID NO:186), LSGPSR (SEQ ID NO:187), ISTPAR (SEQ ID NO:188), LSTPSK (SEQ ID NO:189), MSTPSK (SEQ ID NO:190), VSTPSK (SEQ ID NO:191), LSSPSK (SEQ ID NO:192), LSAPSK (SEQ ID NO:193), LSVPSK (SEQ ID NO:194), LSGPSK (SEQ ID NO:195), LSTPSA (SEQ ID NO:196), ISTPAA (SEQ ID NO:197), MSTPSA (SEQ ID NO:198), VSTPSA (SEQ ID NO:199), LSSPSA (SEQ ID NO:200), LSAPSA (SEQ ID NO:201), LSVPSA (SEQ ID NO:202), and LSGPSA (SEQ ID NO:203).

In some embodiments, the composition includes an fGly-modified antibody, wherein $Z^1$ of the antibody is fGly. In some embodiments, $X^1Z^1X^2Z^2X^3Z^3$ is L(fGly)TPSR (SEQ ID NO:157). In some embodiments, $X^1Z^1X^2Z^2X^3Z^3$ is selected from M(fGly)TPSR (SEQ ID NO:204), V(fGly)TPSR (SEQ ID NO:205), L(fGly)SPSR (SEQ ID NO:206), L(fGly)APSR (SEQ ID NO:207), L(fGly)VPSR (SEQ ID NO:208), L(fGly)GPSR (SEQ ID NO:209), I(fGly)TPAR (SEQ ID NO:210), L(fGly)TPSK (SEQ ID NO:211), M(fGly)TPSK (SEQ ID NO:212), V(fGly)TPSK (SEQ ID NO:213), L(fGly)SPSK (SEQ ID NO:214), L(fGly)APSK (SEQ ID NO:215), L(fGly)VPSK (SEQ ID NO:216), L(fGly)GPSK (SEQ ID NO:217), L(fGly)TPSA (SEQ ID NO:218), I(fGly)TPAA (SEQ ID NO:219), M(fGly)TPSA (SEQ ID NO:220), V(fGly)TPSA (SEQ ID NO:221), L(fGly)SPSA (SEQ ID NO:222), L(fGly)APSA (SEQ ID NO:223), L(fGly)VPSA (SEQ ID NO:224), and L(fGly)GPSA (SEQ ID NO:225).

In some embodiments, the composition includes an antibody conjugate including the antibody covalently bound to the payload, wherein $Z^1$ is fGly'. In some embodiments, $X^1(fGly')X^2Z^2X^3Z^3$ is L(fGly')TPSR (SEQ ID NO:226). In some embodiments, $X^1(fGly')X^2Z^2X^3Z^3$ is selected from M(fGly')TPSR (SEQ ID NO:227), V(fGly')TPSR (SEQ ID NO:228), L(fGly')SPSR (SEQ ID NO:229), L(fGly')APSR (SEQ ID NO:230), L(fGly')VPSR (SEQ ID NO:231), L(fGly')GPSR (SEQ ID NO:232), I(fGly')TPAR (SEQ ID NO:233), L(fGly')TPSK (SEQ ID NO:234), M(fGly')TPSK (SEQ ID NO:235), V(fGly')TPSK (SEQ ID NO:236), L(fGly')SPSK (SEQ ID NO:237), L(fGly')APSK (SEQ ID NO:238), L(fGly')VPSK (SEQ ID NO:239), L(fGly')GPSK (SEQ ID NO:240), L(fGly')TPSA (SEQ ID NO:241), I(fGly')TPAA (SEQ ID NO:242), M(fGly')TPSA (SEQ ID NO:243), V(fGly')TPSA (SEQ ID NO:244), L(fGly')SPSA (SEQ ID NO:245), L(fGly')APSA (SEQ ID NO:246), L(fGly')VPSA (SEQ ID NO:247), and L(fGly')GPSA (SEQ ID NO:248).

In any embodiment, the antibody may be covalently bound to the payload via a hydrazone, oxime, semicarbazone, alkyl, alkenyl, acyloxy, hydrazinyl-indolyl, hydrazinyl-imidazoyl, hydrazinyl-pyrrolyl, hydrazinyl-furanyl or a pyrazalinone linkage.

In any embodiment the antibody may be covalently bound to the payload via a linking group. In some embodiments, the linking group comprises a 4-aminopiperidine derivative (4AP).

In any embodiment the payload may be selected from a drug, a detectable label, a water-soluble polymer, and a synthetic peptide. In some embodiments, the payload is a small molecule drug. In some embodiments, the small molecule drug is a cancer chemotherapeutic agent. In some embodiments, the cancer chemotherapeutic agent is an alkylating agent, a nitrosourea, an antimetabolite, an antitumor antibiotic, a vinca alkaloid, or a steroid hormone. In some embodiments, the water-soluble polymer is poly(ethylene glycol). In some embodiments, the detectable label is an imaging agent. In some embodiments, the payload is a viral fusion inhibitor.

In any embodiment, the constant region of the Ig light chain polypeptide may include the amino acid sequence:

TX¹(fGly')X²Z²X³Z³VA;  (SEQ ID NO: 120)

TVX¹(fGly')X²Z²X³Z³AA;  (SEQ ID NO: 121)

VAX¹(fGly')X²Z²X³Z³AP;  (SEQ ID NO: 122)

AAX¹(fGly')X²Z²X³Z³PSV;  (SEQ ID NO: 123)

APX¹(fGly')X²Z²X³Z³SVF;  (SEQ ID NO: 124)

PSX¹(fGly')X²Z²X³Z³VF;  (SEQ ID NO: 125)

KSX¹(fGly')X²Z²X³Z³GT;  (SEQ ID NO: 126)

KSGX¹(fGly')X²Z²X³Z³TA;  (SEQ ID NO: 127)

GTX$^1$(fGly')X$^2$Z$^2$X$^3$Z$^3$AS; (SEQ ID NO: 128)

TAX$^1$(fGly')X$^2$Z$^2$X$^3$Z$^3$SVV; (SEQ ID NO: 129)

LNX$^1$(fGly')X$^2$Z$^2$X$^3$Z$^3$NF; (SEQ ID NO: 130)

NNX$^1$(fGly')X$^2$Z$^2$X$^3$Z$^3$FY; (SEQ ID NO: 131)

NFX$^1$(fGly')X$^2$Z$^2$X$^3$Z$^3$YP; (SEQ ID NO: 132)

FYX$^1$(fGly')X$^2$Z$^2$X$^3$Z$^3$PR; (SEQ ID NO: 133)

WKVX$^1$(fGly')X$^2$Z$^2$X$^3$Z$^3$DN; (SEQ ID NO: 134)

VDX$^1$(fGly')X$^2$Z$^2$X$^3$Z$^3$N[A/V]; (SEQ ID NO: 135)

N[A/V]X$^1$(fGly')X$^2$Z$^2$X$^3$Z$^3$LQ; (SEQ ID NO: 136)

[A/V]LX$^1$(fGly')X$^2$Z$^2$X$^3$Z$^3$QS; (SEQ ID NO: 137)

LQX$^1$(fGly')X$^2$Z$^2$X$^3$Z$^3$SGN; (SEQ ID NO: 138)

QSX$^1$(fGly')X$^2$Z$^2$X$^3$Z$^3$GN; (SEQ ID NO: 139)

QSGX$^1$(fGly')X$^2$Z$^2$X$^3$Z$^3$NS; (SEQ ID NO: 140)

GNX$^1$(fGly')X$^2$Z$^2$X$^3$Z$^3$SQ; (SEQ ID NO: 141)

NSX$^1$(fGly')X$^2$Z$^2$X$^3$Z$^3$QE; (SEQ ID NO: 142)

SQX$^1$(fGly')X$^2$Z$^2$X$^3$Z$^3$ES; (SEQ ID NO: 143)

QDSX$^1$(fGly')X$^2$Z$^2$X$^3$Z$^3$KD; (SEQ ID NO: 144)

KDX$^1$(fGly')X$^2$Z$^2$X$^3$Z$^3$STY; (SEQ ID NO: 145)

KDSX$^1$(fGly')X$^2$Z$^2$X$^3$Z$^3$TY; (SEQ ID NO: 146)

DSTX$^1$(fGly')X$^2$Z$^2$X$^3$Z$^3$YS; (SEQ ID NO: 147)

TYX$^1$(fGly')X$^2$Z$^2$X$^3$Z$^3$SL; (SEQ ID NO: 148)

EVTX$^1$(fGly')X$^2$Z$^2$X$^3$Z$^3$HQ; (SEQ ID NO: 149)

THX$^1$(fGly')X$^2$Z$^2$X$^3$Z$^3$QG; (SEQ ID NO: 150)

HQX$^1$(fGly')X$^2$Z$^2$X$^3$Z$^3$GL; (SEQ ID NO: 151)

QGX$^1$(fGly')X$^2$Z$^2$X$^3$Z$^3$LSSP; (SEQ ID NO: 152)

GLX$^1$(fGly')X$^2$Z$^2$X$^3$Z$^3$SS; (SEQ ID NO: 153)

GLSX$^1$(fGly')X$^2$Z$^2$X$^3$Z$^3$SP; (SEQ ID NO: 154)

GLSSX$^1$(fGly')X$^2$Z$^2$X$^3$Z$^3$PV; (SEQ ID NO: 155)

SPX$^1$(fGly')X$^2$Z$^2$X$^3$Z$^3$VT. (SEQ ID NO: 156)

Also provided herein is an antibody conjugate containing an antibody covalently bound to a payload, the antibody containing an immunoglobulin (Ig) light chain polypeptide including, in a constant region, an amino acid sequence of the formula: X$^1$(fGly')X$^2$Z$^2$X$^3$Z$^3$, wherein fGly' is an fGly residue covalently bound to the payload; Z$^2$ is proline or alanine; Z$^3$ is an aliphatic amino acid or a basic amino acid; X$^1$ is present or absent, and when present, can be any amino acid; and X$^2$ and X$^3$ are each independently any amino acid, and wherein the constant region of the Ig light chain polypeptide includes the amino acid sequence:

TX$^1$(fGly')X$^2$Z$^2$X$^3$Z$^3$VA; (SEQ ID NO: 120)

TVX$^1$(fGly')X$^2$Z$^2$X$^3$Z$^3$AA; (SEQ ID NO: 121)

VAX$^1$(fGly')X$^2$Z$^2$X$^3$Z$^3$AP; (SEQ ID NO: 122)

AAX$^1$(fGly')X$^2$Z$^2$X$^3$Z$^3$PSV; (SEQ ID NO: 123)

APX$^1$(fGly')X$^2$Z$^2$X$^3$Z$^3$SVF; (SEQ ID NO: 124)

PSX$^1$(fGly')X$^2$Z$^2$X$^3$Z$^3$vF; (SEQ ID NO: 125)

KSX$^1$(fGly')X$^2$Z$^2$X$^3$Z$^3$GT; (SEQ ID NO: 126)

KSGX$^1$(fGly')X$^2$Z$^2$X$^3$Z$^3$TA; (SEQ ID NO: 127)

GTX$^1$(fGly')X$^2$Z$^2$X$^3$Z$^3$AS; (SEQ ID NO: 128)

TAX$^1$(fGly')X$^2$Z$^2$X$^3$Z$^3$SVV; (SEQ ID NO: 129)

LNX$^1$(fGly')X$^2$Z$^2$X$^3$Z$^3$NF; (SEQ ID NO: 130)

NNX$^1$(fGly')X$^2$Z$^2$X$^3$Z$^3$FY; (SEQ ID NO: 131)

NFX$^1$(fGly')X$^2$Z$^2$X$^3$Z$^3$YP; (SEQ ID NO: 132)

FYX$^1$(fGly')X$^2$Z$^2$X$^3$Z$^3$PR; (SEQ ID NO: 133)

WKVX$^1$(fGly')X$^2$Z$^2$X$^3$Z$^3$DN; (SEQ ID NO: 134)

VDX$^1$(fGly')X$^2$Z$^2$X$^3$Z$^3$N[A/V]; (SEQ ID NO: 135)

N[A/V]X$^1$(fGly')X$^2$Z$^2$X$^3$Z$^3$LQ; (SEQ ID NO: 136)

[A/V]LX$^1$(fGly')X$^2$Z$^2$X$^3$Z$^3$QS; (SEQ ID NO: 137)

LQX$^1$(fGly')X$^2$Z$^2$X$^3$Z$^3$SGN; (SEQ ID NO: 138)

-continued

QSX¹(fGly')X²Z²X³Z³GN;  (SEQ ID NO: 139)

QSGX¹(fGly')X²Z²X³Z³NS;  (SEQ ID NO: 140)

GNX¹(fGly')X²Z²X³Z³SQ;  (SEQ ID NO: 141)

NSX¹(fGly')X²Z²X³Z³QE;  (SEQ ID NO: 142)

SQX¹(fGly')X²Z²X³Z³ES;  (SEQ ID NO: 143)

QDSX¹(fGly')X²Z²X³Z³KD;  (SEQ ID NO: 144)

KDX¹(fGly')X²Z²X³Z³STY;  (SEQ ID NO: 145)

KDSX¹(fGly')X²Z²X³Z³TY;  (SEQ ID NO: 146)

DSTX¹(fGly')X²Z²X³Z³YS;  (SEQ ID NO: 147)

TYX¹(fGly')X²Z²X³Z³SL;  (SEQ ID NO: 148)

EVTX¹(fGly')X²Z²X³Z³HQ;  (SEQ ID NO: 149)

THX¹(fGly')X²Z²X³Z³QG;  (SEQ ID NO: 150)

HQX¹(fGly')X²Z²X³Z³GL;  (SEQ ID NO: 151)

QGX¹(fGly')X²Z²X³Z³LSSP;  (SEQ ID NO: 152)

GLX¹(fGly')X²Z²X³Z³SS;  (SEQ ID NO: 153)

GLSX¹(fGly')X²Z²X³Z³SP;  (SEQ ID NO: 154)

GLSSX¹(fGly')X²Z²X³Z³PV;  (SEQ ID NO: 155)
or

SPX¹(fGly')X²Z²X³Z³VT.  (SEQ ID NO: 156)

Also provided herein is a recombinant nucleic acid that includes a nucleotide sequence encoding the light chain constant region of the antibody of the present disclosure, wherein $Z^1$ is cysteine or serine. Also provided herein is a recombinant expression vector containing the nucleic acid encoding the light chain constant region of the antibody of the present disclosure, wherein the light chain constant region-encoding nucleotide sequence is operably linked to a promoter. In some embodiments, the recombinant expression vector further includes a nucleotide sequence encoding an Ig heavy chain polypeptide.

Also provided herein is a host cell genetically modified to express the antibody of the present disclosure, wherein $Z^1$ is cysteine, serine or fGly. In some embodiments, the host cell is genetically modified to express a formylglycine generating enzyme (FGE), in a manner sufficient to convert an Ig light chain polypeptide of the antibody into an fGly-modified Ig light chain polypeptide. In some embodiments, the host cell is a mammalian cell.

Also provided herein is a method of producing an antibody conjugate, including: combining, in a reaction mixture: the composition of any of the embodiments above containing an fGly-modified antibody; and a reactive partner containing a payload and an aldehyde-reactive group, under conditions sufficient for the aldehyde-reactive group to react with an aldehyde group of the fGly residue of the fGly-modified antibody, thereby conjugating the payload to the fGly residue via a covalent linkage to generate an antibody conjugate; and isolating the antibody conjugate from the reaction mixture. In some embodiments, the aldehyde-reactive group is selected from the group consisting of: a hydrazine, hydrazide, aminooxy, semicarbazide, hydrazinyl-indole, hydrazinyl-imidazole, hydrazinyl-pyrrole, hydrazinyl-furan and a pyrazalinone group. In some embodiments reactive partner includes a linking group covalently linking the aldehyde-reactive group with the payload. In some embodiments the linking group includes a 4-aminopiperidine derivative (4AP).

Also provided herein is a formulation that includes: the composition of any of the embodiments above containing an antibody conjugate, or the antibody conjugate of the present disclosure; and a pharmaceutically acceptable excipient.

Also provided is a method of treating an individual for cancer, by administering to an individual a therapeutically effective amount of the composition of any of the embodiments above containing an antibody conjugate or the antibody conjugate of the present disclosure.

BRIEF DESCRIPTION OF THE DRAWINGS

FIG. 1 shows a schematic illustrating scanning insertion of a sulfatase motif (LCTPSR) in a human immunoglobulin (Ig) kappa light chain constant region amino acid sequence (SEQ ID NOS:1-14), according to embodiments of the present disclosure.

FIG. 3 is a table listing percentage of aggregation, measured by size exclusion chromatography (SEC), of an antigen-specific antibody modified with a sulfatase motif insertion adjacent and C-terminal to the indicated position, as defined relative to SEQ ID NO:1, in the constant region of its Ig light chain amino acid sequence, according to embodiments of the present disclosure.

FIGS. 6A-6E are a collection of graphs showing antigen binding activity of an antigen-specific antibody conjugated to a cytotoxic drug, where the antibody was modified by having a sulfatase motif inserted adjacent and C-terminal to the indicated position, as defined relative to SEQ ID NO:1, in the constant region of its Ig light chain amino acid sequence, according to embodiments of the present disclosure.

FIG. 9 shows an amino acid sequence of constant regions of human immunoglobulin kappa light chain polypeptide (SEQ ID NO:1), and location of amino acid variations present in different allotypes ("Km*").

FIGS. 10A-10D show amino acid sequences of human Ig kappa light chain constant region amino acid sequence, with or without an inserted sulfatase motif (underlined), according to embodiments of the present disclosure.

FIGS. 14A-14E shows Table 3, listing the primer sets used to amplify clones, according to embodiments of the present disclosure.

FIG. 15 shows Table 4, listing the conjugation results for light chain tagged antibodies, according to embodiments of the present disclosure.

DEFINITIONS

Figure 2A:
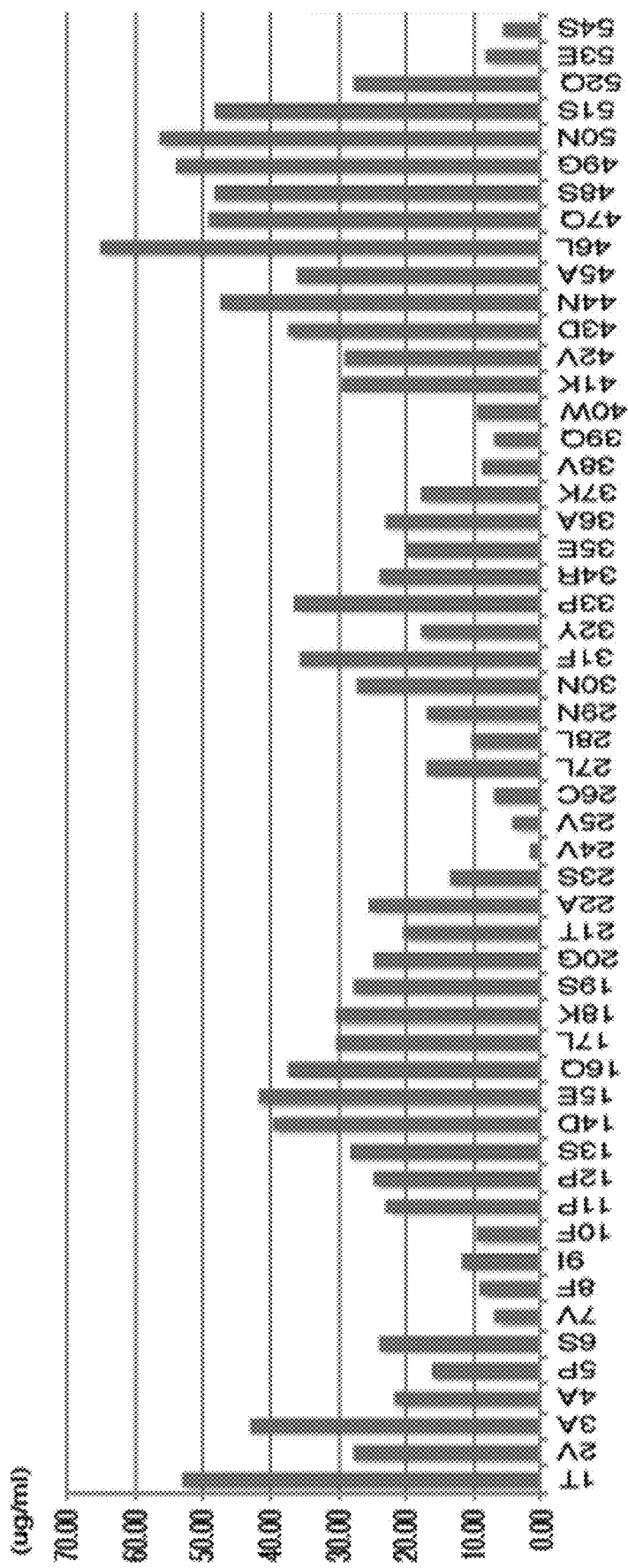
FIGS. 2A and 2B is a graph showing the expression titer (y-axis) of an antigen-specific antibody modified with a sulfatase motif insertion adjacent and C-terminal to the indicated position, as defined relative to SEQ ID NO:1, in the constant region of its Ig light chain amino acid sequence, according to embodiments of the present disclosure. The sulfatase motif is inserted immediately after the amino acid position indicated, as shown schematically in FIG. 1.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are typical of measurements characterizing the disclosed compositions or appropriate to perform the disclosed methods.

The terms "polypeptide," "peptide," and "protein" are used interchangeably herein to refer to a polymeric form of amino acids of any length. Unless specifically indicated otherwise, "polypeptide," "peptide," and "protein" can include genetically coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, proteins which contain at least one N-terminal methionine residue (e.g., to facilitate production in a recombinant bacterial host cell); immunologically tagged proteins; and the like.

"Native amino acid sequence" or "parent amino acid sequence" are used interchangeably herein in the context of an immunoglobulin to refer to the amino acid sequence of the immunoglobulin prior to modification to include a heterologous aldehyde tag.

The term "antibody" is used in the broadest sense and includes monoclonal antibodies, and multispecific antibodies (e.g., bispecific antibodies), humanized antibodies, chimeric antibodies, and antigen-binding antibody fragments (e.g., Fab fragments). A target antigen can have one or more binding sites, also called epitopes, recognized by complementarity determining regions (CDRs) formed by one or more variable regions of an antibody.

"Immunoglobulin polypeptide" as used herein refers to a polypeptide comprising at least a constant region of a light chain polypeptide or at least a constant region of a heavy chain polypeptide.

An immunoglobulin light or heavy chain polypeptide variable region is composed of a framework region (FR) interrupted by three hypervariable regions, also called "complementarity determining regions" or "CDRs". The extent of the framework region and CDRs have been defined (see, "Sequences of Proteins of Immunological Interest," E. Kabat et al., U.S. Department of Health and Human Services, 1991). The framework region of an antibody, that is the combined framework regions of the constituent light and heavy chains, serves to position and align the CDRs. The CDRs are primarily responsible for binding to an epitope of an antigen. An immunoglobuline light chain may have a structure schematically represented, from N- to C-termini, as: FR1-CDR1-FR2-CDR2-FR3-CDR3-FR4-$C_L$, where CDR1, CDR2 and CDR3 are hypervariable regions that interrupt the framework region into four (FR1, FR2, FR3 and FR4) and $C_L$ is the constant region. An immunoglobuline heavy chain may have a structure schematically represented, from N- to C-termini, as: FR1-CDR1-FR2-CDR2-FR3-CDR3-FR4-$C_H1$-H-$C_H2$-$C_H3$, where CDR1, CDR2 and CDR3 are hypervariable regions that interrupt the framework region into four (FR1, FR2, FR3 and FR4), $C_H1$, $C_H2$ and $C_H3$ are constant regions and H is a hinge region.

The term "natural antibody" refers to an antibody in which the heavy and light chains of the antibody have been made and paired by the immune system of a multi-cellular organism. Spleen, lymph nodes, bone marrow and serum are examples of tissues that produce natural antibodies. For example, the antibodies produced by the antibody producing cells isolated from a first animal immunized with an antigen are natural antibodies.

A "parent Ig polypeptide" is a polypeptide comprising an amino acid sequence which lacks a tagged constant region as described herein. The parent polypeptide may comprise a native sequence constant region, or may comprise a constant region with pre-existing amino acid sequence modifications (such as additions, deletions and/or substitutions).

In the context of an Ig polypeptide, the term "constant region" is well understood in the art, and refers to a C-terminal region of an Ig heavy chain, or an Ig light chain. An Ig heavy chain constant region includes CH1, CH2, and CH3 domains (and CH4 domains, where the heavy chain is a μ or an ε heavy chain). In a native Ig heavy chain, the CH1, CH2, CH3 (and, if present, CH4) domains begin immediately after (C-terminal to) the heavy chain variable ($V_H$) region, and are each from about 100 amino acids to about 130 amino acids in length. In a native Ig light chain, the constant region begins begin immediately after (C-terminal to) the light chain variable ($V_L$) region, and is about 100 amino acids to 120 amino acids in length.

In some embodiments, a "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down-regulation of cell surface receptors (e.g. B cell receptor; BCR), etc. Such effector functions generally require the Fc region to be combined with a binding domain (e.g. an antibody variable domain) and can be assessed using various assays that are well known in the art.

Antibody-dependent cell-mediated cytotoxicity" and "ADCC" refer to a cell-mediated reaction in which nonspecific cytotoxic cells that express FcRs (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII The terms "Fc receptor" or "FcR" are used to describe a receptor that binds to the Fc region of an antibody.

The term "humanized antibody" or "humanized immunoglobulin" refers to a non-human (e.g., mouse or rabbit) antibody containing one or more amino acids (in a framework region, a constant region or a CDR, for example) that have been substituted with a correspondingly positioned amino acid from a human antibody. In general, humanized antibodies produce a reduced immune response in a human host, as compared to a non-humanized version of the same antibody. Antibodies can be humanized using a variety of techniques known in the art including, for example, CDR-grafting, veneering or resurfacing, and chain shuffling. In certain embodiments, framework substitutions are identified by modeling of the interactions of the CDR and framework residues to identify framework residues important for antigen binding and sequence comparison to identify unusual framework residues at particular positions.

The term "chimeric antibodies" refer to antibodies whose light and heavy chain genes have been constructed, typically by genetic engineering, from antibody variable and constant region genes belonging to different species. For example, the variable segments of the genes from a mouse monoclonal antibody may be joined to human constant segments, such as gamma 1 and gamma 3. An example of a therapeutic chimeric antibody is a hybrid protein composed of the variable or antigen-binding domain from a mouse antibody and the constant or effector domain from a human antibody, although domains from other mammalian species may be used.

By "genetically-encodable" as used in reference to an amino acid sequence of polypeptide, peptide or protein means that the amino acid sequence is composed of amino acid residues that are capable of production by transcription and translation of a nucleic acid encoding the amino acid sequence, where transcription and/or translation may occur in a cell or in a cell-free in vitro transcription/translation system.

The term "control sequences" refers to DNA sequences that facilitate expression of an operably linked coding sequence in a particular expression system, e.g. mammalian cell, bacterial cell, cell-free synthesis, etc. The control sequences that are suitable for prokaryote systems, for example, include a promoter, optionally an operator sequence, and a ribosome binding site. Eukaryotic cell systems may utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate the initiation of translation. Generally, "operably linked" means that the DNA sequences being linked are contiguous, and, in the case of a secretory leader, contiguous and in reading frame. Linking is accomplished by ligation or through amplification reactions. Synthetic oligonucleotide adaptors or linkers may be used for linking sequences in accordance with conventional practice.

The term "expression cassette" as used herein refers to a segment of nucleic acid, usually DNA, that can be inserted into a nucleic acid (e.g., by use of restriction sites compatible with ligation into a construct of interest or by homologous recombination into a construct of interest or into a host cell genome). In general, the nucleic acid segment comprises a polynucleotide that encodes a polypeptide of interest (e.g., a tagged Ig protein), and the cassette and restriction sites are designed to facilitate insertion of the cassette in the proper reading frame for transcription and translation. Expression cassettes can also comprise elements that facilitate expression of a polynucleotide encoding a polypeptide of interest in a host cell. These elements may include, but are not limited to: a promoter, a minimal promoter, an enhancer, a response element, a terminator sequence, a polyadenylation sequence, and the like.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, at least 75% free, at least 80% free, at least 85% free, at least 90% free, at least 95% free, at least 98% free, or more than 98% free, from other components with which it is naturally associated.

The term "physiological conditions" is meant to encompass those conditions compatible with living cells, e.g., predominantly aqueous conditions of a temperature, pH, salinity, etc. that are compatible with living cells.

"N-terminus" refers to the terminal amino acid residue of a polypeptide having a free amine group, which amine group in non-N-terminus amino acid residues normally forms part of the covalent backbone of the polypeptide.

"C-terminus" refers to the terminal amino acid residue of a polypeptide having a free carboxyl group, which carboxyl group in non-C-terminus amino acid residues normally forms part of the covalent backbone of the polypeptide.

By "internal site" as used in referenced to a polypeptide or an amino acid sequence of a polypeptide means a region of the polypeptide that is not at the N-terminus or at the C-terminus.

As used herein, the terms "treat," "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

A "therapeutically effective amount" refers to an amount effective, at dosages and for periods of time necessary, to achieve the desired therapeutic result. A therapeutically effective amount of a therapeutic agent may vary according to factors such as the disease state, age, sex, and weight of the individual, and the ability of the therapeutic agent to elicit a desired response in the individual. A therapeutically effective amount is also one in which any toxic or detrimental effects of the therapeutic agent are outweighed by the therapeutically beneficial effects.

By "tag" is meant an amino acid sequence that contains an amino acid sequence motif found in sulfatases (hereinafter "sulfatase motif"), which amino acid sequence motif is capable of being converted, by action of a formylglycine generating enzyme (FGE), to contain a 2-formylglycine residue (referred to herein as "fGly"). The fGly residue generated by an FGE is often referred to in the literature as a "formylglycine". Stated differently, the term "tag" is used herein to refer to an amino acid sequence comprising an "unconverted" sulfatase motif (i.e., a sulfatase motif in which the cysteine or serine residues has not been converted to fGly by an FGE, but is capable of being converted). The sulfatase motif may be exchangeable with "FGE substrate motif". A "tagged" polypeptide contains an amino acid sequence motif, e.g., a sulfatase motif, that can be converted by an FGE to contain fGly.

By "conversion" as used in the context of action of a formylglycine generating enzyme (FGE) on a sulfatase motif refers to biochemical modification of a cysteine or serine residue in a sulfatase motif to a formylglycine (fGly) residue (e.g., Cys to fGly, or Ser to fGly).

"Aldehyde tag" or "ald-tag" as used herein, may refer to a tag that contains a sulfatase motif, which has been converted, by action of an FGE, to contain fGly. A converted tag refers to an amino acid sequence comprising a "converted" sulfatase motif (i.e., a sulfatase motif in which the cysteine or the serine residue has been converted to fGly by action of an FGE). An "aldehyde tagged" polypeptide contains an amino acid sequence motif, e.g., a sulfatase motif, that has been converted by an FGE to contain fGly.

By "reactive partner" is meant a molecule or molecular moiety that specifically reacts with another reactive partner to produce a reaction product. Exemplary reactive partners include a cysteine or serine of sulfatase motif and an FGE, which react to form a reaction product of a converted aldehyde tag containing an fGly in lieu of cysteine or serine in the motif. Other exemplary reactive partners include an aldehyde of a formylglycine (fGly) residue of a converted aldehyde tag and an "aldehyde-reactive reactive partner", which comprises an aldehyde-reactive group and a moiety of interest (i.e., a payload, e.g., drug), and which reacts to form a reaction product of a modified aldehyde tagged polypeptide having the payload (e.g., drug) conjugated to the fGly-modified polypeptide via an fGly residue.

By "conjugate" is meant a first moiety that is stably associated with a second moiety. By "stably associated" is meant that a moiety is bound to another moiety or structure under standard conditions. In certain embodiments, the first and second moieties are bound to each other through one or more covalent bonds. The first or the second moiety of a conjugate may be referred to as a "payload".

Before the present disclosure is further described, it is to be understood that the disclosed subject matter is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosed subject matter. The upper and lower limits of these smaller ranges may independently be included in the smaller ranges, and are also encompassed within the disclosed subject matter, subject to any specifically excluded limit in the stated range. Where the stated range includes one or both of the limits, ranges excluding either or both of those included limits are also included in the disclosed subject matter.

Unless defined otherwise, all technical and scientific terms used herein have the same meaning as commonly understood by one of ordinary skill in the art to which the disclosed subject matter belongs. Although any methods and materials similar or equivalent to those described herein can also be used in the practice or testing of the disclosed subject matter, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an antibody" includes a plurality of such antibodies and reference to "the antigen" includes reference to one or more antigens and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the disclosed subject matter, which are, for clarity, described in the context of separate embodiments, may also be provided in combination in a single embodiment. Conversely, various features of the disclosed subject matter, which are, for brevity, described in the context of a single embodiment, may also be provided separately or in any suitable sub-combination. All combinations of the embodiments pertaining to the disclosure are specifically embraced by the disclosed subject matter and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

The publications discussed herein are provided solely for their disclosure prior to the filing date of the present application. Nothing herein is to be construed as an admission that the disclosed subject matter is not entitled to antedate such publication by virtue of prior invention. Further, the dates of publication provided may be different from the actual publication dates which may need to be independently confirmed.

DETAILED DESCRIPTION

As summarized above, an antibody that includes a tag, e.g., a tag containing a sulfatase motif, in an immunoglobulin (Ig) light chain polypeptide is disclosed. The tag includes a substrate motif for a formylglycine-generating enzyme (FGE), where FGE can convert (oxidize) a serine or cysteine residue in the substrate motif to a 2-formylglycine residue (fGly), thereby generating an fGly-modified antibody. An fGly-modified antibody can further react with an aldehyde-reactive partner to generate an antibody conjugate, where a moiety of interest (i.e., a payload, e.g., drug) is bound covalently and site-specifically to the light chain via the fGly.

The tagged antibodies, conjugates, compositions and methods of the present disclosure exploit a naturally-occurring, genetically-encodable sulfatase motif for use as a tag, referred to herein as a "tag", to direct site-specific modification of an Ig polypeptide. The sulfatase motif of the tag, which motif is based on a motif found in active sites of sulfatases, contains a serine or cysteine residue that is capable of being converted (oxidized) to a 2-formylglycine (fGly) residue by action of a formylglycine generating enzyme (FGE) either in a cell-based system in an FGE-expressing host cell (e.g., at the time of translation of an ald tag-containing protein in a cell) or in a cell-free system (e.g., by contacting an ald tag-containing protein with an FGE in a cell-free system). The aldehyde moiety of the resulting fGly residue can be used as a "chemical handle" to facilitate site-specific chemical modification of the Ig polypeptide, and thus site-specific attachment of a payload (e.g., drug). For example, a peptide modified to contain an α-nucleophile-containing moiety (e.g., an aminooxy or hydrazide moiety) can be reacted with the fGly-containing Ig polypeptide to yield a conjugate in which the Ig polypeptide and the peptide are linked by a covalent bond, e.g., a hydrazone or oxime bond, or via alternative aldehyde-specific chemistries such as reductive amination, etc. The reactivity of the aldehyde thus allows for bioorthogonal and chemoselective modification of the Ig polypeptide, and thus provides a site-specific means for chemical modification that in turn can be exploited to provide for site-specific attachment of a payload in the final conjugate.

Tags may be positioned in an Ig light chain polypeptide in any suitable manner such that the tagged Ig light chain polypeptide, an antibody having the tagged light chain polypeptide, or both exhibit one or more desirable properties. The properties may be associated with, e.g., the tagged and/or the fGly-modified antibody produced in vitro (i.e., in a cellular expression system), and/or the antibody conjugate having a payload (e.g., drug) covalently bound to the antibody through fGly. The desirable properties may include, without limitation, higher titer of antibody production, higher conversion rate, higher conjugation yield (e.g., as measured by the average molar ratio of payload to antibody, e.g., drug to antibody), lower aggregation rate, lower immunogenicity, and/or higher stability in serum, relative to reference measures for the respective properties. A tagged, fGly-modified or conjugated antibody of the present disclosure may be characterized in satisfying one or more threshold criteria, e.g., two or more threshold criteria, such as expression titer and/or conjugation yield (e.g., payload-to-antibody ratio (PAR), e.g., the drug-to-antibody ratio, or DAR, where the payload is a drug) that are higher than a threshold titer and/or a threshold yield, respectively.

A tagged or fGly-modified antibody of the present disclosure may exhibit a desirable titer of expression. "Titer of expression", "expression titer" and "titer" are used herein interchangeably, in reference to an antibody, to refer to the amount of antibody secreted in a cell culture supernatant by cultured cells that are genetically modified with suitable expression constructs encoding the antibody. The cells may be genetically modified to coexpress any convenient Ig heavy chain polypeptide with the tagged Ig light chain polypeptide. The cells may be further genetically modified with additional expression constructs encoding enzymes, or any other suitable polypeptide. In some cases, the cells may be genetically modified to express a formylglycine generating enzyme (FGE), as described herein. The threshold titer of expression may be, in some cases, about 5 mg/L or more, e.g., about 6 mg/L or more, about 8 mg/L or more, about 10 mg/L or more, about 15 mg/L or more, about 20 mg/L or more, about 30 mg/L or more, or about 40 mg/L or more. In some embodiments, the threshold titer of expression is in the range of about 5 to about 500 mg/L, e.g., about 6 to about 500 mg/L, about 8 to about 200 mg/L, about 10 to about 200 mg/L, about 20 to about 200 mg/L, or about 30 to about 200 mg/L. The antibody titer may be measured using, e.g., a biosensor chip system, such as a protein A-based biosensor assay run on the BLItz® system (Forte Bio, Calif.).

A tagged or fGly-modified antibody of the present disclosure may exhibit an acceptable level of aggregation in solution. Aggregation may refer to a non-covalent or covalent interaction between antibodies that causes two or more antibodies to physically associate with one another. Thus, the aggregation level of the tagged or fGly-modified antibody may be sufficiently low so as not to interfere with the antigen binding properties, the conjugation yield (as described below), the immunogenicity, etc., of the antibody. In some cases, the tagged or fGly-modified antibody exhibits an aggregation level of about 20% or less, e.g., about 18% or less, about 16% or less, about 14% or less, about 12% or less, about 10% or less, about 5% or less, about 3% or less, about 2% or less, including about 1% or less. In some cases, the tagged or fGly-modified antibody exhibits an aggregation level in the range of about 0% to about 20%, e.g., about 0% to about 16%, about 1% to about 12%, including about 1% to about 10%. Aggregation levels may be measured using, e.g., size exclusion chromatography.

An fGly-modified antibody that includes a converted tag present in each Ig light chain polypeptide constant region, as disclosed herein, may exhibit a desirable conjugation yield as expressed by the average molar ratio of payload to antibody (PAR) (e.g., drug-antibody ratio (DAR), where the payload is a drug), when the fGly-modified antibody is conjugated with a payload, such as a drug, through the fGly in a suitable reaction mixture. The payload prior to conjugation with the fGly-modified antibody may be covalently attached to a suitable reactive group, e.g., an aldehyde-reactive group, that reacts with the aldehyde of the fGly residue of the fGly-modified antibody in the reaction mixture under suitable conditions. In some embodiments, the conjugation yield is about 0.5 or more, e.g., about 0.75 or more, about 1.0 or more, about 1.1 or more, about 1.2 or more, about 1.3 or more, or about 1.6 or more, and up to 2.0.

In some embodiments, the conjugation yield is in the range of about 0.5 to about 2.0, e.g., about 0.5 to about 1.9, about 0.75 to about 1.8, about 1.0 to about 1.8, or about 1.3 to about 1.8. The conjugation yield may be measured by performing, e.g., hydrophobic interaction chromatography (HIC), after a conjugation reaction.

An antibody conjugate of the present disclosure may bind an antigen with a suitable binding activity (e.g., specificity, binding affinity, etc.) compared to the parent antibody (i.e., the antibody without a payload conjugated thereto, or the antibody having an Ig light chain polypeptide without the tag sequence inserted in the constant region). In some cases, the antibody conjugate has binding activity toward an antigen that is substantially the same as the binding activity of a parent antibody that does not have a tag sequence inserted in the constant region of the Ig light chain polypeptide. The binding activity may be measured by, e.g., an enzyme-linked immunosorbent assay (ELISA).

The present antibody conjugates may find use in delivering a conjugated payload (e.g., drug) to a target site, where the antibody conjugate may bind specifically to an antigen specific for, or enriched at, the target site. For example, the antibody conjugate may specifically recognize a tumor antigen and enhance site-specific delivery of a chemotherapeutic drug conjugated to the antibody to the tumor.

Further aspects of the present disclosure are now described.

Tags Containing a Sulfatase Motif

An antibody of the present disclosure includes a tag, i.e., includes an amino acid sequence containing a sulfatase motif which is capable of being converted, by action of FGE, to provide a fGly in the sulfatase motif, in an Ig light chain polypeptide constant region. The tag may include a sulfatase motif having a length of 5 amino acid residues or more, e.g., 6 amino acid residues or more, 7 amino acid residues or more, 8 amino acid residues or more, including 10 amino acid residues or more, and in some cases may have a length of 15 amino acid residues or less, e.g., 12 amino acid residues or less, 11 amino acid residues or less, 10 amino acid residues or less, including 8 amino acid residues or less. In some embodiments, the tag includes a sulfatase motif having a length in the range of 5 to 15 amino acid residues, e.g., 5 to 12 amino acid residues, 5 to 10 amino acid residues, including 6 to 8 residues. In some embodiments, the sulfatase motif includes 5 or 6 amino acid residues.

In some embodiments, the tag includes at least a minimal sulfatase motif (also referred to a "consensus sulfatase motif"), having 5 or 6 amino acid residues, and additional sequence flanking the minimal sulfatase motif. The additional sequence may be N- and/or C-terminal to the minimal sulfatase motif.

In certain embodiments, the sulfatase motif may be described by the formula:

$$X^1Z^1X^2Z^2X^3Z^3 \text{ (SEQ ID NO:478)} \quad (I)$$

where $Z^1$ is cysteine or serine (which can also be represented by (C/S)); $Z^2$ is either a proline or alanine residue (which can also be represented by (P/A)); $Z^3$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), usually A, G, L, V, or I; $X^1$ is present or absent and, when present, can be any amino acid, though usually an aliphatic amino acid, a sulfur-containing amino acid, or a polar, uncharged amino acid, (i.e., other than a aromatic amino acid or a charged amino acid), usually L, M, V, S or T, more usually L, M, S or V; and $X^2$ and $X^3$ independently can be any amino acid, though usually an aliphatic amino acid, a polar, uncharged amino acid, or a sulfur containing amino acid (i.e., other than an aromatic amino acid or a charged amino acid), usually S, T, A, V, G or C, more usually S, T, A, V or G.

Thus, the present disclosure provides an antibody, where the Ig light chain polypeptide of the antibody includes a constant region amino acid sequence modified to provide a tag having at least 5 amino acids and having the formula $X^1Z^1X^2Z^2X^3Z^3$ (SEQ ID NO:478), where $Z^1$ is cysteine or serine; $Z^2$ is a proline or alanine residue; $Z^3$ is an aliphatic amino acid or a basic amino acid; $X^1$ is present or absent and, when present, is any amino acid; $X^2$ and $X^3$ are each independently any amino acid, and where the Ig light chain polypeptide includes a light chain constant region containing one or more, e.g., two or more, or 3 or more, of the amino acid sequences set forth in SEQ ID NOs:46-82, shown in Table 1, as described further below.

It should be noted that, following action of an FGE on the sulfatase motif, $Z^1$ is oxidized to generate a formylglycine (fGly) residue. Furthermore, following both FGE-mediated conversion and reaction with a reactive partner comprising a moiety of interest (i.e., a payload, e.g., drug, detectable label, water soluble polymer, polypeptide, etc.), fGly position at $Z^1$ in the formula above is covalently bound to the payload.

The sulfatase motif of the tag is generally selected so as to be capable of conversion by a selected FGE, e.g., an FGE present in a host cell in which the antibody of the present disclosure is expressed or an FGE which is to be contacted with the antibody of the present disclosure in a cell-free, in vitro method.

Selection of tags and an FGE that provide for conversion of a tag to include an fGly in the target antibody containing a tagged Ig light chain polypeptide can be readily accomplished in light of information available in the art. In general, sulfatase motifs susceptible to conversion by a eukaryotic FGE contain a cysteine and a proline (i.e., a cysteine and proline at $Z^1$ and $Z^2$, respectively, in Formula I above (e.g., $X^1CX^2PX^3Z^3$) and are modified by the "SUMF1-type" FGE (Cosma et al. Cell 2003, 113, (4), 445-56; Dierks et al. Cell 2003, 113, (4), 435-44). Sulfatase motifs susceptible to conversion by a prokaryotic FGE contain either a cysteine or a serine, and a proline in the sulfatase motif (i.e., a cysteine or serine at $Z^1$, and a proline at $Z^2$, respectively, in Formula I above (e.g., $X^1(C/S)X^2PX^3Z^3$) are modified either by the "SUMF1-type" FGE or the "AtsB-type" FGE, respectively (Szameit et al. J Biol Chem 1999, 274, (22), 15375-81). Other sulfatase motifs susceptible to conversion by a prokaryotic FGE contain either a cysteine or a serine, and either a proline or an alanine in the sulfatase motif (i.e., a cysteine or serine at $Z^1$, and a proline or alanine at $Z_2$, respectively, in Formula I or II above (e.g., $X^1CX^2PX^3R$; $X^1SX^2PX^2R$; $X^1CX^2AX^3R$; $X^1SX^2AX^3R$; $CX^1PX^2R$; $SX^1PX^2R$; $CX^1AX^2R$; $SX^1AX^2R$, $X^1CX^2PX^3Z^3$; $X^1SX^2PX^2\ Z^3$; $X^1CX^2AX^3Z^3$; $X^1SX^2AX^3Z^3$; $CX^1PX^2Z^3$; $SX^1PX^2Z^3$; $CX^1AX^2Z^3$; $SX^1AX^2Z^3$), and are susceptible to modification by, for example, can be modified by an FGE of a Firmicutes (e.g., *Clostridium perfringens*) (see Berteau et al. *J. Biol. Chem.* 2006; 281:22464-22470) or an FGE of *Mycobacterium tuberculosis*.

Therefore, for example, where the FGE is a eukaryotic FGE (e.g., a mammalian FGE, including a human FGE), the sulfatase motif is usually of the formula: $X^1CX^2PX^3Z^3$, where $X^1$ may be present or absent and, when present, can be any amino acid, though usually an aliphatic amino acid, a sulfur-containing amino acid, or a polar, uncharged amino acid, (i.e., other than a aromatic amino acid or a charged amino acid), usually L, M, S or V; $X^2$ and $X^3$ independently can be any amino acid, though usually an aliphatic amino acid, a sulfur-containing amino acid, or a polar, uncharged amino acid, (i.e., other than a aromatic amino acid or a charged amino acid), usually S, T, A, V, G, or C, more usually S, T, A, V or G; and $Z^3$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), usually A, G, L, V, or I.

Specific examples of sulfatase motifs include LCTPSR (SEQ ID NO:158), MCTPSR (SEQ ID NO:160), VCTPSR (SEQ ID NO:161), LCSPSR (SEQ ID NO:162), LCAPSR (SEQ ID NO:163), LCVPSR (SEQ ID NO:164), LCGPSR (SEQ ID NO:165), ICTPAR (SEQ ID NO:166), LCTPSK (SEQ ID NO:167), MCTPSK (SEQ ID NO:168), VCTPSK (SEQ ID NO:169), LCSPSK (SEQ ID NO:170), LCAPSK (SEQ ID NO:171), LCVPSK (SEQ ID NO:172), LCGPSK (SEQ ID NO:173), LCTPSA (SEQ ID NO:174), ICTPAA (SEQ ID NO:175), MCTPSA (SEQ ID NO:176), VCTPSA (SEQ ID NO:177), LCSPSA (SEQ ID NO:178), LCAPSA (SEQ ID NO:179), LCVPSA (SEQ ID NO:180), LCGPSA (SEQ ID NO:181), LSTPSR (SEQ ID NO:159), MSTPSR (SEQ ID NO:182), VSTPSR (SEQ ID NO:183), LSSPSR (SEQ ID NO:184), LSAPSR (SEQ ID NO:185), LSVPSR (SEQ ID NO:186), LSGPSR (SEQ ID NO:187), ISTPAR (SEQ ID NO:188), LSTPSK (SEQ ID NO:189), MSTPSK (SEQ ID NO:190), VSTPSK (SEQ ID NO:191), LSSPSK (SEQ ID NO:192), LSAPSK (SEQ ID NO:193), LSVPSK (SEQ ID NO:194), LSGPSK (SEQ ID NO:195), LSTPSA (SEQ ID NO:196), ISTPAA (SEQ ID NO:197), MSTPSA (SEQ ID NO:198), VSTPSA (SEQ ID NO:199), LSSPSA (SEQ ID NO:200), LSAPSA (SEQ ID NO:201), LSVPSA (SEQ ID NO:202), and LSGPSA (SEQ ID NO:203). Other specific sulfatase motifs are readily apparent from the disclosure provided herein.

Antibodies Containing a Tagged Immunoglobulin Light Chain Polypeptide

Figure 1:
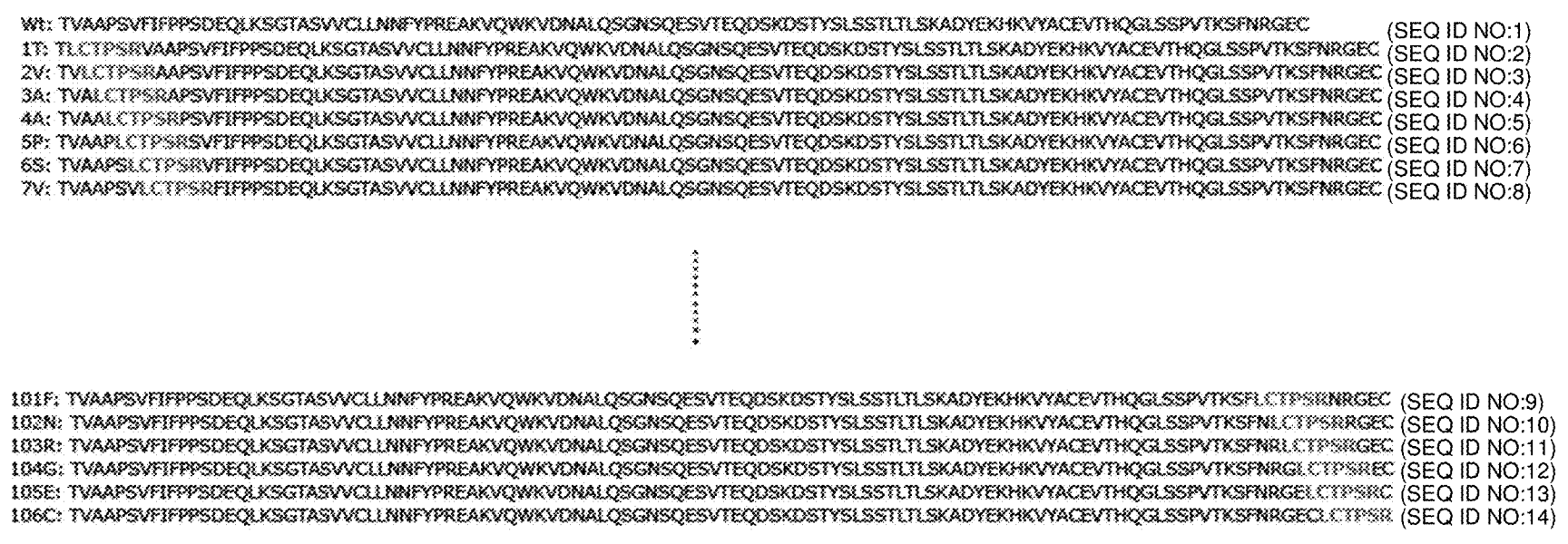

An antibody of the present disclosure contains a tag, as described above, in the amino acid sequence of an Ig light chain polypeptide constant region, where the tag is positioned between two consecutive amino acids in the constant region of a corresponding parent Ig light chain polypeptide, e.g., the Ig light chain polypeptide without the tag in the constant region. In other words, the amino acid sequence of the present tag may be present in an Ig light chain polypeptide such that the tag amino acid sequence is directly flanked N-terminally by a first flanking sequence identical to a first contiguous sequence in a corresponding parent Ig light chain constant region, and C-terminally directly flanked by a second flanking sequence identical to a second contiguous sequence in the corresponding parent Ig light chain constant region, where the first contiguous sequence is more N-terminal to the second contiguous sequence in the parent Ig light chain constant region amino acid sequence, and the first and second contiguous sequences are contiguous in the parent Ig light chain constant region amino acid sequence (see also, e.g., FIG. 1).

The parent light chain polypeptide may be an Ig kappa light chain polypeptide, having an Ig constant region amino acid sequence, e.g., as shown in FIG. 1. Thus, in some cases, the Ig light chain polypeptide is a human Ig light chain polypeptide. In some cases, the Ig light chain constant region is a human Ig light chain constant region. In some cases, the parent Ig light chain polypeptide includes a constant region amino acid sequence 75% or more, e.g., 80% or more, 85% or more, 90% or more, 95% or more, 97% or more, and up to 100% identical to the amino acid sequence set forth in SEQ ID NO:1. Thus, an antibody of the present disclosure, containing a tag, may include an Ig light chain derived from a parent Ig light chain polypeptide that is based on an Ig kappa light chain polypeptide, where the antibody contains an Ig light chain polypeptide that includes a constant region amino acid sequence, exclusive of any tags, that is 75% or more, e.g., 80% or more, 85% or more, 90% or more, 95% or more, 97% or more, and up to 100% identical to the amino acid sequence set forth in SEQ ID NO:1.

The present disclosure contemplates an antibody that includes an Ig light chain based on any suitable allotype, e.g., human allotype, of Ig kappa light chain. The Ig kappa light chain allotypes of interest include, without limitation, Km1 (having V at position 45 and L at position 83 of SEQ ID NO:1); Km1,2 (having L at position 83 of SEQ ID NO:1); and Km3 (corresponding to SEQ ID NO:1). Thus in some cases, the antibody contains an Ig light chain polypeptide that includes a constant region amino acid sequence, exclusive of any tags, that is 75% or more, e.g., 80% or more, 85% or more, 90% or more, 95% or more, 97% or more, and up to 100% identical to the Km1 allotype of Ig kappa light chain having the amino acid sequence set forth in SEQ ID NO:1, where position 45 is V and position 83 is L. In some cases, the antibody contains an Ig light chain polypeptide that includes a constant region amino acid sequence, exclusive of any tags, that is 75% or more, e.g., 80% or more, 85% or more, 90% or more, 95% or more, 97% or more, and up to 100% identical to the Km1,2 allotype of Ig kappa light chain having the amino acid sequence set forth in SEQ ID NO:1, where position 83 is L. In some cases, the antibody contains an Ig light chain polypeptide that includes a constant region amino acid sequence, exclusive of any tags, that is 75% or more, e.g., 80% or more, 85% or more, 90% or more, 95% or more, 97% or more, and up to 100% identical to the Km3 allotype of Ig kappa light chain having the amino acid sequence set forth in SEQ ID NO:1.

In some cases, the tag is positioned within or adjacent a solvent-accessible region of the Ig light chain polypeptide, and in some cases, the tag is not positioned within or adjacent a solvent-accessible region of the Ig light chain polypeptide. Solvent accessible loop of an antibody can be identified by molecular modeling, or by comparison to a known antibody structure. The relative accessibility of amino acid residues can also be calculated using a method of DSSP (Dictionary of Secondary Structure in Proteins; Kabsch and Sander 1983 Biopolymers 22: 2577-637) and solvent accessible surface area of an amino acid may be calculated based on a 3-dimensional model of an antibody, using algorithms known in the art (e.g., Connolly, J. Appl. Cryst. 16, 548 (1983) and Lee and Richards, J. Mol. Biol. 55, 379 (1971), both of which are incorporated herein by reference). Exemplary solvent-accessible loop regions of an Ig light chain (e.g., a human kappa light chain) include: 1) TVAAP (SEQ ID NO:464); 2) PPS; 3) Gly (see, e.g., Gly at position 20 of the human kappa light chain sequence set forth in SEQ ID NO:1, depicted in FIG. 9); 4) YPREA (SEQ ID NO:465); 5) PREA (SEQ ID NO:466); 6) DNALQSGN (SEQ ID NO:467); 7) TEQDSKDST (SEQ ID NO:468); 8) HK; 9) HQGLSS (SEQ ID NO:469); and 10) RGEC (SEQ ID NO:470), as shown in FIG. 9.

The tag of the present disclosure is positioned in the constant region of an Ig light chain polypeptide, e.g., Ig kappa light chain polypeptide, of an antibody so as to provide for an antibody having desirable properties that meet one or more threshold criteria when the antibody includes the tagged, or aldehyde tagged, Ig light chain polypeptide, as described above. An antibody of the present disclosure provides for an antibody titer of about 5 mg/L or greater, and, when the tag is converted, provides for a conjugation efficiency, represented by the average molar ratio of payload to antibody (PAR, e.g., drug-to-antibody ratio (DAR)), of about 0.5 or greater. Thus, the antibody may include a tag in an Ig light chain polypeptide, where the tag contains an amino acid sequence of the formula $X^1Z^1X^2Z^2X^3Z^3$ (SEQ ID NO: 478), where $X^1$, $X^2$, $X^3$, $Z^1$, $Z^2$ and $Z^3$ are as described above, and where the Ig light chain polypeptide includes a constant region containing any one or more (e.g., two or more, or three or more) of the amino acid sequences set forth in SEQ ID NOs:46-82, shown in Table 1. In some embodiments, $Z^3$ is arginine. In some embodiments, $X^1$ is glycine, leucine, isoleucine, methionine, histidine, tyrosine, valine, serine, cysteine or threonine. In some embodiments, $X^2$ and $X^3$ are each independently serine, threonine, alanine, valine, glycine or cysteine. In some embodiments, the tag includes the amino acid sequence LCTPSR (SEQ ID NO:158). In certain embodiments, the Ig light chain polypeptide includes a constant region containing any one or more (e.g., two or more, including three or more) of the amino acid sequences set forth in SEQ ID NOs:83-119, shown in Table 2.

TABLE 1

| Label | Sequence | SEQ ID NO: |
|---|---|---|
| 1T | TX$^1$Z$^1$X$^2$Z$^2$X$^3$Z$^3$VA | 46 |
| 2V | TVX$^1$Z$^1$X$^2$Z$^2$X$^3$Z$^3$AA | 47 |
| 3A | VAX$^1$Z$^1$X$^2$Z$^2$X$^3$Z$^3$AP | 48 |
| 4A | AAX$^1$Z$^1$X$^2$Z$^2$X$^3$Z$^3$PSV | 49 |
| 5P | APX$^1$Z$^1$X$^2$Z$^2$X$^3$Z$^3$SVF | 50 |
| 6S | PSX$^1$Z$^1$X$^2$Z$^2$X$^3$Z$^3$VF | 51 |
| 19S | KSX$^1$Z$^1$X$^2$Z$^2$X$^3$Z$^3$GT | 52 |
| 20G | KSGX$^1$Z$^1$X$^2$Z$^2$X$^3$Z$^3$TA | 53 |
| 21T | GTX$^1$Z$^1$X$^2$Z$^2$X$^3$Z$^3$AS | 54 |
| 22A | TAX$^1$Z$^1$X$^2$Z$^2$X$^3$Z$^3$SVV | 55 |
| 29N | LNX$^1$Z$^1$X$^2$Z$^2$X$^3$Z$^3$NF | 56 |
| 30N | NNX$^1$Z$^1$X$^2$Z$^2$X$^3$Z$^3$FY | 57 |
| 31F | NFX$^1$Z$^1$X$^2$Z$^2$X$^3$Z$^3$YP | 58 |
| 32Y | FYX$^1$Z$^1$X$^2$Z$^2$X$^3$Z$^3$PR | 59 |
| 42V | WKVX$^1$Z$^1$X$^2$Z$^2$X$^3$Z$^3$DN | 60 |
| 43D | VDX$^1$Z$^1$X$^2$Z$^2$X$^3$Z$^3$N[A/V] | 61 |
| 45A | N[A/V]X$^1$Z$^1$X$^2$Z$^2$X$^3$Z$^3$LQ | 62 |
| 46L | [A/V]LX$^1$Z$^1$X$^2$Z$^2$X$^3$Z$^3$QS | 63 |
| 47Q | LQX$^1$Z$^1$X$^2$Z$^2$X$^3$Z$^3$SGN | 64 |
| 48S | QSX$^1$Z$^1$X$^2$Z$^2$X$^3$Z$^3$GN | 65 |
| 49G | QSGX$^1$Z$^1$X$^2$Z$^2$X$^3$Z$^3$NS | 66 |
| 50N | GNX$^1$Z$^1$X$^2$Z$^2$X$^3$Z$^3$SQ | 67 |
| 51S | NSX$^1$Z$^1$X$^2$Z$^2$X$^3$Z$^3$QE | 68 |
| 52Q | SQX$^1$Z$^1$X$^2$Z$^2$X$^3$Z$^3$ES | 69 |
| 60S | QDSX$^1$Z$^1$X$^2$Z$^2$X$^3$Z$^3$KD | 70 |
| 62D | KDX$^1$Z$^1$X$^2$Z$^2$X$^3$Z$^3$STY | 71 |
| 63S | KDSX$^1$Z$^1$X$^2$Z$^2$X$^3$Z$^3$TY | 72 |
| 64T | DSTX$^1$Z$^1$X$^2$Z$^2$X$^3$Z$^3$YS | 73 |
| 65Y | TYX$^1$Z$^1$X$^2$Z$^2$X$^3$Z$^3$SL | 74 |
| 89T | EVTX$^1$Z$^1$X$^2$Z$^2$X$^3$Z$^3$HQ | 75 |
| 90H | THX$^1$Z$^1$X$^2$Z$^2$X$^3$Z$^3$QG | 76 |
| 91Q | HQX$^1$Z$^1$X$^2$Z$^2$X$^3$Z$^3$GL | 77 |
| 92G | QGX$^1$Z$^1$X$^2$Z$^2$X$^3$Z$^3$LSSP | 78 |
| 93L | GLX$^1$Z$^1$X$^2$Z$^2$X$^3$Z$^3$SS | 79 |
| 94S | GLSX$^1$Z$^1$X$^2$Z$^2$X$^3$Z$^3$SP | 80 |
| 95S | GLSSX$^1$Z$^1$X$^2$Z$^2$X$^3$Z$^3$PV | 81 |
| 96P | SPX$^1$Z$^1$X$^2$Z$^2$X$^3$Z$^3$VT | 82 |

([*/*]denotes alternative amino acids (or amino acid sequences) chosen from the amino acid residues (or sequences) separated by "/".)

TABLE 2

| ID | Sequence | SEQ ID NO: |
|---|---|---|
| 1T | TLCTPSRVA | 83 |
| 2V | TVLCTPSRAA | 84 |
| 3A | VALCTPSRAP | 85 |
| 4A | AALCTPSRPSV | 86 |
| 5P | APLCTPSRSVF | 87 |
| 6S | PSLCTPSRVF | 88 |
| 19S | KSLCTPSRGT | 89 |
| 20G | KSGLCTPSRTA | 90 |
| 21T | GTLCTPSRAS | 91 |
| 22A | TALCTPSRSVV | 92 |
| 29N | LNLCTPSRNF | 93 |
| 30N | NNLCTPSRFY | 94 |
| 31F | NFLCTPSRYP | 95 |
| 32Y | FYLCTPSRPR | 96 |
| 42V | WKVLCTPSRDN | 97 |
| 43D | VDLCTPSRN[A/V] | 98 |

TABLE 2-continued

| ID | Sequence | SEQ ID NO: |
|---|---|---|
| 45A | N[A/V]LCTPSRLQ | 99 |
| 46L | [A/V]LLCTPSRQS | 100 |
| 47Q | LQLCTPSRSGN | 101 |
| 48S | QSLCTPSRGN | 102 |
| 49G | QSGLCTPSRNS | 103 |
| 50N | GNLCTPSRSQ | 104 |
| 51S | NSLCTPSRQE | 105 |
| 52Q | SQLCTPSRES | 106 |
| 60S | QDSLCTPSRKD | 107 |
| 62D | KDLCTPSRSTY | 108 |
| 63S | KDSLCTPSRTY | 109 |
| 64T | DSTLCTPSRYS | 110 |
| 65Y | TYLCTPSRSL | 111 |
| 89T | EVTLCTPSRHQ | 112 |
| 90H | THLCTPSRQG | 113 |
| 91Q | HQLCTPSRGL | 114 |
| 92G | QGLCTPSRLSSP | 115 |
| 93L | GLLCTPSRSS | 116 |
| 94S | GLSLCTPSRSP | 117 |
| 95S | GLSSLCTPSRPV | 118 |
| 96P | SPLCTPSRVT | 119 |

([*/*] denotes alternative amino acids (or amino acid sequences) chosen from the amino acid residues (or sequences) separated by "/".)

As described above, the tag may be positioned between two consecutive amino acids in the constant region of a corresponding parent Ig light chain polypeptide, e.g., the Ig light chain polypeptide without the tag in the constant region. Thus, the position of the tag in the Ig light chain amino acid sequence may be defined by the position of the most C-terminal amino acid of the amino acid sequence flanking the tag at its N-terminal end. In some embodiments, the tag is positioned adjacent and C-terminal to an amino acid residue, of an Ig kappa light chain polypeptide, corresponding to one or more (e.g., two or more, including three or more) of residues 1, 2, 3, 4, 5, 6, 19, 20, 21, 22, 29, 30, 31, 32, 42, 43, 45, 46, 47, 48, 49, 50, 51, 52, 60, 62, 63, 64, 65, 89, 90, 91, 92, 93, 94, 95, or 96 of SEQ ID NO:1.

The parent Ig light chain polypeptide may be modified to insert the tag in the amino acid sequence of the constant region such that an antibody that includes the tag in its Ig light chain polypeptide achieves an antibody titer of about 5 mg/L or greater, and/or a conjugation efficiency expressed by the average amount of conjugated moieties (e.g., drugs) relative to the total amount of antibody (e.g., DAR, where the payload is a drug) of about 0.5 or greater. Insertion sites of interest in an Ig light chain polypeptide include the position immediately C-terminal to an amino acid residue, of an Ig kappa light chain polypeptide, corresponding to one or more (e.g., two or more, including three or more) of positions 1, 2, 3, 4, 5, 6, 19, 20, 21, 22, 29, 30, 31, 32, 42, 43, 45, 46, 47, 48, 49, 50, 51, 52, 60, 62, 63, 64, 65, 89, 90, 91, 92, 93, 94, 95, or 96, of SEQ ID NO:1.

In certain embodiments, an antibody of the present disclosure provides for an antibody titer of about 5 mg/L or greater, and, when the tag is converted, a conjugation efficiency (e.g., DAR) of about 1.3 or greater. In some embodiments, the antibody includes a tagged Ig light chain polypeptide, where the tag contains an amino acid sequence of the formula $X^1Z^1X^2Z^2X^3Z^3$ (SEQ ID NO: 478), where $X^1$, $X^2$, $X^3$, $Z^1$, $Z^2$ and $Z^3$ are as described above, and where the Ig light chain polypeptide includes a constant region containing any one or more (e.g., two or more, including three or more) of the amino acid sequences set forth in SEQ ID NOs:47, 49, 50, 53-55, 63, 65-68, 74, 77, 79, 81, and 82, of Table 1. In some embodiments, $Z^3$ is arginine. In some embodiments, $X^1$ is glycine, leucine, isoleucine, methionine, histidine, tyrosine, valine, serine, cysteine or threonine. In some embodiments, $X^2$ and $X^3$ are each independently serine, threonine, alanine, valine, glycine or cysteine. In some embodiments, the tag includes the amino acid sequence LCTPSR (SEQ ID NO:158). In certain embodiments, the Ig light chain polypeptide includes a constant region containing any one or more (e.g., two or more, including three or more) of the amino acid sequences set forth in SEQ ID NOs:84, 86, 87, 90-92, 100, 102-105, 111, 114, 116, 118 and 119, of Table 2.

The tag may be positioned between two consecutive amino acids in the constant region of a corresponding parent Ig light chain polypeptide, e.g., the Ig light chain polypeptide without the tag in the constant region. Thus, the position of the tag in the Ig light chain amino acid sequence may be defined by the position of the most C-terminal amino acid of the amino acid sequence flanking the tag at its N-terminal end. In some embodiments, the tag is positioned adjacent and C-terminal to an amino acid residue, of an Ig kappa light chain polypeptide, corresponding to one or more (e.g., two or more, including three or more) of residues 2, 4, 5, 20, 21, 22, 46, 48, 49, 50, 51, 65, 91, 93, 95, or 96, of SEQ ID NO:1.

In some cases, the parent Ig light chain polypeptide is modified to insert the tag in the amino acid sequence of the constant region such that an antibody that includes the tag in its Ig light chain polypeptide provides for an antibody titer of about 15 mg/L or greater, and, when the tag is converted, provides for a conjugation efficiency (e.g., DAR) of about 1.3 or greater. Insertion sites of interest in an Ig light chain polypeptide include the position immediately C-terminal to an amino acid residue of an Ig kappa light chain polypeptide corresponding to one or more (e.g., two or more, including three or more) of positions 2, 4, 5, 20, 21, 22, 46, 48, 49, 50, 51, 65, 91, 93, 95, or 96, of SEQ ID NO:1.

In some embodiments, the tagged Ig light chain polypeptide may include two or more, such as three or more, tags in the constant region amino acid sequence. Where the Ig light chain polypeptide includes two or more, such as three or more, tags in the constant region amino acid sequence, the position of the tags may be any two or more, such as three or more sites adjacent and C-terminal to an amino acid residue, of an Ig kappa light chain polypeptide, corresponding to one or more (e.g., two or more, including three or more) of residues 2, 4, 5, 20, 21, 22, 46, 48, 49, 50, 51, 65, 91, 93, 95, or 96, of SEQ ID NO:1, provided that there is a sufficient number of amino acid residues corresponding to the parent Ig polypeptide amino acid sequence between any two tags such that the tags do not overlap with each other.

An antibody of the present disclosure generally includes a tagged Ig light chain polypetpide constant region, as described herein, and a variable region ($V_L$), and includes an Ig heavy chain having a constant region ($C_H1$, H, $C_H2$, $C_H3$ regions) and a variable region ($V_H$), where the antibody binds an antigen. In other words, the tagged Ig light chain polypetpide forms an antigen-binding antibody when suitably combined with an Ig heavy chain polypeptide. The Ig heavy chain constant region can include heavy chain constant region sequences of an IgA, IgM, IgD, IgE, $IgG_1$, $IgG_2$, $IgG_3$, or $IgG_4$ isotype heavy chain or any allotypic variant of same, e.g., human heavy chain constant region sequences or mouse heavy chain constant region sequences, a hybrid heavy chain constant region, a synthetic heavy chain constant region, or a consensus heavy chain constant region sequence, etc. The Ig heavy chain can include one or more modifications, e.g., glycosylation, and the like.

In some embodiments, the present antibody includes an Ig heavy chain that does not include a tag, e.g., does not include a tag in the heavy chain constant region. In some embodiments, the antibody includes an Ig heavy chain having one or more, e.g., two or more, including three or more tags, i.e., a tag containing a sulfatase motif, where the tag is positioned within or adjacent a solvent-accessible loop region of the Ig heavy chain constant region. Any suitable Ig heavy chain polypeptides with a tag in the constant region may be used. Suitable Ig heavy chain polypeptides with a tag (i.e., an FGE substrate motif) in the constant region are described in, e.g., US20120183566, which is incorporated herein by reference.

In certain embodiments, an antibody of the present disclosure includes an Ig light chain polypeptide containing an amino acid sequence at least 90%, e.g., at least 95%, at least 97%, at least 99%, including 100% identical to any one of the sequences set forth in SEQ ID NOs:2-7 and 15-45, shown in FIGS. 10A-10D, where the amino acid sequence includes the tag, i.e., the FGE substrate motif: LCTPSR (SEQ ID NO:158). The antibody having a tagged Ig light chain polypeptide may exhibit an antibody titer of about 5 mg/L or greater, e.g., about 10 mg/L or greater, about 15 mg/L or greater, about 20 mg/L or greater, or about 30 mg/L or greater, and, when the tag is converted, a conjugation efficiency (e.g., DAR) of, in some cases, about 0.5 or greater, e.g., about 1.0 or greater, or about 1.3 or greater. The Ig light chain polypeptide may include a variable region ($V_L$), and the antibody may include an Ig heavy chain having a constant region (e.g., an Fc region) and a variable region ($V_H$). The Ig heavy chain constant region can include heavy chain constant region sequences of any suitable isotype (e.g., IgA, IgM, IgD, IgE, $IgG_1$, $IgG_2$, $IgG_3$, or $IgG_4$), allotypic variant of same; human, mouse, hybrid, synthetic, or consensus heavy chain constant region sequences; modified (e.g., glycosylated) heavy chain constant region, etc. In some cases, the Ig heavy chain constant region includes one or more tags.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 1 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:2 ("1T" in FIG. 10A), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tag in its Ig light chain polypeptide may exhibit an antibody titer of about 5 mg/L or greater, e.g., about 10 mg/L or greater, about 15 mg/L or greater, about 20 mg/L or greater, including about 30 mg/L or greater, and, when the tag is converted, a conjugation efficiency (e.g., DAR) of about 0.5 or greater, including about 1.0 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 2 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:3 ("2V" in FIG. 10A), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, including about 20 mg/L or greater, and, when the tag is converted, a conjugation efficiency (e.g., DAR) of about 0.5 or greater, e.g., about 1.0 or greater, about 1.3 or greater, including about 1.6 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 3 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:4 ("3A" in FIG. 10A), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, about 20 mg/L, including about 30 mg/L or greater, and, when the tag is converted, a conjugation efficiency (e.g., DAR) of about 0.5 or greater, including about 1.0 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 4 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:5 ("4A" in FIG. 10A), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, including about 20 mg/L or greater, and, when the tag is converted, a conjugation efficiency (e.g., DAR) of about 0.5 or greater, e.g., about 1.0 or greater, including about 1.3 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 5 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:6 ("5P" in FIG. 10A), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, including about 15 mg/L, and, when the tag is converted, a conjugation efficiency (e.g., DAR) of about 0.5 or greater, e.g., about 1.0 or greater, including about 1.3 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478), inserted adjacent and C-terminal to the amino acid residue at position 6 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:7 ("6S" in FIG. 10A), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, including about 20 mg/L or greater, and, when the tag is converted, a conjugation efficiency (e.g., DAR) of about 0.5 or greater, including about 1.0 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 19 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:15 ("19S" in FIG. 10A), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, including about 20 mg/L or greater, and, when the tag is converted, a conjugation efficiency (e.g., DAR) of about 0.5 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 20 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:16 ("20G" in FIG. 10A), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, including about 20 mg/L or greater, and, when the tag is converted, a conjugation efficiency (e.g., DAR) of about 0.5 or greater, e.g., about 1.0 or greater, including about 1.3 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 21 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:17 ("21T" in FIG. 10A), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, including about 20 mg/L or greater, and, when the tag is converted, a conjugation efficiency (e.g., DAR) of about 0.5 or greater, e.g., about 1.0 or greater, about 1.3 or greater, including about 1.6 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 22 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:18 ("22A" in FIG. 10A), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, including about 20 mg/L or greater, and, when the tag is converted, a conjugation efficiency (e.g., DAR) of about 0.5 or greater, e.g., about 1.0 or greater, about 1.3 or greater, including about 1.6 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 29 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:19 ("29N" in FIG. 10B), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, including about 15 mg/L or greater, and, when the tag is converted, a conjugation efficiency (e.g., DAR) of about 0.5 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 30 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:20 ("30N" in FIG. 10B), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, including about 20 mg/L or greater, and, when the tag is converted, a conjugation efficiency (e.g., DAR) of about 0.5 or greater, including about 1.0 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 31 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:21 ("31F" in FIG. 10B), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, about 20 mg/L or greater, including 30 mg/L or greater, and, when the tag is converted, a conjugation efficiency (e.g., DAR) of about 0.5 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 32 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:22 ("32Y" in FIG. 10B), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, including about 15 mg/L or greater, and, when the tag is converted, a conjugation efficiency (e.g., DAR) of about 0.5 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 42 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:23 ("42V" in FIG. 10B), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, including about 20 mg/L or greater, and, when the tag is converted, a conjugation efficiency (e.g., DAR) of about 0.5 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 43 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:24 ("43D" in FIG. 10B), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, about 20 mg/L or greater, including 30 mg/L or greater, and, when the tag is converted, a conjugation efficiency (e.g., DAR) of about 0.5 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 45 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:25 ("45A" in FIG. 10B), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, about 20 mg/L or greater, including 30 mg/L or greater, and, when the tag is converted, a conjugation efficiency (e.g., DAR) of about 0.5 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 46 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:26 ("46L" in FIG. 10B), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, and, when the tag is converted, a conjugation efficiency (e.g., DAR) of about 0.5 or greater, e.g., about 1.0 or greater, including about 1.3 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 47 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:27 ("47Q" in FIG. 10B), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, about 20 mg/L or greater, including about 30 mg/L or greater, and, when the tag is converted, a conjugation efficiency (e.g., DAR) of about 0.5 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 48 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:28 ("48S" in FIG. 10B), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, about 20 mg/L or greater, including about 30 mg/L or greater, and, when the tag is converted, a conjugation efficiency (e.g., DAR) of about 0.5 or greater, e.g., about 1.0 or greater, including about 1.3 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 49 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:29 ("49G" in FIG. 10C), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, about 20 mg/L or greater, including about 30 mg/L or greater, and, when the tag is converted, a conjugation efficiency (e.g., DAR) of about 0.5 or greater, e.g., about 1.0 or greater, including about 1.3 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 50 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:30 ("50N" in FIG. 10C), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, about 20 mg/L or greater, including about 30 mg/L or greater, and, when the tag is converted, a conjugation efficiency (e.g., DAR) of about 0.5 or greater, e.g., about 1.0 or greater, including about 1.3 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478), inserted adjacent and C-terminal to the amino acid residue at position 51 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:31 ("51S" in FIG. 10C), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, about 20 mg/L or greater, including about 30 mg/L or greater, and, when the tag is converted, a conjugation efficiency (e.g., DAR) of about 0.5 or greater, e.g., about 1.0 or greater, including about 1.3 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 52 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:32 ("52Q" in FIG. 10C), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, including about 20 mg/L or greater, and, when the tag is converted, a conjugation efficiency (e.g., DAR) of about 0.5 or greater, including about 1.0 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 60 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:33 ("60S" in FIG. 10C), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, about 20 mg/L or greater, including about 30 mg/L or greater, and, when the tag is converted, a conjugation efficiency (e.g., DAR) of about 0.5 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 62 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:34 ("62D" in FIG. 10C), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, about 20 mg/L or greater, including about 30 mg/L or greater, and, when the tag is converted, a conjugation efficiency (e.g., DAR) of about 0.5 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 63 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:35 ("63S" in FIG. 10C), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, including about 20 mg/L or greater, and, when the tag is converted, a conjugation efficiency (e.g., DAR) of about 0.5 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 64 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:36 ("64T" in FIG. 10C), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, about 20 mg/L or greater, including about 30 mg/L or greater, and, when the tag is converted, a conjugation efficiency (e.g., DAR) of about 0.5 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 65 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:37 ("65Y" in FIG. 10C), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, including about 15 mg/L or greater, and, when the tag is converted, a conjugation efficiency (e.g., DAR) of about 0.5 or greater, e.g., about 1.0 or greater, including about 1.3 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 89 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:38 ("89T" in FIG. 10C), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, including about 20 mg/L or greater, and, when the tag is converted, a conjugation efficiency (e.g., DAR) of about 0.5 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 90 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:39 ("90H" in FIG. 10D), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, including about 15 mg/L or greater, and, when the tag is converted, a conjugation efficiency (e.g., DAR) of about 0.5 or greater, including about 1.0 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 91 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO40 ("91Q" in FIG. 10D), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, including about 15 mg/L or greater, and, when the tag is converted, a conjugation efficiency (e.g., DAR) of about 0.5 or greater, e.g., about 1.0 or greater, including about 1.3 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) adjacent and C-terminal to the amino acid residue at position 92 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:41 ("92G" in FIG. 10D), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, including about 20 mg/L or greater, and, when the tag is converted, a conjugation efficiency (e.g., DAR) of about 0.5 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 93 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:42 ("93L" in FIG. 10D), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, including about 15 mg/L or greater, and, when the tag is converted, a conjugation efficiency (e.g., DAR) of about 0.5 or greater, e.g., about 1.0 or greater, including about 1.3 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 94 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:43 ("94S" in FIG. 10D), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, including about 15 mg/L or greater, and, when the tag is converted, a conjugation efficiency (e.g., DAR) of about 0.5 or greater, including about 1.0 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 95 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:44 ("95S" in FIG. 10D), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, including about 15 mg/L or greater, and, when the tag is converted, a conjugation efficiency (e.g., DAR) of about 0.5 or greater, e.g., about 1.0 or greater, including about 1.3 or greater.

In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:1, where the Ig light chain polypeptide constant region contains a tag of the formula $X^1Z^1X^2Z^2X^3Z^3$ (SEQ ID NO: 478) inserted adjacent and C-terminal to the amino acid residue at position 96 of SEQ ID NO:1, where $X^1$, $X^2$, $X^3$, $Z^1$, $Z^2$ and $Z^3$ are as described above. In some embodiments, the antibody is a modified antibody, where fGly is at $Z^1$. In some cases, the antibody is part of an antibody conjugate, where fGly' is positioned at $Z^1$, where fGly' is an fGly conjugated to a payload (e.g., drug). In certain embodiments, an antibody of the present disclosure includes an Ig light chain polypeptide containing a constant region amino acid sequence at least 90%, e.g., at least 95%, at least 97%, at least 99%, including 100% identical to the sequence set forth in SEQ ID NO:45 ("96P" in FIG. 10D), where the amino acid sequence includes the tag: LCTPSR (SEQ ID NO:158). In some embodiments, the antibody is a modified antibody, where the tag is converted to L(fGly)TPSR (SEQ ID NO:157). In some embodiments, the antibody is part of an antibody conjugate, where the tag is L(fGly')TPSR (SEQ ID NO: 226), where fGly' is an fGly conjugated to a payload (e.g., drug). The antibody having the tagged Ig light chain polypeptide may exhibit an antibody titer of about 5 mg/L or greater, e.g., about 10 mg/L or greater, about 15 mg/L or greater, including about 20 mg/L or greater, and, when the tag is converted, a conjugation efficiency (e.g., DAR) of about 0.5 or greater, e.g., about 1.0 or greater, about 1.3 or greater, including about 1.6 or greater.

The antibody of the present disclosure, or a modified form thereof (e.g., fGly-modified antibody or antibody conjugate), as described herein, may be provided in a suitable composition. Thus, the present disclosure provides a composition that includes an antibody, e.g., a plurality of members of an antibody, or a modified form thereof, of the present disclosure. The composition may include any other suitable components (e.g., buffers, stabilizers, preservatives, and the like) that are compatible with the antibody, or the modified form thereof. In some cases, the composition includes an aqueous medium, such as water, or an aqueous buffer. In some cases, the composition includes a suitable salt (i.e., is a saline solution). In some embodiments, the composition is a reconstitutable storage-stable powder or liquid composed of the present antibody and optionally any buffer or salt components. In some cases, the composition is a pharmaceutical composition, as described further below.

An antibody of the present disclosure can have any of a variety of antigen-binding specificities. The antibody can bind any of a variety of antigens, including, e.g., an antigen present on a cancer cell; an antigen present on an autoimmune cell; an antigen present on a pathogenic microorganism; an antigen present on a virus-infected cell (e.g., a human immunodeficiency virus-infected cell), e.g., CD4 or gp120; an antigen present on a diseased cell; and the like. For example, the present antibody can bind an antigen, as noted above, where the antigen is present on the surface of the cell.

For example, an antibody of the present disclosure can specifically bind an antigen present on a cancer cell. Non-limiting examples of cancer antigens that can be recognized and bound (e.g., specifically bound) by an antibody of the present disclosure include antigens present on carcinomas, prostate cancer cells, breast cancer cells, colorectal cancer cells, melanoma cells, T-cell leukemia cells, T-cell lymphoma cells, B-cell lymphoma cells, non-Hodgkin's lymphoma cells, and the like.

Non-limiting examples of antigens present on particular cancer cells include, e.g., CA125, CA15-3, CA19-9, L6, Lewis Y, Lewis X, alpha fetoprotein, CA 242, placental alkaline phosphatase, prostate specific antigen, prostatic acid phosphatase, epidermal growth factor, MAGE-1, MAGE-2, MAGE-3, MAGE-4, anti-transferrin receptor, p97, MUC1-KLH, HER2, CEA, gp100, MART1, prostate-specific antigen, human chorionic gonadotropin, IL-2 receptor, EphB2, CD19, CD20, CD22, CD52, CD33, CD38, CD40, mucin, P21, MPG, and Neu oncogene product. In some embodiments, the antigen is CD19. In other embodiments, the antigen is CD22.

Non-limiting examples of antibodies that can be modified to include a tag, as described herein, include, but are not limited to, an anti-CD19 antibody, and an anti-CD22 antibody.

fGly-Modified Antibodies

A tagged antibody, as described above, may be modified, e.g., by oxidation of the side chain of a cysteine or serine residue in the tag into an aldehyde side chain, such that the tag is converted to a converted tag containing a 2-formylglycine residue (fGly), as described above, to generate a fGly-modified antibody. Where the Ig light chain polypeptide includes a tag containing a formylglycine generating enzyme (FGE) substrate motif of formula I, as described above, $Z^1$ may be modified to fGly through the action of FGE, to generate a converted tag that includes an amino acid sequence of the formula $X^1(fGly)X^2Z^2X^3Z^3$, where $X^1$, $X^2$, $X^3$, $Z^2$, and $Z^3$ are as described above.

The enzyme that oxidizes cysteine or serine in a sulfatase motif to fGly is referred to herein as a formylglycine generating enzyme (FGE). As discussed above, "FGE" is used herein to refer to fGly-generating enzymes that mediate conversion of a cysteine (C) of a sulfatase motif to fGly as well as fGly-generating enzymes that mediate conversion of serine (S) of a sulfatase motif to fGly. It should be noted that in general, the literature refers to fGly-generating enzymes that convert a C to fGly in a sulfatase motif as FGEs, and refers to enzymes that convert S to fGly in a sulfatase motif as Ats-B-like. However, for purposes of the present disclosure "FGE" is used generically to refer to both types of fGly-generating enzymes, with the understanding that an appropriate FGE will be selected according to the target reactive partner containing the appropriate sulfatase motif (i.e., C-containing or S-containing).

In general, the FGE used to facilitate conversion of cysteine or serine to fGly in a sulfatase motif of a tag of a target polypeptide is selected according to the sulfatase motif present in the tag. The FGE can be native to the host cell in which the tag-containing polypeptide is expressed, or the host cell can be genetically modified to express an appropriate FGE. In some embodiments it may be desired to use a sulfatase motif compatible with a human FGE (e.g., the SUMF1-type FGE, see, e.g., Cosma et al. Cell 113, 445-56 (2003); Dierks et al. Cell 113, 435-44 (2003)), and express the aldehyde tagged protein in a human cell that expresses the FGE or in a host cell, usually a mammalian cell, genetically modified to express a human FGE.

In general, an FGE for use in the methods disclosed herein can be obtained from naturally occurring sources or synthetically produced. For example, an appropriate FGE can be derived from biological sources which naturally produce an FGE or which are genetically modified to express a recombinant gene encoding an FGE. Nucleic acids encoding a number of FGEs are known in the art and readily available (see, e.g., Preusser et al. 2005 J. Biol. Chem. 280(15):14900-10 (Epub 2005 Jan. 18); Fang et al. 2004 J Biol Chem. 79(15):14570-8 (Epub 2004 Jan. 28); Landgrebe et al. Gene. 2003 Oct 16; 316:47-56; Dierks et al. 1998 FEBS Lett. 423(1):61-5; Dierks et al. Cell. 2003 May 16; 113(4):435-44; Cosma et al. (2003 May 16) Cell 113(4):445-56; Baenziger (2003 May 16) Cell 113(4):421-2 (review); Dierks et al. Cell. 2005 May 20; 121(4):541-52; Roeser et al. (2006 Jan. 3)Proc Natl Acad Sci USA 103(1):81-6; Sardiello et al. (2005 Nov. 1) Hum Mol Genet. 14(21):3203-17; WO 2004/072275; WO 2008/036350; U.S. Patent Publication No. 2008/0187956; and GenBank Accession No. NM_182760. Accordingly, the disclosure here provides for recombinant host cells genetically modified to express an FGE that is compatible for use with a tag of a target polypeptide. In certain embodiments, the FGE used may be a naturally occurring enzyme (may have a wild type amino acid sequence). In other embodiments, the FGE used may be non-naturally occurring, in which case it may, in certain cases, have an amino acid sequence that is at least 80% identical, at least 90% identical or at least 95% identical to that of a wild type enzyme. Because FGEs have been studied structurally and functionally and the amino acid sequences of several examples of such enzymes are available, variants that retain enzymatic activity should be readily designable.

Where a cell-free method is used to convert a sulfatase motif-containing polypeptide, an isolated FGE can be used. Any convenient protein purification procedures may be used to isolate an FGE, see, e.g., Guide to Protein Purification, (Deuthser ed.) (Academic Press, 1990). For example, a lysate may be prepared from a cell that produces a desired FGE, and purified using HPLC, exclusion chromatography, gel electrophoresis, affinity chromatography, and the like.

Any suitable method of generating a tagged antibody having a sulfatase motif in its Ig polypeptide, e.g., Ig light chain polypeptide, and converting the tag to include an fGly residue, may be used, e.g., as described in US20120183566, which is incorporated herein by reference.

Thus, the present disclosure includes an fGly-modified antibody that includes a converted tag in an fGly-modified Ig light chain polypeptide, e.g., fGly-modified Ig kappa light chain polypeptide, where the converted tag contains an amino acid sequence of the formula:

$$X^1(fGly)X^2Z^2X^3Z^3 \quad (II)$$

where fGly is a formylglycine residue; $Z^2$ is either a proline or alanine residue (which can also be represented by (P/A)); $Z^3$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), usually A, G, L, V, or I; $X^1$ is present or absent and, when present, can be any amino acid, though usually an aliphatic amino acid, a sulfur-containing amino acid, or a polar, uncharged amino acid, (i.e., other than a aromatic amino acid or a charged amino acid), usually L, M, V, S or T, more usually L, M, S or V; and $X^2$ and $X^3$ independently can be any amino acid, though usually an aliphatic amino acid, a polar, uncharged amino acid, or a sulfur containing amino acid (i.e., other than an aromatic amino acid or a charged amino acid), usually S, T, A, V, G or C, more usually S, T, A, V or G.

As the converted tag may be derived from an unconverted tag, e.g., through the oxidation of a cysteine or serine in the sulfatase motif of a tag via the action of FGE, the position of the converted tag may be defined by the position of the tag in the Ig light chain polypeptide, as described above. Thus in some embodiments, an fGly-modified antibody of the present disclosure includes an fGly-modified Ig light chain polypeptide that includes a converted tag having an amino acid sequence of the formula $X^1Z^1X^2Z^2X^3Z^3$ (SEQ ID NO: 478), where $X^1$, $X^2$, $X^3$, $Z^2$ and $Z^3$ are as described above, and where $Z^1$ is fGly, and where the fGly-modified Ig light chain polypeptide includes a constant region containing any one or more (e.g., two or more, including three or more) of the amino acid sequences set forth in SEQ ID NOs:46-82, shown in Table 1, where $Z^1$ is fGly and $X^1$, $X^2$, $X^3$, $Z^2$ and $Z^3$ are as described above. In some embodiments, the converted tag contained in the fGly-modified Ig light chain polypeptide has the amino acid sequence L(fGly)TPSR (SEQ ID NO:157). In some embodiments, the fGly-modified Ig light chain polypeptide includes a constant region containing any one or more (e.g., two or more, including three or more) of the amino acid sequences set forth in SEQ ID NOs:83-119, shown in Table 2, where Cys is substituted with fGly. As described above, the antibody containing a converted tag in an Ig light chain polypeptide constant region may exhibit a conjugation efficiency, represented by the average molar ratio of payload to antibody (e.g., drug to antibody (DAR)), of about 0.5 or greater.

In some cases, the present antibody containing an converted tag in an Ig light chain polypeptide constant region provides for a conjugation efficiency, represented by the average amount of conjugated moieties (e.g., drugs) relative to the total amount of antibody, of 1.3 or greater. In such cases, the fGly-modified Ig light chain polypeptide includes a constant region containing any one or more (e.g., two or more, including three or more) of the amino acid sequences set forth in SEQ ID NOs:47, 49, 50, 53-55, 63, 65-68, 74, 77, 79, 81, and 82, of Table 1, where $Z^1$ is fGly and $X^1$, $X^2$, $X^3$, $Z^2$ and $Z^3$ are as described above. In some cases, where the tag is LCTPSR (SEQ ID NO:158), the fGly-modified Ig light chain polypeptide includes a constant region containing any one or more (e.g., two or more, including three or more) of the amino acid sequences set forth in SEQ ID NOs:84, 86, 87, 90-92, 100, 102-105, 111, 114, 116, 118 and 119, of Table 2, where Cys is substituted with fGly.

Antibody Conjugates

An antibody containing an fGly-modified Ig light chain polypeptide, as described above, may be modified to covalently attach a moiety of interest (i.e., a payload, e.g., drug) to the antibody in a site-specific manner, to produce an antibody conjugate. As described above, the aldehyde moiety of the fGly residue in the converted tag of an Ig light chain polypeptide provides a bioorthogonal reactive side chain with which an aldehyde-reactive group attached to a payload, e.g., a drug functionalized with an aldehyde-reactive group, can react in a chemoselective manner to form a covalent bond between the payload (e.g., drug) and the Ig light chain polypeptide via the fGly residue, to form an Ig light chain polypeptide conjugate. A payload conjugated to an antibody of the present disclosure includes any suitable moiety (e.g., drug, detectable label, water soluble polymer, polypeptide, etc.) that, prior to conjugation to an fGly-modified antibody, can be functionalized to from an aldehyde-reactive reactive partner that includes an aldehyde-reactive group attached to the payload.

Thus, the present disclosure includes an antibody conjugate that includes a modified tag in an Ig light chain polypeptide conjugate, e.g., Ig kappa light chain polypeptide conjugate, where the modified tag contains an amino acid sequence of the formula:

$$X^1(fGly')X^2Z^2X^3Z^3 \quad (III)$$

where fGly' is a formylglycine residue modified with a payload (e.g., drug) covalently attached thereto; $Z^2$ is either a proline or alanine residue (which can also be represented by (P/A)); $Z^3$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), usually A, G, L, V, or I; $X^1$ is present or absent and, when present, can be any amino acid, though usually an aliphatic amino acid, a sulfur-containing amino acid, or a polar, uncharged amino acid, (i.e., other than a aromatic amino acid or a charged amino acid), usually L, M, V, S or T, more usually L, M, S or V; and $X^2$ and $X^3$ independently can be any amino acid, though usually an aliphatic amino acid, a polar, uncharged amino acid, or a sulfur containing amino acid (i.e., other than an aromatic amino acid or a charged amino acid), usually S, T, A, V, G or C, more usually S, T, A, V or G.

As the modified tag, having a payload (e.g., drug) conjugated thereto, may be derived from a converted tag, e.g., through the reaction of a aldehyde-reactive reactive partner containing the payload (e.g., drug with the aldehyde group of fGly, the position of the modified tag may be defined by the position of the converted tag in the Ig light chain polypeptide, which in turn may be defined by the position of the tag in the Ig light chain polypeptide, as described above. Thus in some embodiments, an antibody conjugate of the present disclosure includes an Ig light chain polypeptide conjugate that includes a modified tag having an amino acid sequence of the formula $X^1Z^1X^2Z^2X^3Z^3$ (SEQ ID NO: 478), where $X^1$, $X^2$, $X^3$, $Z^2$ and $Z^3$ are as described above, and where $Z^1$ is fGly', where fGly' is a formylglycine residue modified with a payload (e.g., drug) covalently attached thereto, and where the Ig light chain polypeptide conjugate includes a constant region containing any one of the amino acid sequences set forth in SEQ ID NOs:46-82, shown in Table 1, where $Z^1$ is fGly', where fGly' is a formylglycine residue modified with a payload (e.g., drug) covalently attached thereto, and where $X^1$, $X^2$, $X^3$, $Z^2$ and $Z^3$ are as described above. In some embodiments, the antibody conjugate includes an Ig light chain polypeptide conjugate having the amino acid sequence L(fGly')TPSR (SEQ ID NO: 226) in the constant region. In some embodiments, the Ig light chain polypeptide conjugate includes a constant region containing any one of the amino acid sequences set forth in SEQ ID NOs:83-119, shown in Table 2, where Cys is substituted with fGly', where fGly' is a formylglycine residue modified with a payload (e.g., drug) covalently attached thereto.

The structure of fGly' may vary, and may depend on the structure of the aldehyde-reactive group used to react a reactive partner containing the payload (e.g., drug) with the aldehyde side chain of the fGly residue in a converted tag of an fGly-modified Ig light chain polypeptide. fGly' may include any suitable linkage between the Ig polypeptide backbone and the payload (e.g., drug). In some cases, the payload (e.g., drug) is covalently bound to the converted tag through the fGly, which is modified, through its reaction with the aldehyde-reactive group, to form a hydrazone, oxime, semicarbazone (e.g., thiosemicarbozone), alkyl, alkenyl, acyloxy, hydrazinyl-indolyl, hydrazinyl-imidazoyl, hydrazinyl-pyrrolyl, hydrazinyl-furanyl or a pyrazalinone-derived linkage, and derivatives of such linkages, with the payload (e.g., drug). A hydrazinyl-indolyl linkage may include, e.g., a partially unsaturated pyrazole or pyridazine ring, or a partially unsaturated pyridazine or 1,2-diazepine ring. A pyrazalinone-derived linkage may include a cyclic linkage derived from a pyrazalinone. In some cases, a hydrazinyl-substituted heteroaryl ring-derived linkage includes a cyclic linkage derived from, e.g., a hydrazinyl-substituted 5-membered heteroaryl ring compound, where one or more atoms in the ring is a heteroatom (e.g., N, O or S). The hydrazinyl-substituted heteroaryl ring-derived linkage may include a hydrazinyl-imidazoyl, hydrazinyl-pyrrolyl, or a hydrazinyl-furanyl linkage. Suitable linkages between the fGly of a converted tag and the payload are described in, e.g., US20120183566, US20140141025, and WO2014074218, each of which is incorporated herein by reference.

The payload (e.g., drug), in some cases, may be covalently bound to the fGly of a converted tag via one or more linking groups, in addition to the covalent linkage formed by a reaction between the aldehyde-reactive group and the aldehyde group of fGly of the converted tag. Thus the linking group may serve as a spacer between the payload (e.g., drug) and the covalent linkage with the modified fGly of the tag in the Ig light chain polypeptide conjugate. The linking group may be any suitable linking group. In some cases, the linking group includes polyethylene glycol (PEG); amino acids; alkyl groups, including substituted alkyl groups; a protease cleavable group; esters; acyloxy groups, including substituted acyloxy groups, etc. Suitable linking groups are described in, e.g., US20150157736, which is incorporated by reference herein. In some embodiments, the linking group includes a 4-aminopiperidine (4AP) derivative.

An antibody conjugate of the present disclosure can include: 1) Ig heavy chain constant region that is not conjugated to a payload (e.g., drug); and an Ig light chain constant region conjugated to a payload (e.g., drug) of interest; or 2) an Ig heavy chain constant region conjugated to a payload (e.g., drug); and an Ig light chain constant region conjugated to a payload (e.g., drug). A subject antibody conjugate can also include $V_H$ and/or $V_L$ domains.

An antibody conjugate can have any of a variety of antigen-binding specificities, as described above, including, e.g., an antigen present on a cancer cell; an antigen present on an autoimmune cell; an antigen present on a pathogenic microorganism; an antigen present on a virus-infected cell (e.g., a human immunodeficiency virus-infected cell), e.g., CD4 or gp120; an antigen present on a diseased cell; and the like. For example, an antibody conjugate can bind an antigen, as noted above, where the antigen is present on the surface of the cell. The binding specificity, affinity, etc., of the antibody conjugate may be determined by at least the light and heavy chain variable region CDR sequences and/or the light and heavy chain variable regions (including the framework regions) included in the antibody conjugate. Thus the binding specificity, affinity, etc., of the antibody conjugate typically may have substantially the same antigen binding specificity, affinity, etc., as an antibody that may not be conjugated to a payload, or be tagged, and which has at least the same light and heavy chain variable region CDR sequences and/or the same light and heavy chain variable regions as the antibody conjugate.

An antibody conjugate of the present disclosure can bind antigen with a suitable binding affinity, e.g., from about $5\times10^{-6}$ M to about $10^{-7}$ M, from about $10^{-7}$ M to about $5\times10^{-7}$ M, from about $5\times10^{-7}$ M to about $10^{-8}$ M, from about $10^{-8}$ M to about $5\times10^{-8}$ M, from about $5\times10^{-8}$ M to about $10^{-9}$ M, or a binding affinity greater than $10^{-9}$ M.

As non-limiting examples, a subject antibody conjugate can bind an antigen present on a cancer cell (e.g., a tumor-specific antigen; an antigen that is over-expressed on a cancer cell; etc.), and the attached payload can be a cytotoxic compound (e.g., a cytotoxic small molecule, a cytotoxic synthetic peptide, etc.). For example, a subject antibody conjugate can be specific for CD19, where the attached payload is a cytotoxic compound (e.g., a cytotoxic small molecule, a cytotoxic synthetic peptide, etc.). As another example, a subject antibody conjugate can be specific for CD22, where the attached payload can be a cytotoxic compound (e.g., a cytotoxic small molecule, a cytotoxic synthetic peptide, etc.).

As further non-limiting examples, a subject antibody conjugate can bind an antigen present on a cell infected with a virus (e.g., where the antigen is encoded by the virus; where the antigen is expressed on a cell type that is infected by a virus; etc.), and the payload can be a viral fusion inhibitor. For example, a subject antibody conjugate can bind CD4, and the attached payload can be a viral fusion inhibitor. As another example, a subject antibody conjugate can bind gp120, and the attached payload can be a viral fusion inhibitor.

As described above, a payload conjugated to an antibody of the present disclosure includes any suitable moiety (e.g., drug, detectable label, water soluble polymer, polypeptide, etc.) that, prior to conjugation to an fGly-modified antibody, can be functionalized to from an aldehyde-reactive reactive partner that includes an aldehyde-reactive group attached to the payload.

An antibody conjugate of the present disclosure can include, as the payload (e.g., drug), any of a variety of compounds, as described above, e.g., a drug (e.g., a peptide drug, a small molecule drug, and the like), a water-soluble polymer, a detectable label, a synthetic peptide, etc. In general, the payload or payloads (e.g., drug or drugs) can provide for one or more of a wide variety of functions or features. Moieties of interest include, without limitation, detectable labels (e.g., dye labels (e.g., chromophores, fluorophores), biophysical probes (spin labels, nuclear magnetic resonance (NMR) probes), Förster Resonance Energy Transfer (FRET)-type labels (e.g., at least one member of a FRET pair, including at least one member of a fluorophore/quencher pair), Bioluminescence Resonance Energy Transfer (BRET)-type labels (e.g., at least one member of a BRET pair), immunodetectable tags (e.g., FLAG (e.g., DYKDDDDK (SEQ ID NO:249)), His(6), and the like), localization tags (e.g., to identify association of a tagged polypeptide at the tissue or molecular cell level (e.g., association with a tissue type, or particular cell membrane)), and the like); light-activated dynamic moieties (e.g., azobenzene mediated pore closing, azobenzene mediated structural changes, photodecaging recognition motifs); water soluble polymers (e.g., PEGylation); purification tags (e.g., to facilitate isolation by affinity chromatography (e.g., attachment of a FLAG epitope, e.g., DYKDDDDK (SEQ ID NO:249)); membrane localization domains (e.g., lipids or glycophosphatidylinositol (GPI)-type anchors); immobilization tags (e.g., to facilitate attachment of the polypeptide to a surface, including selective attachment); drugs (e.g., to facilitate drug targeting, e.g., through attachment of the drug to an antibody); toxins; targeted delivery moieties, (e.g., ligands for binding to a target receptor (e.g., to facilitate viral attachment, attachment of a targeting protein present on a liposome, etc.)), other molecules for delivery to the cell and which can provide for a pharmacological activity or can serve as a target for delivery of other molecules, and the like.

Also contemplated is a covalently attached payload (e.g., drug) that comprises one of a pair of binding partners (e.g., a ligand, a ligand-binding portion of a receptor, a receptor-binding portion of a ligand, etc.). For example, the payload can comprise a polypeptide that serves as a viral receptor and, upon binding with a viral envelope protein or viral capsid protein, facilitates attachment of virus to the cell surface with which the antibody conjugate is associated, e.g., is bound. Alternatively, the payload comprises an antigen that is specifically bound by an antibody (e.g., monoclonal antibody), to facilitate detection and/or separation of host cells bound to the antibody conjugate containing the payload.

Water-Soluble Polymers

In some cases, an antibody conjugate comprises a covalently linked payload that is a water-soluble polymer. A moiety of particular interest is a water-soluble polymer. A "water-soluble polymer" refers to a polymer that is soluble in water and is usually substantially non-immunogenic, and usually has an atomic molecular weight greater than about 1,000 Daltons. The methods and compositions described herein can be used to attach one or more water-soluble polymers to a tagged and converted polypeptide. Attachment of a water-soluble polymer (e.g., PEG) of a polypeptide, particularly a pharmaceutically active (therapeutic) polypeptide can be desirable as such modification can increase therapeutic index by increasing serum half-life as a result of increased proteolytic stability and/or decreased renal clearance. Additionally, attachment of one or more polymers (e.g., PEGylation) can reduce immunogenicity of protein pharmaceuticals.

In some embodiments, the water-soluble polymer has an effective hydrodynamic molecular weight of greater than about 10,000 Da, greater than about 20,000 to 500,000 Da, greater than about 40,000 Da to 300,000 Da, greater than about 50,000 Da to 70,000 Da, usually greater than about 60,000 Da. In some embodiments, the water-soluble polymer has an effective hydrodynamic molecular weight of from about 10 kDa to about 20 kDa, from about 20 kDa to about 25 kDa, from about 25 kDa to about 30 kDa, from about 30 kDa to about 50 kDa, or from about 50 kDa to about 100 kDa. By "effective hydrodynamic molecular weight" is intended the effective water-solvated size of a polymer chain as determined by aqueous-based size exclusion chromatography (SEC). When the water-soluble polymer contains polymer chains having polyalkylene oxide repeat units, such as ethylene oxide repeat units, each chain can have an atomic molecular weight of between about 200 Da and about 80,000 Da, or between about 1,500 Da and about 42,000 Da, with 2,000 to about 20,000 Da being of particular interest. Unless referred to specifically, molecular weight is intended to refer to atomic molecular weight. Linear, branched, and terminally charged water soluble polymers (e.g., PEG) are of particular interest.

Polymers useful as moieties to be conjugated to an fGly-modified antibody to form an antibody conjugate can have a wide range of molecular weights, and polymer subunits. These subunits may include a biological polymer, a synthetic polymer, or a combination thereof. Examples of such water-soluble polymers include: dextran and dextran derivatives, including dextran sulfate, P-amino cross linked dextrin, and carboxymethyl dextrin, cellulose and cellulose derivatives, including methylcellulose and carboxymethyl cellulose, starch and dextrines, and derivatives and hydroylactes of starch, polyalklyene glycol and derivatives thereof, including polyethylene glycol, methoxypolyethylene glycol, polyethylene glycol homopolymers, polypropylene glycol homopolymers, copolymers of ethylene glycol with propylene glycol, wherein said homopolymers and copolymers are unsubstituted or substituted at one end with an alkyl group, heparin and fragments of heparin, polyvinyl alcohol and polyvinyl ethyl ethers, polyvinylpyrrolidone, aspartamide, and polyoxyethylated polyols, with the dextran and dextran derivatives, dextrine and dextrine derivatives. It will be appreciated that various derivatives of the specifically recited water-soluble polymers are also contemplated.

Water-soluble polymers such as those described above are well known, particularly the polyalkylene oxide based polymers such as polyethylene glycol "PEG". Suitable polymers include, without limitation, those containing a polyalkylene oxide, polyamide alkylene oxide, or derivatives thereof, including polyalkylene oxide and polyamide alkylene oxide comprising an ethylene oxide repeat unit of the formula —(CH$_2$—CH$_2$—O)—. Further exemplary polymers of interest include a polyamide having a molecular weight greater than about 1,000 Daltons of the formula —[C(O)—X—C(O)—NH—Y—NH]n— or —[NH—Y—NH—C(O)—X—C(O)]$_n$—, where X and Y are divalent radicals that may be the same or different and may be branched or linear, and n is a discrete integer from 2-100, usually from 2 to 50, and where either or both of X and Y comprises a biocompatible, substantially non-antigenic water-soluble repeat unit that may be linear or branched. Further exemplary water-soluble repeat units comprise an ethylene oxide of the formula —(CH$_2$—CH$_2$—O)— or —(CH$_2$—CH$_2$—O)—. The number of such water-soluble repeat units can vary significantly, with the usual number of such units being from 2 to 500, 2 to 400, 2 to 300, 2 to 200, 2 to 100, and most usually 2 to 50. An exemplary embodiment is one in which one or both of X and Y is selected from: —((CH$_2$)$_{n1}$—(CH$_2$—CH$_2$—O)$_{n2}$—(CH$_2$)— or —((CH$_2$)$_{n1}$—(O—CH$_2$—CH$_2$)$_{n2}$—(CH$_2$)$_{n-1}$—), where n1 is 1 to 6, 1 to 5, 1 to 4 and most usually 1 to 3, and where n2 is 2 to 50, 2 to 25, 2 to 15, 2 to 10, 2 to 8, and most usually 2 to 5. A further exemplary embodiment is one in which X is —($CH_2$—$CH_2$)—, and where Y is —($CH_2$—$CH_2$—$CH_2$—O)$_3$—$CH_2$—$CH_2$—$CH_2$— or —($CH_2$—$CH_2$—$CH_2$—(O—$CH_2$—$CH_2$)$_3$—$CH_2$)—.

The polymer can include one or more spacers or linkers. Exemplary spacers or linkers include linear or branched moieties comprising one or more repeat units employed in a water-soluble polymer, diamino and or diacid units, natural or unnatural amino acids or derivatives thereof, as well as aliphatic moieties, including alkyl, aryl, heteroalkyl, heteroaryl, alkoxy, and the like, which can contain, for example, up to 18 carbon atoms or even an additional polymer chain.

The polymer moiety, or one or more of the spacers or linkers of the polymer moiety when present, may include polymer chains or units that are biostable or biodegradable. For example, polymers with repeat linkages have varying degrees of stability under physiological conditions depending on bond lability. Polymers with such bonds can be categorized by their relative rates of hydrolysis under physiological conditions based on known hydrolysis rates of low molecular weight analogs, e.g., from less stable to more stable, e.g., polyurethanes (—NH—C(O)—O—)>polyorthoesters (—O—C((OR)(R'))—O—)>polyamides (—C(O)—NH—). Similarly, the linkage systems attaching a water-soluble polymer to a target molecule may be biostable or biodegradable, e.g., from less stable to more stable: carbonate (—O—C(O)—O—)>ester (—C(O)—O—)>urethane (—NH—C(O)—O—)>orthoester (—O—C((OR)(R'))—O—)>amide (—C(O)—NH—). In general, it may be desirable to avoid use of sulfated polysaccharide, depending on the lability of the sulfate group. In addition, it may be less desirable to use polycarbonates and polyesters. These bonds are provided by way of example, and are not intended to limit the types of bonds employable in the polymer chains or linkage systems of the water-soluble polymers useful in the modified aldehyde tagged polypeptides disclosed herein.

Synthetic Peptides

In some cases, an antibody conjugate comprises a covalently linked peptide, e.g., a peptide covalently linked to fGly of a converted tag of an Ig light chain polypeptide of an antibody. Suitable peptides include, but are not limited to, cytotoxic peptides; angiogenic peptides; anti-angiogenic peptides; peptides that activate B cells; peptides that activate T cells; anti-viral peptides; peptides that inhibit viral fusion; peptides that increase production of one or more lymphocyte populations; anti-microbial peptides; growth factors; growth hormone-releasing factors; vasoactive peptides; anti-inflammatory peptides; peptides that regulate glucose metabolism; an anti-thrombotic peptide; an anti-nociceptive peptide; a vasodilator peptide; a platelet aggregation inhibitor; an analgesic; and the like.

Where the covalently attached moiety is a peptide, the peptide can be chemically synthesized to include a group reactive with a converted fGly-containing Ig polypeptide. A suitable synthetic peptide has a length of from about 5 amino acids to about 100 amino acids, or longer than 100 amino acids; e.g., a suitable peptide has a length of from about 5 amino acids (aa) to about 10 aa, from about 10 aa to about 15 aa, from about 15 aa to about 20 aa, from about 20 aa to about 25 aa, from about 25 aa to about 30 aa, from about 30 aa to about 40 aa, from about 40 aa to about 50 aa, from about 50 aa to about 60 aa, from about 60 aa to about 70 aa, from about 70 aa to about 80 aa, from about 80 aa to about 90 aa, or from about 90 aa to about 100 aa.

A peptide can be modified to contain an α-nucleophile-containing moiety (e.g., an aminooxy or hydrazide moiety), e.g., can be reacted with the fGly-containing Ig polypeptide to yield a conjugate in which the aldehyde-tagged Ig polypeptide and peptide are linked by a hydrazone or oxime bond, respectively. Exemplary methods of synthesizing a peptide, such that the synthetic peptide comprising a reactive group reactive with a converted aldehyde tag, are described above.

Suitable peptides include, but are not limited to, hLF-11 (an 11-amino acid N-terminal fragment of lactoferrin), an anti-microbial peptide; granulysin, an anti-microbial peptide; Plectasin (NZ2114; SAR 215500), an anti-microbial peptide; viral fusion inhibitors such as Fuzeon (enfuvirtide), TRI-1249 (T-1249; see, e.g., Matos et al. (2010) PLoS One 5:e9830), TRI-2635 (T-2635; see, e.g., Eggink et al. (2009) J. Biol. Chem. 284:26941), T651, and TRI-1144; C5a receptor inhibitors such as PMX-53, JPE-1375, and JSM-7717; POT-4, a human complement factor C3 inhibitor; Pancreate (an INGAP derivative sequence, a HIP-human proislet protein); somatostatin; a somatostatin analog such as DEBIO 8609 (Sanvar), octreotide, octreotide (C2L), octreotide QLT, octreotide LAR, Sandostatin LAR, SomaLAR, Somatuline (lanreotide), see, e.g., Deghenghi et al. (2001) Endocrine 14:29; TH9507 (Tesamorelin, a growth hormone-releasing factor); POL7080 (a protegrin analog, an anti-microbial peptide); relaxin; a corticotropin releasing factor agonist such as urotensin, sauvagine, and the like; a heat shock protein derivative such as DiaPep277; a human immunodeficiency virus entry inhibitor; a heat shock protein-20 mimic such as AZX100; a thrombin receptor activating peptide such as TP508 (Chrysalin); a urocortin 2 mimic (e.g., a CRF2 agonist) such as urocortin-2; an immune activator such as Zadaxin (thymalfasin; thymosin-α1), see, e.g., Sjogren (2004) J. Gastroenterol. Hepatol. 19:S69; a hepatitis C virus (HCV) entry inhibitorE2 peptide such as HCV3; an atrial natriuretic peptide such as HANP (Sun 4936; carperitide); an annexin peptide; a defensin (anti-microbial peptide) such as hBD2-4; a defensin (anti-microbial peptide) such as hBD-3; a defensin (anti-microbial peptide) such as PMX-30063; a histatin (anti-microbial peptide) such as histatin-3, histatin-5, histatin-6, and histatin-9; a histatin (anti-microbial peptide) such as PAC-113; an indolicidin (anti-microbial peptide) such as MX-594AN (Omniganin; CLS001); an indolicidin (anti-microbial peptide) such as Omnigard (MBI-226; CPI-226); an anti-microbial peptide such as an insect cecropin; an anti-microbial peptide such as a lactoferrin (talactoferrin); an LL-37/cathelicidin derivative (an anti-microbial peptide) such as P60.4 (OP-145); a magainin (an anti-microbial peptide) such as Pexiganan (MSI-78; Suponex); a protegrin (an anti-microbial peptide) such as IB-367 (Iseganan); an agan peptide; a beta-natriuretic peptide such as Natrecor, or Noratak (Nesiritide), or ularitide; bivalarudin (Angiomax), a thrombin inhibitor; a C peptide derivative; a calcitonin such as Miacalcin (Fortical); an enkephalin derivative; an erythropoiesis-stimulating peptide such as Hematide; a gap junction modulator such as Danegaptide (ZP1609); a gastrin-releasing peptide; a ghrelin; a glucagon-like peptide; a glucagon-like peptide-2 analog such as ZP1846 or ZP1848; a glucosaminyl muramyl dipeptide such as GMDP; a glycopeptide antibiotic such as Oritavancin; a teicoplanin derivative such as Dalbavancin; a gonadotropin releasing hormone (GnRH) such as Zoladex (Lupon) or Triptorelin; a histone deacetylase (HDAC) inhibitor depsipeptide such as PM02734 (Irvalec); an integrin such as eptifibatide; an insulin analog such as Humulog; a kahalalide depsipeptide such as PM02734; a kallikrein inhibitor such as Kalbitor (ecallantide); an antibiotic such as Telavancin; a lipopeptide such as Cubicin or MX-2401; a lutenizing hormone releasing hormone (LHRH) such as goserelin; an LHRH synthetic decapeptide agonist analog such as Treistar (triptorelin pamoate); an LHRH such as Eligard; an M2 protein channel peptide inhibitor; metreleptin; a melanocortin receptor agonist peptide such as bremalanotide/PT-141; a melanocortin; a muramyl tripeptide such as Mepact (mifamurtide); a myelin basic protein peptide such as MBP 8298 (dirucotide); an N-type voltage-gated calcium channel blocker such as Ziconotide (Prialt); a parathyroid hormone peptide; a parathyroid analog such as 768974; a peptide hormone analog such as UGP281; a prostaglandin F2-α receptor inhibitor such as PDC31; a protease inhibitor such as PPL-100; surfaxin; a thrombospondin-1 (TSP-1) mimetic such as CVX-045 or ABT 510; a vasoactive intestinal peptide; vasopressin; a Y2R agonist peptide such as RG7089; obinepeptide; and TM30339.

Drugs as a Payload Conjugated to an Antibody

The payload conjugated to an antibody of the present disclosure may be any of a number of drugs. Exemplary drugs include small molecule drugs and peptide drugs. Thus, the present disclosure provides drug-antibody conjugates, where a drug is covalently linked to fGly of a converted tag of an Ig light chain polypeptide of an antibody.

"Small molecule drug" as used herein refers to a compound, e.g., an organic compound, which exhibits a pharmaceutical activity of interest and which is generally of a molecular weight of no greater than about 800 Da, or no greater than 2000 Da, but can encompass molecules of up to 5 kDa and can be as large as about 10 kDa. A small inorganic molecule refers to a molecule containing no carbon atoms, while a small organic molecule refers to a compound containing at least one carbon atom.

"Peptide drug" as used herein refers to amino-acid containing polymeric compounds, and is meant to encompass naturally-occurring and non-naturally-occurring peptides, oligopeptides, cyclic peptides, polypeptides, and proteins, as well as peptide mimetics. The peptide drugs may be obtained by chemical synthesis or be produced from a genetically encoded source (e.g., recombinant source). Peptide drugs can range in molecular weight, and can be from 200 Da to 10 kDa or greater in molecular weight.

In some cases, the drug is a cancer chemotherapeutic agent. For example, where an antibody has specificity for a tumor cell, the antibody can be modified as described herein to include an aldehyde tag, can be subsequently converted to an fGly-modified antibody, and can then be conjugated to a cancer chemotherapeutic agent. Cancer chemotherapeutic agents include non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones. Peptidic compounds can also be used.

Suitable cancer chemotherapeutic agents include dolastatin and active analogs and derivatives thereof; and auristatin and active analogs and derivatives thereof. See, e.g., WO 96/33212, WO 96/14856, and U.S. Pat. No. 6,323,315. For example, dolastatin 10 or auristatin PE can be included in an antibody-drug conjugate of the present disclosure. Suitable cancer chemotherapeutic agents also include maytansinoids and active analogs and derivatives thereof (see, e.g., EP 1391213; and Liu et al (1996) *Proc. Natl. Acad. Sci.* USA 93:8618-8623); and duocarmycins and active analogs and derivatives thereof (e.g., including the synthetic analogues, KW-2189 and CB 1-TM1). In some cases, the cancer chemotherapeutic agent includes a pyrrolobenzodiazepine compound.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; aziridinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation; therefore compounds that bind to the estrogen receptor are used to block this activity. Corticosteroids may inhibit T cell proliferation.

Other suitable chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

Taxanes are suitable for use. "Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers suitable for use include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-γ; (8) colony-stimulating factors; and (9) inhibitors of angiogenesis.

Formulations

The antibody conjugates of the present disclosure can be formulated in a variety of different ways. In general, where the antibody conjugate is an antibody-drug conjugate, the antibody conjugate is formulated in a manner compatible with the drug conjugated to the Ig polypeptide (e.g., Ig light chain polypeptide), the condition to be treated, and the route of administration to be used.

The antibody conjugate (e.g., antibody-drug conjugate) can be provided in any suitable form, e.g., in the form of a pharmaceutically acceptable salt, and can be formulated for any suitable route of administration, e.g., oral, topical or parenteral administration. Where the antibody conjugate is provided as a liquid injectable (such as in those embodiments where they are administered intravenously or directly into a tissue), the antibody conjugate can be provided as a ready-to-use dosage form, or as a reconstitutable storage-stable powder or liquid composed of pharmaceutically acceptable carriers and excipients.

Methods for formulating antibody conjugates can be adapted from those available in the art. For example, antibody conjugates can be provided in a pharmaceutical composition comprising an effective amount of an antibody conjugate and a pharmaceutically acceptable carrier (e.g., saline). The pharmaceutical composition may optionally include other additives (e.g., buffers, stabilizers, preservatives, and the like). Of particular interest in some embodiments are formulations that are suitable for administration to a mammal, particularly those that are suitable for administration to a human.

Nucleic Acids, Expression Vectors and Host Cells

The present disclosure provides a nucleic acid encoding Ig light chain polypeptides containing a tag, as well as constructs and host cells containing the nucleic acid. Such nucleic acids comprise a sequence of DNA having an open reading frame that encodes a tagged Ig light chain polypeptide and, in most embodiments, is capable, under appropriate conditions, of being expressed. "Nucleic acid" encompasses DNA, cDNA, mRNA, and vectors comprising such nucleic acids.

The present disclosure provides a recombinant nucleic acid comprising a nucleotide sequence encoding a tagged Ig light chain polypeptide, as described above. The recombinant nucleic acid can include:

1) a nucleotide sequence encoding a tagged Ig light chain constant region (and not an Ig light chain variable region, i.e., where the recombinant nucleic acid lacks a nucleotide sequence encoding an Ig $V_L$ domain);

2) a nucleotide sequence encoding a tagged Ig polypeptide, where the Ig polypeptide comprises an Ig $V_L$ domain and a tagged Ig light chain constant region;

3) a nucleotide sequence encoding an Ig heavy chain constant region (and not an Ig heavy chain variable region, i.e., where the recombinant nucleic acid lacks a nucleotide sequence encoding an Ig $V_H$ domain); and a nucleotide sequence encoding a tagged Ig light chain constant region (and not an Ig light chain variable region, i.e., where the recombinant nucleic acid lacks a nucleotide sequence encoding an Ig $V_L$ domain);

4) a nucleotide sequence encoding a tagged Ig heavy chain constant region, as described above, (and not an Ig heavy chain variable region, i.e., where the recombinant nucleic acid lacks a nucleotide sequence encoding an Ig $V_H$ domain); and a nucleotide sequence encoding a tagged Ig light chain constant region (and not an Ig light chain variable region, i.e., where the recombinant nucleic acid lacks a nucleotide sequence encoding an Ig $V_L$ domain);

5) a nucleotide sequence encoding a first tagged Ig polypeptide, where the first aldehyde-tagged Ig polypeptide comprises an Ig $V_H$ domain and a tagged Ig heavy chain constant region; and a nucleotide sequence encoding a second aldehyde-tagged Ig polypeptide, where the second tagged Ig polypeptide comprises an Ig $V_L$ domain and a tagged Ig light chain constant region;

6) a nucleotide sequence encoding a first Ig polypeptide, where the first Ig polypeptide comprises an Ig $V_H$ domain and an Ig heavy chain constant region; and a nucleotide sequence encoding a second Ig polypeptide, where the second Ig polypeptide includes a tag, where the second Ig polypeptide comprising an Ig $V_L$ domain and a tagged Ig light chain constant region.

The present disclosure provides a recombinant expression vector comprising a nucleic acid as described above, where the nucleotide sequence encoding the Ig polypeptide(s) is operably linked to a promoter. In some embodiments, where a subject recombinant expression vector encodes both Ig heavy and light chains (with or without Ig variable regions), the heavy and light chain-encoding sequences can be operably linked to the same promoter, or to separate promoters.

Where a recombinant expression vector includes a nucleotide sequence encoding a heavy chain variable ($V_H$) region and/or a light chain variable ($V_L$) region, it will be appreciated that a large number of $V_H$ and $V_L$ amino acid sequences, and nucleotide sequences encoding same, are known in the art, and can be used. See, e.g., Kabat et al., Sequences of Proteins of Immunological Interest, 5th Ed. Public Health Service, National Institutes of Health, Bethesda, Md. (1991).

In those instances in which a recombinant expression vector comprises a nucleotide sequence encoding an Ig heavy or Ig light chain without variable region sequences, the vector can include an insertion site for an Ig variable region 5' of the Ig polypeptide-encoding nucleotide sequence. For example, a recombinant expression vector can comprise, in order from 5' to 3':

1) an insertion site for a nucleotide sequence encoding a $V_L$ domain; and a nucleotide sequence encoding a tagged Ig light chain constant region; or 2) an insertion site for a nucleotide sequence encoding a $V_H$ domain; and a nucleotide sequence encoding an Ig heavy chain constant region, which may or may not include a tag.

Nucleic acids contemplated herein can be provided as part of a vector (also referred to as a construct), a wide variety of which are known in the art. Exemplary vectors include, but are not limited to, plasmids; cosmids; viral vectors (e.g., retroviral vectors); non-viral vectors; artificial chromosomes (yeast artificial chromosomes (YAC's), BAC's, etc.); minichromosomes; and the like. The choice of vector will depend upon a variety of factors such as the type of cell in which propagation is desired and the purpose of propagation.

Vectors can provide for extrachromosomal maintenance in a host cell or can provide for integration into the host cell genome. Vectors are amply described in numerous publications well known to those in the art, including, e.g., Short Protocols in Molecular Biology, (1999) F. Ausubel, et al., eds., Wiley & Sons. Vectors may provide for expression of the nucleic acids encoding a polypeptide of interest (e.g., a tagged polypeptide, an FGE, etc.), may provide for propagating the subject nucleic acids, or both.

Exemplary vectors that may be used include but are not limited to those derived from recombinant bacteriophage DNA, plasmid DNA or cosmid DNA. For example, plasmid vectors such as pBR322, pUC 19/18, pUC 118, 119 and the M13 mp series of vectors may be used. Bacteriophage vectors may include λgt10, λgt11, λgt18-23, λZAP/R and the EMBL series of bacteriophage vectors. Cosmid vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors. Alternatively, recombinant virus vectors may be engineered, including but not limited to those derived from viruses such as herpes virus, retroviruses, vaccinia virus, poxviruses, adenoviruses, adeno-associated viruses, or bovine papilloma virus.

For expression of a protein of interest (e.g., a tagged Ig polypeptide or an FGE), an expression cassette may be employed. Thus, the present invention provides a recombinant expression vector comprising a subject nucleic acid. The expression vector provides a transcriptional and translational regulatory sequence, and may provide for inducible or constitutive expression, where the coding region is operably linked under the transcriptional control of the transcriptional initiation region, and a transcriptional and translational termination region. These control regions may be native to the gene encoding the polypeptide (e.g., the Ig polypeptide or the FGE), or may be derived from exogenous sources. In general, the transcriptional and translational regulatory sequences may include, but are not limited to, promoter sequences, ribosomal binding sites, transcriptional start and stop sequences, translational start and stop sequences, and enhancer or activator sequences. In addition to constitutive and inducible promoters, strong promoters (e.g., T7, CMV, and the like) find use in the constructs described herein, particularly where high expression levels are desired in an in vivo (cell-based) or in an in vitro expression system. Further exemplary promoters include mouse mammary tumor virus (MMTV) promoters, Rous sarcoma virus (RSV) promoters, adenovirus promoters, the promoter from the immediate early gene of human CMV (Boshart et al., Cell 41:521-530, 1985), and the promoter from the long terminal repeat (LTR) of RSV (Gorman et al., Proc. Natl. Acad. Sci. USA 79:6777-6781, 1982). The promoter can also be provided by, for example, a 5'UTR of a retrovirus.

Expression vectors generally have convenient restriction sites located near the promoter sequence to provide for the insertion of nucleic acid sequences encoding proteins of interest. A selectable marker operative in the expression host may be present to facilitate selection of cells containing the vector. In addition, the expression construct may include additional elements. For example, the expression vector may have one or two replication systems, thus allowing it to be maintained in organisms, for example in mammalian or insect cells for expression and in a prokaryotic host for cloning and amplification. In addition the expression construct may contain a selectable marker gene to allow the selection of transformed host cells. Selection genes are well known in the art and will vary with the host cell used.

Expression constructs encoding tagged Ig polypeptides can also be generated using amplification methods (e.g., a polymerase chain reaction (PCR)), where at least one amplification primer (i.e., at least one of a forward or reverse primer) includes a nucleic acid sequence encoding an aldehyde tag. For example, an amplification primer having a tag amino acid sequence-encoding nucleotide sequence is designed to provide for amplification of a nucleic acid encoding an Ig polypeptide. The extension product that results from polymerase-mediated synthesis from the tagged forward primer produces a nucleic acid amplification product encoding a fusion protein composed of a tagged Ig polypeptide. The amplification product is then inserted into an expression construct of choice to provide a tagged polypeptide expression construct.

Host Cells

The present disclosure provides genetically modified host cells comprising a subject nucleic acid, including a genetically modified host cell comprising a recombinant expression vector as described above. Any of a number of suitable host cells can be used in the production of an antibody containing the present tagged Ig light chain polypeptide. The host cell used for production of an antibody containing the tagged Ig polypeptide can optionally provide for FGE-mediated conversion, so that the antibody produced contains an fGly-modified Ig polypeptide, where the tag is converted to contain fGly, following expression and modification by FGE. Alternatively the host cell can provide for production of an antibody containing a tagged and unconverted Ig light chain polypeptide (e.g., due to lack of expression of an FGE that facilitates conversion of the tag).

The aldehyde moiety of a converted tag can be used for a variety of applications including, but not limited to, visualization using fluorescence or epitope labeling (e.g., electron microscopy using gold particles equipped with aldehyde reactive groups); protein immobilization (e.g., protein microarray production); protein dynamics and localization studies and applications; and conjugation of proteins with a payload (e.g., moieties that improve a parent protein's half-life (e.g., poly(ethylene glycol)), targeting moieties (e.g., to enhance delivery to a site of action), and biologically active moieties (e.g., a therapeutic moiety).

In general, the polypeptides described herein may be expressed in prokaryotes or eukaryotes in accordance with conventional ways, depending upon the purpose for expression. Thus, the present invention further provides a host cell, e.g., a genetically modified host cell that comprises a nucleic acid encoding a tagged polypeptide. The host cell can further optionally comprise a recombinant FGE, which may be endogenous or heterologous to the host cell. Thus, in some cases, the host cell is genetically modified to express an FGE.

Host cells for production (including large scale production) of a tagged and unconverted, or (where the host cell expresses a suitable FGE) tagged and converted Ig polypeptide, or for production of an FGE (e.g., for use in a cell-free method) can be selected from any of a variety of available host cells. Exemplary host cells include those of a prokaryotic or eukaryotic unicellular organism, such as bacteria (e.g., *Escherichia coli* strains, *Bacillus* spp. (e.g., *B. subtilis*), and the like) yeast or fungi (e.g., *S. cerevisiae*, *Pichia* spp., and the like), and other such host cells can be used. Exemplary host cells originally derived from a higher organism such as insects, vertebrates, particularly mammals, (e.g. CHO, HEK, and the like), may be used as the expression host cells.

Suitable mammalian cell lines include, but are not limited to, HeLa cells (e.g., American Type Culture Collection (ATCC) No. CCL-2), CHO cells (e.g., ATCC Nos. CRL9618 and CRL9096), CHO DG44 cells (Urlaub (1983) *Cell* 33:405), CHO-K1 cells (ATCC CCL-61), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Specific expression systems of interest include bacterial, yeast, insect cell and mammalian cell derived expression systems. Representative systems from each of these categories are provided below.

The product can be recovered by any appropriate means known in the art. Further, any convenient protein purification procedures may be employed, where suitable protein purification methodologies are described in Guide to Protein Purification, (Deuthser ed.) (Academic Press, 1990). For example, a lysate may prepared from a cell comprising the expression vector expressing the tagged Ig polypeptide, and purified using high performance liquid chromatography (HPLC), exclusion chromatography, gel electrophoresis, affinity chromatography, and the like.

Methods

Methods for Conversion and Modification of a Tag

Conversion of a tag, e.g., a sulfatase motif in a tag, present in a tagged Ig polypeptide of an antibody can be accomplished by cell-based (in vivo) or cell-free methods (in vitro). Similarly, modification of a converted tag of a tagged polypeptide can be accomplished by cell-based (in vivo) or cell-free methods (in vitro). These are described in more detail below.

"In Vivo" Host Cells Conversion and Modification

Conversion of a tag, e.g., a sulfatase motif in a tag, of an aldehyde tagged polypeptide of an antibody can be accomplished by expression of the tagged polypeptide in a cell that contains a suitable FGE. In this embodiment, conversion of the cysteine or serine of the tag occurs during or following translation in the host cell. The FGE of the host cell can be endogenous to the host cell, or the host cell can be recombinant for a suitable FGE that is heterologous to the host cell. FGE expression can be provided by an expression system endogenous to the FGE gene (e.g., expression is provided by a promoter and other control elements present in the native FGE gene of the host cell), or can be provided by from a recombinant expression system in which the FGE coding sequence is operably linked to a heterologous promoter to provide for constitutive or inducible expression.

Conditions suitable for use to accomplish conjugation of a reactive partner moiety to a tagged polypeptide are similar to those described in Mahal et al. (1997 May 16) Science 276(5315):1125-8.

In some instances, where the present method is carried out in a cell, the cell is in vitro, e.g., in in vitro cell culture, e.g., where the cell is cultured in vitro in a single-cell suspension or as an adherent cell. In some embodiments, the cell is cultured in the presence of an oxidation reagent that can activate FGE. In some embodiments, a cell expressing an FGE is cultured in the presence of a suitable amount of $Cu^{2+}$ in the culture medium. In certain aspects, the $Cu^{2+}$ is present in the cell culture medium at a concentration of from 1 nM to 100 mM, such as from 0.1 μM to 10 mM, from 1 μM to 1 mM, from 2 μM to 500 μM, from 4 μM to 300 μM, or from 5 μM to 200 μM (e.g., from 10 μM to 150 μM). The culture medium may be supplemented with any suitable copper salt to provide for the $Cu^{2+}$. Suitable copper salts include, but are not limited to, copper sulfate (i.e., copper(II) sulfate, $CuSO_4$), copper citrate, copper tartrate, copper nitrate, and any combination thereof.

"In Vitro" (Cell-Free) Conversion and Modification

In vitro (cell-free) conversion of a tag, e.g., a sulfatase motif in a tag, of a tagged Ig polypeptide of an antibody can be accomplished by contacting a tagged polypeptide with an FGE under conditions suitable for conversion of a cysteine or serine of a sulfatase motif of the tag to an fGly. For example, nucleic acid encoding a tagged Ig polypeptide can be expressed in an in vitro transcription/translation system in the presence of a suitable FGE to provide for production of tagged and converted Ig polypeptides.

Alternatively, isolated, unconverted, tagged Ig polypeptide can be isolated following recombinant production in a host cell lacking a suitable FGE or by synthetic production. The isolated tagged Ig polypeptide is then contacted with a suitable FGE under conditions to provide for tag conversion. The tagged Ig polypeptide can be unfolded by methods known in the art (e.g., using heat, adjustment of pH, chaotropic agents, (e.g., urea, and the like), organic solvents (e.g., hydrocarbons: octane, benzene, chloroform), etc.) and the denatured protein contacted with a suitable FGE. The tagged Ig polypeptide can then be refolded under suitable conditions.

With respect to modification of tagged and converted Ig polypeptide of an antibody, e.g., to covalently and site-specifically attach a payload (e.g., drug) thereto, modification is normally carried out in vitro. An antibody containing a converted aldehyde tagged Ig polypeptide is isolated from a production source (e.g., recombinant host cell production, synthetic production), and contacted with a reactive partner-containing drug or other moiety under conditions suitable to provide for conjugation of the drug or other moiety to the fGly of the tag in the Ig polypeptide, e.g., Ig light chain polypeptide, of the antibody.

In some instances, a combination of cell-based conversion and cell-free conversion is carried out, to generate a converted tag; followed by cell-free modification of the converted tag. In some embodiments, a combination of cell-free conversion and cell-based conversion is carried out.

Method of Producing an Antibody Conjugate

Aspects of the present disclosure include a method of producing an antibody conjugate, as described herein. In general terms, the method may include combining, in a reaction mixture, an fGly-modified antibody having a converted tag in its Ig light chain polypeptide, as described above, and a reactive partner, e.g., an aldehyde-reactive reactive partner, that includes the payload (e.g., drug) and an aldehyde-reactive group. In some cases, the reactive partner may be represented by the formula: P-(L)-R, where P is the payload covalently linked to R, an aldehyde-reactive group, through an optional linking group L. Under suitable conditions, the aldehyde-reactive group may react with the aldehyde group of the fGly in the converted tag of the fGly-modified antibody ("A") in the reaction mixture, to form a covalent linkage between the payload (e.g., drug) and the fGly-modified antibody at the fGly residue of the converted tag (which may be represented by the formula: P-(L)-A, or P-(L)-A-(L)-P, etc., depending on the number of tags present in each of the Ig polypeptides of the antibody). The reaction may be carried out in any suitable condition, such as those described in, e.g., US20120183566, US20140141025 and WO2014074218, each of which is incorporated herein by reference.

The payload (P) may be any suitable moiety (e.g., drug, water-soluble polymer, detectable label, synthetic peptide, etc.) as described above, and may be a compound that can be functionalized with an aldehyde-reactive group. The aldehyde-reactive group (R) may be any suitable functional group suitable for carrying out a conjugation reaction between the present fGly-modified antibody and the reactive partner. In some cases, the aldehyde-reactive group is an α-nucleophile, such as an aminooxy or hydrazide group. Suitable aldehyde-reactive groups include, without limitation, a hydrazine compound, hydrazide compound, aminooxy compound, semicarbazide (e.g., thiosemicarbazide) compound, hydrazinyl-indole compound, hydrazinyl-imidazole compound, hydrazinyl-pyrrole compound, hydrazinyl-furan compound, and a pyrazalinone compound.

In some embodiments, the reactive partner includes a payload (P) (e.g., drug) attached to an aldehyde-reactive group (R) that is based on a hydrazinyl-indole group, and can be produced using any suitable method, e.g., as described in US20140141025, which is incorporated herein by reference. A hydrazinyl-indole-containing reactive partner may react with an aldehyde of fGly in a converted tag in an fGly-modified antibody, as described herein, where the hydrazine of the hydrazinyl-indole coupling moiety undergoes an intramolecular cyclization to form a partially unsaturated pyrazole or pyridazine ring, to covalently attach the payload (e.g., drug) to the antibody Ig light chain polypeptide. Alternatively, the hydrazine of the hydrazinyl-indole coupling moiety may undergo an intramolecular cyclization to form a partially unsaturated pyridazine or 1,2-diazepine ring, to covalently attach the payload (e.g., drug) to the antibody Ig light chain polypeptide.

In some cases, the reactive partner includes a payload (P) (e.g., drug) attached to an aldehyde-reactive group (R) based on a pyrazalinone group, and can be produced using any suitable method, e.g., as described in WO2014074218, which is incorporated herein by reference. A pyrazalinone-containing reactive partner may react with an aldehyde of fGly in a converted tag in an fGly-modified antibody, as described herein, to covalently attach the payload (e.g., drug) of the reactive partner to the antibody Ig light chain polypeptide through a cyclic linkage.

In some cases, the reactive partner includes a payload (P) (e.g., drug) attached to an aldehyde-reactive group (R) based on a hydrazinyl-substituted heteroaryl ring compound, such as a hydrazinyl-substituted 5-membered heteroaryl ring compound, where one or more atoms in the ring is a heteroatom (e.g., N, O or S). The hydrazinyl-substituted heteroaryl ring compound may include a hydrazinyl-imidazole compound, hydrazinyl-pyrrole compound, or a hydrazinyl-furan compound. Thus, a hydrazinyl-substituted heteroaryl ring compound (e.g., a hydrazinyl-imidazole compound, hydrazinyl-pyrrole compound, a hydrazinyl-furan compound) may react with an aldehyde of fGly in a converted tag in an fGly-modified antibody, as described herein, to covalently attach the payload (e.g., drug) to the antibody Ig light chain polypeptide through a cyclic linkage.

The reactive partner may further include a linking group (L) bridging the payload (P) (e.g., drug) and the aldehyde-reactive group (R) through covalent bonds. The linking group may be any suitable linking group. In some cases, the linking group includes polyethylene glycol (PEG); amino acids; alkyl groups, including substituted alkyl groups; a protease cleavable group; esters; acyloxy groups, including substituted acyloxy groups, etc. Suitable linking groups and methods of using the same to bridge a payload (e.g., drug) and an aldehyde-reactive group are described in, e.g., US20150157736, which is incorporated by reference herein. In some embodiments, the linking group includes a 4-aminopiperidine (4AP) derivative.

In some cases, the payload is a drug, e.g., a peptide drug. In some cases, peptide drugs to be conjugated to a tagged and converted Ig polypeptide of an fGly-modified antibody can be modified to incorporate an aldehyde-reactive group for reaction with an aldehyde of the fGly residue of the tagged and converted Ig polypeptide. Since the methods of tagged and converted polypeptide modification are compatible with conventional chemical processes, any of a wide variety of commercially available reagents can be used to accomplish conjugation. For example, aminooxy, hydrazide, hydrazine, thiosemicarbazide, hydrazinyl-indole, hydrazinyl-imidazole, hydrazinyl-pyrrole, hydrazinyl-furan or pyrazalinone derivatives of a number of moieties of interest are suitable reactive partners, and are readily available or can be generated using standard chemical methods.

Where the drug is a peptide drug, the reactive moiety (e.g., aminooxy or hydrazide can be positioned at an N-terminal region, the N-terminus, a C-terminal region, the C-terminus, or at a position internal to the peptide. For example, one method involves synthesizing a peptide drug having an aminooxy group. In this example, the peptide is synthesized from a Boc-protected precursor. An amino group of a peptide can react with a compound comprising a carboxylic acid group and oxy-N-Boc group. As an example, the amino group of the peptide reacts with 3-(2,5-dioxopyrrolidin-1-yloxy)propanoic acid. Other variations on the compound comprising a carboxylic acid group and oxy-N-protecting group can include different number of carbons in the alkylene linker and substituents on the alkylene linker. The reaction between the amino group of the peptide and the compound comprising a carboxylic acid group and oxy-N-protecting group occurs through standard peptide coupling chemistry. Examples of peptide coupling reagents that can be used include, but not limited to, DCC (dicyclohexylcarbodiimide), DIC (diisopropylcarbodiimide), di-p-toluoyl-carbodiimide, BDP (1-benzotriazole diethylphosphate-1-cyclohexyl-3-(2-morpholinylethyl)carbodiimide), EDC (1-(3-dimethylaminopropyl-3-ethyl-carbodiimide hydrochloride), cyanuric fluoride, cyanuric chloride, TFFH (tetramethyl fluoroformamidinium hexafluorophosphate), DPPA (diphenylphosphorazidate), BOP (benzotriazol-1-yloxytris(dimethylamino)phosphonium hexafluorophosphate), HBTU (O-benzotriazol-1-yl-N,N,N',N'-tetramethyluronium hexafluorophosphate), TBTU (O-benzotriazol-1-yl-N,N,N', N'-tetramethyluronium tetrafluoroborate), TSTU (O—(N-succinimidyl)-N,N,N',N'-tetramethyluronium tetrafluoroborate), HATU (N-[(dimethylamino)-1-H-1,2,3-triazolo[4,5, 6]-pyridin-1-ylmethylene]- -N-methylmethanaminium hexafluorophosphate N-oxide), BOP—Cl (bis(2-oxo-3-oxazolidinyl)phosphinic chloride), PyBOP ((1-H-1,2,3-benzotriazol-1-yloxy)-tris(pyrrolidino)phosphonium tetrafluorophopsphate), BrOP (bromotris(dimethylamino) phosphonium hexafluorophosphate), DEPBT (3-(diethoxyphosphoryloxy)-1,2,3-benzotriazin-4(3H)-one) PyBrOP (bromotris(pyrrolidino)phosphonium hexafluorophosphate). As a non-limiting example, HOBt and DIC can be used as peptide coupling reagents.

Deprotection to expose the amino-oxy functionality is performed on the peptide comprising an N-protecting group. Deprotection of the N-oxysuccinimide group, for example, occurs according to standard deprotection conditions for a cyclic amide group. Deprotecting conditions can be found in Greene and Wuts, Protective Groups in Organic Chemistry, 3rd Ed., 1999, John Wiley & Sons, NY and Harrison et al. Certain deprotection conditions include a hydrazine reagent, amino reagent, or sodium borohydride. Deprotection of a Boc protecting group can occur with TFA. Other reagents for deprotection include, but are not limited to, hydrazine, methylhydrazine, phenylhydrazine, sodium borohydride, and methylamine. The product and intermediates can be purified by conventional means, such as HPLC purification.

The ordinarily skilled artisan will appreciate that factors such as pH and steric hindrance (i.e., the accessibility of the aldehyde tag to reaction with a reactive partner of interest) are of importance. Modifying reaction conditions to provide for optimal conjugation conditions is well within the skill of the ordinary artisan, and is routine in the art. In general, it is normally desirable to conduct conjugation reactions at a pH below 7, with a pH of about 5.5, about 6, about 6.5, usually about 5.5 being optimal. Where conjugation is conducted with a tagged and converted polypeptide present in or on a living cell, the conditions are selected so as to be physiologically compatible. For example, the pH can be dropped temporarily for a time sufficient to allow for the reaction to occur but within a period tolerated by the cell having an aldehyde tag (e.g., from about 30 min to 1 hour). Physiological conditions for conducting modification of tagged and converted polypeptides on a cell surface can be similar to those used in a ketone-azide reaction in modification of cells bearing cell-surface azides (see, e.g., U.S. Pat. No. 6,570,040).

Small molecule compounds containing, or modified to contain, an α-nucleophilic group that serves as a reactive partner with an aldehyde of an fGly of a converted tag are also contemplated for use as drugs in the Ig-drug conjugates of the present disclosure. General methods are known in the art for chemical synthetic schemes and conditions useful for synthesizing a compound of interest (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Thus small molecules having an aminooxy or hydrazone group for reaction with an aldehyde of an fGly of a tagged and converted Ig polypeptide are available or can be readily synthesized. An aminooxy or hydrazone group can be installed onto a small molecule using standard synthetic chemistry techniques.

Method of Treating an Individual

The antibody-drug conjugates of the present disclosure find use in treatment of a condition or disease in a subject that is amenable to treatment by administration of the parent drug (i.e., the drug prior to conjugation to the antibody). By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease; and/or (iii) relief, that is, causing the regression of clinical symptoms.

In the context of cancer, the term "treating" includes any or all of: reducing growth of a solid tumor, inhibiting replication of cancer cells, reducing overall tumor burden, and ameliorating one or more symptoms associated with a cancer. Thus, the present disclosure provides methods for delivering a cancer chemotherapeutic agent to an individual having a cancer. The methods are useful for treating a wide variety of cancers, including carcinomas, sarcomas, leukemias, and lymphomas. The cancer treated by the present method may be a cancer of a variety of tissues organs, such as, without limitation, cancer of the lungs, liver, breast, prostate, ovary, kidney, brain, colon, intestine, spleen, stomach, mouth, throat, skin, blood cells, etc.

The antibody to which the payload, e.g., drug, such as a cancer chemotherapeutic agent, is bound may specifically bind to an antigen associated with cell(s) or tissue(s) that are to be targeted and acted upon by the payload.

The present method may include administering to an individual a therapeutically effective amount of an antibody conjugate, e.g., an antibody-drug conjugate, as described herein. The antibody conjugate may be in any suitable formulation, e.g., formulated with a pharmaceutically acceptable excipient, as described herein.

The subject to be treated can be one that is in need of therapy, where the host to be treated is one amenable to treatment using the parent drug. Accordingly, a variety of subjects may be amenable to treatment using an antibody-drug conjugates disclosed herein. Generally such subjects are "mammals", with humans being of particular interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys.

The amount of antibody-drug conjugate administered can be initially determined based on guidance of a dose and/or dosage regimen of the parent drug. In general, the antibody-drug conjugates can provide for targeted delivery and/or enhanced serum half-life of the bound drug, thus providing for at least one of reduced dose or reduced administrations in a dosage regimen. Thus the antibody-drug conjugates can provide for reduced dose and/or reduced administration in a dosage regimen relative to the parent drug prior to being conjugated in an Ig-drug conjugate of the present disclosure.

Furthermore, as noted above, because the antibody-drug conjugates can provide for controlled stoichiometry of drug delivery, dosages of antibody-drug conjugates can be calculated based on the number of drug molecules provided on a per antibody-drug conjugate basis.

In some embodiments, multiple doses of an antibody-drug conjugate are administered. The frequency of administration of an antibody-drug conjugate can vary depending on any of a variety of factors, e.g., severity of the symptoms, etc. For example, in some embodiments, an Ig-drug conjugate is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

EXAMPLES

The following examples are put forth so as to provide those of ordinary skill in the art with a complete disclosure and description of how to make and use the disclosed subject matter, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Production of Tagged Ig Light Chain Constructs and Antibodies Containing Tagged Light Chains Positions within the constant region of human kappa light chain was systematically scanned by a tag insertion. A collection of tagged light chain constructs were generated by inserting the tag sequence: LCTPSR (SEQ ID NO:158) between adjacent amino acids at different sites in the light chain constant region (FIG. 1). Each construct also contained a light chain variable region of an antibody specific for a cell surface antigen. The entire length of the light chain constant region was scanned, to generate 106 variants, each having the tag inserted at a different position (see, e.g., FIGS. 10A-10D). Each light chain variant was provided in an expression vector for expression in Chinese hamster ovary (CHO) cells.

Methods and Materials

Figure 11:
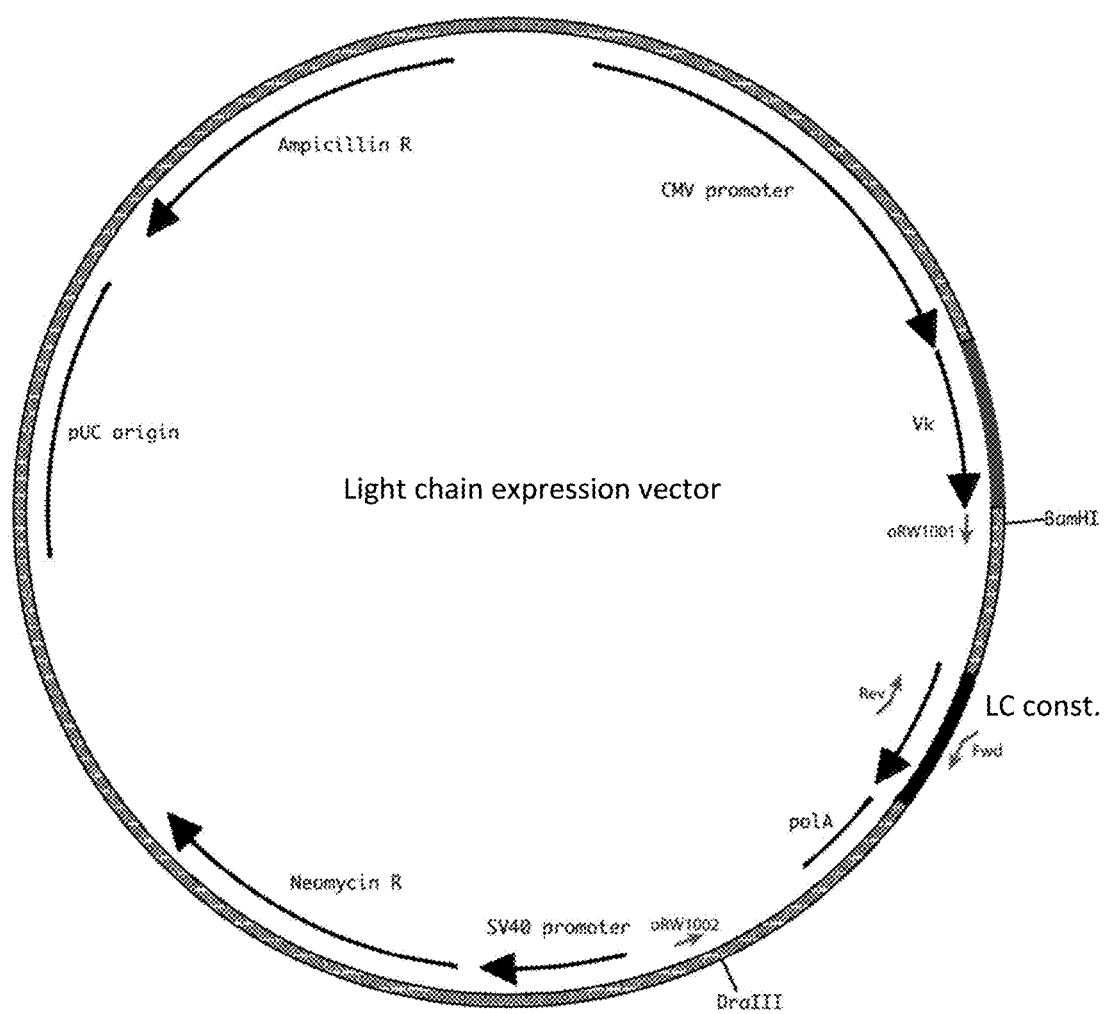
FIG. 11 shows a vector map of an expression vector encoding a light chain polypeptide of an antigen-specific antibody, according to embodiments of the present disclosure.

Light chain expression vector for the antigen-specific antibody was generated and digested with BamHI and DraIII in order to remove wild type human kappa light chain constant region (FIG. 11). The digested plasmid DNA was purified by gel electrophoresis and QIAquick gel extraction kit (Qiagen, MD). The purified plasmid backbone was used for cloning variant human kappa light chain constant genes containing a tag in various positions.

Figure 13A:
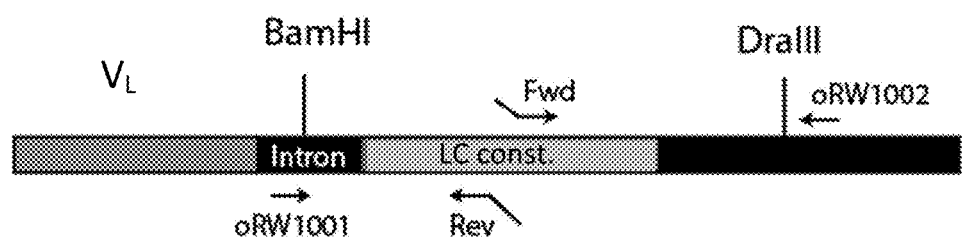
FIGS. 13A and 13B are a collection of schematic diagrams showing the PCR primers and assembly strategy of DNA fragments, according to embodiments of the present disclosure.
Figure 13B:
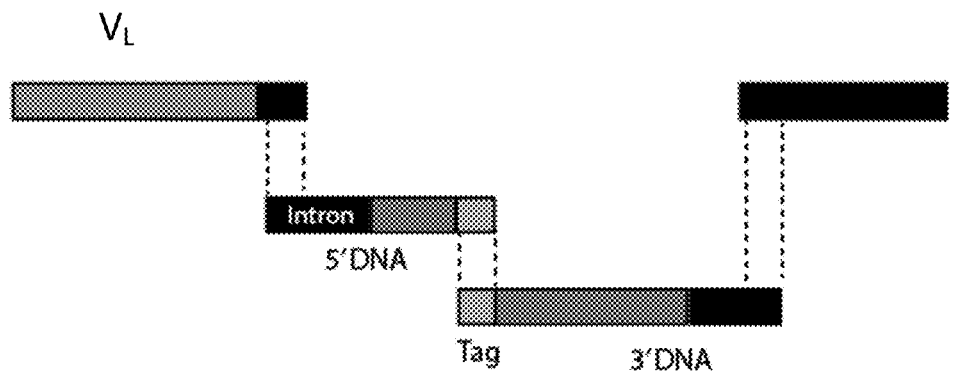

For inserting a tag into human kappa light chain constant region, two PCR amplifications were performed using the light chain expression vector as a template with Phusion DNA polymerase (New England Biolabs, MA). PCR cycling condition included a preheating step at 98° C. for 1 min, followed by 30 cycle of 98° C. for 10 seconds, 60° C. for 10 seconds, 72° C. for 20 seconds followed by 72° C. for 1 min for final extension. PCR amplification for the 5' part of human kappa light chain constant region was performed using a reverse primer (Table 3, in FIGS. 14A-14E, and FIG. 13A) with oRW1001 (5' TCAAACGTGAGTAGAATT-TAAACTTT 3' (SEQ ID NO:250)) and the 3' part of the DNA fragments were amplified using a forward primer and oRW1002 (5' AAAGGGCGAAAAACCGTCTATCAGG 3' (SEQ ID NO:251)) (Table 3 and FIG. 13A). All pairs of forward and reverse primers were designed to insert a tag sequence, LCTPSR (SEQ ID NO:158), throughout the human kappa light chain constant region (Table 3 in FIGS. 14A-14E). The amplified 5' DNA fragment and the corresponding 3' DNA fragment had compatible overlaps for assembly, as shown in the FIG. 13B. The amplified 5' and 3' DNA fragments were combined resulting in total 106 pairs of DNA mixture. The vector was linearized using BamHI and DraIII, and was added to the DNA mixtures. The reaction was subjected to Gibson assembly using Gibson assembly master mix (New England Biolabs, MA) according to the manufacturer's protocol.

The assembled DNA was transformed into E. coli Top10 chemically competent cells (Thermo Fisher Scientific) by the heat shock method. For this purpose 3 μl of the assembled plasmid DNA was added to 50 μl of chemically competent E. coli Top10 and the mixture was incubated on ice for 30 minutes and then subjected to a heat shock at 42° C. for 45 seconds. Then, the suspension was immediately placed on ice for one minute and 500 μl of SOC medium (Teknova, CA) was added. This mixture was incubated for 1 hour at 37° C. on shaker. These cells were plated on LB agar media (Teknova, CA) with antibiotic carbenicillin (100 μg/ml) as selection marker and grown overnight at 37° C. incubator. Colonies appeared on the agar plate were individually picked and inoculated into 3 ml of LB broth and grown at 37° C. for overnight followed by plasmid DNA purification using plasmid DNA isolation kit (Qiagen, Germany) according to the manufacturer's protocol. All 106 clones' DNA sequence integrity was confirmed by sending out to a sequencing service vendor (Sequetech, CA).

Example 2

Analysis of Expression Titer of Antibodies with a Tag in the Light Chain

The effect of inserting a tag at different positions along the light chain on the titer of expression of the antibody was tested by transfecting CHO cells (ExpiCHO™ cells) with an expression vector containing each of the variant light chains generated as described in Example 1, together with a second expression vector encoding the heavy chain polypeptide of the antigen-specific antibody, and a third expression vector encoding a formylglycine generating enzyme (FGE). Then the amount of antibodies secreted into the culture medium by cells expressing antibodies having the tag inserted along different positions of the light chain constant region was measured. The measured antibody titer showed that insertion position affected efficiency of expression from the CHO cells (FIGS. 2A and 2B).

Figure 2B:
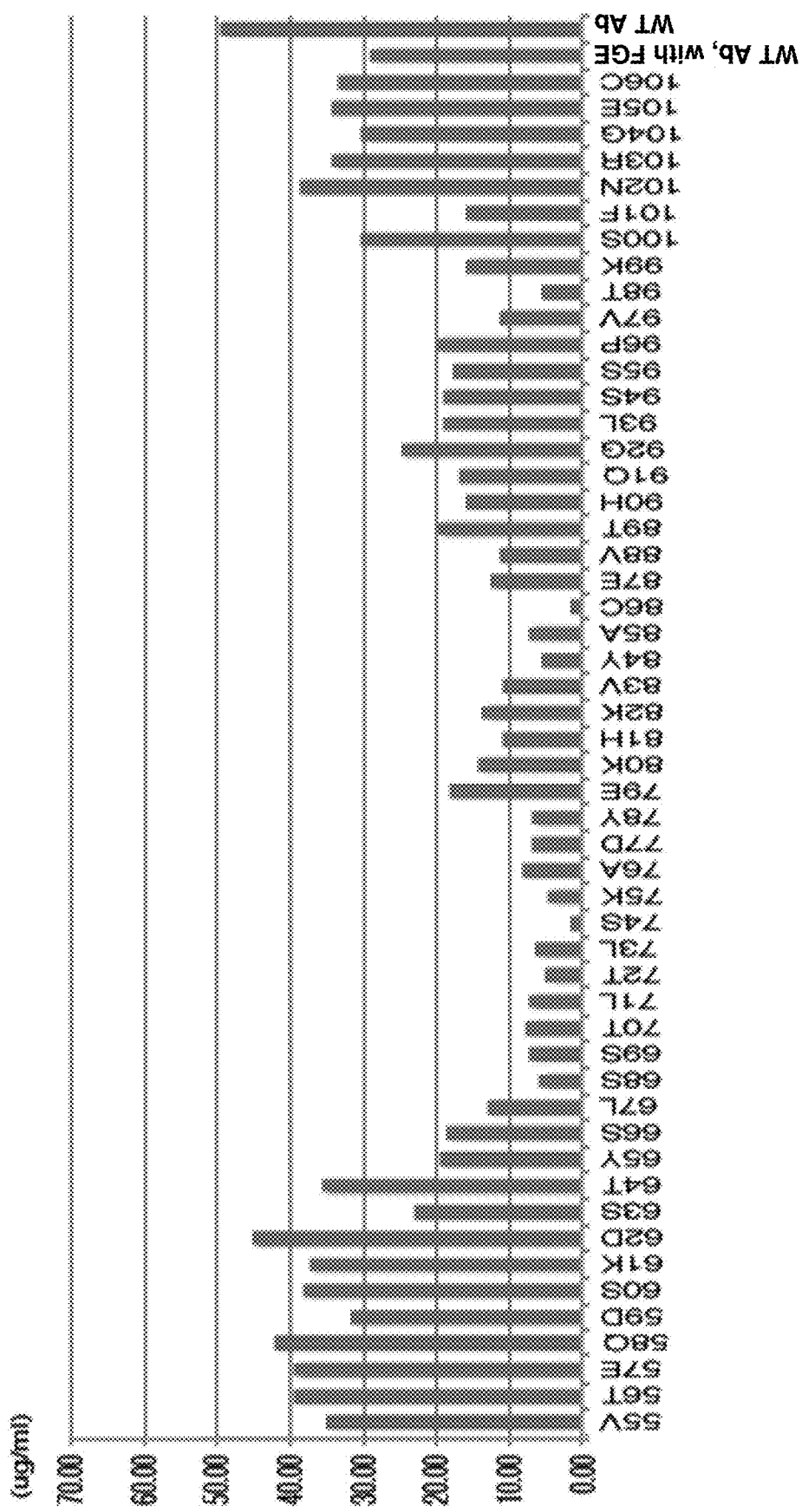

FIGS. 2A and 2B: The expression titer (y-axis), in ExpiCHO™ cells, of variant tagged antibodies, each having a sulfatase motif inserted adjacent and C-terminal to the position indicated, as defined relative to SEQ ID NO:1, in the constant region of its Ig light chain amino acid sequence. The titer of expression of control antibodies having no tag insertion in the light chain, from cells where FGE is co-expressed ("WT Ab with FGE") or not co-expressed ("WT Ab"), is shown in FIG. 2B.

Materials and Methods

Figure 12:
FIG. 12 shows a vector map for an expression vector encoding a heavy chain polypeptide of an antigen-specific antibody.

Expi-CHO—S cells were maintained routinely in 150 ml shaking flask in CHO expression medium (Thermo Fisher Scientific) at 37° C., and 8% $CO_2$. One day before transfection Expi-CHO—S cells were seeded into fresh CHO expression medium with the final cell density of $4 \times 10^6$ cells/ml. On next day, the cell number in the suspension culture was determined by using TC20 cell counter (Bio-Rad, CA) and adjusted the cell density to $6 \times 10^6$ cells/ml by adding additional CHO expression medium. At this step, 100 mM of $CuSO_4$ was supplemented to a final concentration of 100 μM. 6 ml of cells were seeded in a disposable mini-bioreactor tube (Corning, NY) for transfection. 1.8 ug of the expression vector for the heavy chain (FIG. 12) and 1.5 ug of FGE expression plasmid DNA were mixed with 2.7 ug of the light chain expression vector, as described above, in 240 μl of Opti-SFM (Thermo Fisher Scientific, CA) followed by combining with lipofectamine mixture containing 19.2 ul of Expi-ChoFectamine in 240 ul of Opti-SFM.

The Expi-CHO Fectamine and DNA complex was directly added to the cells and briefly mixed by swirling. After culturing at 37° C., and 8% $CO_2$ with 180 rpm orbital shaking for a day, 36 μl of enhancer solution and 960 μl of feed provided in the Expi-CHO transfection kit (Thermo Fisher Scientific, CA) was added to the cell and the cells were kept at 37° C. and 8% $CO_2$ with 180 rpm orbital agitation. After 4 days, additional 960 ul of feed was added to the cell and the cells were kept in the same culture condition for 5 days more. The culture supernatant was harvested by centrifugation and filtration with 0.45 μm PES filter followed by IgG quantification with Blitz system (Forte Bio, CA) using protein A biosensor chips (FIGS. 2A and 2B).

Example 3

Analysis of Aggregation of Antibodies with a Tag in the Light Chain

The effect of inserting a tag at different positions along the light chain on aggregation of the tagged antibodies, each having a sulfatase motif inserted adjacent and C-terminal to the position indicated, as defined relative to SEQ ID NO:1, in the constant region of its Ig light chain amino acid sequence, was tested (FIG. 3). To determine aggregation, samples were analyzed using analytical size exclusion chromatography (SEC; Tosoh #08541) with a mobile phase of 300 mM NaCl, 25 mM sodium phosphate pH 6.8.

Example 4

Analysis of Conjugation Efficiency of Antibodies with a Tag in the Light Chain

Figure 4:
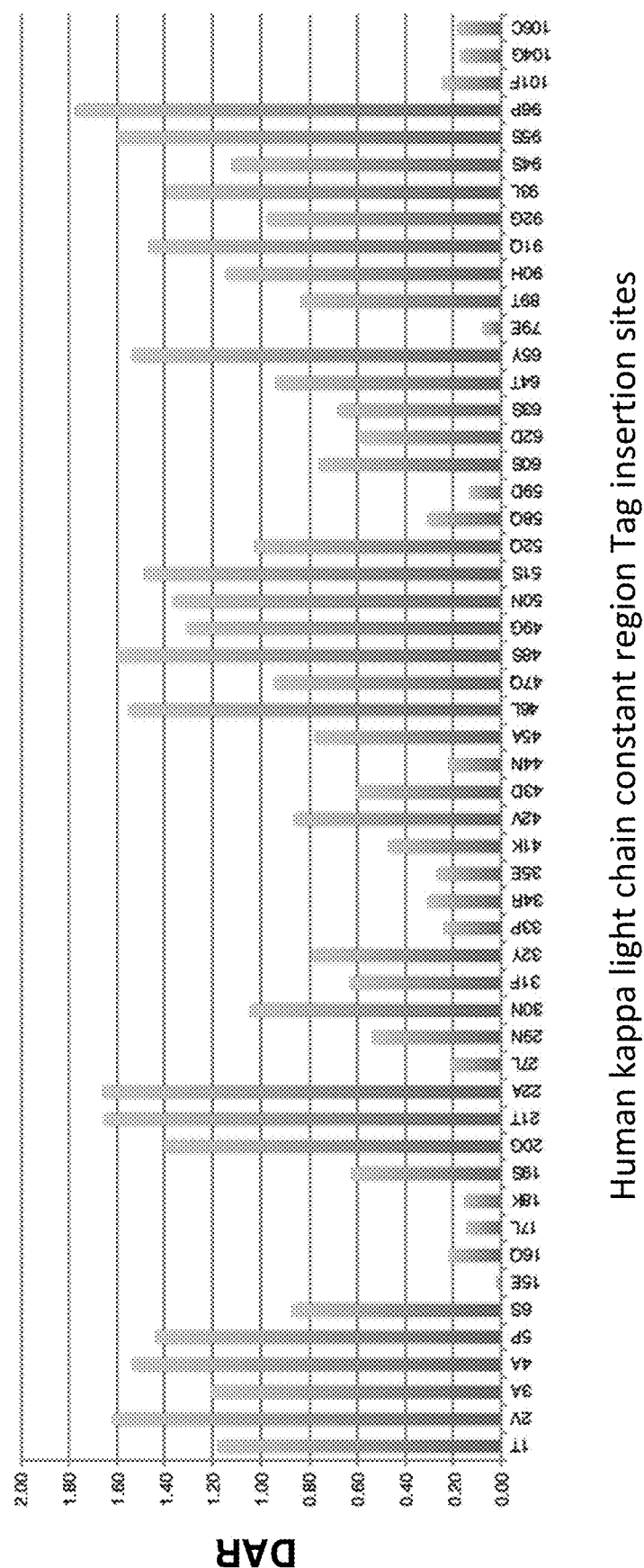
FIG. 4 is a graph showing the drug-to-antibody ratio (DAR) for an antigen-specific antibody conjugated to a hydrophobic payload, where the antibody was modified by having a sulfatase motif inserted adjacent and C-terminal to the indicated position, as defined relative to SEQ ID NO:1, in the constant region of its Ig light chain amino acid sequence, according to embodiments of the present disclosure.

A subset of insertion sites selected based on the titer, as shown in Example 2, was chosen to study the conjugation efficiency, as measured by the drug-to-antibody ratio (DAR). Antibodies having a tagged (fGly-containing) light chain polypeptide were conjugated with a hydrophobic payload, a detectable label which serves as a surrogate for drug. Measurement of DAR of the tagged antibodies after conjugation with the hydrophobic payload showed variable conjugation efficiency across the different insertion sites (FIG. 4).

Figure 5:
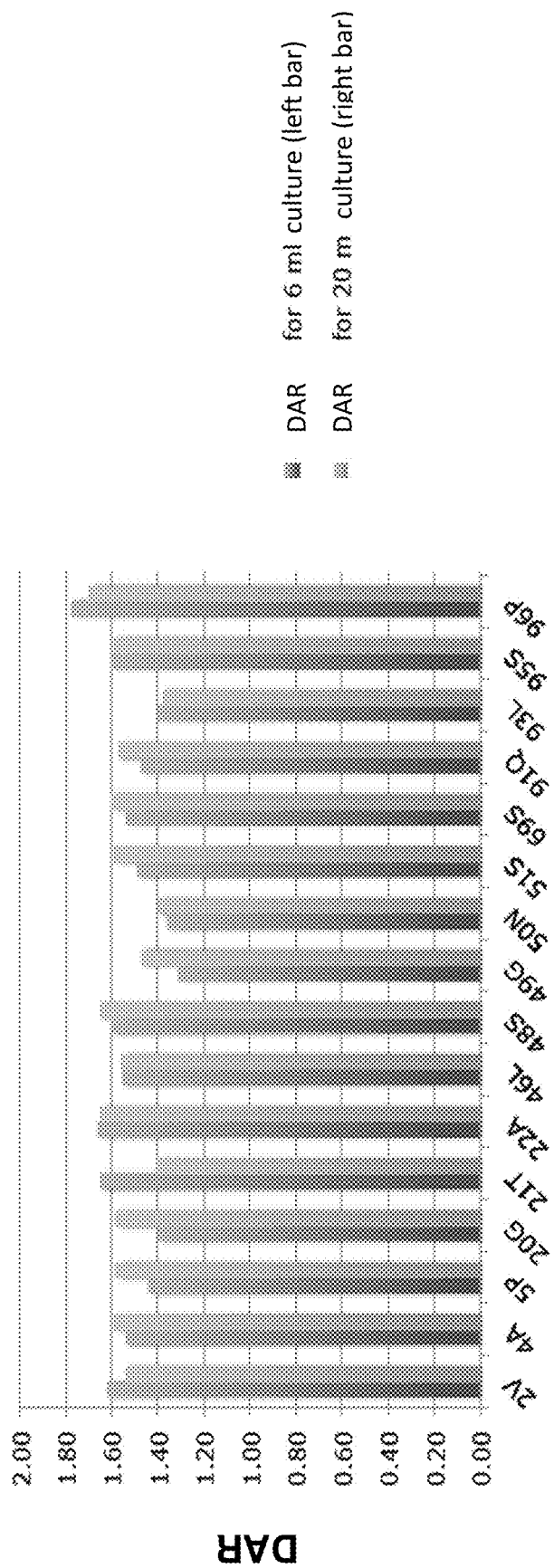
FIG. 5 is a graph showing DAR of for an antigen-specific antibody conjugated to a hydrophobic payload, where the antibody was modified by having a sulfatase motif inserted adjacent and C-terminal to the indicated position, as defined relative to SEQ ID NO:1, in the constant region of its Ig light chain amino acid sequence, according to embodiments of the present disclosure.
Figure 6E:
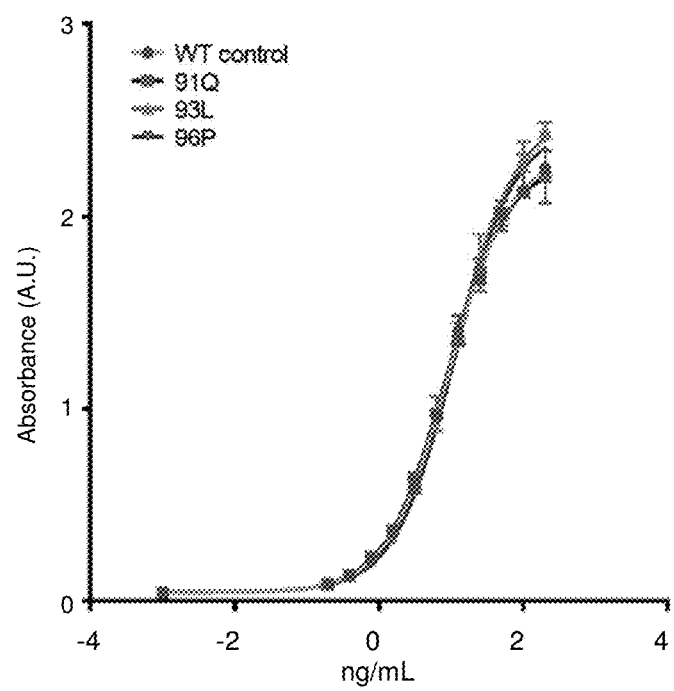
Figure 7A:
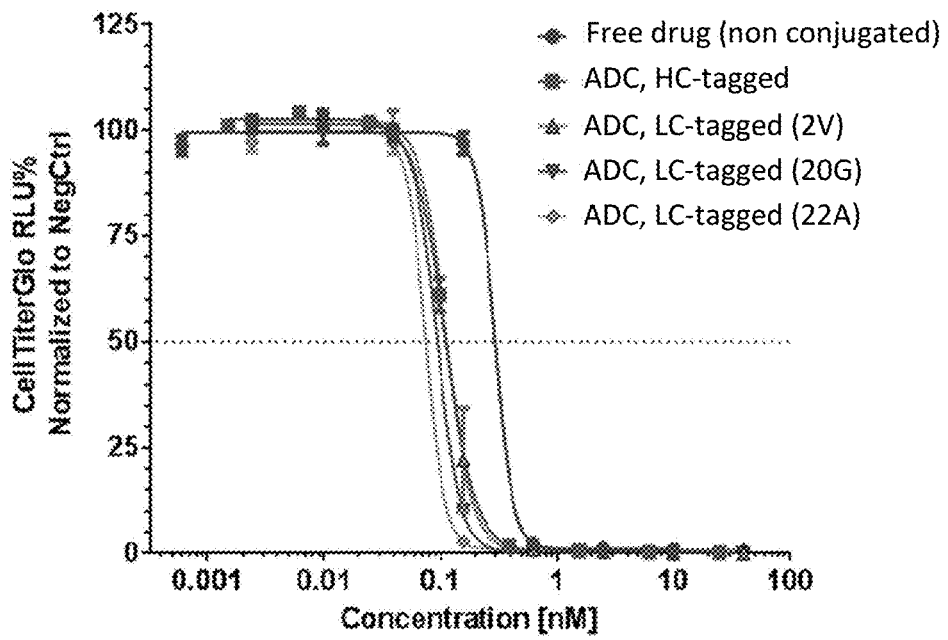
FIGS. 7A-7B are a collection of graphs showing efficacy of a cytotoxic drug conjugated to an antigen-specific antibody having a sulfatase motif inserted adjacent and C-terminal to the indicated position, as defined relative to SEQ ID NO:1, in the constant region of its Ig light chain amino acid sequence, according to embodiments of the present disclosure.
Figure 7B:
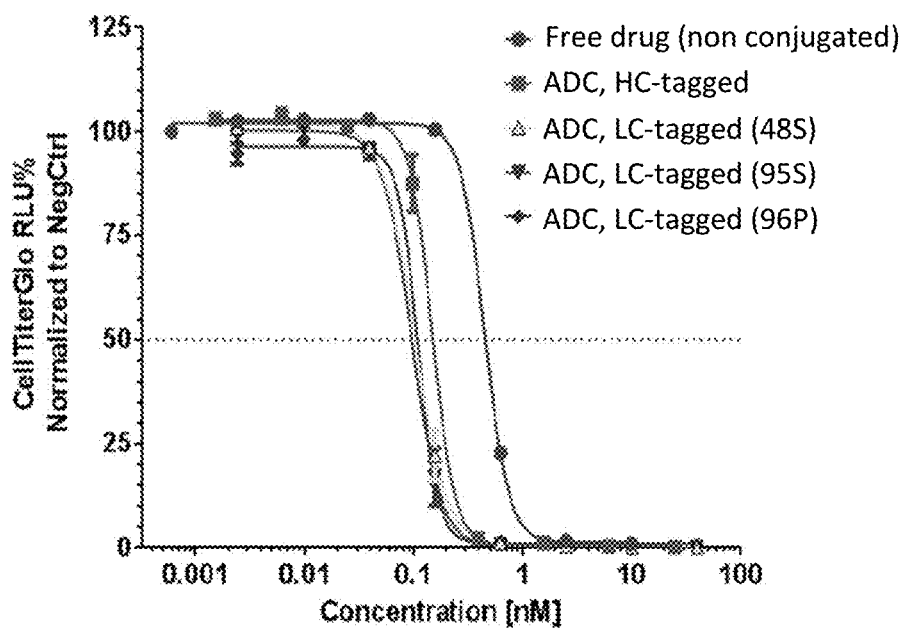
Figure 8A:
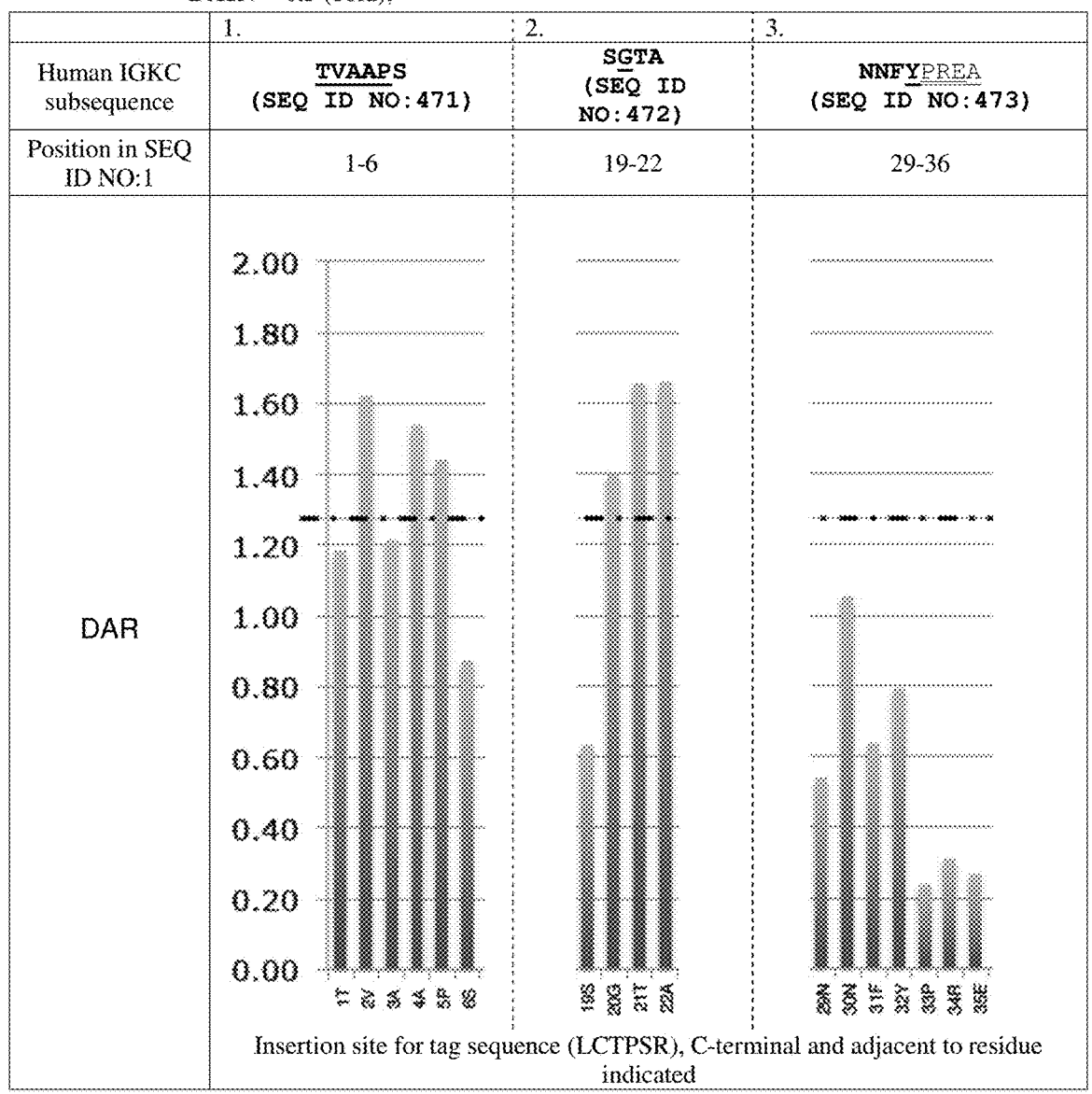
FIGS. 8A-8C is a table comparing solvent accessible loop regions in relation to the DAR observed upon conjugation of an antigen-specific antibody to a cytotoxic drug (hydrophobic payload), where the antibody was modified by having a sulfatase motif inserted adjacent and C-terminal to the indicated position, as defined relative to SEQ ID NO:1, in the constant region of its Ig light chain amino acid sequence, according to embodiments of the present disclosure.
Figure 8B:
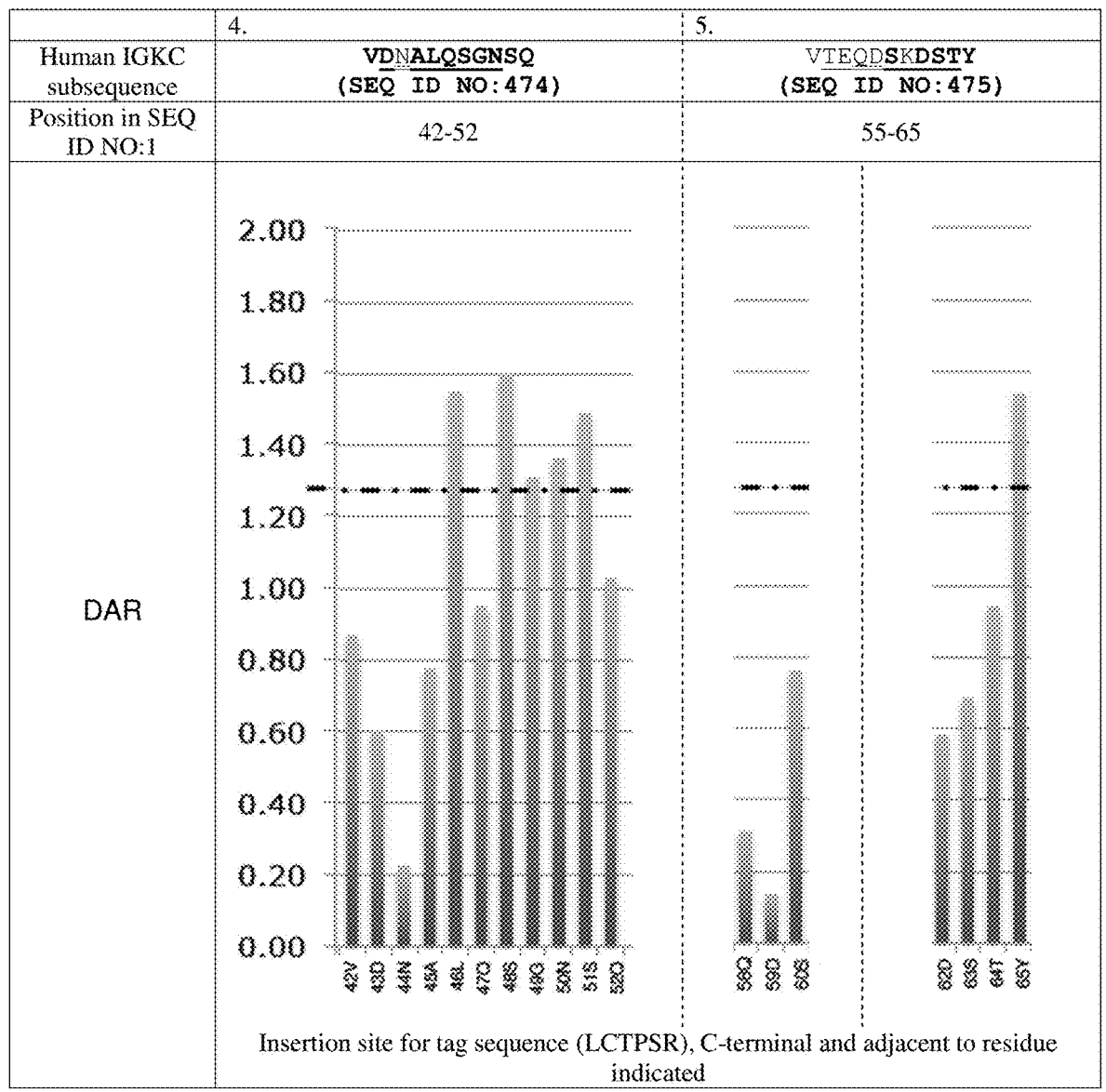
Figure 8C:
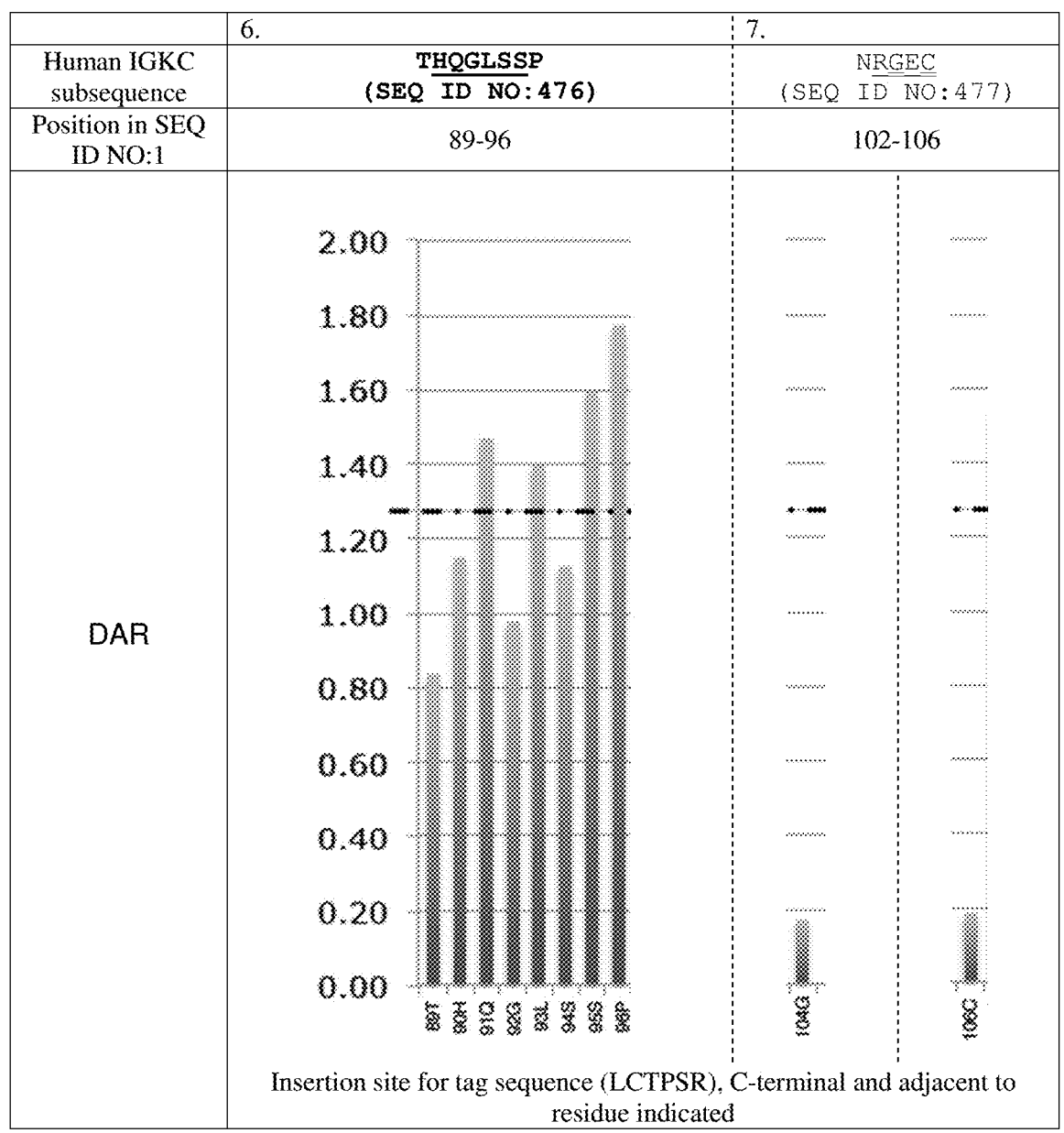

The conjugation yield of light chain-tagged antibodies expressed in ExpiCHO™ cells in a 6 ml culture volume in a tube was similar to the conjugation efficiency when expressed in ExpiCHO™ cells in a 20 ml culture volume in a flask, showing that the conjugation efficiency of the light-chain tagged antibody with a hydrophobic payload was consistent between tagged antibodies produced under different culture conditions (FIG. 5).

Materials and Methods

To determine the drug-to-antibody ratio (DAR) of the final product, antibody-drug conjugates (ADCs) were examined by analytical HIC (Tosoh #14947) with mobile phase A: 1.5 M ammonium sulfate, 25 mM sodium phosphate pH 7.0, and mobile phase B: 25% isopropanol, 18.75 mM sodium phosphate pH 7.0.

Example 5

Functional Properties of Antibody-Drug Conjugates

Select light chain-tagged antibody-drug conjugates were tested for antigen binding using ELISA. All light chain-tagged antibody-drug conjugates tested had antigen binding properties similar to the parent antibody (FIGS. 6A-6E).

Select light chain-tagged antibodies conjugated to a cytotoxic drug were tested for cytotoxic activity towards cells expressing the antigen on the cell surface. All light chain-tagged antibody-drug conjugates tested exhibited enhanced cytotoxicity compared to free drug, and similar potency as a heavy chain-tagged antibody-drug conjugate.

Materials and Methods

Light chain-tagged antibody (1 mg/mL) was conjugated to a hydrophobic payload (cytotoxic drug) functionalized with an aldehyde-reactive group (360 mol. equivalents drug:antibody) for 16-24 h at 37° C. in 50 mM sodium citrate, 50 mM NaCl pH 5.5 containing 0.85% dimethylacetamide (DMA). Unconjugated drug was removed by repeated buffer exchange using a centrifugal concentrator with a molecular weight cutoff (MWCO) of 10 kD.

While the present disclosure has been described with reference to the specific embodiments thereof, it should be understood by those skilled in the art that various changes may be made and equivalents may be substituted without departing from the true spirit and scope of the present disclosure. In addition, many modifications may be made to adapt a particular situation, material, composition of matter, process, process step or steps, to the objective, spirit and scope of the present disclosure. All such modifications are intended to be within the scope of the claims appended hereto.

What is claimed is:

1. An immunoglobulin (Ig) kappa light chain polypeptide comprising, in a constant region, an amino acid sequence selected from:
   i) SEQ ID NO: 2, SEQ ID NO: 4, SEQ ID NO: 17, SEQ ID NO: 18, SEQ ID NO: 26, SEQ ID NO: 28, SEQ ID NO: 31, SEQ ID NO: 37, SEQ ID NO: 44, and SEQ ID NO: 45;
   wherein the cysteine residue in the sequence LCTPSR (SEQ ID NO: 158) is oxidized to fGly.

2. The Ig kappa light chain polypeptide of claim 1, wherein the fGly is covalently bound to a payload.

3. The Ig kappa light chain polypeptide of claim 2, wherein the fGly is covalently bound to the payload via a hydrazone, oxime, semicarbazone, alkyl, alkenyl, acyloxy, hydrazinyl-indolyl, hydrazinyl-imidazoyl, hydrazinyl-pyrrolyl, hydrazinyl-furanyl or a pyrazalinone linkage.

4. The Ig kappa light chain polypeptide of claim 2, wherein the fGly is covalently bound to the payload via a linking group.

5. The Ig kappa light chain polypeptide of claim 4, wherein the linking group comprises a 4-aminopiperidine derivative (4AP).

6. The Ig kappa light chain polypeptide of claim 2, wherein the payload is a drug, a detectable label, a water-soluble polymer, a viral fusion inhibitor, or a synthetic peptide.

7. The Ig kappa light chain polypeptide of claim 6, wherein the drug is a small molecule drug.

8. The Ig kappa light chain polypeptide of claim 7, wherein the small molecule drug is a cancer chemotherapeutic agent.

9. The Ig kappa light chain polypeptide of claim 8, wherein the cancer chemotherapeutic agent is an alkylating agent, a nitrosourea, an antimetabolite, an antitumor antibiotic, a *vinca* alkaloid, or a steroid hormone.

10. The Ig kappa light chain polypeptide of claim 6, wherein the water-soluble polymer is poly(ethylene glycol).

11. The Ig kappa light chain polypeptide of claim 6, wherein the detectable label is an imaging agent.

12. A recombinant nucleic acid comprising a nucleotide sequence encoding the Ig kappa light chain polypeptide of claim 1.

13. A recombinant expression vector comprising the nucleic acid of claim 12, wherein the nucleotide sequence encoding the Ig kappa light chain polypeptide is operably linked to a promoter.

14. A host cell genetically modified to express the Ig kappa light chain polypeptide of claim 1.

15. The host cell of claim 14, genetically modified to express a formylglycine generating enzyme (FGE), in a manner sufficient to convert the Ig kappa light chain polypeptide into an fGly-modified Ig kappa light chain polypeptide.

16. The host cell of claim 15, wherein the host cell is a mammalian cell.

17. An antibody comprising the Ig kappa light chain polypeptide of claim 1.

18. The antibody of claim 17, wherein the antibody specifically binds a tumor antigen on a cancer cell.

19. A formulation comprising: the antibody of claim 18 and a pharmaceutically acceptable excipient.

20. The Ig kappa light chain polypeptide of claim 1, comprising, in the constant region, the amino acid sequence of SEQ ID NO: 2, wherein the cysteine residue in the sequence LCTPSR (SEQ ID NO: 158) is oxidized to fGly.

21. The Ig kappa light chain polypeptide of claim 1, comprising, in the constant region, the amino acid sequence of SEQ ID NO: 4, wherein the cysteine residue in the sequence LCTPSR (SEQ ID NO: 158) is oxidized to fGly.

22. The Ig kappa light chain polypeptide of claim 1, comprising, in the constant region, the amino acid sequence of SEQ ID NO: 17, wherein the cysteine residue in the sequence LCTPSR (SEQ ID NO: 158) is oxidized to fGly.

23. The Ig kappa light chain polypeptide of claim 1, comprising, in the constant region, the amino acid sequence of SEQ ID NO: 18, wherein the cysteine residue in the sequence LCTPSR (SEQ ID NO: 158) is oxidized to fGly.

24. The Ig kappa light chain polypeptide of claim 1, comprising, in the constant region, the amino acid sequence of SEQ ID NO: 26, wherein the cysteine residue in the sequence LCTPSR (SEQ ID NO: 158) is oxidized to fGly.

25. The Ig kappa light chain polypeptide of claim 1, comprising, in the constant region, the amino acid sequence of SEQ ID NO: 28, wherein the cysteine residue in the sequence LCTPSR (SEQ ID NO: 158) is oxidized to fGly.

26. The Ig kappa light chain polypeptide of claim 1, comprising, in the constant region, the amino acid sequence of SEQ ID NO: 31, wherein the cysteine residue in the sequence LCTPSR (SEQ ID NO: 158) is oxidized to fGly.

27. The Ig kappa light chain polypeptide of claim 1, comprising, in the constant region, the amino acid sequence of SEQ ID NO: 37, wherein the cysteine residue in the sequence LCTPSR (SEQ ID NO: 158) is oxidized to fGly.

28. The Ig kappa light chain polypeptide of claim 1, comprising, in the constant region, the amino acid sequence of SEQ ID NO: 44, wherein the cysteine residue in the sequence LCTPSR (SEQ ID NO: 158) is oxidized to fGly.

29. The Ig kappa light chain polypeptide of claim 1, comprising, in the constant region, the amino acid sequence of SEQ ID NO: 45, wherein the cysteine residue in the sequence LCTPSR (SEQ ID NO: 158) is oxidized to fGly.

\* \* \* \* \*